(12) United States Patent
Subramanyam et al.

(10) Patent No.: US 10,723,727 B2
(45) Date of Patent: Jul. 28, 2020

(54) TUBULYSIN ANALOGS AND METHODS FOR THEIR PREPARATION

(71) Applicants: PFIZER INC., New York, NY (US); CovX Technologies Ireland Limited, Ringaskiddy, Co. Cork (IE)

(72) Inventors: Chakrapani Subramanyam, South Glastonbury, CT (US); Lawrence N. Tumey, Vestal, NY (US); Longfei Xie, Groton, CT (US); Carolyn Leverett, Groton, CT (US); Beth C. Vetelino, North Stonington, CT (US); Sai Chetan K. Sukuru, Glastonbury, CT (US); Sarah Hudson, San Diego, CA (US); Venkata Ramana Doppalapudi, San Dieto, CA (US); Abhijit S. Bhat, Winchester, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 16/072,291

(22) PCT Filed: Jan. 27, 2017

(86) PCT No.: PCT/IB2017/050462
§ 371 (c)(1),
(2) Date: Jul. 24, 2018

(87) PCT Pub. No.: WO2017/134547
PCT Pub. Date: Aug. 10, 2017

(65) Prior Publication Data
US 2018/0362519 A1    Dec. 20, 2018

Related U.S. Application Data

(60) Provisional application No. 62/322,328, filed on Apr. 14, 2016, provisional application No. 62/289,485, filed on Feb. 1, 2016.

(51) Int. Cl.
| | | |
|---|---|---|
| *A61K 31/426* | (2006.01) |
| *A61K 31/427* | (2006.01) |
| *A61K 31/4025* | (2006.01) |
| *A61K 47/65* | (2017.01) |
| *C07D 277/56* | (2006.01) |
| *C07D 417/12* | (2006.01) |
| *A61P 35/00* | (2006.01) |
| *C07D 277/42* | (2006.01) |
| *A61K 47/68* | (2017.01) |

(52) U.S. Cl.
CPC ............ *C07D 417/12* (2013.01); *A61K 47/65* (2017.08); *A61K 47/6803* (2017.08); *A61P 35/00* (2018.01); *C07D 277/42* (2013.01); *C07D 277/56* (2013.01)

(58) Field of Classification Search
CPC ............... A61K 31/426; A61K 31/427; A61K 31/4025; A61K 47/65; A61K 47/6803; C07D 277/56; C07D 417/12; A61P 35/00
USPC .................. 514/365; 548/204, 205, 200, 518
See application file for complete search history.

(56) References Cited

U.S. PATENT DOCUMENTS

| | | | |
|---|---|---|---|
| 4,816,397 A | 3/1989 | Boss et al. |
| 4,816,567 A | 3/1989 | Cabilly et al. |
| 5,545,806 A | 8/1996 | Lonberg et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 2006/0205670 A1 | 9/2006 | Bradshaw et al. |
| 2011/0027274 A1 | 2/2011 | Cheng et al. |
| 2014/0363452 A1 | 12/2014 | Doroski et al. |

FOREIGN PATENT DOCUMENTS

| | | | |
|---|---|---|---|
| EP | 0171496 A2 | 2/1986 | |
| EP | 0173494 A2 | 3/1986 | |
| EP | 0184187 A2 | 6/1986 | |
| EP | 0404097 A2 | 12/1990 | |
| WO | WO-2008138561 A1 * | 11/2008 | ............. C07K 5/021 |

OTHER PUBLICATIONS

Beidler, et al., "Cloning and High Level Expression of a Chimeric Antibody With Specificity for Human Carcinoembryonic Antigen", The Journal of Immunology, 1988, 4053-4060, 141(11).

Better, et al., "*Escherichia coli* Secretion of an Active Chimeric Antibody Fragment", Science, 1988, 1041-1043, 240.

Chothia, et al., "Canonical Structures for the Hypervariable Regions of Immunoglobulins", Journal of Molecular Biology, 1987, 901-917, 196.

Holliger, et al., "Diabodies": Samll bivalent and bispecific antibody fragments, PNAS, 1993, 6444-6448, 90.

Hoogenboom, et al., "By-passing Immunisation Human Antibodies from Synthetic Repertoires of Germline VH Gene Segments Rearranged in Vitro", Journal of Molecular Biology, 1992, 381-388, 227.

Jespers, et al., "Guiding the Selection of Human Antibodies from Phage Display Repertoires to a Single Epitope of an Antigen", Bio/Technology, 1994, 899-903, 12.

Jones, et al., "Replacing the complementarity-determing regions in a human antibody with those from a mouse", Nature, 1986, 522-525, 321.

Kabat, "Origins of Antibody Complementarity and Specificity—Hypervariable Regions and the Minigene Hypothesis", The Journal of Immunology, 1980, 961-969, 125.

(Continued)

*Primary Examiner* — Matthew P Coughlin
*Assistant Examiner* — Sagar Patel
(74) *Attorney, Agent, or Firm* — David Rubin

(57) ABSTRACT

The present invention is directed to novel cytotoxic tubulysin analogs and derivatives, to antibody drug conjugates thereof, and to methods for using the same to treat medical conditions including cancer.

7 Claims, 3 Drawing Sheets

(56) References Cited

OTHER PUBLICATIONS

Kozbor, et al., "The production of monoclonal antibodies from human lymphocytes", Immunology Today, 1983, 72-79, 4(3).
Laguzza, et al., "New Antitumor Monoclonal Antibody-Vinca Conjugates LY203725 and Related Compounds: Design, Preparation, and Representative in Vivo Activity", Journal Med. Chem., 1989, 548-555, 32.
Langer, "New Methods of Drug Delivery", Science, 1990, 1527-1532, 249.
Liu, et al., Production of a mouse-human chimeric monoclonal antibody to CD20 with potent Fc-dependent biologic activity, Journal of Immunology, 1987, 3521-3526, 139.
Liu, et al., "Chimeric mouse-human IgG1 antibody that can mediate lysis of cancer cells", PNAS, 1987, 3439-3443, 84.
Lonberg et al., "Human Antibodies from Transgenic Mice", Intern. Rev. Immunol., 1995, 65-93, 13.
Marks, et al., "By-passing Immunization, Human Antibodies from V-gene Libraries Displayed on Phage", J. Mol. Biol, 1991, 581-597, 222.
Morrison, "Transfectomas Provide Novel Chimeric Antibodies", Science, 1985, 1202-1207, 229.
Nishimura, et al., "Recombinant Human-Mouse Chimeric Monoclonal Antibody Specific for Common Acute Lymphocytic Leukemia Antigen", Cancer Research, 1987, 999-1005, 999.
Oi, "Chimeric Antibodies", BioTechniques, 1986, 214-221, 4(3).
Olsson et al., "Human-Human Monoclonal Antibody-Producing Hybridomas: Technical Aspects", Methods of Enzymology, 1982, 3-16, 92.
Presta, "Antibody engineering", Current Opinion in Structural Biology, 1992, 593-596, 1992.
Riechmann, et al., "Reshaping human antibodies for therapy", Nature, 1988, 323-327, 332.
Sasse, et al., "Tubulysins, New Cytostatic Peptides from Myxobacteria Acting on Microtubuli Production, Isolation, Physico-chemical and Biological Properties", The Journal of Antibiotics, 2000, 879-895, 53(9).
Schroder, et al., "Formation of the Peptide Bond", Methods of Peptide, 1965, 76-136.
Shaw, et al., "Mouse/Human Chimeric Antibodies to a Tumor-Associated Antigen: Biologic Activity of the Four Human IgG Subclasses", Journal of the National Cancer Institute, 1988, 1553-1559, 80(19).
Sun, et al., "Chimeric antibody with human constant regions and mouse variable regions directed against carcinoma-associated antigen 17-1A", PNAS, 1987, 214-218, 84.
Teng, et al., "Construction and testing of mouse-human heteromyelomas for human monoclonal antibody production", PNAS, 1983, 7308-7312, 80.
Verhoeyen, et al., "Reshaping Human Antibodies: Grafting an Antilysozyme Activity", Science, 1988, 1534-1536, 239.
Wood, et a., "The synthesis and in vivo assembly of functional antibodies in yeast", Nature, 1985, 446-449, 314.
International Search Report dated Jun. 1, 2017 for International Application No. PCT/IB2017/050462, filed Jan. 27, 2017.
Written Opinion of the International Searching Authority for International Application No. PCT/IB2017/050462, filed Jan. 27, 2017.

* cited by examiner

In vivo efficacy of ADCs in N87-Xenograft

Plasma stability of ADCs

FIG. 3

In vivo Stability of ADCs (as measured by DAR)

| Example | DAR at 0 h post-dose | DAR at 72 h post-dose | % DAR remaining at 72 h |
|---|---|---|---|
| ADC#1 | 3.8 | 0.6 | 16% |
| ADC#2 | 1.8 | 1.7 | 95% |
| ADC#10 | 4.0 | 3.2 | 80% |

TUBULYSIN ANALOGS AND METHODS FOR THEIR PREPARATION

CROSS-REFERENCE TO RELATED APPLICATIONS

This Application is the national stage filing under 35 U.S.C. 371 of Patent Cooperation Treaty Patent Application No. PCT/IB2017/050462, filed Jan. 27, 2017, which claims the benefit of priority from U.S. Provisional Application No. 62/289,485 filed Feb. 1, 2016 and U.S. Provisional Application No. 62/322,328 filed Apr. 14, 2016, the contents of each of which are hereby incorporated by reference in their entirety.

FIELD OF THE INVENTION

The present invention is directed to novel natural product-derived and/or tubulysin-based compounds useful as payloads in antibody-drug-conjugates (ADCs), and payload-linker compounds useful in connection with ADCs. The present invention further relates to compositions including the aforementioned payloads, payload-linkers and ADCs, and methods for using these payloads, payload-linkers and ADCs, to treat pathological conditions including cancer.

BACKGROUND

Conjugation of drugs to antibodies, either directly or via linkers, involves a consideration of a variety of factors, including the identity and location of the chemical group for conjugation of the drug, the mechanism of drug release, the structural elements providing drug release, and the structural modification to the released free drug. In addition, if the drug is to be released after antibody internalization, the mechanism of drug release must be consonant with the intracellular trafficking of the conjugate.

While a number of different drug classes have been tried for delivery via antibodies, only a few drug classes have proved efficacious as antibody drug conjugates, while having a suitable toxicity profile.

Tubulysins are a class of potent antimitotic agents isolated from myxobacteria (J. Antibiot. 2000, 53, 879). Tubulysins prevent the assembly of the tubulins into microtubules and have been evaluated as payloads for delivery as an ADC (US 2011/0027274 A1, WO2015/157592A1, WO14080251). However, there remains a need for additional tubulysins with improved properties.

SUMMARY OF THE INVENTION

The present invention relates to compounds and pharmaceutical compositions containing them, to their preparation, and to uses for the compounds, primarily but not exclusively anti-cancer agents. Specifically, the present invention relates to a compound or compounds of formula (I):

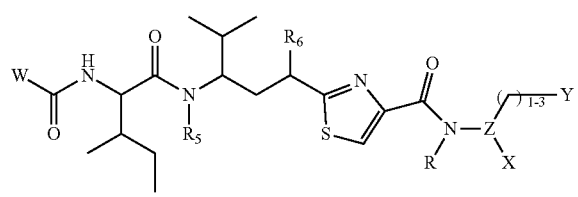

(I)

or a pharmaceutically acceptable salt thereof, wherein:

W is selected from:

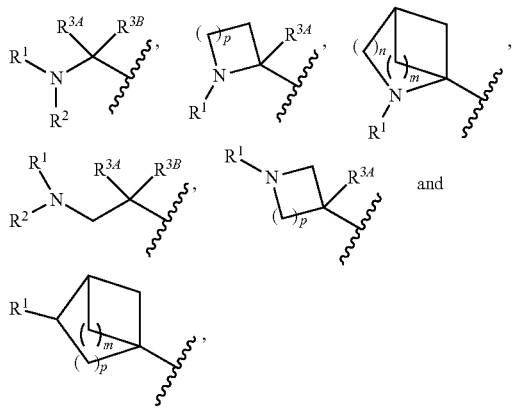

where:

m is 1-3;

n is 1-2; and p is 1-4;

$R^1$ is selected from hydrogen, $C_1$-$C_8$ alkyl and $C_1$-$C_8$ haloalkyl;

$R^2$ is selected from hydrogen, $C_1$-$C_8$ alkyl and $C_1$-$C_8$ haloalkyl;

each $R^{3A}$ and $R^{3B}$ is independently selected from $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen and aralkyl; or $R^{3A}$ and $R^{3B}$ taken together are selected from $C_2$-$C_8$ alkylene and $C_1$-$C_8$ heteroalkylene;

$R^5$ is selected from hydrogen, $C_1$-$C_8$ alkyl, $C_1$-$C_8$ haloalkyl, $C_3$-$C_8$ carbocyclyl, $C_3$-$C_8$ heterocyclyl, aryl, heteroaralkyl, aralkyl, where $R^5$ is optionally substituted with —$(C(R)_2)_m$NR$^1$R$^2$;

$R^6$ is selected from hydrogen, OR$^7$, OC(O)R$^7$, OC(O)NR$^7$R$^8$, NR$^7$R$^8$, N(R$^7$)C(O)R$^7$, N(R$^7$) C(O)OR$^7$, N(R)C(O)NR$^7$R$^8$, N(R$^7$)SO$_2$R, and N(R$^7$)SO$_2$NR$^7$R$^8$, where R$^7$ and R$^8$ are each independently selected from hydrogen, $C_1$-$C_8$ alkyl, $C_3$-$C_8$ carbocyclyl, $C_3$-$C_8$ heterocyclyl, aryl, heteroaralkyl and aralkyl; or R$^7$ and R$^8$, together with the nitrogen to which they are joined form $C^3$-$C^{10}$ heterocyclyl, and where one or more of R$^7$ and R$^8$ are optionally substituted with one or more substituents selected from halogen, NR$_2$, CN, OH and OC$_1$-$C_8$ alkyl;

Z is N or CR$^2$;

Y is selected from aryl, $C_3$-$C_8$ heterocyclyl and $C_5$-$C_{14}$ heteroaryl, where Y is optionally substituted with one or more R$^{11}$, or Y is selected from:

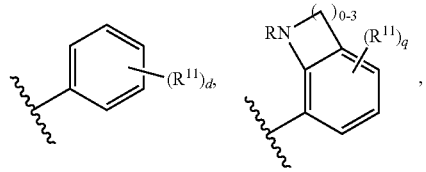

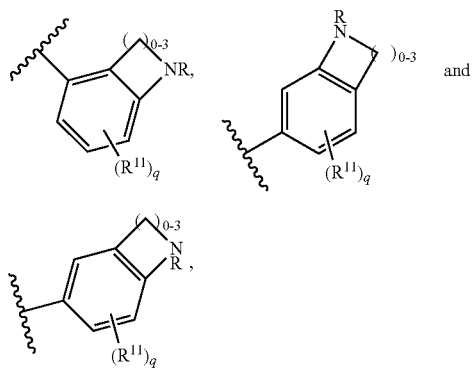 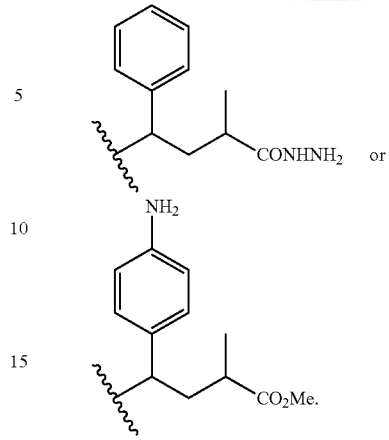

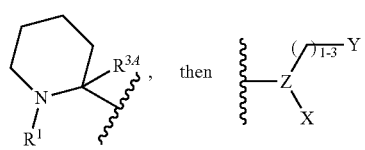

where
d is 1-5;
q is 1-3; and
each $R^{11}$ is independently selected from hydrogen, $C_1$-$C_8$ alkyl, $C_1$-$C_8$ haloalkyl, halogen, —CN, —OH, —C(R)$_2$)$_t$ONRR, —(C(R)$_2$)$_t$—NRR, (C(R)$_2$)$_t$—C(O)R, (C(R)$_2$)$_t$—CONR$^8$R$^9$, —(C(R)$_2$)$_t$C(O)NRNRR, —(C(R)$_2$)$_t$C(O)N(R)OH, —(C(R)$_2$)$_t$SH, —(C(R)$_2$)$_t$—N(R)—C(O)R, —(C(R)$_2$)$_t$N(R)—C(O)OR, —(C(R)$_2$)$_t$—N(R)—SO$_2$R, —(C(R)$_2$)$_t$N(R)C(O)NR$^8$R$^9$, —(C(R)$_2$)$_t$SO$_2$NR$^8$R$^9$, and —(C(R)$_2$)$_t$N(R)SO$_2$NR$^8$R$^9$, where each t is independently 0-3; and X is selected from hydrogen, —C(O)OR, $C_1$-$C_6$ alkyl, $C_6$-$C_{14}$ aryl, $C_5$-$C_4$ heteroaryl, $C_3$-$C_6$ carbocyclyl, $C_3$-$C_8$ heterocyclyl, —$C_1$-$C_6$ alkyl-$C_6$-$C_{14}$ aryl, and —$C_1$-$C_6$alkyl-$C_5$-$C_{14}$heteroaryl, where X is optionally substituted with 1-3 substituents independently selected from, halogen, —OH, —C(O)OR, —CON(R)OH, —ONR$^2$, —NR$^8$R$^9$, —COR, —CONR$^2$, —CONRNRR, —SH, —N(R)—COR, —N(R)—C(O)OR, —N(R)—SO$_2$R, —N(R)—CONR$^8$R$^9$, —SO$_2$—NR$^8$R$^9$, —N(R)—SO$_2$ NR$^8$R$^9$, —P(O)(OR)$_2$, and —S(O)(OR)$_2$, where each R is independently hydrogen, $C_1$-$C_8$ alkyl or $C_1$-$C_8$ haloalkyl;

and related linker-payloads and antibody drug conjugates;
provided that when $R^6$ is —OC(O)R or —OR and W is:

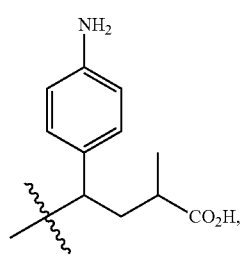

is not:

In another aspect, the present invention relates to an antibody drug conjugate compound of formula III wherein the antibody AB is selected from: trastuzumab, trastuzumab mutants (for instance the trastuzumab mutants disclosed herein or in international patent application PCT/IB2012/056234), oregovomab, edrecolomab, cetuximab, a humanized monoclonal antibody to the vitronectin receptor ($\alpha_v\beta_3$), alemtuzumab, anti-HLA-DR antibodies including a humanized anti-HLA-DR antibody for the treatment of non-Hodgkin's lymphoma, 131I Lym-1, anti-HLA-Dr10 antibodies including a murine anti-HLA-Dr10 antibody for the treatment of non-Hodgkin's lymphoma, anti-cd33 antibodies, anti-cd22 antibodies including a humanized anti-CD22 mAb for the treatment of Hodgkin's Disease or non-Hodgkin's lymphoma, labetuzumab, bevacizumab, ibritumomab tiuxetan, ofatumumab, panitumumab, rituximab, tositumomab, ipilimumab, and gemtuzumab.

In another aspect, the present invention relates to a compound or compounds of formula II or III wherein L comprises one or more independently selected amino acid di-radicals, preferably one or more independently selected amino acid diradicals selected from the group consisting of valine, citrulline, phenylalanine, lysine, alanine and glycine.

According to another aspect, the present invention relates to a compound or compounds of formula II or III wherein L is capable of being cleaved from P, or a radical comprising P, by an intracellular protease.

According to an additional aspect, the present invention relates to a compound or compounds of formula III wherein the antibody is attached to an amino acid di-radical via a cysteine residue of the antibody via a sulphur or sulphur-sulphur bond, a lysine residue of ther antibody via an amide bond, or a glutamine residue via an amide bond. Preferably, the antibody is a monoclonal antibody, a chimeric antibody, a humanized antibody, a bispecific antibody or an antibody fragment.

According to still another aspect, the present invention relates to a pharmaceutical composition of a compound or compounds of formula III and/or a salt or salts thereof, comprising an effective amount of the compound(s) or salt(s) and a pharmaceutically acceptable diluent, carrier or excipient. Such pharmaceutical compositions may additionally include a therapeutically effective amount of a chemotherapeutic agent selected from the group consisting of a tubulin-forming inhibitor, a topoisomerase inhibitor, and a DNA binder.

According to another aspect, the present invention relates to a method for killing or inhibiting the proliferation of tumor cells or cancer cells comprising treating tumor cells or cancer cells in a patient with an amount of the compound of formula III, and/or a salt or salts thereof, said amount being effective to kill or inhibit the proliferation of the tumor cells or cancer cells.

Another aspect of the invention relates to a method of using an effective amount of any one of the aforementioned compounds and/or any one of the aforementioned antibody drug conjugates to treat cancer by administering to a patient in need thereof an effective amount of said compound and/or conjugate.

BRIEF DESCRIPTION OF THE DRAWINGS

FIG. 3 provides in vivo stability data for antibody drug conjugates of the present invention (as measured by DAR).

DETAILED DESCRIPTION

Figure 1:
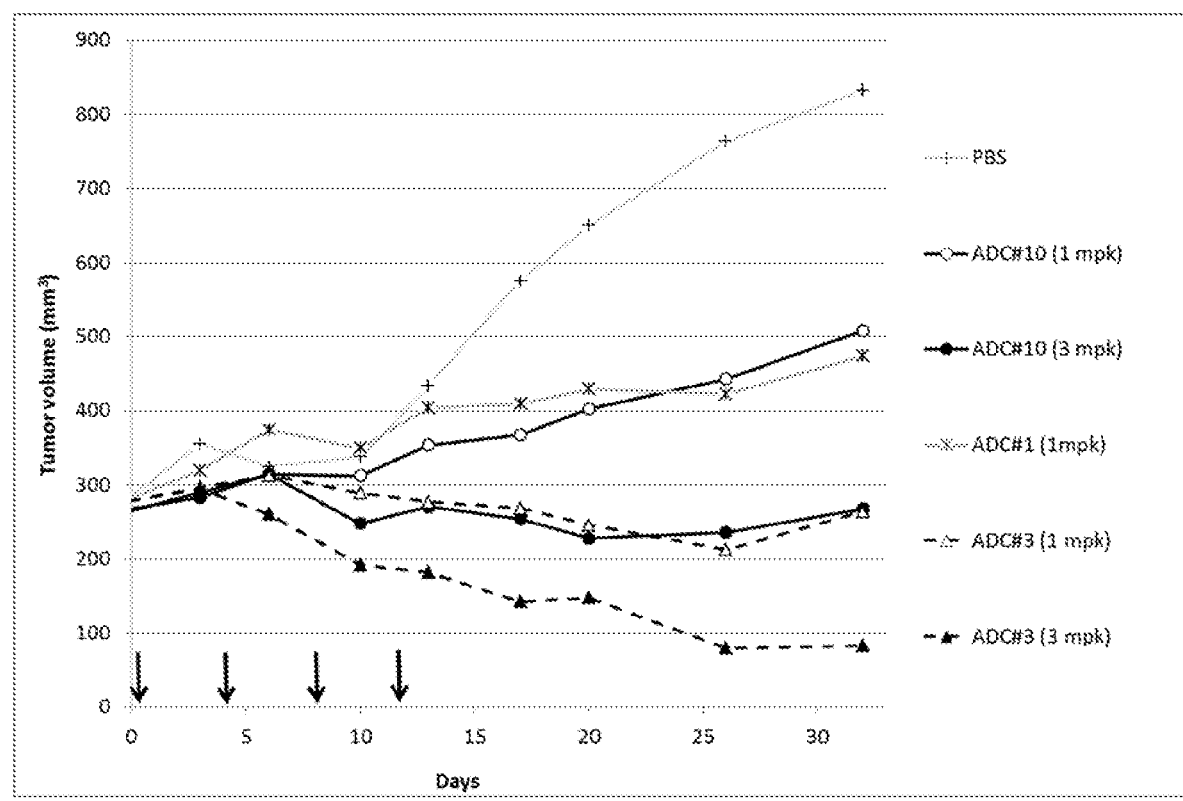
FIG. 1 depicts the in vivo efficacy of antibody drug conjugates of the present invention, using a N87-xenograft model.

The present invention is directed to cytotoxic tubulysin analogs, to antibody drug conjugates comprising said cytotoxic tubulysin analogs, and to methods for using the same to treat cancer and other pathological conditions. The invention also relates to methods of using such compounds and/or conjugates in vitro, in situ, and in vivo for the detection, diagnosis, or treatment of mammalian cells, or associated pathological conditions.

Definitions and Abbreviations

Unless stated otherwise, the following terms and phrases as used herein are intended to have the following meanings. When trade names are used herein, the trade name includes the product formulation, the generic drug, and the active pharmaceutical ingredient(s) of the trade name product, unless otherwise indicated by context.

The term "antibody" (or "Ab" or "AB") herein is used in the broadest sense and specifically covers intact monoclonal antibodies, polyclonal antibodies, monospecific antibodies, multispecific antibodies (e.g., bispecific antibodies), and antibody fragments that exhibit the desired biological activity. An intact antibody has primarily two regions: a variable region and a constant region. The variable region binds to and interacts with a target antigen. The variable region includes a complementary determining region (CDR) that recognizes and binds to a specific binding site on a particular antigen. The constant region may be recognized by and interact with the immune system (see, e.g., Janeway et al., 2001, Immuno. Biology, 5th Ed., Garland Publishing, New York). An antibody can be of any type or class (e.g., IgG, IgE, IgM, IgD, and IgA) or subclass (e.g., IgG1, IgG2, IgG3, IgG4, IgA1 and IgA2). The antibody can be derived from any suitable species. In some embodiments, the antibody is of human or murine origin. An antibody can be, for example, human, humanized or chimeric.

Trastuzumab refers to a monoclonal antibody that interferes with the HER2/neu receptor, such as Herclon, Herceptin or a modified form of these antibodies.

The terms "specifically binds" and "specific binding" refer to antibody binding to a predetermined antigen. Typically, the antibody binds with an affinity of at least about $1 \times 10^7$ $M^{-1}$, and binds to the predetermined antigen with an affinity that is at least two-fold greater than its affinity for binding to a non-specific antigen (e.g., BSA, casein) other than the predetermined antigen or a closely-related antigen.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method. The term "monoclonal antibodies" specifically includes "chimeric" antibodies in which a portion of the heavy and/or light chain is identical to or homologous with the corresponding sequence of antibodies derived from a particular species or belonging to a particular antibody class or subclass, while the remainder of the chain(s) is identical to or homologous with the corresponding sequences of antibodies derived from another species or belonging to another antibody class or subclass, as well as fragments of such antibodies, so long as they exhibit the desired biological activity.

An "intact antibody" is one which comprises an antigen-binding variable region as well as a light chain constant domain ($C_L$) and heavy chain constant domains, $C_{H1}$, $C_{H2}$, $C_{H3}$ and $C_{H4}$, as appropriate for the antibody class. The constant domains may be native sequence constant domains (e.g., human native sequence constant domains) or amino acid sequence variants thereof. An intact antibody may have one or more "effector functions", which refers to those biological activities attributable to the Fc region (e.g., a native sequence Fc region or amino acid sequence variant Fc region) of an antibody. Examples of antibody effector functions include complement dependent cytotoxicity, antibody-dependent cell-mediated cytotoxicity (ADCC) and antibody-dependent cell-mediated phagocytosis.

An "antibody fragment" comprises a portion of an intact antibody, preferably comprising the antigen-binding or variable region thereof. Examples of antibody fragments include Fab, Fab', F(ab')$_2$, and Fv fragments, diabodies, triabodies, tetrabodies, linear antibodies, single-chain antibody molecules, scFv, scFv-Fc, multispecific antibody fragments formed from antibody fragment(s), a fragment(s) produced by a Fab expression library, or an epitope-binding fragments of any of the above which immuno specifically bind to a target antigen (e.g., a cancer cell antigen, a viral antigen or a microbial antigen).

The term "variable" in the context of an antibody refers to certain portions of the variable domains of the antibody that differ extensively in sequence and are used in the binding and specificity of each particular antibody for its particular antigen. This variability is concentrated in three segments called "hypervariable regions" in the light chain and the heavy chain variable domains. The more highly conserved portions of variable domains are called the framework regions (FRs). The variable domains of native heavy and light chains each comprise four FRs connected by three hypervariable regions.

The term "hypervariable region" when used herein refers to the amino acid residues of an antibody which are responsible for antigen-binding. The hypervariable region generally comprises amino acid residues from a "complementarity determining region" or "CDR" (e.g., residues 24-34 (L1), 50-56 (L2) and 89-97 (L3) in the light chain variable domain and 31-35 (H1), 50-65 (H2) and 95-102 (L3) in the heavy chain variable domain; Kabat et al. (Sequences of Proteins of Immunological Interest, 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the light chain variable domain and 26-32 (H1), 53-55 (142) and 96-101 (H3) in the heavy chain variable domain; Chothia and Lesk, 1987, J. Mol. Biol. 196:901-917). FR residues are those variable domain residues other than the hypervariable region residues as herein defined.

A "single-chain Fv" or "scFv" antibody fragment comprises the $V_H$ and $V_L$ domains of an antibody, wherein these domains are present in a single polypeptide chain.

Typically, the Fv polypeptide further comprises a polypeptide linker between the $V_H$ and $V_L$ domains which enables the scFv to form the desired structure for antigen binding. For a review of scFv, see Pluckthun in The Pharmacology of Monoclonal Antibodies, vol. 113, Rosenburg and Moore eds., Springer-Verlag, New York, pp. 269-315 (1994).

The term "diabody" refers to small antibody fragments with two antigen-binding sites, which fragments comprise a variable heavy domain ($V_H$) connected to a variable light domain ($V_L$) in the same polypeptide chain. By using a linker that is too short to allow pairing between the two domains on the same chain, the domains are forced to pair with the complementary domains of another chain and create two antigen-binding sites. Diabodies are described more fully in, for example, EP 0 404 097; WO 93/11161; and Hollinger et al., 1993, Proc. Natl. Acad. Sci. USA 90:6444-6448.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., 1986, Nature 321:522-525; Riechmann et al., 1988, Nature 332:323-329; and Presta, 1992, Curr. Op. Struct. Biol. 2:593-596.

As used herein, "isolated" means separated from other components of (a) a natural source, such as a plant or animal cell or cell culture, or (b) a synthetic organic chemical reaction mixture. As used herein, "purified" means that when isolated, the isolate contains at least 95%, and in another aspect at least 98%, of a compound (e.g., a conjugate) by weight of the isolate. An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is a tumor cell, e.g., a breast, ovarian, stomach, endometrial, salivary gland, lung, kidney, colon, thyroid, pancreatic or bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may inhibit the growth of and/or kill existing cancer cells, it may be cytostatic and/or cytotoxic. For cancer therapy, efficacy can, for example, be measured by assessing the time to disease progression (TTP) and/or determining the response rate (RR).

The term "substantial amount" refers to a majority, i.e. greater than 50% of a population, of a mixture or a sample.

The term "intracellular metabolite" refers to a compound resulting from a metabolic process or reaction inside a cell on an antibody-drug conjugate (ADC). The metabolic process or reaction may be an enzymatic process such as proteolytic cleavage of a peptide linker of the ADC. Intracellular metabolites include, but are not limited to, antibodies and free drug which have undergone intracellular cleavage after entry, diffusion, uptake or transport into a cell.

The terms "intracellularly cleaved" and "intracellular cleavage" refer to a metabolic process or reaction inside a cell on an ADC or the like, whereby the covalent attachment, e.g., the linker, between the drug moiety and the antibody is broken, resulting in the free drug, or other metabolite of the conjugate dissociated from the antibody inside the cell. The cleaved moieties of the ADC are thus intracellular metabolites.

The term "bioavailability" refers to the systemic availability (i.e., blood/plasma levels) of a given amount of a drug administered to a patient. Bioavailability is an absolute term that indicates measurement of both the time (rate) and total amount (extent) of drug that reaches the general circulation from an administered dosage form.

The term "cytotoxic activity" refers to a cell-killing, a cytostatic or an anti-proliferative effect of a ADC or an intracellular metabolite of said ADC. Cytotoxic activity may be expressed as the $IC_{50}$ value, which is the concentration (molar or mass) per unit volume at which half the cells survive.

A "disorder" is any condition that would benefit from treatment with a drug or antibody-drug conjugate. This includes chronic and acute disorders or diseases including those pathological conditions which predispose a mammal to the disorder in question. Non-limiting examples of disorders to be treated herein include benign and malignant cancers; leukemia and lymphoid malignancies, neuronal, glial, astrocytal, hypothalamic and other glandular, macrophagal, epithelial, stromal and blastocoelic disorders; and inflammatory, angiogenic and immunologic disorders.

The terms "cancer" and "cancerous" refer to or describe the physiological condition or disorder in mammals that is typically characterized by unregulated cell growth. A "tumor" comprises one or more cancerous cells.

Examples of a "patient" include, but are not limited to, a human, rat, mouse, guinea pig, monkey, pig, goat, cow, horse, dog, cat, bird and fowl. In an exemplary embodiment, the patient is a human.

The terms "treat" or "treatment," unless otherwise indicated by context, refer to therapeutic treatment and prophylactic measures to prevent relapse, wherein the object is to inhibit or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already having the condition or disorder as well as those prone to have the condition or disorder.

In the context of cancer, the term "treating" includes any or all of inhibiting growth of tumor cells, cancer cells, or of a tumor; inhibiting replication of tumor cells or cancer cells, lessening of overall tumor burden or decreasing the number of cancerous cells, and ameliorating one or more symptoms associated with the disease.

In the context of an autoimmune disease, the term "treating" includes any or all of inhibiting replication of cells associated with an autoimmune disease state including, but not limited to, cells that produce an autoimmune antibody, lessening the autoimmune-antibody burden and ameliorating one or more symptoms of an autoimmune disease.

In the context of an infectious disease, the term "treating" includes any or all of: inhibiting the growth, multiplication or replication of the pathogen that causes the infectious disease and ameliorating one or more symptoms of an infectious disease.

The term "package insert" is used to refer to instructions customarily included in commercial packages of therapeutic products, that contain information about the indication(s), usage, dosage, administration, contraindications and/or warnings concerning the use of such therapeutic products.

As used herein, the terms "cell," "cell line," and "cell culture" are used interchangeably and all such designations include progeny. The words "transformants" and "transformed cells" include the primary subject cell and cultures or progeny derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

Unless otherwise indicated, the term "alkyl" by itself or as part of another term refers to a straight chain or branched, saturated hydrocarbon having the indicated number of carbon atoms (e.g., "$C_1$-$C_8$" alkyl refers to an alkyl group having from 1 to 8 carbon atoms; "$C_1$-$C_6$" alkyl refers to an alkyl group having from 1 to 6 carbon atoms, and so on). When the number of carbon atoms is not indicated, the alkyl group has from 1 to 8 carbon atoms, preferably from 1 to 6 carbon atoms. Representative straight chain $C_1$-$C_8$ alkyls include, but are not limited to, methyl, ethyl, n-propyl, n-butyl, n-pentyl, n-hexyl, n-heptyl and n-octyl; while branched $C_1$-$C_8$ alkyls include, but are not limited to, -isopropyl, -sec-butyl, -isobutyl, -tent-butyl, -isopentyl, and -2-methylbutyl; unsaturated $C_2$-$C_8$ alkyls include, but are not limited to, vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexyl, 2-hexyl, 3-hexyl, acetylenyl, propynyl, 1-butynyl, 2-butynyl, 1-pentynyl, 2-pentynyl and 3-methyl-1-butynyl.

Unless otherwise indicated, "alkylene," by itself of as part of another term, refers to a saturated, branched or straight chain or cyclic hydrocarbon radical of the stated number of carbon atoms, typically 1-18 carbon atoms, and having two monovalent radical centers derived by the removal of two hydrogen atoms from the same or two different carbon atoms of a parent alkane. Typical alkylene radicals include, but are not limited to: methylene (—$CH_2$—), 1,2-ethylene (—$CH_2CH_2$—), 1,3-propylene (—$CH_2CH_2CH_2$—), 1,4-butylene (—$CH_2CH_2CH_2CH_2$—), and the like. A "$C_1$-$C_{10}$" straight chain alkylene is a straight chain, saturated hydrocarbon group of the formula —$(CH_2)_{1-10}$—. Examples of a $C_1$-$C_{10}$ alkylene include methylene, ethylene, propylene, butylene, pentylene, hexylene, heptylene, ocytylene, nonylene and decalene. In certain embodiments of the invention, alkylenes have from 1 to 9, from 1 to 8, from 1 to 7, and from 1 to 6 carbons.

"Alkenyl" refers to an alkyl group, as defined herein, consisting of at least two carbon atoms and at least one carbon-carbon double bond. Representative examples include, but are not limited to, ethenyl, 1-propenyl, 2-propenyl, 1-, 2-, or 3-butenyl, and the like. "Alkenylene" refers to a di-valent form of alkenyl.

Unless otherwise indicated, the term "heteroalkyl," by itself or in combination with another term, means, unless otherwise stated, a stable straight or branched chain hydrocarbon, or combinations thereof, fully saturated or containing from 1 to 3 degrees of unsaturation, consisting of the stated number of carbon atoms and from one to three heteroatoms selected from the group consisting of O, N, Si, S and/or P, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Up to two heteroatoms may be consecutive.

"Halo" or "halogen" refers to fluoro, chloro, bromo and iodo.

"Halo($C_{1-6}$-alkyl)" refers to $C_{1-6}$-alkyl groups substituted with 1 to 3 or 1 to 2 halo groups, wherein $C_{1-6}$-alkyl and halo are as defined herein. The term includes, for example, $CF_3$.

The term "epoxy", or "epoxy group" or "epoxy residue" with be known to those skilled in the art to refer to a three member ring comprising to carbon atoms and an oxygen atom linked by single bonds as follows:

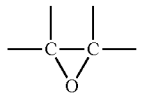

Accordingly, the term "epoxide" refers to a compound that comprise at least one epoxy group as herein before defined.

Unless otherwise indicated, the term "heteroalkylene" by itself or as part of another substituent means a divalent group derived from heteroalkyl (as discussed above). For heteroalkylene groups, heteroatoms can also occupy either or both of the chain termini.

Unless otherwise indicated, "aryl," by itself or an part of another term, means a substituted or unsubstituted monovalent aromatic hydrocarbon radical of 6 to 20 carbon atoms, preferably from 6 to 14 carbon atoms, derived by the removal of one hydrogen atom from a single carbon atom of a parent aromatic ring system. Typical aryl groups include, but are not limited to, radicals derived from benzene, substituted benzene, naphthalene, anthracene, biphenyl, and the like. A substituted aromatic group (e.g., an aryl group) can be substituted with one or more, preferably 1 to 5, of the following groups: $C_1$-$C_8$ alkyl, —O—($C_1$-$C_8$ alkyl), —C(O)R', —OC(O)R', —C(O)OR', —C(O)$NH_2$, —C(O)NHR', —C(O)N(R')$_2$, —NHC(O)R', —S(O)$_2$R', —S(O)R', —OH, halogen, —$N_3$, —$NH_2$, —NH(R'), —N(R')$_2$ and —CN; wherein each R' is independently selected from —H, $C_1$-$C_8$ alkyl, $C_1$-$C_8$ heteroalkyl and aryl, preferably unsubstituted aryl. In some embodiments, a substituted aromatic group can further include one or more of: —NHC(=NH)$NH_2$, —NHCON$H_2$, —S(=O)$_2$R' and —SR'.

The term "heteroaryl" as used herein refers to an aromatic heterocycle ring of 5 to 14 members, such as 5 to 6 members, having at least one heteroatom selected from nitrogen, oxygen and sulfur, and containing at least 1 carbon atom. Heteroaryls may be monocyclic, bicyclic, or tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, and quinoxalinyl. Heteroaryls are optionally substituted. Typical substituents include, but are not limited to, —X, —R, —O—, —OR, —SR, —S—, —$NR_2$, —$NR_3$, =NR, —$CX_3$, —CN, —OCN, —SCN, —N=C=O, —NCS, —NO, —$NO_2$, =$N_2$, —$N_3$, —NRC(=O)R, —C(=O)$NR_2$, —$SO_3$—$SO_3H$, —S(=O)$_2$R, —OS(=O)$_2$OR, —S(=O)$_2$NR, —S(=O)R, —OP(=O)(OR)$_2$, —P(=O)(OR)$_2$, —$PO_{32}$—$PO_3H2$, —$AsO_2H2$, —C(=O)R, —C(=O)X, —C(=S)R, —$CO_2R$, —$CO_2$—, —C(=S)OR, —C(=O)SR, —C(=S)SR, —C(=O)$NR_2$, —C(=S)$NR_2$, —C(=NR)$NR_2$, $C_1$-$C_{20}$ heteroalkyl, $C_6$-$C_{20}$ aryl, $C_3$-$C_8$ heterocyclyl, a protecting group or a prodrug moiety, where each X is independently a halogen: —F, —Cl, —Br, or —I; and each R is independently —H or $C_1$-$C_6$ alkyl.

The terms "arylene", "heteroarylene" refer to divalent versions of "aryl" and "heteroaryl" respectively, and other terms incorporating "aryl" and "heteroaryl".

"Hydroxy" refers to the group —OH.

"Substituted alkyl" means an alkyl in which one or more hydrogen atoms are each independently replaced with a substituent. Typical substituents include, but are not limited to, —X, —R, —O—, —OR, —SR, —S—, —$NR_2$, —$NR_3$, =NR, —$CX_3$, —CN, —OCN, —SCN, —N=C=O, —NCS, —NO, —$NO_2$, =$N_2$, —$N_3$, —NRC(=O)R, —C(=O)$NR_2$, —$SO_3$, —$SO_3H$, —S(=O)$_2$R, —OS(=O)$_2$OR, —S(=O)$_2$NR, —S(=O)R, —OP(=O)(OR)$_2$, —P(=O)(OR)$_2$, —$PO_{32}$—$PO_3H2$, —$AsO_2H2$, —C(=O)R, —C(=O)X, —C(=S)R, —$CO_2R$, —$CO_2$—, —C(=S)OR, —C(=O)SR, —C(=S)SR, —C(=O)$NR_2$, —C(=S)$NR_2$, —C(=NR)$NR_2$, $C_1$-$C_{20}$ heteroalkyl, $C_6$-$C_{20}$ aryl, $C_3$-$C_8$ heterocyclyl, a protecting group or a prodrug moiety, where each X is independently a halogen: —F, —Cl, —Br, or —I; and each R is independently —H or $C_1$-$C_6$ alkyl. A substituted alkyl substituted with a halogen is sometimes referred to herein as a haloalkyl. Aryl, alkylene, heteroalkylene and other groups containing or not containing an alkyl or alkylene moiety as described herein may also be similarly substituted.

Unless otherwise indicated, "aralkyl" by itself or part of another term, means an alkyl group, as defined above, substituted with an aryl group, as defined above.

Unless otherwise indicated, "$C_3$-$C_8$heterocyclyl" by itself or as part of another term, refers to a monovalent or divalent substituted or unsubstituted aromatic or non-aromatic monocyclic or bicyclic ring system having from 3 to 8 carbon atoms (also referred to as ring members) and one to four heteroatom ring members independently selected from N, O, P or S, and derived by removal of one hydrogen atom from a ring atom of a parent ring system.

Similarly, unless otherwise indicated, "$C_3$-$C_{10}$heterocyclyl" by itself or as part of another term, refers to a monovalent or divalent substituted or unsubstituted aromatic or non-aromatic monocyclic or bicyclic ring system having from 3 to 10 carbon atoms (also referred to as ring members) and one to four heteroatom ring members independently selected from N, O, P or S, and derived by removal of one hydrogen atom from a ring atom of a parent ring system. One or more N, C or S atoms in the heterocyclyl can be oxidized. The ring that includes the heteroatom can be aromatic or nonaromatic. Heterocyclyl groups with more than 10 carbons, for instance rings or ring systems with 11, 12, 13, 14, 15, 16, 17, 18, 19 or 20 carbons, are also possible and are encompassed, along with $C_3$-$C_{10}$heterocyclyls, when the term "heterocyclyl" is employed without reference to a specific number of carbons. Similarly, heterocyclyl groups with less than 3 carbons, for instance rings with 1 or 2, are possible and are encompassed when the term "heterocyclyl" is employed without reference to a specific number of carbons. The term "heterocycloalkyl" refers to non-aromatic heterocyclyl rings or ring systems where all carbon atoms are saturated (i.e., bonded to a hydrogen or another substituent as noted below, with no double or triple bonds). In certain embodiments heterocycloalkyl groups typically have 3 to 5 members and 1 to 2 heteroatoms. In certain embodiments heterocycloalkyl can be epoxy.

Unless otherwise noted, the heterocyclyl is attached to its pendant group at any heteroatom or carbon atom that results in a stable structure. Representative examples of a $C_3$-$C_8$ heterocyclyl include, but are not limited to, tetrahyrofuranyl, oxetanyl, pyranyl, pyrrolidinyl, piperidinyl, benzofuranyl, benzothiophene, indolyl, benzopyrazolyl, pyrrolyl, thiophenyl (thiopene), furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A $C_3$-$C_8$ heterocyclyl, or a $C_3$-$C_{10}$ heterocyclyl, can be substituted with up to seven groups including, but not limited to, $C_1$-$C_8$ alkyl, $C_1$-$C_8$ heteroalkyl, —OR', aryl, —C(O)R', —OC(O)R', —C(O)OR', —C(O)NH$_2$, —C(O)NHR', —C(O)N(R')$_2$, —NHC(O)R', —S(=O)$_2$R', —S(O)R', halogen, —N$_3$, —NH$_2$, —NH(R'), —N(R')$_2$ and —CN; wherein each R' is independently selected from —H, $C_1$-$C_8$ alkyl, $C_1$-$C_8$ heteroalkyl and aryl. In some embodiments, a substituted heterocyclyl can also include one or more of: —NHC(=NH)NH$_2$, —NHCONH$_2$, —S(=O)$_2$R' and —SR'.

Unless otherwise indicated, "heteroaralkyl" by itself or part of another term, means an alkyl group, as defined above, substituted with an aromatic heterocyclyl group, as defined above.

Unless otherwise indicated, "$C_3$-$C_8$ carbocyclyl" by itself or as part of another term, is a 3-, 4-, 5-, 6-, 7- or 8-membered monovalent or divalent, substituted or unsubstituted, saturated or unsaturated non-aromatic monocyclic or bicyclic carbocyclic ring derived by the removal of one hydrogen atom or two hydrogen atoms from a ring atom of a parent ring system. Similarly, unless otherwise indicated, "$C_3$-$C_{10}$ carbocyclyl" by itself or as part of another term, is a 3-, 4-, 5-, 6-, 7-, 8-, 9- or 10-membered monovalent or divalent, substituted or unsubstituted, saturated or unsaturated non-aromatic monocyclic or bicyclic carbocyclic ring derived by the removal of one hydrogen atom from a ring atom of a parent ring system. Representative $C_3$-$C_8$ carbocyclyl include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, cyclooctadienyl, bicyclo(111)pentane, and bicyclo(222)octane. A $C_3$-$C_8$ carbocyclyl group, or a $C_3$-$C_{10}$ carbocyclyl group, can be unsubstituted or substituted with up to seven groups including, but not limited to, $C_1$-$C_8$ alkyl, $C_1$-$C_8$ heteroalkyl, —OR', aryl, —C(O)R', —OC(O)R', —C(O)OR', —C(O)NH$_2$, —C(O)NHR', —C(O)N(R')$_2$, —NHC(O)R', —S(=O)$_2$R', —S(=O)R', —OH, -halogen, —N$_3$, —NH$_2$, —NH(R'), —N(R')$_2$ and —CN; where each R' is independently selected from —H, $C_1$-$C_8$ alkyl, $C_1$-$C_8$ heteroalkyl and aryl. Carbocyclyl groups with more than 10 carbons, for instance ring systems with 11, 12, 13, 14, 15, 16, 17, 18, 19 or 20 carbons, are also possible and are encompassed, along with $C_3$-$C_{10}$ carbocyclyl, when the term "carbocyclyl" is employed without reference to a specific number of carbons. The term "cycloalkyl" refers to carbocyclyl rings or ring systems where all carbon atoms are saturated (i.e., bonded to a hydrogen or another substituent as noted below, with no double or triple bonds).

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

Stereochemical definitions and conventions used herein generally follow S. P. Parker, Ed., McGraw-Hill Dictionary of Chemical Terms, McGraw-Hill Book Company, New York (1984); and Eliel and Wilen, Stereochemistry of Organic Compounds, John Wiley & Sons, Inc., New York (1994). Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another.

A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

An amino acid "derivative" includes an amino acid having substitutions or modifications by covalent attachment of a parent amino acid, such as, e.g., by alkylation, glycosylation, acetylation, phosphorylation, and the like. Further included within the definition of "derivative" is, for example, one or more analogs of an amino acid with substituted linkages, as well as other modifications known in the art.

A "natural amino acid" refers to arginine, glutamine, phenylalanine, tyrosine, tryptophan, lysine, glycine, alanine, histidine, serine, proline, glutamic acid, aspartic acid, threonine, cysteine, methionine, leucine, asparagine, isoleucine, and valine, unless otherwise indicated by context.

The phrase "pharmaceutically acceptable salt," as used herein, refers to pharmaceutically acceptable organic or inorganic salts of a compound. The compound typically contains at least one amino group, and accordingly acid addition salts can be formed with this amino group. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

The terms "loading" or "drug loading" or "payload loading" represent or refer to the average number of payloads ("payload" and "payloads" are used interchangeably herein with "drug" and "drugs") per antibody in an ADC molecule.

Drug loading may range from 1 to 20 drugs per antibody. This is sometimes referred to as the DAR, or drug to antibody ratio. Compositions of the ADCs described herein typically have DAR's of from 1-20, and in certain embodiments from 1-8, from 2-8, from 2-6, from 2-5 and from 2-4. Typical DAR values are 2, 4, 6 and 8. The average number of drugs per antibody, or DAR value, may be characterized by conventional means such as UV/visible spectroscopy, mass spectrometry, ELISA assay, and HPLC. The quantitative DAR value may also be determined. In some instances, separation, purification, and characterization of homogeneous ADCs having a particular DAR value may be achieved by means such as reverse phase HPLC or electrophoresis. DAR may be limited by the number of attachment sites on the antibody. For example, where the attachment is a cysteine thiol, an antibody may have only one or several cysteine thiol groups, or may have only one or several sufficiently reactive thiol groups through which a Linker unit may be attached. In some embodiments, the cysteine thiol is a thiol group of a cysteine residue that forms an interchain disulfide bond. In some embodiments, the cysteine thiol is a thiol group of a cysteine residue that does not form an interchain disulfide bond. Typically, fewer than the theoretical maximum of drug moieties are conjugated to an antibody during a conjugation reaction. An antibody may contain, for example, many lysine residues that do not react with a linker or linker intermediate. Only the most reactive lysine groups may react with a reactive linker reagent.

Generally, antibodies do not contain many, if any, free and reactive cysteine thiol groups which may be linked to a drug via a linker. Most cysteine thiol residues in the antibodies exist as disulfide bridges and must be reduced with a reducing agent such as dithiothreitol (DTT). The antibody may be subjected to denaturing conditions to reveal reactive nucleophilic groups such as lysine or cysteine. The loading (drug/antibody ratio) of an ADC may be controlled in several different manners, including: (i) limiting the molar excess of drug-linker relative to the antibody, (ii) limiting the conjugation reaction time or temperature, and (iii) partial or limiting reductive conditions for cysteine thiol modification. Where more than one nucleophilic group reacts with a drug-linker then the resulting product is a mixture of ADCs with a distribution of one or more drugs moieties per antibody. The average number of drugs per antibody may be calculated from the mixture by, for example, dual ELISA antibody assay, specific for antibody and specific for the drug. Individual ADCs may be identified in the mixture by mass spectroscopy, and separated by HPLC, e.g., hydrophobic interaction chromatography.

Below is a list of abbreviations and definitions that may not otherwise be defined or described in this application: DMSO (refers to dimethyl sulfoxide), HRMS (refers to high resolution mass spectrometry), DAD (refers to diode array detection), TFA (refers to 2,2,2-trifluoroacetic acid or trifluoroacetic acid), TFF (refers to tangential flow filtration), EtOH (refers to ethanol), MW (refers to molecular weight), HPLC (refers to high performance liquid chromatography), prep HPLC (refers to preparative high performance liquid chromatography), etc. (refers to and so forth), trityl (refers 1,1',1''-ethane-1,1,1-triyltribenzene), THF (refers to tetrahydrofuran), NHS (refers to 1-Hydroxy-2,5-pyrrolidinedione), Cbz (refers to carboxybenzyl), eq. (refers to equivalent), n-BuLi (refers to n-butyllithium), OAc (refers to acetate), MeOH (refers to methanol), i-Pr (refers to isopropyl or propan-2-yl), NMM (refers to 4-methylmorpholine), and "-" (in a table refers to no data available at this time).

As used herein, "—PABC-" or "PABC" refers to the structure:

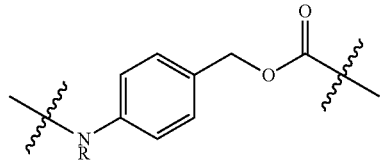

or variants thereof.

As used herein, "—PABA-" or "PABA" refers to the structure:

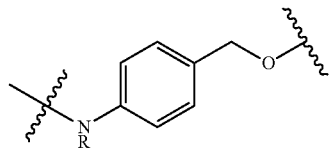

or variants thereof.

Compounds and Antibody Drug Conjugates Thereof
According to one aspect, the present invention relates to a compound or compounds of formula (I):

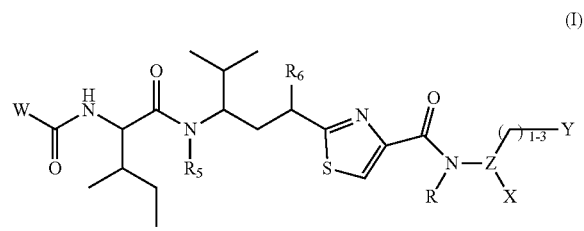

(I)

or a pharmaceutically acceptable salt thereof, wherein:
W is selected from:

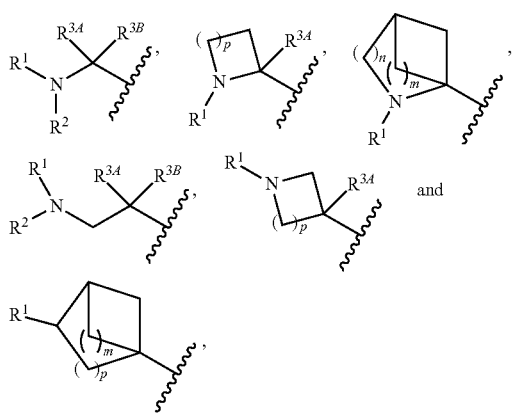

where:
m is 1-3;
n is 1-2; and
p is 1-4;
$R^1$ is selected from hydrogen, $C_1$-$C_8$ alkyl and $C_1$-$C_8$ haloalkyl;

$R^2$ is selected from hydrogen, $C_1$-$C_8$ alkyl and $C_1$-$C_8$ haloalkyl;

each $R^{3A}$ and $R^{3B}$ is independently selected from $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen and aralkyl; or $R^{3A}$ and $R^{3B}$ taken together are selected from $C_2$-$C_8$ alkylene and $C_1$-$C_8$ heteroalkylene;

$R^5$ is selected from hydrogen, $C_1$-$C_8$ alkyl, $C_1$-$C_8$ haloalkyl, $C_3$-$C_8$ carbocyclyl, $C_3$-$C_8$ heterocyclyl, aryl, heteroaralkyl, aralkyl, where $R^5$ is optionally substituted with —$(C(R)_2)_m$ $NR^1R^2$;

$R^6$ is selected from hydrogen, $OR^7$, $OC(O)R^7$, $OC(O)$ $NR^7R^8$, $NR^7R^8$, $N(R^7)C(O)R^7$, $N(R^7)$ $C(O)OR^7$, $N(R)C(O)$ $NR^7R^8$, $N(R^7)SO_2R$, and $N(R^7)SO_2NR^7R^8$, where $R^7$ and $R^8$ are each independently selected from hydrogen, $C_1$-$C_8$ alkyl, $C_3$-$C_8$ carbocyclyl, $C_3$-$C_8$ heterocyclyl, aryl, heteroaralkyl and aralkyl; or $R^7$ and $R^8$, together with the nitrogen to which they are joined form $C^3$-$C^{10}$ heterocyclyl, and where one or more of $R^7$ and $R^8$ are optionally substituted with one or more substituents selected from halogen, $NR_2$, CN, OH and $OC_1$-$C_8$ alkyl;

Z is N or $CR^2$;

Y is selected from aryl, $C_3$-$C_8$ heterocyclyl and $C_5$-$C_{14}$ heteroaryl, where Y is optionally substituted with one or more $R^{11}$, or Y is selected from:

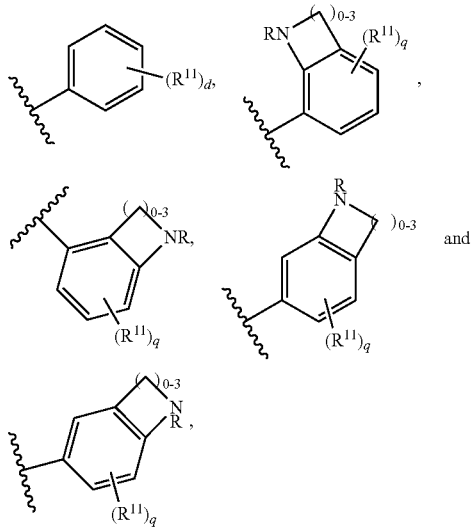

where
d is 1-5;
q is 1-3; and
each $R^{11}$ is independently selected from hydrogen, $C_1$-$C_8$ alkyl, $C_1$-$C_8$ haloalkyl, halogen, —CN,
—OH, —$(C(R)_2)_t$ONRR, —$(C(R)_2)_t$—NRR, $(C(R)_2)_t$—C(O)R, $(C(R)_2)_t$—$CONR^8R^9$, —$(C(R)_2)_tC(O)$ NRNRR, —$(C(R)_2)_tC(O)N(R)OH$, —$(C(R)_2)_t$SH, —$(C(R)_2)_t$—N(R)—C(O)R, —$(C(R)_2)_tN(R)$—C(O) OR, —$(C(R)_2)_t$—N(R)—$SO_2R$, —$(C(R)_2)_tN(R)C(O)$ $NR^8R^9$, —$(C(R)_2)_t$$SO_2NR^8R^9$, and —$(C(R)_2)_tN(R)$ $SO_2NR^8R^9$, where each t is independently 0-3; and X is selected from hydrogen, —C(O)OR, $C_1$-$C_6$ alkyl, $C_6$-$C_{14}$ aryl, $C_5$-$C_4$ heteroaryl, $C_3$-$C_6$ carbocyclyl, $C_3$-$C_8$ heterocyclyl, —$C_1$-$C_6$ alkyl-$C_6$-$C_{14}$ aryl, and —$C_1$-$C_6$alkyl-$C_5$-$C_{14}$heteroaryl, where X is optionally substituted with 1-3 substituents independently selected from, halogen, —OH, —C(O)OR, —CON(R)OH, —$ONR^2$, —$NR^8R^9$, —COR, —$CONR^2$, —CONRNRR, —SH, —N(R)—COR, —N(R)—C(O)OR, —N(R)—$SO_2R$, —N(R)—$CONR^8R^9$, —$SO_2$—$NR^8R^9$, —N(R)—$SO_2$ $NR^8R^9$, —P(O)(OR)$_2$, and —S(O)(OR)$_2$, where each R is independently hydrogen, $C_1$-$C_8$ alkyl or $C_1$-$C_8$ haloalkyl;

provided that when $R^6$ is —OC(O)R or —OR and W is:

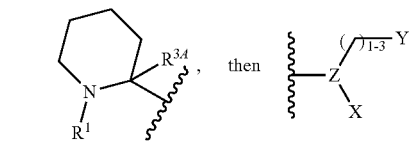

is not:

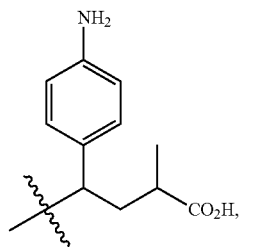

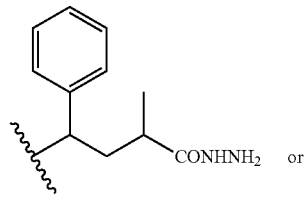

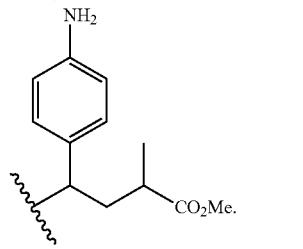

Additional aspects of the invention include a compound or compounds of formula (II):

$$L-P \qquad (II)$$

or a pharmaceutically acceptable salt thereof, wherein:
L is the linker moiety $L^1$-$L^2$-$L^3$, where L is bound to P through $R^6$;
P is a radical of formula:

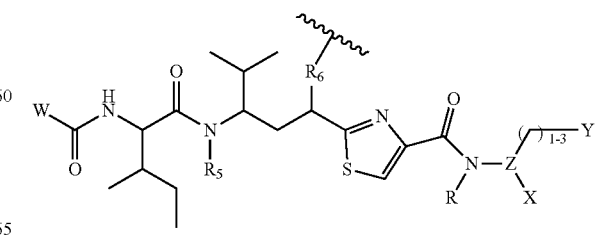

W is selected from:

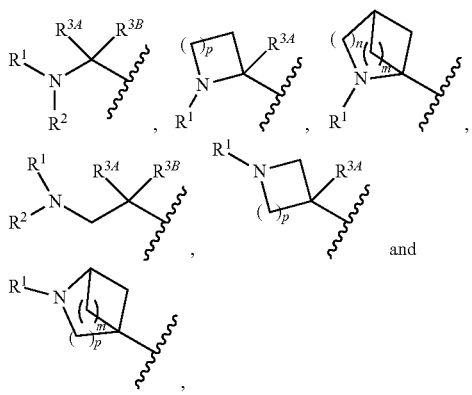

where:
m is 1-3;
n is 1-2; and
p is 1-4;
$R^1$ is selected from hydrogen, $C_1$-$C_8$ alkyl and $C_1$-$C_8$ haloalkyl; $R^2$ is selected from hydrogen, $C_1$-$C_8$ alkyl and $C_1$-$C_8$ haloalkyl;
each $R^{3A}$ and $R^{3B}$ is independently selected from $C_1$-$C_8$ alkyl, $C_1$-$C_8$ haloalkyl, $C_3$-$C_8$ carbocyclyl, $C_1$-$C_{10}$ heterocyclyl, aryl, heteroalkyl, halogen and aralkyl; or $R^{3A}$ and $R^{3B}$ taken together are selected from $C_2$-$C_8$ alkylene and $C_1$-$C_8$ heteroalkylene;
$R^5$ is selected from hydrogen, $C_1$-$C_8$ alkyl, $C_1$-$C_8$ haloalkyl, $C_3$-$C_8$ carbocyclyl, $C_3$-$C_8$ heterocyclyl, aryl, heteroaralkyl, aralkyl, where $R^5$ is optionally substituted with —$(C(R)_2)_m NR^1R^2$;
$R^6$ is selected from —OC(O)N(*)$R^7$, —O—, —NR—, —N(*)C(O)$R^7$, —N(*)C(O)O$R^7$, —N(*)C(O)N$R^7R^8$, —N(*)SO$_2$R and —N(*)SO$_2$N$R^7R^8$, where * is a bond to L, and where $R^7$ and $R^8$ are each independently selected from hydrogen, $C_1$-$C_8$ alkyl, $C_3$-$C_8$ carbocyclyl, $C_3$-$C_8$ heterocyclyl, aryl, heteroaralkyl and aralkyl; or $R^7$ and $R^8$, together with the nitrogen to which they are joined form $C^3$-$C^{10}$ heterocyclyl, and where one or more of $R^7$ and $R^8$ are optionally substituted with one or more substituents selected from halogen, $NR_2$, CN, OH and $OC_1$-$C_8$ alkyl;
Z is N or $CR^2$;
Y is selected from aryl, $C_3$-$C_8$ heterocyclyl and $C_5$-$C_{14}$ heteroaryl, where Y is optionally substituted with one or more $R^{11}$, or
Y is selected from:

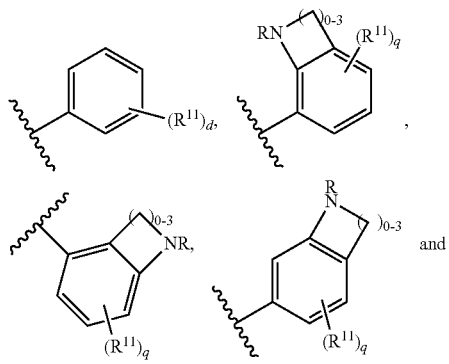

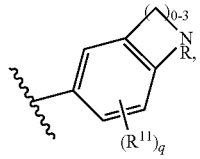

where
d is 1-5;
q is 1-3; and
each $R^{11}$ is independently selected from hydrogen, $C_1$-$C_8$ alkyl, $C_1$-$C_8$ haloalkyl, halogen, —CN, —OH, —$(C(R)_2)_t$ONRR, —$(C(R)_2)_t$—NRR, $(C(R)_2)_t$—C(O)R, $(C(R)_2)_t$—CONR$^8$R$^9$, —$(C(R)_2)_t$C(O)NRNRR, —$(C(R)_2)_t$C(O)N(R)OH, —$(C(R)_2)_t$SH, —$(C(R)_2)_t$—N(R)—C(O)R, —$(C(R)_2)_t$N(R)—C(O)OR, —$(C(R)_2)_t$—N(R)—SO$_2$R, —$(C(R)_2)_t$N(R)C(O)NR$^8$R$^9$, —$(C(R)_2)_t$SO$_2$NR$^8$R$^9$, and —$(C(R)_2)_t$N(R)SO$_2$NR$^8$R$^9$, where each t is independently 0-3; and
X is selected from hydrogen, —C(O)OR, $C_1$-$C_6$ alkyl, $C_6$-$C_{14}$ aryl, $C_5$-$C_4$ heteroaryl, $C_3$-$C_6$ carbocyclyl, $C_3$-$C_8$ heterocyclyl, —$C_1$-$C_6$ alkyl-$C_6$-$C_{14}$ aryl, and —$C_1$-$C_6$alkyl-$C_5$-$C_{14}$heteroaryl, where X is optionally substituted with 1-3 substituents independently selected from, halogen, —OH, —C(O)OR, —CON(R)OH, —ONR$^2$, —NR$^8$R$^9$, —COR, —CONR$^2$, —CONRNRR, —SH, —N(R)—COR, —N(R)—C(O)OR, —N(R)—SO$_2$R, —N(R)—CONR$^8$R$^9$, —SO$_2$—NR$^8$R$^9$, —N(R)—SO$_2$ NR$^8$R$^9$, —P(O)(OR)$_2$, and —S(O)(OR)$_2$, where each R is independently hydrogen, $C_1$-$C_8$ alkyl or $C_1$-$C_8$ haloalkyl;
$L^1$ is selected from: -halogen, —NR$_2$,

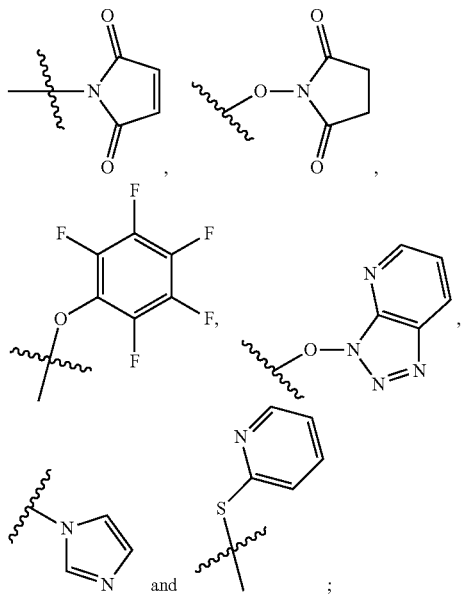

$L^2$ is $L^{2A}$-$L^{2B}$-$L^{2C}$ or $L^{2C}$-$L^{2B}$-$L^{2A}$, where:
$L^{2A}$ comprises one or more components selected from:
—$C_1$-$C_6$alkyl-, —C(O)—$C_1$-$C_6$alkyl-, —$C_1$-$C_6$alkyl(OCH$_2$CH$_2$)$_{1-6}$—, —C(O)—$C_1$-$C_6$alkyl-NRC(O)$C_1$-$C_6$alkyl-, —$C_1$-$C_6$alkyl(OCH$_2$CH$_2$)$_{1-6}$—, —NRC(O) $C_1$-$C_6$alkyl-, —C(O)—, and —C(O)—O—$C_1$-$C_6$alkyl-S—, or $L^{2A}$ is absent;
$L^{2B}$ is AA$_{0-aa}$, where AA is a natural or non-natural amino acid and aa is 12; and $L^{2C}$ is selected from -PABA- and -PABC-, or $L^{2C}$ is absent; and $L^3$ is —$CR_2NR$—, or $L^3$ is absent.

Further aspects of the invention include a compound or compounds of formula (II):

L-P    (II)

or a pharmaceutically acceptable salt thereof, wherein:

L is the linker moiety $L^1$-$L^2$-$L^3$, where L is bound to P through $R^{11}$;

P is a radical of formula:

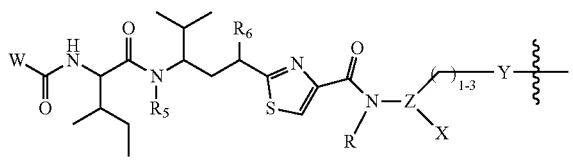

W is selected from:

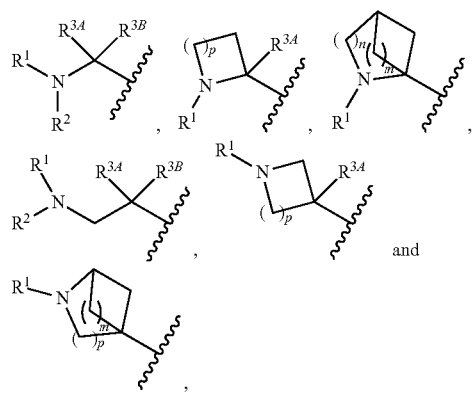

where:
m is 1-3;
n is 1-2; and
p is 1-4;

$R^1$ is selected from hydrogen, $C_1$-$C_8$ alkyl and $C_1$-$C_8$ haloalkyl;

$R^2$ is selected from hydrogen, $C_1$-$C_8$ alkyl and $C_1$-$C_8$ haloalkyl;

each $R^{3A}$ and $R^{3B}$ is independently selected from $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen and aralkyl; or $R^{3A}$ and $R^{3B}$ taken together are selected from $C_2$-$C_8$ alkylene and $C_1$-$C_8$ heteroalkylene;

$R^5$ is selected from hydrogen, $C_1$-$C_8$ alkyl, $C_1$-$C_8$ haloalkyl, $C_3$-$C_8$ carbocyclyl, $C_3$-$C_8$ heterocyclyl, aryl, heteroaralkyl, aralkyl, where $R^5$ is optionally substituted with —$(C(R)_2)_m$NR$^1$R$^2$;

$R^6$ is selected from hydrogen, $OR^7$, $OC(O)R^7$, $OC(O)NR^7R^8$, $NR^7R^8$, $N(R^7)C(O)R^7$, $N(R^7)C(O)OR^7$, $N(R)C(O)NR^7R^8$, $N(R^7)SO_2R$, and $N(R^7)SO_2NR^7R^8$, where $R^7$ and $R^8$ are each independently selected from hydrogen, $C_1$-$C_8$ alkyl, $C_3$-$C_8$ carbocyclyl, $C_3$-$C_8$ heterocyclyl, aryl, heteroaralkyl and aralkyl; or $R^7$ and $R^8$, together with the nitrogen to which they are joined form $C^3$-$C^{10}$ heterocyclyl, and where one or more of $R^7$ and $R^8$ are optionally substituted with one or more substituents selected from halogen, $NR_2$, CN, OH and $OC_1$-$C_8$ alkyl; Z is N or $CR^2$;

Y is selected from aryl, $C_3$-$C_8$ heterocyclyl and $C_5$-$C_{14}$ heteroaryl, where Y is optionally substituted with one or more $R^{11}$, or Y is selected from:

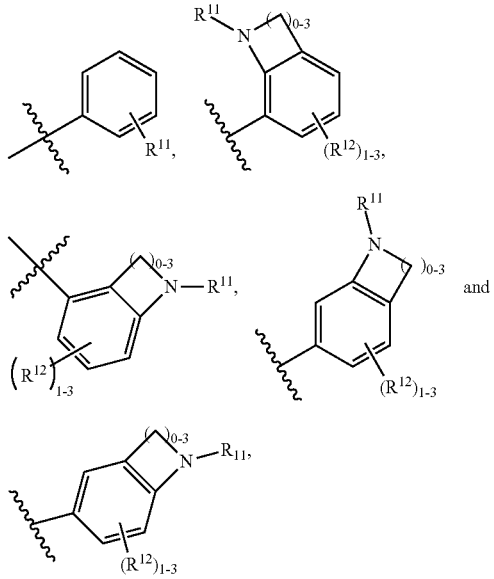

where $R^{11}$ is selected from: —$(C(R)_2)_tO$—, —$(C(R)_2)_tON(R)$—, —$(C(R)_2)_tNR$—, —$(C(R)_2)_t(R)C=N$—, —$C(R)_2)_tC(O)NR$—, —$(C(R)_2)_tC(O)N(R)O$—, —$(C(R)_2)_tS$—, —$(C(R)_2)_tN(*)C(O)OR$, —$(C(R)_2)_tN(*)SO_2R$, —$(C(R)_2)_t$—$N(*)C(O)NR^8R^9$, —$(C(R)_2)_tSO_2$—$N(*)R$, —$(C(R)_2)_tN(*)SO_2NR^8R^9$, where * is a bond to L, or $R^{11}$ is a bond if $R^{11}$ is directly bound to N;

each $R^{12}$ is independently selected from: hydrogen, —OH, —CN and $CF_3$;

and where each t is independently 0-3

X is selected from hydrogen, —C(O)OR, $C_1$-$C_6$ alkyl, $C_6$-$C_{14}$ aryl, $C_5$-$C_4$ heteroaryl, $C_3$-$C_6$ carbocyclyl, $C_3$-$C_8$ heterocyclyl, —$C_1$-$C_6$ alkyl-$C_6$-$C_4$ aryl, and —$C_1$-$C_6$alkyl-$C_5$-$C_{14}$heteroaryl, where X is optionally substituted with 1-3 substituents independently selected from, halogen, —OH, —C(O)OR, —CON(R)OH, —$ONR^2$, —$NR^8R^9$, —COR, —$CONR^2$, —CONRNRR, —SH, —N(R)—COR, —N(R)—C(O)OR, —N(R)—$SO_2R$, —N(R)—$CONR^8R^9$, —$SO_2$—$NR^8R^9$, —N(R)—$SO_2 NR^8R^9$, —$P(O)(OR)_2$, and —$S(O)(OR)_2$, where each R is independently hydrogen, $C_1$-$C_8$ alkyl or $C_1$-$C_8$ haloalkyl;

$L^1$ is selected from: -halogen, —$NR_2$,

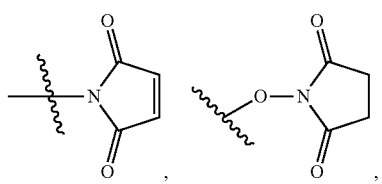

-continued

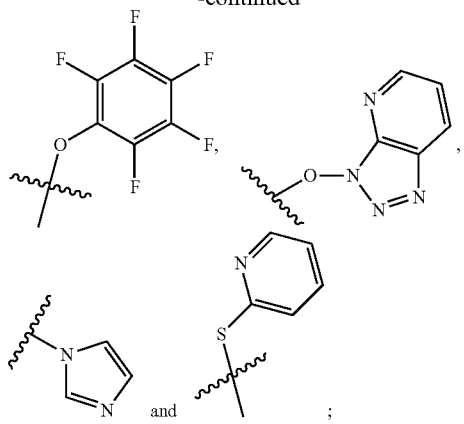

L² is L²ᴬ-L²ᴮ-L²ᶜ or L²ᶜ-L²ᴮ-L²ᴬ, where:
  L²ᴬ comprises one or more components selected from:
  —C(O)—C₁-C₆alkyl-, —C(O)—C₁-C₆alkyl(OCH₂CH₂)₁₋₆—, —C(O)—C₁-C₆alkyl-NRC(O)C₁-C₆alkyl-, —C(O)—C₁-C₆alkyl(OCH₂CH₂)₁₋₆—NRC(O)C₁-C₆alkyl-, —C(O)—C₁₋₆alkyl-C(O)—, —C(O)—C₁₋₆alkyl(OCH₂CH₂)₁₋₆—C(O)—, —NRC(O)-phenyl-O—C₁₋₆alkyl-, —N═CR-phenyl-O—C₁₋₆alkyl-, —N═CR-phenyl-O—C₁₋₆alkyl-C(O)—, -, and —C(O)—O—C₁-C₆alkyl-S—, or L²ᴬ is absent;
  L²ᴮ is AA₀₋ₐₐ, where AA is a natural or non-natural amino acid and aa is 12; and
  L²ᶜ is selected from -PABA- and -PABC-, or L²ᶜ is absent; and
L³ is selected from one or more of: —CO—, —NR—, —C₁-C₆alkyl-, —NR—C₁-C₆alkyl- and —NR—C₁-C₆-alkyl-NR—, or L³ is absent;
provided that when R⁵ is C₁-C₆ alkyl, R⁶ is —OC(O)R, W is:

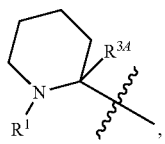

X is

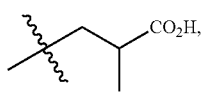 [SMILES: *CC(C)C(=O)O]

Y is

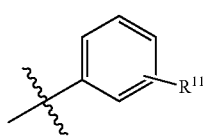

and R¹¹ is —(C(R)₂)ₜ—NR— (t=0), then L is not selected from:

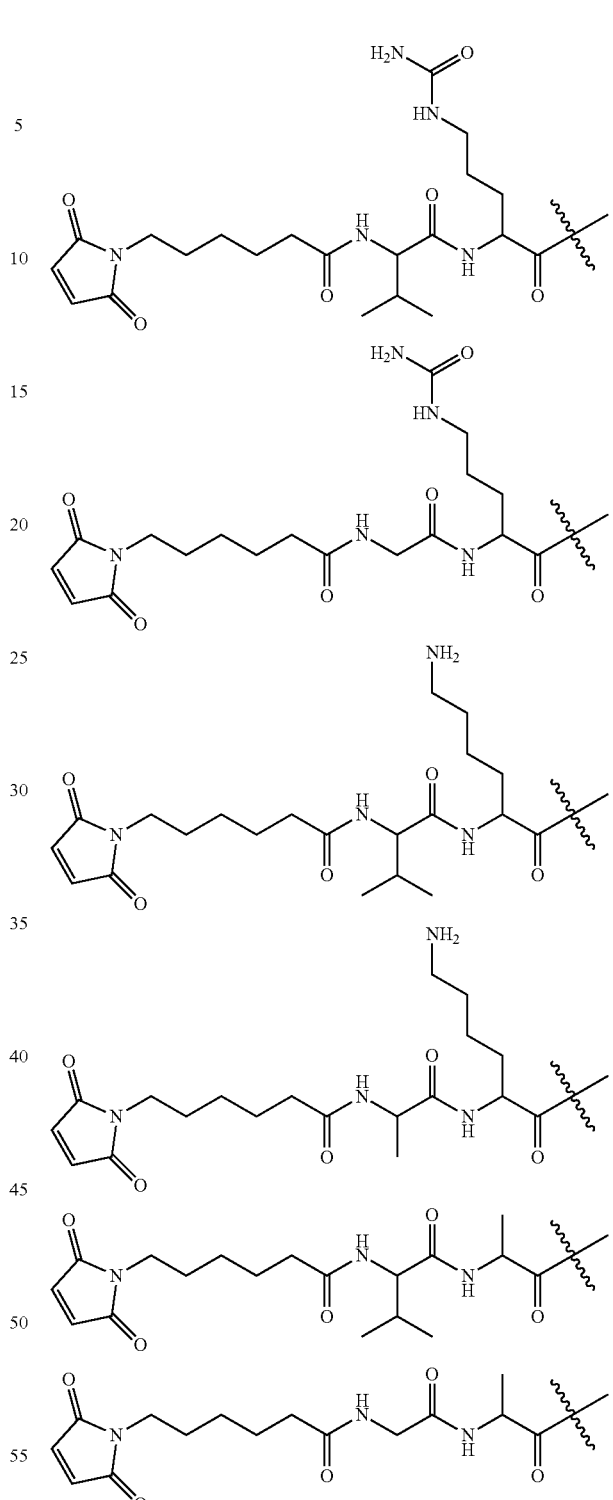

Still further aspects of the invention include a compound or compounds of formula (II):

$$L\text{-}P \qquad (II)$$

or a pharmaceutically acceptable salt thereof, wherein:
L is the linker moiety L¹-L²-L³, where L is bound to P through X;

P is a radical of formula:

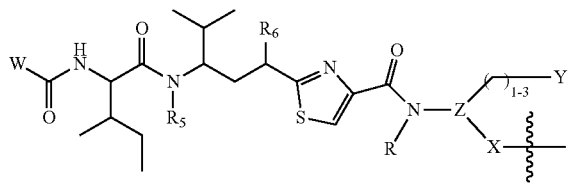

W is selected from:

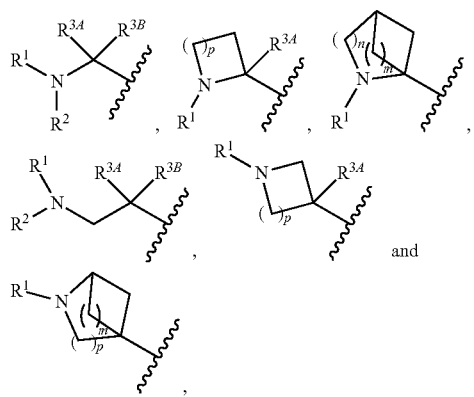

where:
  m is 1-3;
  n is 1-2; and
  p is 1-4;

$R^1$ is selected from hydrogen, $C_1$-$C_8$ alkyl and $C_1$-$C_8$ haloalkyl;

$R^2$ is selected from hydrogen, $C_1$-$C_8$ alkyl and $C_1$-$C_8$ haloalkyl;

each $R^{3A}$ and $R^{3B}$ is independently selected from $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen and aralkyl; or $R^{3A}$ and $R^{3B}$ taken together are selected from $C_2$-$C_8$ alkylene and $C_1$-$C_8$ heteroalkylene;

$R^5$ is selected from hydrogen, $C_1$-$C_8$ alkyl, $C_1$-$C_8$ haloalkyl, $C_3$-$C_8$ carbocyclyl, $C_3$-$C_8$ heterocyclyl, aryl, heteroaralkyl, aralkyl, where $R^5$ is optionally substituted with —$(C(R)_2)_m$NR$^1$R$^2$;

$R^6$ is selected from hydrogen, OR$^7$, OC(O)R$^7$, OC(O)NR$^7$R$^8$, NR$^7$R$^8$, N(R$^7$)C(O)R$^7$, N(R$^7$) C(O)OR$^7$, N(R)C(O)NR$^7$R$^8$, N(R$^7$)SO$_2$R, and N(R$^7$)SO$_2$NR$^7$R$^8$, where $R^7$ and $R^8$ are each independently selected from hydrogen, $C_1$-$C_8$ alkyl, $C_3$-$C_8$ carbocyclyl, $C_3$-$C_8$ heterocyclyl, aryl, heteroaralkyl and aralkyl; or $R^7$ and $R^8$, together with the nitrogen to which they are joined form $C^3$-$C^{10}$ heterocyclyl, and where one or more of $R^7$ and $R^8$ are optionally substituted with one or more substituents selected from halogen, NR$_2$, CN, OH and OC$_1$-$C_8$ alkyl;

Z is CR$^2$;

Y is selected from aryl, $C_3$-$C_8$ heterocyclyl and $C_5$-$C_{14}$ heteroaryl, where Y is optionally substituted with one or more $R^1$ or Y is selected from:

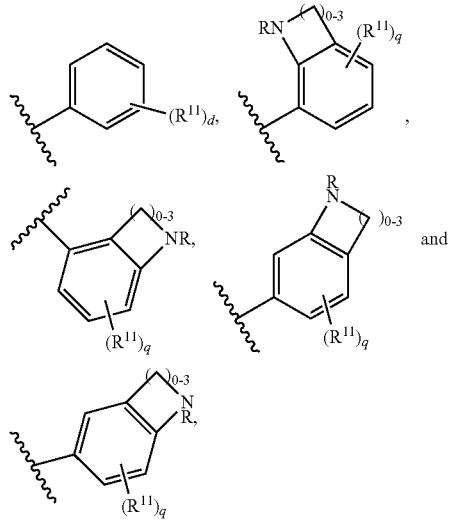

where
  d is 1-5;
  q is 1-3; and
  each $R^{11}$ is independently selected from hydrogen, $C_1$-$C_8$ alkyl, $C_1$-$C_8$ haloalkyl, halogen, —CN, —OH, —$(C(R)_2)_t$ONRR, —$(C(R)_2)_t$—NRR, $(C(R)_2)_t$—C(O)R, $(C(R)_2)_t$—CONR$^8$R$^9$, —$(C(R)_2)_t$C(O)NRNRR, —$(C(R)_2)_t$C(O)N(R)OH, —$(C(R)_2)_t$SH, —$(C(R)_2)_t$—N(R)—C(O)R, —$(C(R)_2)_t$N(R)—C(O)OR, —$(C(R)_2)_t$N(R)—SO$_2$R, —$(C(R)_2)_t$N(R)C(O)NR$^8$R$^9$, —$(C(R)_2)_t$SO$_2$NR$^8$R$^9$, and —$(C(R)_2)_t$N(R)SO$_2$NR$^8$R$^9$, where each t is independently 0-3; and X is selected from —$C_1$-$C_6$ alkyl-C(O)—, —$C_1$-$C_6$ alkyl-C(O)NR—, —$C_1$-$C_6$ alkyl-N(*)C(O)OR, —$C_1$-$C_6$alkyl-N(*)SO$_2$R, $C_1$-$C_6$alkyl-N(*)CONR$^8$R$^9$, and —$C_1$-$C_6$alkylN(*)SO$_2$NR$^8$R$^9$, where * is a bond to L;

$L^1$ is selected from: -halogen, —NR$_2$,

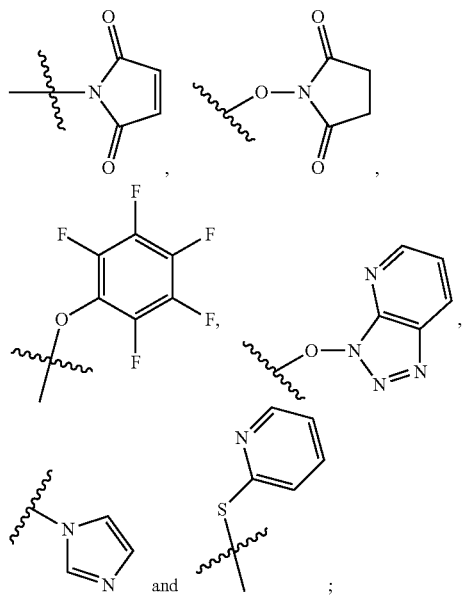

$L^2$ is $L^{2A}$-$L^{2B}$-$L^{2C}$ or $L^{2C}$-$L^{2B}$-$L^{2A}$, where:

$L^{2A}$ comprises one or more components selected from: —C(O)—$C_1$-$C_6$alkyl-, —C(O)—$C_1$-$C_6$alkyl(OCH$_2$CH$_2$)$_{1-6}$—, —C(O)—$C_1$-$C_6$alkyl-NRC(O)$C_1$-$C_6$alkyl-, —C(O)—$C_1$-$C_6$alkyl(OCH$_2$CH$_2$)$_{1-6}$—NRC(O) $C_1$-$C_6$alkyl-, —C(O)—$C_1$-$C_6$alkyl-C(O)—, —C(O)—$C_1$-$C_6$alkyl(OCH$_2$CH$_2$)$_{1-6}$—C(O)—, —N=CR-phenyl-O—$C_1$-$C_6$alkyl-, —N=CR-phenyl-O—$C_1$-$C_6$alkyl-C(O)—, —C(O)—O—$C_1$-$C_6$alkyl-S— and —S—, or $L^{2A}$ is absent;

$L^{2B}$ is $AA_{0-aa}$, where AA is a natural or non-natural amino acid and aa is 12; and $L^{2C}$ is selected from -PABA- and -PABC-, or $L^{2C}$ is absent; and $L^3$ is selected from one or more of: —O—, —NR—, —$C_1$-$C_6$alkyl- and —NR—$C_1$-$C_6$alkyl-, or $L^3$ is absent.

Additional aspects of the invention include a compound or compounds of formula (III):

(AB)-(L-P)$_b$     (III)

or a pharmaceutically acceptable salt thereof, wherein:
L is the linker moiety $L^1$-$L^2$-$L^3$, where L is bound to P through $R^6$;
P is a radical of formula:

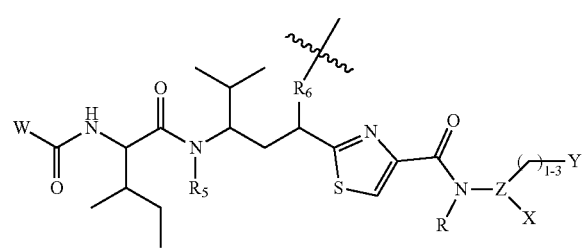

W is selected from:

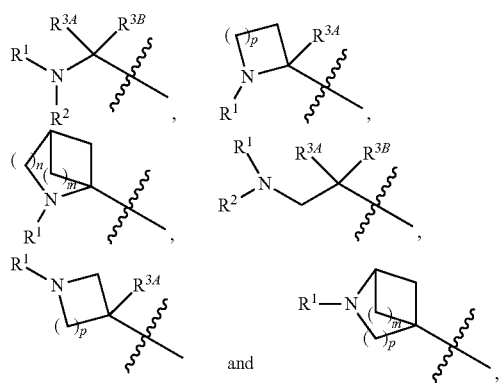

where:
m is 1-3;
n is 1-2; and
p is 1-4;
$R^1$ is selected from hydrogen, $C_1$-$C_8$ alkyl and $C_1$-$C_8$ haloalkyl; $R^2$ is selected from hydrogen, $C_1$-$C_8$ alkyl and $C_1$-$C_8$ haloalkyl;
each $R^{3A}$ and $R^{3B}$ is independently selected from $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen and aralkyl; or $R^{3A}$ and $R^{3B}$ taken together are selected from $C_2$-$C_8$ alkylene and $C_1$-$C_8$ heteroalkylene;

$R^5$ is selected from hydrogen, $C_1$-$C_8$ alkyl, $C_1$-$C_8$ haloalkyl, $C_3$-$C_8$ carbocyclyl, $C_3$-$C_8$ heterocyclyl, aryl, heteroaralkyl, aralkyl, where $R^5$ is optionally substituted with —(C(R)$_2$)$_m$NR$^1$R$^2$;

$R^6$ is selected from —OC(O)N(*)R$^7$, —O—, —NR—, —N(*)C(O)R$^7$, —N(*)C(O)OR$^7$, —N(*)C(O)NR$^7$R$^8$, —N(*)SO$_2$R and —N(*)SO$_2$NR$^7$R$^8$, where * is a bond to L, and where $R^7$ and $R^8$ are each independently selected from hydrogen, $C_1$-$C_8$ alkyl, $C_3$-$C_8$ carbocyclyl, $C_3$-$C_8$ heterocyclyl, aryl, heteroaralkyl and aralkyl; or $R^7$ and $R^8$, together with the nitrogen to which they are joined form $C^3$-$C^{10}$ heterocyclyl, and where one or more of $R^7$ and $R^8$ are optionally substituted with one or more substituents selected from halogen, NR$_2$, CN, OH and O$C_1$-$C_8$ alkyl;

Z is N or CR$^2$;
Y is selected from aryl, $C_3$-$C_8$ heterocyclyl and $C_5$-$C_{14}$ heteroaryl, where Y is optionally substituted with one or more $R^{11}$, or
Y is selected from:

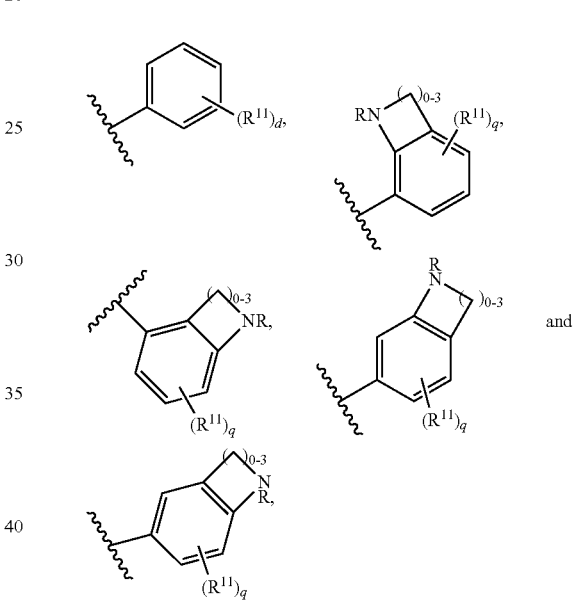

where
d is 1-5;
q is 1-3; and
each $R^{11}$ is independently selected from hydrogen, $C_1$-$C_8$ alkyl, $C_1$-$C_8$ haloalkyl, halogen, —CN, —OH, —(C(R)$_2$)$_t$ONRR, —(C(R)$_2$)$_t$—NRR, (C(R)$_2$)$_t$—C(O)R, (C(R)$_2$)$_t$—CONR$^8$R$^9$, —(C(R)$_2$)$_t$C(O)NRNRR, —(C(R)$_2$)$_t$C(O)N(R)OH, —(C(R)$_2$)$_t$SH, —(C(R)$_2$)$_t$—N(R)—C(O)R, —(C(R)$_2$)$_t$N(R)—C(O)OR, —(C(R)$_2$)$_t$—N(R)—SO$_2$R, —(C(R)$_2$)$_t$N(R)C(O)NR$^8$R$^9$, —(C(R)$_2$)$_t$SO$_2$NR$^8$R$^9$, and —(C(R)$_2$)$_t$N(R)SO$_2$NR$^8$R$^9$, where each t is independently 0-3; and X is selected from hydrogen, —C(O)OR, $C_1$-$C_6$ alkyl, $C_6$-$C_{14}$ aryl, $C_5$-$C_{14}$ heteroaryl, $C_3$-$C_6$ carbocyclyl, $C_3$-$C_8$ heterocyclyl, —$C_1$-$C_6$ alkyl-$C_6$-$C_{14}$ aryl, and —$C_1$-$C_6$alkyl-$C_5$-$C_{14}$heteroaryl, where X is optionally substituted with 1-3 substituents independently selected from, halogen, —OH, —C(O)OR, —CON(R)OH, —ONR$^2$, —NR$^8$R$^9$, —COR, —CONR$^2$, —CONRNRR, —SH, —N(R)—COR, —N(R)—C(O)OR, —N(R)—SO$_2$R, —N(R)—CONR$^8$R$^9$, —SO$_2$—NR$^8$R$^9$, —N(R)—SO$_2$ NR$^8$R$^9$, —P(O)(OR)$_2$, and —S(O)(OR)$_2$, where each R is independently hydrogen, $C_1$-$C_8$ alkyl or $C_1$-$C_8$ haloalkyl;

$L^1$ is selected from: a bond to AB, —NR$_2$-(bond to AB) and;

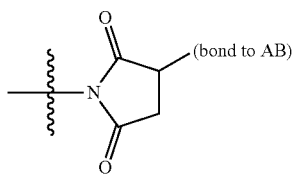

$L^2$ is $L^{2A}$-$L^{2B}$-$L^{2C}$ or $L^{2C}$-$L^{2B}$-$L^{2A}$, where:
$L^{2A}$ comprises one or more components selected from:
—C(O)—C$_1$-C$_6$alkyl-, —C$_1$-C$_6$alkyl(OCH$_2$CH$_2$)$_{1-6}$—,
—C(O)—C$_1$-C$_6$alkyl-NRC(O)C$_1$-C$_6$alkyl-, —C$_1$-C$_6$alkyl(OCH$_2$CH$_2$)$_{1-6}$—NRC(O)C$_1$-C$_6$alkyl-,
—C(O)—, and —C(O)—O—C$_1$-C$_6$alkyl-S—, or $L^{2A}$ is absent;
$L^{2B}$ is AA$_{0-aa}$, where AA is a natural or non-natural amino acid and aa is 12; and
$L^{2C}$ is selected from -PABA- and -PABC-, or $L^{2C}$ is absent; and
$L^3$ is —CR$_2$NR—, or $L^3$ is absent; and
b is 1-20.

Further aspects of the invention include a compound or compounds of formula (III):

or a pharmaceutically acceptable salt thereof, wherein:
L is the linker moiety $L^1$-$L^2$-$L^3$, where L is bound to P through $R^{11}$;
P is a radical of formula:

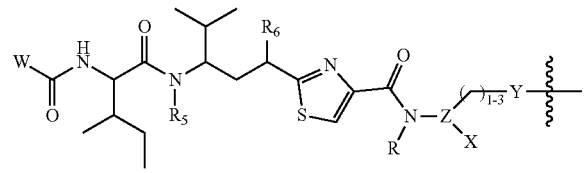

W is selected from:

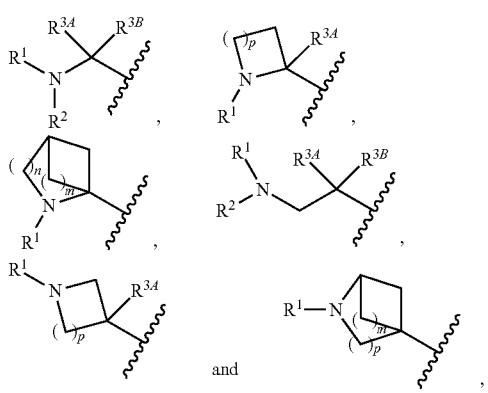

where:
m is 1-3;
n is 1-2; and
p is 1-4;
$R^1$ is selected from hydrogen, C$_1$-C$_8$ alkyl and C$_1$-C$_8$ haloalkyl;

$R^2$ is selected from hydrogen, C$_1$-C$_8$ alkyl and C$_1$-C$_8$ haloalkyl;
each $R^{3A}$ and $R^{3B}$ is independently selected from C$_1$-C$_8$ alkyl, C$_1$-C$_8$ haloalkyl, C$_3$-C$_8$ carbocyclyl, C$_1$-C$_{10}$ heterocyclyl, aryl, heteroaralkyl, halogen and aralkyl; or $R^{3A}$ and $R^{3B}$ taken together are selected from C$_2$-C$_8$ alkylene and C$_1$-C$_8$ heteroalkylene;
$R^5$ is selected from hydrogen, C$_1$-C$_8$ alkyl, C$_1$-C$_8$ haloalkyl, C$_3$-C$_8$ carbocyclyl, C$_3$-C$_8$ heterocyclyl, aryl, heteroaralkyl, aralkyl, where $R^5$ is optionally substituted with —(C(R)$_2$)$_m$NR$^1$R$^2$;
$R^6$ is selected from hydrogen, OR$^7$, OC(O)R$^7$, OC(O)NR$^7$R$^8$, NR$^7$R$^8$, N(R$^7$)C(O)R$^7$, N(R$^7$) C(O)OR$^7$, N(R)C(O)NR$^7$R$^8$, N(R$^7$)SO$_2$R, and N(R$^7$)SO$_2$NR$^7$R$^8$, where R$^7$ and R$^8$ are each independently selected from hydrogen, C$_1$-C$_8$ alkyl, C$_3$-C$_8$ carbocyclyl, C$_3$-C$_8$ heterocyclyl, aryl, heteroaralkyl and aralkyl; or R$^7$ and R$^8$, together with the nitrogen to which they are joined form C$^3$-C$^{10}$ heterocyclyl, and where one or more of R$^7$ and R$^8$ are optionally substituted with one or more substituents selected from halogen, NR$_2$, CN, OH and OC$_1$-C$_8$ alkyl;
Z is N or CR$^2$;
Y is selected from aryl, C$_3$-C$_8$ heterocyclyl and C$_5$-C$_{14}$ heteroaryl, where Y is optionally substituted with one or more R$^{11}$, or
Y is selected from

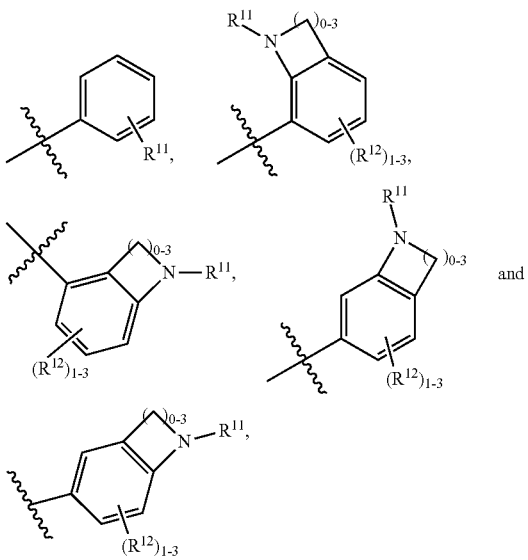

where
$R^{11}$ is selected from: —(C(R)$_2$)$_t$O—, —(C(R)$_2$)$_t$ON(R)—, —(C(R)$_2$)$_t$NR—, —(C(R)$_2$)$_t$(R)C=N—, —C(R)$_2$)$_t$C(O)NR—, —(C(R)$_2$)$_t$C(O)N(R)O—, —(C(R)$_2$)$_t$S—, —(C(R)$_2$)$_t$N(*)C(O)OR, —(C(R)$_2$)$_t$N(*) SO$_2$R, —(C(R)$_2$)$_t$N(*)C(O)NR$^8$R$^9$, —(C(R)$_2$)$_t$SO$_2$—N (*)R, —(C(R)$_2$)$_t$N(*)SO$_2$NR$^8$R$^9$, where * is a bond to L, or $R^{11}$ is a bond if $R^{11}$ is directly bound to N;
each $R^{12}$ is independently selected from: hydrogen, —OH, —CN and CF$_3$;
where each t is independently 0-3;
X is selected from hydrogen, —C(O)OR, C$_1$-C$_6$ alkyl, C$_6$-C$_{14}$ aryl, C$_5$-C$_{14}$ heteroaryl, C$_3$-C$_6$ carbocyclyl, C$_3$-C$_8$ heterocyclyl, —C$_1$-C$_6$ alkyl-C$_6$-C$_{14}$ aryl, and —C$_1$-C$_6$alkyl-C$_5$-C$_{14}$heteroaryl, where X is optionally substituted with 1-3 substituents independently selected from, halogen, —OH, —C(O)OR, —CON(R)OH, —ONR², —NR⁸R⁹, —COR, —CONR², —CONRNRR, —SH, —N(R)—COR, —N(R)—C(O)OR, —N(R)—SO₂R, —N(R)—CONR⁸R⁹, —SO₂—NR⁸R⁹, —N(R)—SO₂ NR⁸R⁹, —P(O)(OR)₂, and —S(O)(OR)₂, where each R is independently hydrogen, $C_1$-$C_8$ alkyl or $C_1$-$C_8$ haloalkyl;

$L^1$ is selected from: a bond to AB, —NR₂— (bond to AB) and

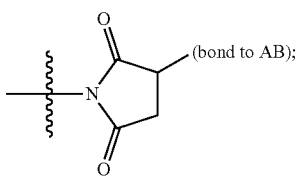

$L^2$ is $L^{2A}$-$L^{2B}$-$L^{2C}$ or $L^{2C}$-$L^{2B}$-$L^{2A}$, where:
  $L^{2A}$ comprises one or more components selected from: —C(O)—$C_1$-$C_6$alkyl-, —C(O)—$C_1$-$C_6$alkyl(OCH₂CH₂)₁₋₆—, —C(O)—$C_1$-$C_6$alkyl-NRC(O)$C_1$-$C_6$alkyl-, —C(O)—$C_1$-$C_6$alkyl(OCH₂CH₂)₁₋₆—NRC(O)$C_1$-$C_6$alkyl-, —C(O)—$C_{1-6}$alkyl-C(O)—, —C(O)—$C_{1-6}$alkyl(OCH₂CH₂)₁₋₆—C(O)—, —NRC(O)-phenyl-O—$C_{1-6}$alkyl-, —N═CR-phenyl-O—$C_{1-6}$alkyl-, —N═CR-phenyl-O—$C_{1-6}$alkyl-C(O)—, -, and —C(O)—O—$C_1$-$C_6$alkyl-S—, or $L^{2A}$ is absent;
  $L^{2B}$ is $AA_{0-aa}$, where AA is a natural or non-natural amino acid and aa is 12; and
  $L^{2C}$ is selected from -PABA- and -PABC-, or $L^{2C}$ is absent; and $L^3$ is selected from one or more of: —CO—, —NR—, —$C_1$-$C_6$alkyl-, —NR—$C_1$-$C_6$alkyl- and —NR—$C_1$-$C_6$-alkyl-NR—, or $L^3$ is absent; and b is 1-20.

provided that when $R^5$ is $C_1$-$C_6$ alkyl, $R^6$ is —OC(O)R, W is:

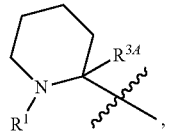,

X is

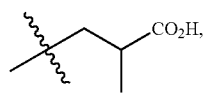 [SMILES: *CC(C)C(=O)O]

$R^{11}$ is —(C(R)₂)$_t$—NR— (t=0) and Y is

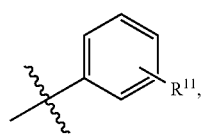

then L is not selected from:

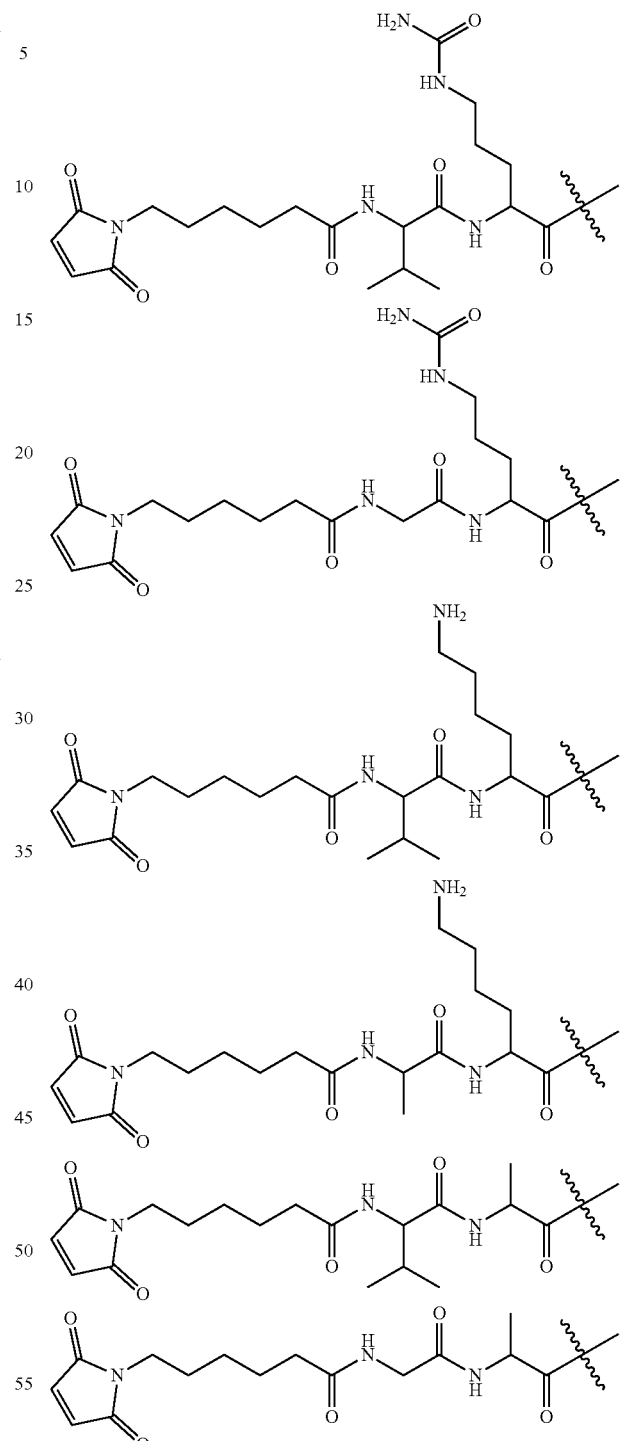

Still further aspects of the invention include a compound or compounds of formula (III):

(AB)-(L-P)$_b$     (III)

or a pharmaceutically acceptable salt thereof, wherein:
L is the linker moiety $L^1$-$L^2$-$L^3$, where L is bound to P through X;

P is a radical of formula:

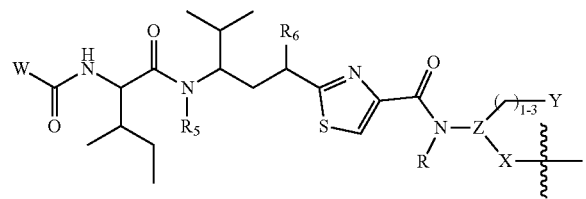

W is selected from:

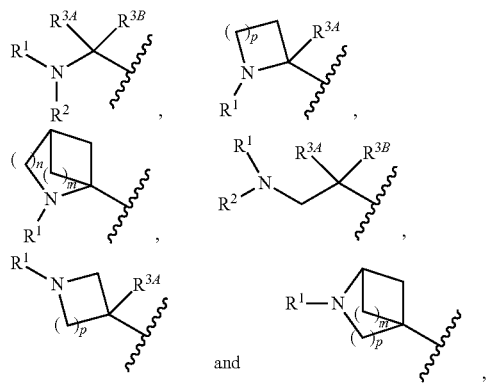

where:
  m is 1-3;
  n is 1-2; and
  p is 1-4;
$R^1$ is selected from hydrogen, $C_1$-$C_8$ alkyl and $C_1$-$C_8$ haloalkyl;

$R^2$ is selected from hydrogen, $C_1$-$C_8$ alkyl and $C_1$-$C_8$ haloalkyl;

each $R^{3A}$ and $R^{3B}$ is independently selected from $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen and aralkyl; or $R^{3A}$ and $R^{3B}$ taken together are selected from $C_2$-$C_8$ alkylene and $C_1$-$C_8$ heteroalkylene;

$R^5$ is selected from hydrogen, $C_1$-$C_8$ alkyl, $C_1$-$C_8$ haloalkyl, $C_3$-$C_8$ carbocyclyl, $C_3$-$C_8$ heterocyclyl, aryl, heteroaralkyl, aralkyl, where $R^5$ is optionally substituted with —$(C(R)_2)_m$NR$^1$R$^2$;

$R^6$ is selected from hydrogen, OR$^7$, OC(O)R$^7$, OC(O)NR$^7$R$^8$, NR$^7$R$^8$, N(R$^7$)C(O)R$^7$, N(R$^7$) C(O)OR$^7$, N(R)C(O)NR$^7$R$^8$, N(R$^7$)SO$_2$R, and N(R$^7$)SO$_2$NR$^7$R$^8$, where $R^7$ and $R^8$ are each independently selected from hydrogen, $C_1$-$C_8$ alkyl, $C_3$-$C_8$ carbocyclyl, $C_3$-$C_8$ heterocyclyl, aryl, heteroaralkyl and aralkyl; or $R^7$ and $R^8$, together with the nitrogen to which they are joined form $C^3$-$C^{10}$ heterocyclyl, and where one or more of $R^7$ and $R^8$ are optionally substituted with one or more substituents selected from halogen, NR$_2$, CN, OH and OC$_1$-$C_8$ alkyl;

Z is CR$^2$;

Y is selected from aryl, $C_3$-$C_8$ heterocyclyl and $C_5$-$C_{14}$ heteroaryl, where Y is optionally substituted with one or more $R^{11}$, or Y is selected from:

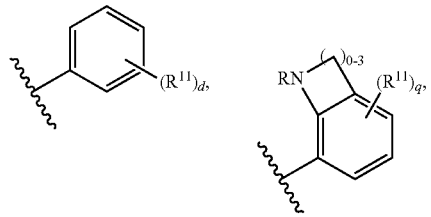

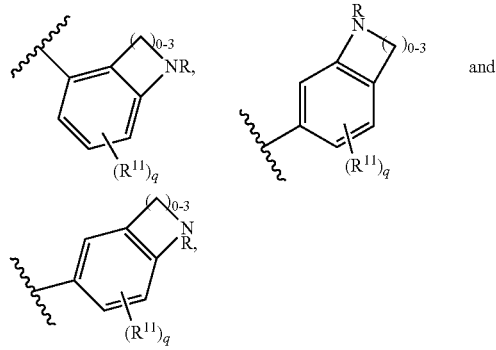

where
  d is 1-5;
  q is 1-3; and
  each $R^{11}$ is independently selected from hydrogen, $C_1$-$C_8$ alkyl, $C_1$-$C_8$ haloalkyl, halogen, —CN, —OH, —(C(R)$_2$)$_t$ONRR, —(C(R)$_2$)$_t$—NRR, (C(R)$_2$)$_t$—C(O)R, (C(R)$_2$)$_t$—CONR$^8$R$^9$, —(C(R)$_2$)$_t$C(O)NRNRR, —(C(R)$_2$)$_t$C(O)N(R)OH, —(C(R)$_2$)$_t$SH, —(C(R)$_2$)$_t$—N(R)—C(O)R, —(C(R)$_2$)$_t$N(R)—C(O)OR, —(C(R)$_2$)$_t$—N(R)—SO$_2$R, —(C(R)$_2$)$_t$N(R)C(O)NR$^8$R$^9$, —(C(R)$_2$)$_t$SO$_2$NR$^8$R$^9$, and —(C(R)$_2$)$_t$N(R)SO$_2$NR$^8$R$^9$, where each t is independently 0-3; and X is selected from —$C_1$-$C_6$ alkyl-C(O)—, —$C_1$-$C_6$ alkyl-C(O)NR—, —$C_1$-$C_6$ alkyl-N(*)C(O)OR, —$C_1$-$C_6$alkyl-N(*)SO$_2$R, $C_1$-$C_6$alkyl-N(*)CONR$^8$R$^9$, and —$C_1$-$C_6$alkylN(*)SO$_2$NR$^8$R$^9$, where * is a bond to L;

$L^1$ is selected from: a bond to AB, —NR$_2$-(bond to AB) and

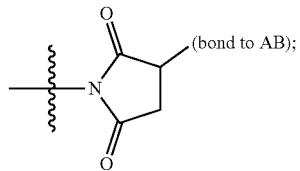

$L^2$ is $L^{2A}$-$L^{2B}$L$^{2C}$ or $L^{2C}$-$L^{2B}$-$L^{2A}$, where:
  $L^{2A}$ comprises one or more components selected from: —C(O)—$C_1$-$C_6$alkyl-, —C(O)—$C_1$-$C_6$alkyl (OCH$_2$CH$_2$)$_{1-6}$—, —C(O)—$C_1$-$C_6$alkyl-NRC(O)C$_1$-$C_6$alkyl-, —C(O)—$C_1$-$C_6$alkyl(OCH$_2$CH$_2$)$_{1-6}$—NRC(O) $C_1$-$C_6$alkyl-, —C(O)—$C_1$-$C_6$alkyl-C(O)—, —C(O)—$C_1$-$C_6$alkyl(OCH$_2$CH$_2$)$_{1-6}$—C(O)—, —N=CR-phenyl-O—$C_1$-$C_6$alkyl-, —N=CR-phenyl-O—$C_1$-$C_6$alkyl-C(O)—, —C(O)—O—$C_1$-$C_6$alkyl-S— and —S—, or $L^{2A}$ is absent;
  $L^{2B}$ is AA$_{0-aa}$, where AA is a natural or non-natural amino acid and aa is 12; and
  $L^{2C}$ is selected from -PABA- and -PABC-, or $L^{2C}$ is absent; and
$L^3$ is selected from one or more of: —O—, —NR—, —$C_1$-$C_6$alkyl- and —NR—$C_1$-$C_6$alkyl-, or $L^3$ is absent; and
b is 1-20.

It is to be noted that divalent variables recited in the above are meant to depict, where appropriate, the positioning of such radicals in multiple orientations within the molecule. Thus, for instance, to cite but a single example, the $L^2$ moiety "—PABC-Cit-Val-C(O)—$C_{1-6}$alkyl-" between $L^1$ and $L^3$ can be positioned as $L^1$-PABC-Cit-Val-C(O)—$C_{1-6}$alkyl-$L^3$ or as $L^1$-$C_{1-6}$alkyl-C(O)-Val-Cit-PABC-$L^3$. Similarly, $L^2$ is defined herein as comprising $L^{2A}$-$L^{2B}$-$L^{2C}$, which construct may likewise be positioned in multiple orientations.

Thus, in certain embodiments there is provided an ADC of the formula III' having the following sequence of components:

AB-$L^1$-$L^2$-$L^3$-P;

AB-$L^1$-$L^{2A}$-$L^{2B}$-$L^{2C}$-$L^3$-P; or

AB-$L^1$-$L^{2C}$-$L^{2B}$-$L^{2A}$-$L^3$-P.

In the above, $L^3$ is shown as typically binding to the payload P, but it is noted that $L^3$ and/or $L^2$ may be absent, with the result being that P may be directly bound to $L^2$ or $L^1$.

Certain chemical groups and moieties described herein are preferred, depending on circumstances. Thus, in certain embodiments of the invention, including with respect to the various payloads, linker-payloads and ADCs described and claimed herein, one or more (or all, or none) of the following may apply: In certain embodiments of the invention $R^1$ is preferably methyl.

In certain embodiments of the invention $R^2$ is preferably methyl.

In certain embodiments of the invention $R^{3A}$ is preferably methyl.

In certain embodiments of the invention $R^{3B}$ is preferably methyl.

In certain embodiments of the invention $R^5$ is preferably methyl.

In certain embodiments of the invention $R^6$ is preferably —O—C(O)—$CH_3$, —OH, —NH—C(O)$CH_3$, —O—C(O)$NR^8R^9$ where $R^8$ and $R^9$ are each independently hydrogen or $C_1$-$C_8$ alkyl, and —NH—C(O)$NR^8R^9$ where $R^8$ and $R^9$ are each independently hydrogen or $C_1$-$C_8$ alkyl.

In certain embodiments of the invention W is preferably selected from

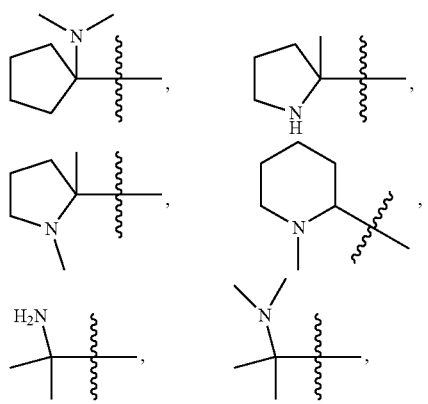

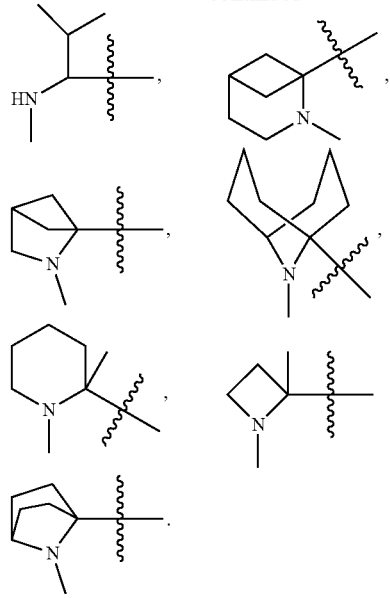

In certain embodiments of the invention of formula I, X is hydrogen, —$C_1$-$C_6$ alkyl or —$C_6$-$C_{14}$ aryl.

In certain embodiments of the invention of formula I, X is $C_1$-$C_6$ alkyl substituted with one or more of: —C(O)OR, —P(O)(OR)$_2$, —COR and —OH.

In certain embodiments of the invention X is selected from hydrogen, —C(O)OR, $C_1$-$C_6$ alkyl, $C_6$-$C_{14}$ aryl, $C_5$-$C_4$ heteroaryl, $C_3$-$C_6$ carbocyclyl, $C_3$-$C_8$ heterocyclyl, —$C_1$-$C_6$ alkyl-$C_6$-$C_{14}$ aryl, and —$C_1$-$C_6$alkyl-$C_6$-$C_{14}$heteroaryl, where X is optionally substituted with 1-3 substituents independently selected from, halogen, —OH, —C(O)OR, —CON(R)OH, —$ONR^2$, —$NR^8R^9$, —COR, —$CONR^2$, —CONRNRR, —SH, —N(R)—COR, —N(R)—C(O)OR, —N(R)—$SO_2R$, —N(R)—$CONR^8R^9$, —$SO_2$—$NR^8R^9$, —N(R)—$SO_2$ $NR^8R^9$, —P(O)(OR)$_2$, and —S(O)(OR)$_2$, where each R is independently hydrogen, $C_1$-$C_8$ alkyl or $C_1$-$C_8$ haloalkyl;

In certain embodiments of the invention Y is aryl, preferably phenyl.

In certain embodiments of the invention Y is aryl substituted with —NRR, preferably phenyl substituted with —$NH_2$.

In certain embodiments of the invention where the compound is not linked to an antibody via is $R^{11}$, $R^{11}$ is preferably hydrogen or $NH_2$. In certain embodiments of the invention where the compound is linked to an antibody via is $R^{11}$, $R^{11}$ is preferably —NH—.

In certain embodiments of the invention Z is —$CH_2$, or Z is —N.

In certain embodiments of the invention m is 1, m is 2 or m is 3.

In certain embodiments of the invention n is 1 or n is 2.

In certain embodiments of the invention p is 1, p is 2, p is 3 or p is 4.

In certain embodiments of the invention q is 1, q is 2 or q is 3.

In certain embodiments of the invention q' is 1, q' is 2, q' is 3, q' is 4 or q' is 5.

In certain embodiments, the present invention relates to any of the aforementioned antibody drug conjugates and attendant definitions, wherein the antibody drug conjugate comprises between 2, 3, 4, 5, 6, 7, 8, 9 or 10 compounds of the invention.

In certain embodiments, the present invention relates to any of the aforementioned antibody drug conjugates and attendant definitions, wherein the antibody drug conjugate comprises 3 or 4 compounds of the invention.

The quaternary amine containing compounds of the present invention present invention bear distinct advantages in that they can be cleared much faster from systemic circulation thus mitigating any adverse events. Also, the use of site specific conjugates alleviate the instability of the acetate ($R^6$=—OC(O)R) in vitro and in vivo and help improve in vivo efficacy. In addition compound of the invention where $R^6$=OC(O)NRR, —NRC(O) help alleviate generation of inactive metabolites. Yet another advantage of the invention is in their ability to be linked to antibodies through multiple points, as the payload (P) can be reacted with appropriately modified linker molecules bearing amine, alcohol and other groups to obtain payload-linkers.

The Antibody Unit (Ab or AB)

As noted above, the term "antibody" (or "Ab" or "AB") herein is used in the broadest sense and specifically covers intact monoclonal antibodies, polyclonal antibodies, monospecific antibodies, multispecific antibodies (e.g., bispecific antibodies), and antibody fragments that exhibit the desired biological activity. In addition, while certain aspects of the invention described herein refer to antibody drug conjugates, it is further envisioned that the antibody portion of the conjugate might be replaced with anything that specifically binds or reactively associates or complexes with a receptor, antigen or other receptive moiety associated with a given target-cell population. For example, instead of containing an antibody a conjugates of the invention could contain a targeting molecule that binds to, complexes with, or reacts with a receptor, antigen or other receptive moiety of a cell population sought to be therapeutically or otherwise biologically modified. Example of such molecules include smaller molecular weight proteins, polypeptide or peptides, lectins, glycoproteins, non-peptides, vitamins, nutrient-transport molecules (such as, but not limited to, transferrin), or any other cell binding molecule or substances. In certain aspects, the antibody or other such targeting molecule acts to deliver a drug to the particular target cell population with which the antibody or other targeting molecule interacts.

In another aspect, the present invention relates to an antibody drug conjugate compound of formulae III or III' wherein the antibody AB is selected from: trastuzumab, trastuzumab mutants (for instance the trastuzumab mutants disclosed herein or in international patent application PCT/IB2012/056234), oregovomab, edrecolomab, cetuximab, a humanized monoclonal antibody to the vitronectin receptor ($\alpha_v\beta_3$), alemtuzumab, anti-HLA-DR antibodies including a humanized anti-HLA-DR antibody for the treatment of non-Hodgkin's lymphoma, 131I Lym-1, anti-HLA-Dr10 antibodies including a murine anti-HLA-Dr10 antibody for the treatment of non-Hodgkin's lymphoma, anti-cd33 antibodies, anti-cd22 antibodies including a humanized anti-CD22 mAb for the treatment of Hodgkin's Disease or non-Hodgkin's lymphoma, labetuzumab, bevacizumab, ibritumomab tiuxetan, ofatumumab, panitumumab, rituximab, tositumomab, ipilimumab, and gemtuzumab.

Heteroatoms that may be present on an antibody unit include sulfur (in one embodiment, from a sulfhydryl group of an antibody), oxygen (in one embodiment, from a carbonyl, carboxyl or hydroxyl group of an antibody) and nitrogen (in one embodiment, from a primary or secondary amino group of an antibody). These hetero atoms can be present on the antibody in the antibody's natural state, for example a naturally-occurring antibody, or can be introduced into the antibody via chemical modification.

In one embodiment, an antibody unit has a sulfhydryl group and the antibody unit bonds via the sulfhydryl group's sulfur atom.

In another embodiment, the antibody has lysine residues that can react with activated esters (such esters include, but are not limited to, N-hydroxysuccinimide, pentafluorophenyl, and p-nitrophenyl esters) and thus form an amide bond consisting of the nitrogen atom of the antibody unit and a carbonyl.

In yet another aspect, the antibody unit has one or more lysine residues that can be chemically modified to introduce one or more sulfhydryl groups. The reagents that can be used to modify lysines include, but are not limited to, N-succinimidyl S-acetylthioacetate (SATA) and 2-Iminothiolane hydrochloride (Traut's Reagent).

In another embodiment, the antibody unit can have one or more carbohydrate groups that can be chemically modified to have one or more sulfhydryl groups.

In yet another embodiment, the antibody unit can have one or more carbohydrate groups that can be oxidized to provide an aldehyde group (see, e.g., Laguzza, et al., 1989, J. Med. Chem. 32(3):548-55). The corresponding aldehyde can form a bond with a reactive site such as, for example, hydrazine and hydroxylamine. Other protocols for the modification of proteins for the attachment or association of drugs are described in Coligan et al., Current Protocols in Protein Science, vol. 2, John Wiley & Sons (2002) (incorporated herein by reference).

When the conjugates comprise non-immunoreactive protein, polypeptide, or peptide units instead of an antibody, useful non-immunoreactive protein, polypeptide, or peptide units include, but are not limited to, transferrin, epidermal growth factors ("EGF"), bombesin, gastrin, gastrin-releasing peptide, platelet-derived growth factor, IL-2, IL-6, transforming growth factors ("TOP"), such as TGF-α and TGF-β, vaccinia growth factor ("VGF"), insulin and insulin-like growth factors I and II, somatostatin, lectins and apoprotein from low density lipoprotein.

Useful polyclonal antibodies are heterogeneous populations of antibody molecules derived from the sera of immunized animals. Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture.

Useful monoclonal antibodies include, but are not limited to, human monoclonal antibodies, humanized monoclonal antibodies, antibody fragments, or chimeric monoclonal antibodies. Human monoclonal antibodies may be made by any of numerous techniques known in the art (e.g., Teng et al., 1983, Proc. Natl. Acad. Sci. USA. 80:7308-7312; Kozbor et al., 1983, Immunology Today 4:72-79; and Olsson et al., 1982, Meth. Enzymol. 92:3-16).

The antibody can also be a bispecific antibody. Methods for making bispecific antibodies are known in the art and are discussed infra.

The antibody can be a functionally active fragment, derivative or analog of an antibody that immunospecifically binds to target cells (e.g., cancer cell antigens, viral antigens, or microbial antigens) or other antibodies that bind to tumor cells or matrix. In this regard, "functionally active" means that the fragment, derivative or analog is able to elicit anti-anti-idiotype antibodies that recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay) (for location of the CDR sequences, see, e.g., Kabat et al., 1991, Sequences of Proteins of Immunological Interest, Fifth Edition, National Institute of Health, Bethesda, Md.; Kabat E et al., 1980, J. Immunology 125(3):961-969).

Other useful antibodies include fragments of antibodies such as, but not limited to, F(ab')$_2$ fragments, Fab fragments, Fvs, single chain antibodies, diabodies, triabodies, tetrabodies, scFv, scFv-FV, or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as for example, those having a variable region derived from a murine monoclonal and human immunoglobulin constant regions. (See, e.g., U.S. Pat. Nos. 4,816,567; and 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Cancer. Res. 47:999-1005; Wood et al., 1985, Nature 314:446-449; and Shaw et al., 1988, J. Natl. Cancer Inst. 80:1553-1559; Morrison, 1985, Science 229:1202-1207; Oi et al., 1986, BioTechniques 4:214; U.S. Pat. No. 5,225,539; Jones et al., 1986, Nature 321:552-525; Verhoeyan et al., 1988, Science 239:1534; and Beidler et al., 1988, J. Immunol. 141:4053-4060; each of which is incorporated herein by reference in its entirety.

Completely human antibodies are particularly desirable and can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, 1995, Int. Rev. Immunol. 13:65-93. For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; 5,545,806; each of which is incorporated herein by reference in its entirety. Other human antibodies can be obtained commercially from, for example, Abgenix, Inc. (now Amgen, Freemont, Calif.) and Medarex (Princeton, N.J.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. (See, e.g., Jespers et al., 1994, Biotechnology 12:899-903). Human antibodies can also be produced using various techniques known in the art, including phage display libraries (see, e.g., Hoogenboom and Winter, 1991, J. Mol. Biol. 227:381; Marks et al., 1991, J. Mol. Biol. 222:581; Quan and Carter, 2002, The rise of monoclonal antibodies as therapeutics, In Anti-IgE and Allergic Disease, Jardieu and Fick, eds., Marcel Dekker, New York, N.Y., Chapter 20, pp. 427-469).

In other embodiments, the antibody is a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, preferably at least 10, 20 or 50 amino acid portion of the protein) that is not from an antibody. Preferably, the antibody or fragment thereof is covalently linked to the other protein at the N-terminus of the constant domain.

Antibodies include analogs and derivatives that are either modified, i.e., by the covalent attachment of any type of molecule as long as such covalent attachment permits the antibody to retain its antigen binding immunospecificity. For example, but not by way of limitation, derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques including, but not limited to, specific chemical cleavage, acetylation, formylation, metabolic synthesis in the presence of tunicamycin, etc. Additionally, the analog or derivative can contain one or more unnatural amino acids.

Antibodies can have modifications (e.g., substitutions, deletions or additions) in amino acid residues that interact with Fc receptors. In particular, antibodies can have modifications in amino acid residues identified as involved in the interaction between the anti-Fc domain and the FcRn receptor (see, e.g., International Publication No. WO 97/34631, which is incorporated herein by reference in its entirety).

Antibodies immunospecific for a cancer cell antigen can be obtained commercially or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, literature publications, or by routine cloning and sequencing.

In a specific embodiment, known antibodies for the treatment of cancer can be used. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing. Examples of antibodies available for the treatment of cancer include, but are not limited to, OVAREX which is a murine antibody for the treatment of ovarian cancer; PANOREX (Glaxo Wellcome, N.C.) which is a murine $IgG_{2a}$ antibody for the treatment of colorectal cancer; Cetuximab ERBITUX (Imclone Systems Inc., NY) which is an anti-EGFR IgG chimeric antibody for the treatment of epidermal growth factor positive cancers, such as head and neck cancer; Vitaxin (MedImmune, Inc., MD) which is a humanized antibody for the treatment of sarcoma; CAMPATH I/H (Leukosite, Mass.) which is a humanized $IgG_1$ antibody for the treatment of chronic lymphocytic leukemia (CLL); SMART ID10 (Protein Design Labs, Inc., CA) which is a humanized anti-HLA-DR antibody for the treatment of non-Hodgkin's lymphoma; ONCOLYM (Techniclone, Inc., CA) which is a radiolabeled murine anti-HLA-Dr10 antibody for the treatment of non-Hodgkin's lymphoma; ALLOMUNE (BioTransplant, Calif.) which is a humanized anti-CD2 mAb for the treatment of Hodgkin's Disease or non-Hodgkin's lymphoma; and CEACIDE (Immunomedics, N.J.) which is a humanized anti-CEA antibody for the treatment of colorectal cancer.

In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

The Linker Unit (L)

A linker (sometimes referred to as "[linker]" herein) is a bifunctional compound which can be used to link a drug and an antibody to form an antibody drug conjugate (ADC). Such conjugates are useful, for example, in the formation of immunoconjugates directed against tumor associated antigens. Such conjugates allow the selective delivery of cytotoxic drugs to tumor cells.

In an ADC the linker serves to attach the payload to the antibody.

In one aspect, a second section of the linker unit is introduced which has a second reactive site e.g., an electrophilic group that is reactive to a nucleophilic group present on an antibody unit (e.g., an antibody). Useful nucleophilic groups on an antibody include but are not limited to, sulfhydryl, hydroxyl and amino groups. The heteroatom of the nucleophilic group of an antibody is reactive to an electrophilic group on a linker unit and forms a covalent bond to a linker unit. Useful electrophilic groups include, but are not limited to, maleimide and haloacetamide groups. The electrophilic group provides a convenient site for antibody attachment.

In another embodiment, a linker unit has a reactive site which has a nucleophilic group that is reactive to an electrophilic group present on an antibody. Useful electrophilic groups on an antibody include, but are not limited to, aldehyde and ketone carbonyl groups. The heteroatom of a nucleophilic group of a linker unit can react with an electrophilic group on an antibody and form a covalent bond to the antibody. Useful nucleophilic groups on a linker unit include, but are not limited to, hydrazide, oxime, amino, hydrazine, thiosemicarbazone, hydrazine carboxylate, and arylhydrazide. The electrophilic group on an antibody provides a convenient site for attachment to a linker unit.

Amino functional groups are also useful reactive sites for a linker unit because they can react with carboxylic acid, or activated esters of a compound to form an amide linkage.

Typically, the peptide-based compounds of the invention can be prepared by forming a peptide bond between two or more amino acids and/or peptide fragments. Such peptide bonds can be prepared, for example, according to the liquid phase synthesis method (see, e.g., Schroder and Lubke, "The Peptides", volume 1, pp 76-136, 1965, Academic Press) that is well known in the field of peptide chemistry.

In the context of the invention, particularly but not limited to linker components such as $L^1$, $L^2$ (including $L^{2A}$, $L^{2B}$ and $L^{2C}$) and $L^3$, the language "selected from one or more of" or "one or more of" indicates that multiple components, which may be the same or different, are or may be arranged sequentially. Thus, for example, $L^3$ may be —$C_{1-6}$alkyl-, —NR— or the other individually listed components, but also —$C_{1-6}$alkyl-NR—, or any other combination of 2 or more listed components.

Synthesis of Compounds and Antibody Drug Conjugates Thereof

The compounds and conjugates of the invention can be made using the synthetic procedures outlined below in the Exemplification. As described in more detail below, the compounds and conjugates of the invention can be prepared using a section of a linker unit having a reactive site for binding to the compound. In one aspect, a second section of the linker unit is introduced which has a second reactive site e.g., an electrophilic group that is reactive to a nucleophilic group present on an antibody unit (e.g., an antibody). Useful nucleophilic groups on an antibody include but are not limited to, sulfhydryl, hydroxyl and amino groups. The heteroatom of the nucleophilic group of an antibody is reactive to an electrophilic group on a linker unit and forms a covalent bond to a linker unit. Useful electrophilic groups include, but are not limited to, maleimide and haloacetamide groups. The electrophilic group provides a convenient site for antibody attachment.

In another embodiment, a linker unit has a reactive site which has a nucleophilic group that is reactive to an electrophilic group present on an antibody. Useful electrophilic groups on an antibody include, but are not limited to, aldehyde and ketone carbonyl groups. The heteroatom of a nucleophilic group of a linker unit can react with an electrophilic group on an antibody and form a covalent bond to the antibody. Useful nucleophilic groups on a linker unit include, but are not limited to, hydrazide, oxime, amino, hydrazine, thiosemicarbazone, hydrazine carboxylate, and arylhydrazide. The electrophilic group on an antibody provides a convenient site for attachment to a linker unit.

Amino functional groups are also useful reactive sites for a linker unit because they can react with carboxylic acid, or activated esters of a compound to form an amide linkage. Typically, the peptide-based compounds of the invention can be prepared by forming a peptide bond between two or more amino acids and/or peptide fragments. Such peptide bonds can be prepared, for example, according to the liquid phase synthesis method (see, e.g., Schroder and Lubke, "The Peptides", volume 1, pp 76-136, 1965, Academic Press) that is well known in the field of peptide chemistry.

As described in more detail below, the conjugates can be prepared using a section of the linker having a reactive site for binding to a compound of the invention and introducing another section of the linker unit having a reactive site for an antibody. In one aspect, a linker unit has a reactive site which has an electrophilic group that is reactive with a nucleophilic group present on an antibody unit, such as an antibody. The electrophilic group provides a convenient site for antibody attachment. Useful nucleophilic groups on an antibody include but are not limited to, sulfhydryl, hydroxyl and amino groups. The heteroatom of the nucleophilic group of an antibody is reactive to an electrophilic group on a linker unit and forms a covalent bond to a linker unit. Useful electrophilic groups include, but are not limited to, maleimide and haloacetamide groups.

In another embodiment, a linker unit has a reactive site which has a nucleophilic group that is reactive with an electrophilic group present on an antibody unit. The electrophilic group on an antibody provides a convenient site for attachment to a linker unit. Useful electrophilic groups on an antibody include, but are not limited to, aldehyde and ketone carbonyl groups. The heteroatom of a nucleophilic group of a linker unit can react with an electrophilic group on an antibody and form a covalent bond to the antibody. Useful nucleophilic groups on a linker unit include, but are not limited to, hydrazide, oxime, amino, hydrazine, thiosemicarbazone, hydrazine carboxylate, and arylhydrazide.

Conjugation with Transglutaminase

In certain embodiments, a compound of the invention may be covalently crosslinked to an Fc-containing or Fab-containing polypeptide engineered with an acyl donor glutamine-containing tag (e.g., Gln-containing peptide tags or Q-tags) or an endogenous glutamine made reactive (i.e., the ability to form a covalent bond as an acyl donor in the presence of an amine and a transglutaminase) by polypeptide engineering (e.g., via amino acid deletion, insertion, substitution, mutation, or any combination thereof on the polypeptide), in the presence of transglutaminase, provided that the compound of the invention comprises an amine donor agent (e.g., small molecule comprising or attached to a reactive amine), thereby forming a stable and homogenous population of an engineered Fc-containing polypeptide conjugate with the amine donor agent being site-specifically conjugated to the Fc-containing or Fab-containing polypeptide through the acyl donor glutamine-containing tag or the exposed/accessible/reactive endogenous glutamine. For example, compounds of the invention may be conjugated as described in International Patent Application Serial No. PCT/IB2011/054899 (published as WO2012/059882), and in International Patent Application Serial No. PCT/IB2014/063566 (published as WO2015/015448), the entire contents of which applications are incorporated herein by reference. In certain embodiments, to facilitate conjugation of the compound of the invention to an Fc-containing or Fab-containing polypeptide engineered with an acyl donor glutamine-containing tag or an endogenous glutamine made reactive by polypeptide engineering in the presence of transglutaminase, $L^1$ is $NH_2$.

Conjugation to the Human Light Chain Kappa Domain Constant Region

In certain embodiments, a compound of the invention may be covalently attached to the side chain of $K^{188}$ of the human light chain kappa domain constant region ($CL_K$) (full light chain numbering according to Kabat). For example, compounds of the invention may be conjugated as described in U.S. patent application Ser. No. 13/180,204, whose entire contents are incorporated herein by reference. In certain embodiments, to facilitate conjugation to K188 $CL_K$, $L^1$ is

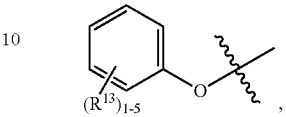

where each $R^{13}$ is independently selected from: F, Cl, I, Br, $NO_2$, CN and $CF_3$.

In certain embodiments, the invention provides for a composition comprising a compound of the invention covalently conjugated to an antibody (or antigen binding portion thereof), wherein at least about 50%, or at least about 60%, or at least about 70%, or at least about 80%, or at least about 90% of the compound of the invention in the composition is conjugated to the antibody or antigen binding portion thereof at $K^{188}$ $CL_K$.

In certain embodiments, the compounds of the invention may be conjugated to the combining site of a catalytic antibody, such as aldolase antibodies, or antigen binding portion thereof. Aldolase antibodies contain combining site portions that, when unencumbered (for example by conjugation), catalyze an aldol addition reaction between an aliphatic ketone donor and an aldehyde acceptor. The contents of US Patent Application Publication No. US 2006/205670 are incorporated herein by reference, in particular pages 78-118 describing linkers, and paragraphs [0153]-[0233] describing antibodies, useful fragments, variants and modifications thereof, h38C$_2$, combining sites and complimentary determining regions (CDRs), and related antibody technology. The term "combining site" includes the CDRs and the adjacent framework residues that are involved in antigen binding.

Compositions and Methods of Administration

In other embodiments, another aspect of the invention relates to pharmaceutical compositions including an effective amount of a compound of the invention and/or antibody drug conjugate thereof and a pharmaceutically acceptable carrier or vehicle. In certain embodiments, the compositions are suitable for veterinary or human administration.

The present pharmaceutical compositions can be in any form that allows for the composition to be administered to a patient. For example, the composition can be in the form of a solid or liquid. Typical routes of administration include, without limitation, parenteral, ocular and intra-tumor. Parenteral administration includes subcutaneous injections, intravenous, intramuscular or intrasternal injection or infusion techniques. In one aspect, the compositions are administered parenterally. In a specific embodiment, the compositions are administered intravenously.

Pharmaceutical compositions can be formulated so as to allow a compound of the invention and/or antibody drug conjugate thereof to be bioavailable upon administration of the composition to a patient. Compositions can take the form of one or more dosage units, where for example, a tablet can be a single dosage unit, and a container of a compound of the invention and/or antibody drug conjugate thereof in liquid form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors.

Relevant factors include, without limitation, the type of animal (e.g., human), the particular form of a compound of the invention and/or antibody drug conjugate thereof, the manner of administration, and the composition employed.

The pharmaceutically acceptable carrier or vehicle can be solid or particulate, so that the compositions are, for example, in tablet or powder form. The carrier(s) can be liquid. In addition, the carrier(s) can be particulate.

The composition can be in the form of a liquid, e.g., a solution, emulsion or suspension. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates, phosphates or amino acids and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of a compound of the invention and/or antibody drug conjugate thereof that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a compound of the invention and/or antibody drug conjugate thereof such that a suitable dosage will be obtained. Typically, this amount is at least about 0.01% of a compound of the invention and/or antibody drug conjugate thereof by weight of the composition. In an exemplary embodiment, pharmaceutical compositions are prepared so that a parenteral dosage unit contains from about 0.01% to about 2% by weight of the amount of a compound of the invention and/or antibody drug conjugate thereof.

For intravenous administration, the composition can comprise from about 0.01 to about 100 mg of a compound of the invention and/or antibody drug conjugate thereof per kg of the patient's body weight. In one aspect, the composition can include from about 1 to about 100 mg of a compound of the invention and/or antibody drug conjugate thereof per kg of the patient's body weight. In another aspect, the amount administered will be in the range from about 0.1 to about 25 mg/kg of body weight of a compound of the invention and/or antibody drug conjugate thereof.

Generally, the dosage of a compound of the invention and/or antibody drug conjugate thereof administered to a patient is typically about 0.01 mg/kg to about 20 mg/kg of the patient's body weight. In one aspect, the dosage administered to a patient is between about 0.01 mg/kg to about 10 mg/kg of the patient's body weight. In another aspect, the dosage administered to a patient is between about 0.1 mg/kg and about 10 mg/kg of the patient's body weight. In yet another aspect, the dosage administered to a patient is between about 0.1 mg/kg and about 5 mg/kg of the patient's body weight. In yet another aspect the dosage administered is between about 0.1 mg/kg to about 3 mg/kg of the patient's body weight. In yet another aspect, the dosage administered is between about 1 mg/kg to about 3 mg/kg of the patient's body weight.

A compound of the invention and/or antibody drug conjugate thereof can be administered by any convenient route, for example by infusion or bolus injection. Administration can be systemic or local. Various delivery systems are known, e.g., encapsulation in liposomes, microparticles, microcapsules, capsules, etc., and can be used to administer a compound of the invention and/or antibody drug conjugate thereof. In certain embodiments, more than one compound of the invention and/or antibody drug conjugate thereof is administered to a patient.

In specific embodiments, it can be desirable to administer one or more compounds of the invention and/or antibody drug conjugates thereof locally to the area in need of treatment. This can be achieved, for example, and not by way of limitation, by local infusion during surgery; topical application, e.g., in conjunction with a wound dressing after surgery; by injection; by means of a catheter; or by means of an implant, the implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue. In another embodiment, administration can be by direct injection at the site (or former site) of a manifestation of an autoimmune disease.

In yet another embodiment, the compound of the invention and/or antibody drug conjugate thereof can be delivered in a controlled release system, such as but not limited to, a pump or various polymeric materials can be used. In yet another embodiment, a controlled-release system can be placed in proximity of the target of the compound of the invention and/or antibody drug conjugate thereof, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer (Science 249:1527-1533 (1990)) can be used.

The term "carrier" refers to a diluent, adjuvant or excipient, with which a compound or antibody drug conjugate thereof is administered. Such pharmaceutical carriers can be liquids, such as water and oils, including those of petroleum, animal, vegetable or synthetic origin. The carriers can be saline, and the like. In addition, auxiliary, stabilizing and other agents can be used. In one embodiment, when administered to a patient, the compound or conjugate and pharmaceutically acceptable carriers are sterile. Water is an exemplary carrier when the compound or conjugate are administered intravenously. Saline solutions and aqueous dextrose and glycerol solutions can also be employed as liquid carriers, particularly for injectable solutions. The present compositions, if desired, can also contain minor amounts of wetting or emulsifying agents, or pH buffering agents.

The present compositions can take the form of solutions, pellets, powders, sustained-release formulations, or any other form suitable for use. Other examples of suitable pharmaceutical carriers are described in "Remington's Pharmaceutical Sciences" by E. W. Martin.

In an embodiment, the compound of the invention and/or antibody drug conjugate thereof are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a compound of the invention and/or antibody drug conjugate thereof is to be administered by infusion, it can be dispensed, for example, with an infusion bottle containing sterile pharmaceutical grade water or saline. Where the compound of the invention and/or antibody drug conjugate thereof is administered by injection, an ampoule of sterile water for injection or saline can be provided so that the ingredients can be mixed prior to administration.

The composition can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

Whether in solid or liquid form, the present compositions can include a pharmacological agent used in the treatment of cancer.

Therapeutics Uses of Compounds and Antibody Drug Conjugates Thereof

Another aspect of the invention relates to a method of using the compounds of the invention and antibody drug conjugates thereof for treating cancer.

The compounds of the invention and/or antibody drug conjugates thereof are useful for inhibiting the multiplication of a tumor cell or cancer cell, causing apoptosis in a tumor or cancer cell, or for treating cancer in a patient. The compounds of the invention and/or antibody drug conjugates thereof can be used accordingly in a variety of settings for the treatment of animal cancers. Said conjugates can be used to deliver a compound of the invention to a tumor cell or cancer cell. Without being bound by theory, in one embodiment, the antibody of the conjugate binds to or associates with a cancer-cell or a tumor-cell-associated antigen, and the conjugate can be taken up (internalized) inside a tumor cell or cancer cell through receptor-mediated endocytosis or other internalization mechanism. The antigen can be attached to a tumor cell or cancer cell or can be an extracellular matrix protein associated with the tumor cell or cancer cell. In certain embodiments, once inside the cell, one or more specific peptide sequences are enzymatically or hydrolytically cleaved by one or more tumor cell or cancer cell-associated proteases, resulting in release of a compound of the invention from the conjugate. The released compound of the invention is then free to migrate within the cell and induce cytotoxic or cytostatic activities. The conjugate also can be cleaved by an intracellular protease to release a compound of the invention. In an alternative embodiment, the compound of the invention is cleaved from conjugate outside the tumor cell or cancer cell, and the compound of the invention subsequently penetrates the cell.

In certain embodiments, the conjugates provide conjugation-specific tumor or cancer drug targeting, thus reducing general toxicity of the compounds of the invention.

In another embodiment, the antibody unit binds to the tumor cell or cancer cell.

In another embodiment, the antibody unit binds to a tumor cell or cancer cell antigen which is on the surface of the tumor cell or cancer cell.

In another embodiment, the antibody unit binds to a tumor cell or cancer cell antigen which is an extracellular matrix protein associated with the tumor cell or cancer cell.

The specificity of the antibody unit for a particular tumor cell or cancer cell can be important for determining those tumors or cancers that are most effectively treated.

Particular types of cancers that can be treated with a compound of the invention and/or antibody drug conjugate thereof include but are not limited to, carcinomas of the bladder, breast, cervix, colon, endometrium, kidney, lung, esophagus, ovary, prostate, pancreas, skin, stomach, and testes; and blood born cancers including but not limited to leukemias and lymphomas.

Multi-Modality Therapy for Cancer.

Cancers, including, but not limited to, a tumor, metastasis, or other disease or disorder characterized by uncontrolled cell growth, can be treated or inhibited by administration of a compound of the invention and/or antibody drug conjugate thereof.

In other embodiments, methods for treating cancer are provided, including administering to a patient in need thereof an effective amount of a compound of the invention and/or antibody drug conjugate thereof and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. A compound of the invention and/or antibody drug conjugate thereof can be administered to a patient that has also undergone surgery as treatment for the cancer.

In some embodiments, the patient also receives an additional treatment, such as radiation therapy. In a specific embodiment, the compound of the invention and/or antibody drug conjugate thereof is administered concurrently with the chemotherapeutic agent or with radiation therapy. In another specific embodiment, the chemotherapeutic agent or radiation therapy is administered prior or subsequent to administration of a compound of the invention and/or antibody drug conjugate thereof.

A chemotherapeutic agent can be administered over a series of sessions. Any one or a combination of the chemotherapeutic agents, such a standard of care chemotherapeutic agent(s), can be administered.

Additionally, methods of treatment of cancer with a compound of the invention and/or antibody drug conjugate thereof are provided as an alternative to chemotherapy or radiation therapy where the chemotherapy or the radiation therapy has proven or can prove too toxic, e.g., results in unacceptable or unbearable side effects, for the subject being treated. The patient being treated can, optionally, be treated with another cancer treatment such as surgery, radiation therapy or chemotherapy, depending on which treatment is found to be acceptable or bearable.

The compounds of the invention and/or antibody drug conjugates thereof can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stem cells are harvested and purged of all cancer cells, the animal's remaining bone-marrow cell population is then eradicated via the administration of a high dose of a compound of the invention and/or antibody drug conjugate thereof with or without accompanying high dose radiation therapy, and the stem cell graft is infused back into the animal. Supportive care is then provided while bone marrow function is restored and the patient recovers.

The invention is further described in the following examples, which are in not intended to limit the scope of the invention.

Released Species

Further embodiments of the invention include the chemical species released, inside or in the vicinity of the cancer cell or tumor cell by what is believed to be enzymatic and/or hydrolytic cleavage by one or more cancer cell or tumor cell-associated proteases. Such compounds include the species described herein, and also include compounds such as those described below.

A compound of formula (III):

(AB)-(L-P)$_b$          (III)

or a pharmaceutically acceptable salt thereof, wherein:
L is the linker moiety $L^1$-$L^2$-$L^3$, where L is bound to P through $R^6$;
P is a radical of formula:

W is selected from:

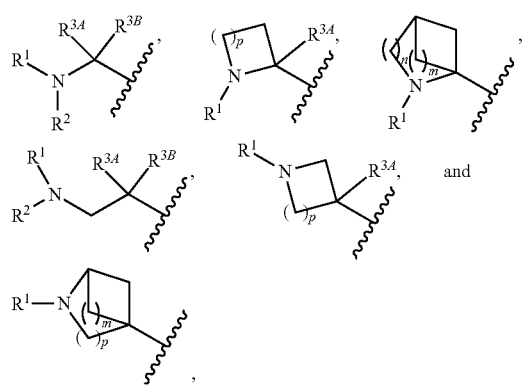

where:
m is 1-3;
n is 1-2; and
p is 1-4;
$R^1$ is selected from hydrogen, $C_1$-$C_8$ alkyl and $C_1$-$C_8$ haloalkyl;
$R^2$ is selected from hydrogen, $C_1$-$C_8$ alkyl and $C_1$-$C_8$ haloalkyl;
each $R^{3A}$ and $R^{3B}$ is independently selected from $C_1$-$C_8$ alkyl, $C_1$-$C_8$ haloalkyl, $C_3$-$C_8$ carbocyclyl, $C_1$-$C_{10}$ heterocyclyl, aryl, heteroaralkyl, halogen and aralkyl; or $R^{3A}$ and $R^{3B}$ taken together are selected from $C_2$-$C_8$ alkylene and $C_1$-$C_8$ heteroalkylene;
$R^5$ is selected from hydrogen, $C_1$-$C_8$ alkyl, $C_1$-$C_8$ haloalkyl, $C_3$-$C_8$ carbocyclyl, $C_3$-$C_8$ heterocyclyl, aryl, heteroaralkyl, aralkyl, where $R^5$ is optionally substituted with —$(C(R)_2)_m$NR$^1$R$^2$;
$R^6$ is selected from —OC(O)N(*)R$^7$, —O—, —NR—, —N(*)C(O)R$^7$, —N(*)C(O)OR$^7$, —N(*)C(O)NR$^7$R$^8$, —N(*)SO$_2$R and —N(*)SO$_2$NR$^7$R$^8$, where * is a bond to L, and where $R^7$ and $R^8$ are each independently selected from hydrogen, $C_1$-$C_8$ alkyl, $C_3$-$C_8$ carbocyclyl, $C_3$-$C_8$ heterocyclyl, aryl, heteroaralkyl and aralkyl; or $R^7$ and $R^8$, together with the nitrogen to which they are joined form $C^3$-$C^{10}$ heterocyclyl, and where one or more of $R^7$ and $R^8$ are optionally substituted with one or more substituents selected from halogen, NR$_2$, CN, OH and OC$_1$-$C_8$ alkyl;
Z is N or CR$^2$;
Y is selected from aryl, $C_3$-$C_8$ heterocyclyl and $C_5$-$C_{14}$ heteroaryl, where Y is optionally substituted with one or more $R^{11}$, or
Y is selected from:

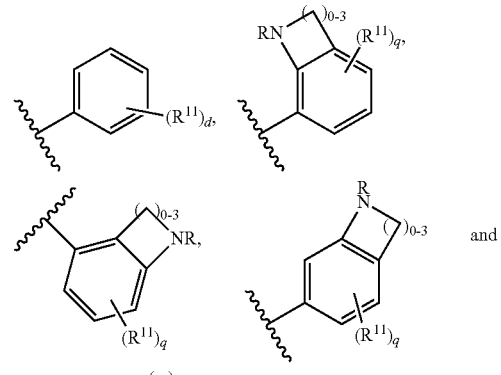

where
d is 1-5;
q is 1-3; and
each $R^{11}$ is independently selected from hydrogen, $C_1$-$C_8$ alkyl, $C_1$-$C_8$ haloalkyl, halogen, —CN, —OH, —(C(R)$_2$)$_t$ONRR, —(C(R)$_2$)$_t$—NRR, (C(R)$_2$)$_t$—C(O)R, (C(R)$_2$)$_t$—CONR$^8$R$^9$, —(C(R)$_2$)$_t$C(O)NRNRR, —(C(R)$_2$)$_t$C(O)N(R)OH, —(C(R)$_2$)$_t$SH, —(C(R)$_2$)$_t$—N(R)—C(O)R, —(C(R)$_2$)$_t$N(R)—C(O)OR, —(C(R)$_2$)$_t$—N(R)—SO$_2$R, —(C(R)$_2$)$_t$N(R)C(O)NR$^8$R$^9$, —(C(R)$_2$)

$_t$SO$_2$NR$^8$R$^9$, and —(C(R)$_2$)$_t$N(R)SO$_2$NR$^8$R$^9$, where each t is independently 0-3; and X is selected from hydrogen, —C(O)OR, C$_1$-C$_6$ alkyl, C$_6$-C$_{14}$ aryl, C$_5$-C$_{14}$ heteroaryl, C$_3$-C$_6$ carbocyclyl, C$_3$-C$_8$ heterocyclyl, —C$_1$-C$_6$ alkyl-C$_6$-C$_{14}$ aryl, and —C$_1$-C$_6$alkyl-C$_5$-C$_{14}$heteroaryl, where X is optionally substituted with 1-3 substituents independently selected from, halogen, —OH, —C(O)OR, —CON(R)OH, —ONR$^2$, —NR$^8$R$^9$, —COR, —CONR$^2$, —CONRNRR, —SH, —N(R)—COR, —N(R)—C(O)OR, —N(R)—SO$_2$R, —N(R)—CONR$^8$R$^9$, —SO$_2$—NR$^8$R$^9$, —N(R)—SO$_2$ NR$^8$R$^9$, —P(O)(OR)$_2$, and —S(O)(OR)$_2$, where each R is independently hydrogen, C$_1$-C$_8$ alkyl or C$_1$-C$_8$ haloalkyl;

L$^1$ is selected from: -acid, —NR-acid and

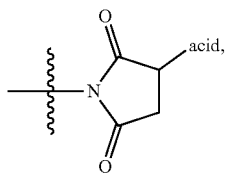

where acid is an amino acid residue selected from —SCH$_2$CH(COOH)(NH$_2$), —NH(CH$_2$)$_4$CH(COOH)(NH$_2$) and —C(O)(CH$_2$)$_2$CH(COOH)(NH$_2$);

L$^2$ is L$^{2A}$-L$^{2B}$-L$^{2C}$ or L$^{2C}$-L$^{2B}$-L$^{2A}$, where:

L$^{2A}$ comprises one or more components selected from: —C(O)—C$_1$-C$_6$alkyl-, —C$_1$-C$_6$alkyl(OCH$_2$CH$_2$)$_{1-6}$—, —C(O)—C$_1$-C$_6$alkyl-NRC(O)C$_1$-C$_6$alkyl-, —C$_1$-C$_6$alkyl(OCH$_2$CH$_2$)$_{1-6}$—NRC(O)C$_1$-C$_6$alkyl-, —C(O)—, and —C(O)—O—C$_1$-C$_6$alkyl-S—, or L$^{2A}$ is absent;

L$^{2B}$ is AA$_{0-aa}$, where AA is a natural or non-natural amino acid and aa is 12; and L$^{2C}$ is selected from -PABA- and -PABC-, or L$^{2C}$ is absent; and L$^3$ is —CR$_2$NR—, or L$^3$ is absent; and b is 1-20.

A compound of formula (III):

(AB)-(L-P)$_b$     (III)

or a pharmaceutically acceptable salt thereof, wherein:

L is the linker moiety L$^1$-L$^2$-L$^3$, where L is bound to P through R$^{11}$;

P is a radical of formula:

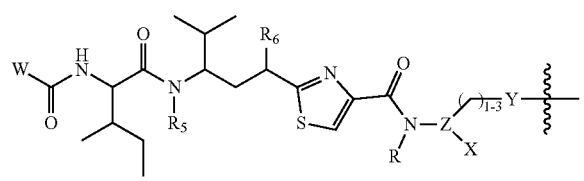

W is selected from:

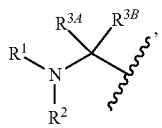 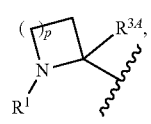 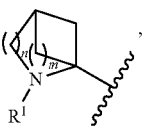

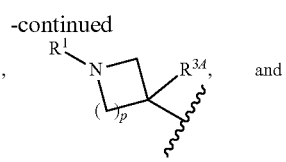

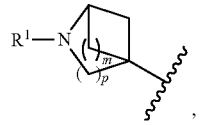

where:

m is 1-3;

n is 1-2; and p is 1-4;

R$^1$ is selected from hydrogen, C$_1$-C$_8$ alkyl and C$_1$-C$_8$ haloalkyl; R$^2$ is selected from hydrogen, C$_1$-C$_8$ alkyl and C$_1$-C$_8$ haloalkyl;

each R$^{3A}$ and R$^{3B}$ is independently selected from C$_1$-C$_8$ alkyl, C$_1$-C$_8$ haloalkyl, C$_3$-C$_8$ carbocyclyl, C$_1$-C$_{10}$ heterocyclyl, aryl, heteroaralkyl, halogen and aralkyl; or R$^{3A}$ and R$^{3B}$ taken together are selected from C$_2$-C$_8$ alkylene and C$_1$-C$_8$ heteroalkylene;

R$^5$ is selected from hydrogen, C$_1$-C$_8$ alkyl, C$_1$-C$_8$ haloalkyl, C$_3$-C$_8$ carbocyclyl, C$_3$-C$_8$ heterocyclyl, aryl, heteroaralkyl, aralkyl, where R$^5$ is optionally substituted with —(C(R)$_2$)$_m$NR$^1$R$^2$;

R$^6$ is selected from hydrogen, OR$^7$, OC(O)R$^7$, OC(O)NR$^7$R$^8$, NR$^7$R$^8$, N(R$^7$)C(O)R$^7$, N(R$^7$) C(O)OR$^7$, N(R)C(O)NR$^7$R$^8$, N(R$^7$)SO$_2$R, and N(R$^7$)SO$_2$NR$^7$R$^8$, where R$^7$ and R$^8$ are each independently selected from hydrogen, C$_1$-C$_8$ alkyl, C$_3$-C$_8$ carbocyclyl, C$_3$-C$_8$ heterocyclyl, aryl, heteroaralkyl and aralkyl; or R$^7$ and R$^8$, together with the nitrogen to which they are joined form C$^3$-C$^{10}$ heterocyclyl, and where one or more of R$^7$ and R$^8$ are optionally substituted with one or more substituents selected from halogen, NR$_2$, CN, OH and OC$_1$-C$_8$ alkyl;

Z is N or CR$^2$;

Y is selected from aryl, C$_3$-C$_8$ heterocyclyl and C$_5$-C$_{14}$ heteroaryl, where Y is optionally substituted with one or more R$^{11}$, or Y is selected from

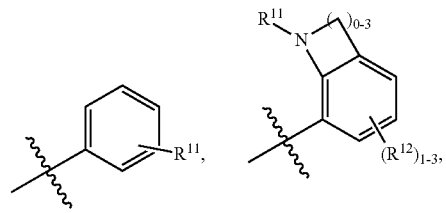

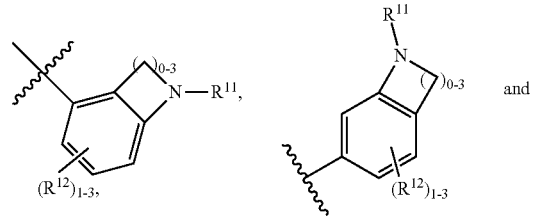

-continued

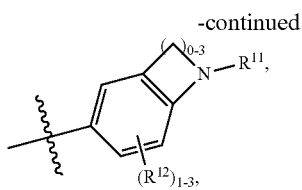

where

R[11] is selected from: —(C(R)$_2$)$_t$O—, —(C(R)$_2$)$_t$ON(R)—, —(C(R)$_2$)$_t$NR—, —(C(R)$_2$)$_t$(R)C=N—, —C(R)$_2$)$_t$C(O)NR—, —(C(R)$_2$)$_t$C(O)N(R)O—, —(C(R)$_2$)$_t$S—, —(C(R)$_2$)$_t$N(*)C(O)OR, —(C(R)$_2$)$_t$N(*)SO$_2$R, —(C(R)$_2$)$_t$N(*)C(O)NR$^8$R$^9$, —(C(R)$_2$)$_t$SO$_2$—N(*)R, —(C(R)$_2$)$_t$N(*)SO$_2$NR$^8$R$^9$, where * is a bond to L, or R[11] is a bond if R[11] is directly bound to N;

each R[12] is independently selected from: hydrogen, —OH, —CN and CF$_3$;

where each t is independently 0-3;

X is selected from hydrogen, —C(O)OR, C$_1$-C$_6$ alkyl, C$_6$-C$_{14}$ aryl, C$_5$-C$_{14}$ heteroaryl, C$_3$-C$_6$ carbocyclyl, C$_3$-C$_8$ heterocyclyl, —C$_1$-C$_6$ alkyl-C$_6$-C$_{14}$ aryl, and —C$_1$-C$_6$alkyl-C$_5$-C$_{14}$heteroaryl, where X is optionally substituted with 1-3 substituents independently selected from, halogen, —OH, —C(O)OR, —CON(R)OH, —ONR$^2$, —NR$^8$R$^9$, —COR, —CONR$^2$, —CONRNRR, —SH, —N(R)—COR, —N(R)—C(O)OR, —N(R)—SO$_2$R, —N(R)—CONR$^8$R$^9$, —SO$_2$—NR$^8$R$^9$, —N(R)—SO$_2$ NR$^8$R$^9$, —P(O)(OR)$_2$, and —S(O)(OR)$_2$, where each R is independently hydrogen, C$_1$-C$_8$ alkyl or C$_1$-C$_8$ haloalkyl;

L[1] is selected from: -acid, —NR— acid and

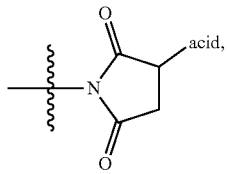

where acid is an amino acid residue selected from —SCH$_2$CH(COOH)(NH$_2$), —NH(CH$_2$)$_4$CH(COOH)(NH$_2$) and —C(O)(CH$_2$)$_2$CH(COOH)(NH$_2$);

L[2] is L$^{2A}$-L$^{2B}$-L$^{2C}$ or L$^{2C}$-L$^{2B}$-L$^{2A}$, where:

L$^{2A}$ comprises one or more components selected from: —C(O)—C$_1$-C$_6$alkyl-, —C(O)—C$_1$-C$_6$alkyl(OCH$_2$CH$_2$)$_{1-6}$—, —C(O)—C$_1$-C$_6$alkyl-NRC(O)C$_1$-C$_6$alkyl-, —C(O)—C$_1$-C$_6$alkyl(OCH$_2$CH$_2$)$_{1-6}$—NRC(O)C$_1$-C$_6$alkyl-, —C(O)—C$_{1-6}$alkyl-C(O)—, —C(O)—C$_{1-6}$alkyl(OCH$_2$CH$_2$)$_{1-6}$—C(O)—, —NRC(O)-phenyl-O—C$_{1-6}$alkyl-, —N=CR-phenyl-O—C$_{1-6}$alkyl-, —N=CR-phenyl-O—C$_{1-6}$alkyl-C(O)—, -, and —C(O)—O—C$_1$-C$_6$alkyl-S—, or L$^{2A}$ is absent;

L$^{2B}$ is AA$_{0-aa}$, where AA is a natural or non-natural amino acid and aa is 12; and L$^{2C}$ is selected from -PABA- and -PABC-, or L$^{2C}$ is absent; and L[3] is selected from one or more of: —CO—, —NR—, —C$_1$-C$_6$alkyl-, —NR—C$_1$-C$_6$alkyl- and —NR—C$_1$-C$_6$-alkyl-NR—, or L[3] is absent; and b is 1-20.

provided that when R[5] is C$_1$-C$_6$ alkyl, R[6] is —OC(O)R, W is:

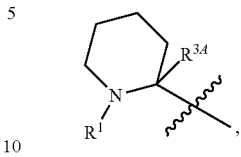

X is

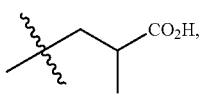

R[11] is —(C(R)$_2$)$_t$—NR— (t=0) and Y is

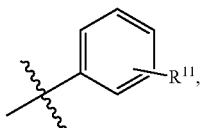

then L is not selected from:

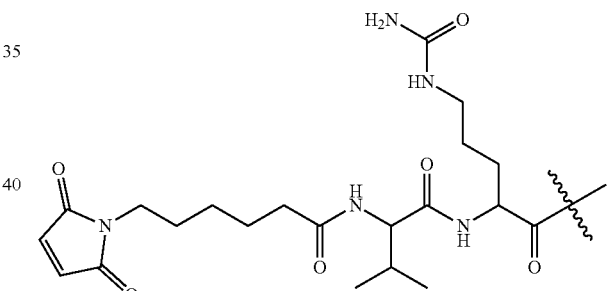

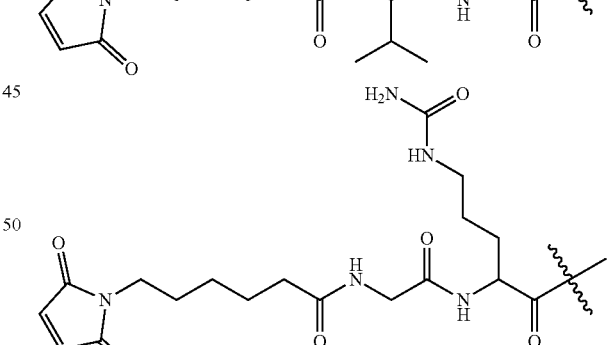

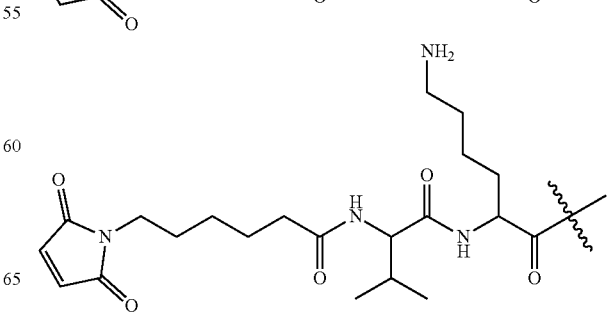

-continued

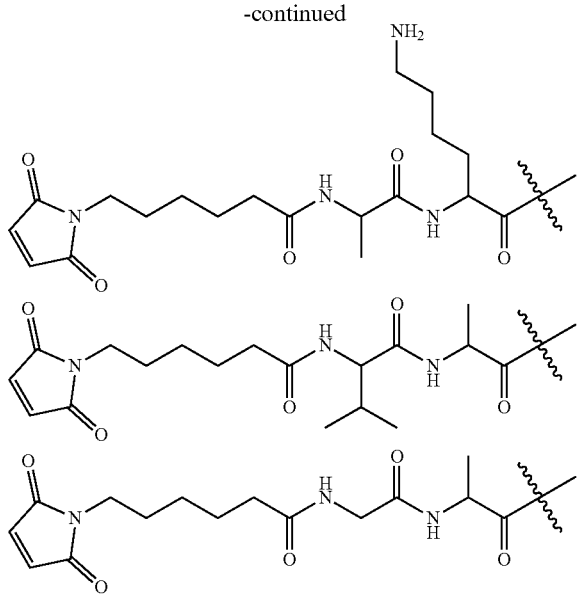

A compound of formula (III):

(AB)-(L-P)$_b$ (III)

or a pharmaceutically acceptable salt thereof, wherein:
L is the linker moiety L$^1$-L$^2$-L$^3$, where L is bound to P through X;
P is a radical of formula:

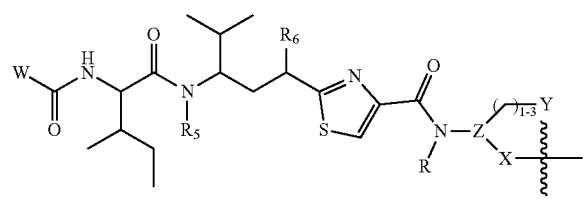

W is selected from:

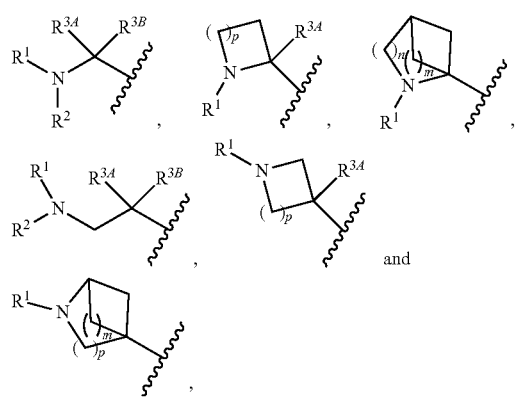

where:
m is 1-3;
n is 1-2; and
p is 1-4;
R$^1$ is selected from hydrogen, C$_1$-C$_8$ alkyl and C$_1$-C$_8$ haloalkyl;

R$^2$ is selected from hydrogen, C$_1$-C$_8$ alkyl and C$_1$-C$_8$ haloalkyl;
each R$^{3A}$ and R$^{3B}$ is independently selected from C$_1$-C$_8$ alkyl, C$_1$-C$_8$ haloalkyl, C$_3$-C$_8$ carbocyclyl, C$_1$-C$_{10}$ heterocyclyl, aryl, heteroaralkyl, halogen and aralkyl; or R$^{3A}$ and R$^{3B}$ taken together are selected from C$_2$-C$_8$ alkylene and C$_1$-C$_8$ heteroalkylene;
R$^5$ is selected from hydrogen, C$_1$-C$_8$ alkyl, C$_1$-C$_8$ haloalkyl, C$_3$-C$_8$ carbocyclyl, C$_3$-C$_8$ heterocyclyl, aryl, heteroaralkyl, aralkyl, where R$^5$ is optionally substituted with —(C(R)$_2$)$_m$NR$^1$R$^2$;
R$^6$ is selected from hydrogen, OR$^7$, OC(O)R$^7$, OC(O)NR$^7$R$^8$, NR$^7$R$^8$, N(R$^7$)C(O)R$^7$, N(R$^7$) C(O)OR$^7$, N(R)C(O)NR$^7$R$^8$, N(R$^7$)SO$_2$R, and N(R$^7$)SO$_2$NR$^7$R$^8$, where R$^7$ and R$^8$ are each independently selected from hydrogen, C$_1$-C$_8$ alkyl, C$_3$-C$_8$ carbocyclyl, C$_3$-C$_8$ heterocyclyl, aryl, heteroaralkyl and aralkyl; or R$^7$ and R$^8$, together with the nitrogen to which they are joined form C$^3$-C$^{10}$ heterocyclyl, and where one or more of R$^7$ and R$^8$ are optionally substituted with one or more substituents selected from halogen, NR$_2$, CN, OH and OC$_1$-C$_8$ alkyl;
Z is CR$^2$;
Y is selected from aryl, C$_3$-C$_8$ heterocyclyl and C$_5$-C$_{14}$ heteroaryl, where Y is optionally substituted with one or more R$^{11}$, or
Y is selected from:

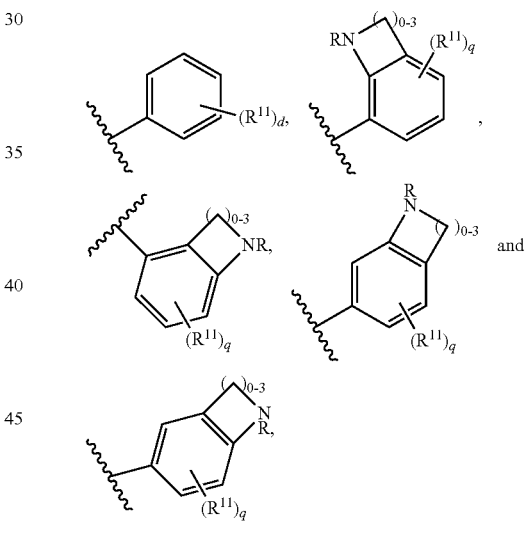

where
d is 1-5;
q is 1-3; and
each R$^{11}$ is independently selected from hydrogen, C$_1$-C$_8$ alkyl, C$_1$-C$_8$ haloalkyl, halogen, —CN, —OH, —(C(R)$_2$)$_t$ONRR, —(C(R)$_2$)$_t$—NRR, (C(R)$_2$)$_t$—C(O)R, (C(R)$_2$)$_t$—CONR$^8$R$^9$, —(C(R)$_2$)$_t$C(O)NRNRR, —(C(R)$_2$)$_t$C(O)N(R)OH, —(C(R)$_2$)$_t$SH, —(C(R)$_2$)$_t$—N(R)—C(O)R, —(C(R)$_2$)$_t$N(R)—C(O)OR, —(C(R)$_2$)$_t$—N(R)—SO$_2$R, —(C(R)$_2$)$_t$N(R)C(O)NR$^8$R$^9$, —(C(R)$_2$)$_t$SO$_2$NR$^8$R$^9$, and —(C(R)$_2$)$_t$N(R)SO$_2$NR$^8$R$^9$, where each t is independently 0-3; and
X is selected from —C$_1$-C$_6$ alkyl-C(O)—, —C$_1$-C$_6$ alkyl-C(O)NR—, —C$_1$-C$_6$ alkyl-N(*)C(O)OR, —C$_1$-C$_6$alkyl-N(*)SO$_2$R, C$_1$-C$_6$alkyl-N(*)CONR$^8$R$^9$, and —C$_1$-C$_6$alkylN(*)SO$_2$NR$^8$R$^9$, where * is a bond to L;
L$^1$ is selected from: -acid, —NR-acid and

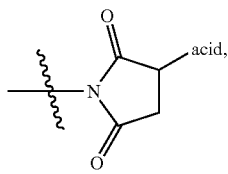

where acid is an amino acid residue selected from —SCH$_2$CH(COOH)(NH$_2$), —NH(CH$_2$)$_4$CH(COOH)(NH$_2$) and —C(O)(CH$_2$)$_2$CH(COOH)(NH$_2$);

L$^2$ is L$^{2A}$-L$^{2B}$-L$^{2C}$ or L$^{2C}$-L$^{2B}$-L$^{2A}$, where:

L$^{2A}$ comprises one or more components selected from: —C(O)—C$_1$-C$_6$alkyl-, —C(O)—C$_1$-C$_6$alkyl(OCH$_2$CH$_2$)$_{1-6}$—, —C(O)—C$_1$-C$_6$alkyl-NRC(O)C$_1$-C$_6$alkyl-, —C(O)—C$_1$-C$_6$alkyl(OCH$_2$CH$_2$)$_{1-6}$—NRC(O) C$_1$-C$_6$alkyl-, —C(O)—C$_1$-C$_6$alkyl-C(O)—, —C(O)—C$_1$-C$_6$alkyl(OCH$_2$CH$_2$)$_{1-6}$—C(O)—, —N=CR-phenyl-O—C$_1$-C$_6$alkyl-, —N=CR-phenyl-O—C$_1$-C$_6$alkyl-C(O)—, —C(O)—O—C$_1$-C$_6$alkyl-S— and —S—, or L$^{2A}$ is absent;

L$^{2B}$ is AA$_{0-aa}$, where AA is a natural or non-natural amino acid and aa is 12; and L$^{2C}$ is selected from -PABA- and -PABC-, or L$^{2C}$ is absent; and L$^3$ is selected from one or more of: —O—, —NR—, —C$_1$-C$_6$alkyl- and —NR—C$_1$-C$_6$alkyl-, or L$^3$ is absent; and b is 1-20.

EXAMPLES

General Methods
Synthetic Experimental Procedures:

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.). Mass spectrometry data is reported from either liquid chromatography-mass spectrometry (LC-MS) or atmospheric pressure chemical ionization (APCI). Chemical shifts for nuclear magnetic resonance (NMR) data are expressed in parts per million (ppm, δ) referenced to residual peaks from the deuterated solvents employed.

For syntheses referencing procedures in other Examples or Methods, reaction Protocol (length of reaction and temperature) may vary. In general, reactions were followed by thin layer chromatography, LC-MS or HPLC, and subjected to work-up when appropriate. Purifications may vary between experiments: in general, solvents and the solvent ratios used for eluents/gradients were chosen to provide appropriate retention times. Unless otherwise specified, reverse phase HPLC fractions were concentrated via lyophilization/Freeze-drying. Intermediate and final compounds were stored at (0° C.) or room temperature in closed vials or flasks under nitrogen. Compound names were generated with ACD Labs software.

Abbreviations for solvents and/or reagents is based on American Chemical Society guidelines and is highlighted below:
Ac=Acetyl
Boc=N-tert-butoxycarbonyl
CDI=N,N'-Carbonyldiimidazole
DCC=1,3-Dicyclohexylcarbodiimide
DCE=Dichloroethane
DCM=Dichloromethane
DEA=N,N-Diethylamine
DEAD=Diethyl azodicarboxylate
DIAD=Diisopropyl azodicarboxylate
DIBAL-H=Diisobutylaluminium hydride
DIPEA=N,N-Diisopropylethylamine
DMA=Dimethylacetamide
DMAP=4-Dimethylaminopyridine
DME=Dimethoxyethane
DMF=N,N-Dimethylformamide
DMSO=Dimethyl sulfoxide
DPPA=Diphenylphosphoryl azide
EDCl=1-Ethyl-3-(3-dimethylaminopropyl)carbodiimide
EtOAc=Ethyl acetate
Fmoc=Fluorenylmethyloxycarbonyl
h=hour
HATU=o-(7-azabenzotriazol-1-yl)-N,N,N',N'-tetramethyluronium hexafluorophosphate
HBTU=N,N,N',N'-Tetramethyl-O-(1H-benzotriazol-1-yl)uronium hexafluorophosphate
HOAc=Acetic acid
HOAt=1-Hydroxy-7-azabenzotriazole
HOBt=1-Hydroxybenzotriazole hydrate
LDA=Lithium diisopropylamide
Me=Methyl
MS=Molecular Sieves
MTBE=Methyl tert-butyl ether
n-BuLi=n-Butyllithium
NBS=N-Bromosuccinimide
NMM=N-methyl morpholine
Ph=Phenyl
PPTS=Pyridinium p-Toluenesulfonate
p-TsOH=p-Toluenesulfonic acid
rt=room temperature
TBAI=Tetrabutylammonium Iodide
TEA=Triethylamine
Tf=Trifluoromethanesulfonate
TFA=TFA
THF=Tetrahydrofuran
TPTU=O-(2-Oxo-1 (2H)pyridyl)-N,N,N,'N'-tetramethyluronium tetrafluoroborate
Purification Methods:

Method A: Column: Waters Sunfire, C18, 19×100 mm I.D., 5 μm; Mobile phase A: 0.05% TFA in water (v/v); Mobile phase B: 0.05% TFA in acetonitrile (v/v); Gradient: variable, increasing gradient of B in A over 10 to 20 minutes. Flow rate 25 mL/minute. Detection: DAD 215 nm MS (+) range 160-1000 daltons; Instrument: Waters FractionLynx.

Method B: Column: Phenomenex Luna C18 (2), 150×21.2 mm I.D., 5 μm; Mobile phase A: 0.1% formic acid in water (v/v); Mobile phase B: 0.1% formic acid in acetonitrile (v/v); Gradient: variable, increasing gradient of B in A over 10 to 20 minutes. Flow rate: 27 mL/minute. Temperature: not controlled; Detection: DAD 215 nm, 254 nm; MS (+) range 150-2000 daltons; Instrument: Waters FractionLynx.

Method C: Column: Phenomenex Gemini, N×C18, 150×21.2 mm I.D., 5 μm; Mobile phase A: 0.02% ammonium Hydroxide in water (v/v); Mobile phase B: 0.02% ammonium hydroxide in acetonitrile (v/v); Gradient: variable, increasing gradient of B in A over 10 to 20 minutes. Flow rate: 27 mL/minute. Temperature: not controlled; Detection: DAD 215 nm, 254 nm; Injection Volume: variable; Instrument: Waters FractionLynx.

Method D: Column: Phenomenex Luna C18 (2), 150×21.2 mm I.D., 5 μm; Mobile phase A: 0.02% TFA in water (v/v); Mobile phase B: 0.02% TFA in acetonitrile (v/v); Gradient: variable, increasing gradient of B in A over 10 to 20 minutes. Flow rate: 27 mL/minute. Temperature: 45° C.; Detection: DAD 215 nm, 254 nm; MS (+) range 150-2000 daltons; Instrument: Waters FractionLynx.

Method E: Column: Waters Sunfire, C18, 19×100 mm I.D., 5 μm; Mobile phase A: 0.05% TFA in water (v/v); Mobile phase B: 0.05% TFA in acetonitrile (v/v); Flow rate 25 mL/minute. Detection: DAD 215 nm; MS (+) range 160-1000 daltons; Instrument: Waters FractionLynx.

Method F: Column: Waters X Bridge N×C18, 100×19 mm I.D., 5 μm; Mobile phase A: 0.03% ammonium hydroxide in water (v/v); Mobile phase B: 0.02% ammonium hydroxide in acetonitrile (v/v); Gradient: variable, increasing gradient of B in A over 10 to 20 minutes. Flow rate: 25 mL/minute. Temperature: not controlled; Detection: DAD 215 nm, 254 nm; Injection Volume: variable; Instrument: Waters FractionLynx.

Method G: Column: Phenomenex Gemini, C18, 30×100 mm I.D., 5 μm; Mobile phase A: 0.02% acetic acid in water (v/v); Mobile phase B: 0.02% acetic acid in acetonitrile (v/v); Gradient: 0% to 95% B over 20 minutes; Flow rate: 20 mL/minute. Temperature: not controlled; Detection: DAD 215 nm, 254 nm; Injection Volume: variable; Instrument: Gilson.

Method H: Column: Phenomenex Gemini, C18, 30×100 mm, 5 μm; Mobile phase A: 0.02% TFA in water (v/v); Mobile phase B: 0.02% TFA in acetonitrile (v/v); Gradient: 0% to 95% B over 20 minutes; Flow rate: 20 mL/minute. Temperature: not controlled; Detection: DAD 215 nm, 254 nm; Injection Volume: variable; Instrument: Gilson.

Analytical Protocols:

Protocol A: Column: Atlantis dC18, 50×4.6 mm I.D., 5 μm; Mobile phase A: 0.05% TFA in water (v/v); Mobile phase B: 0.05% TFA in acetonitrile (v/v); Gradient: 5% to 95% B over 4.0 minutes, linear; then hold at 95% B over 1 minute. Flow rate: 2 mL/minute. Temperature: room temperature; Detection: DAD 215 nm; MS (+) range 160-1000 daltons; injection volume 3 uL; Instrument: Waters 996 PDA.

Protocol B: Column: Waters Acquity UPLC HSS T3, C18, 2.1×50 mm I.D., 1.7 μm; Mobile phase A: 0.1% formic acid in water (v/v); Mobile phase B: 0.1% formic acid in acetonitrile (v/v); Gradient: 5% B over 0.1 minute, 5% to 95% B over 2.5 minutes, 95% B over 0.35 minute; Flow rate: 1.25 mL/minute. Temperature: 60° C.; Detection: 200-450 nm; MS (+) range 100-2000 daltons; Injection volume: 5 μL; Instrument: Waters Acquity.

Protocol C: Column: Waters Acquity UPLC HSS T3, C18, 2.1×50 mm I.D., 1.7 μm; Mobile phase A: 0.1% formic acid in water (v/v); Mobile phase B: 0.1% formic acid in acetonitrile (v/v); Gradient: 5% B over 0.1 minute, 5% to 95% B over 1.5 minute, 95% B over 0.35 minute; Flow rate: 1.25 mL/minute. Temperature: 60° C.; Detection: 200-450 nm; MS (+) range 100-2000 daltons; Injection volume: 5 μL; Instrument: Waters Acquity.

Protocol D: Column: Phenomenex Luna C18 (2), 150×3.0 mm I.D., 5 μm; Mobile phase A: 0.1% formic acid in water (v/v); Mobile phase B: 0.1% formic acid in acetonitrile (v/v); Gradient: 5% B over 1.5 minutes, 5% to 100% B over 8.5 minutes, then 100% B for 1 minute; Flow rate: 0.75 mL/minute. Temperature: 45° C.; Detection: DAD 215 nm, 254 nm; MS (+) range 150-2000 daltons; Injection volume: 10 μL; Instrument: Agilent 1200 LCMS.

Protocol E: Column: Waters XBridge C18, 4.6×50 I.D., 5 μm; Mobile phase A: 0.03% ammonium hydroxide in water (v/v); Mobile phase B: 0.03% ammonium hydroxide in acetonitrile (v/v); Gradient: 95.0% A/5.0% B linear to 5% A/95% B over 4.0 minutes, then 5% A/95% B for 1 minute; Flow rate: 2 mL/minute. Detection: PDA 215 nm; MS (+) range 150-2000 daltons; Injection volume: 4 μL; Instrument: Waters 2795/H-Class/Acquity.

Protocol F: Column: Phenomenex Gemini-NX, C18, 4.6 mm×50 mm I.D., 110A, 3 μm, Mobile phase A: 0.1% formic acid in water (v/v); Mobile phase B: 0.1% formic acid in acetonitrile (v/v); Gradient 5%; to 100% B over 0.0-4.10 min; hold at 100% B from 4.10-4.50 min; Flow rate: 1.25 mL/minute. Temperature: 60° C.; Detection: 200-450 nm; MS (+) range 100-2000 daltons; Injection volume: 5 μL; Instrument: Waters Acquity.

Synthesis of Intermediates

Preparation of ethyl 2-[(1R,3R)-3-{[N-(tert-butoxycarbonyl)-L-isoleucyl](methyl)amino}-1-hydroxy-4-methylpentyl]-1,3-thiazole-4-carboxylate (# A1)

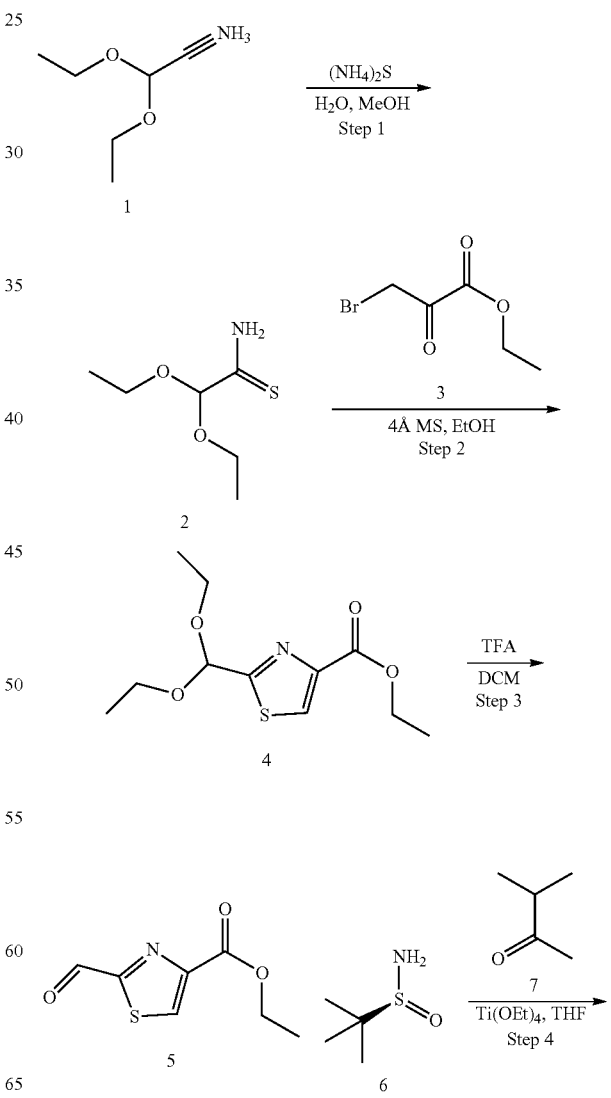

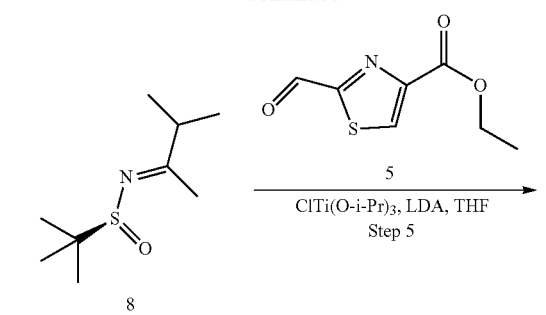
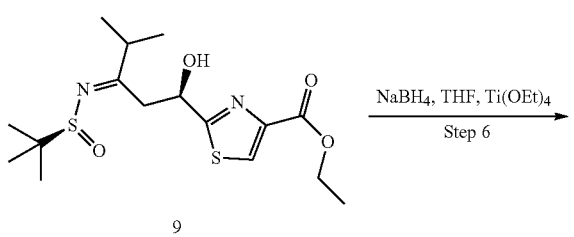
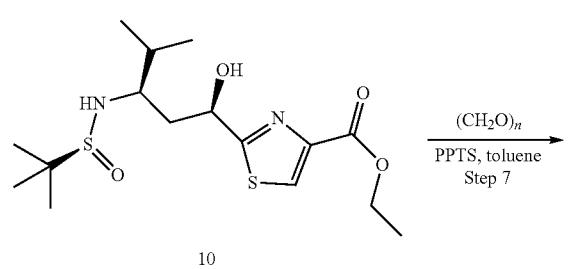
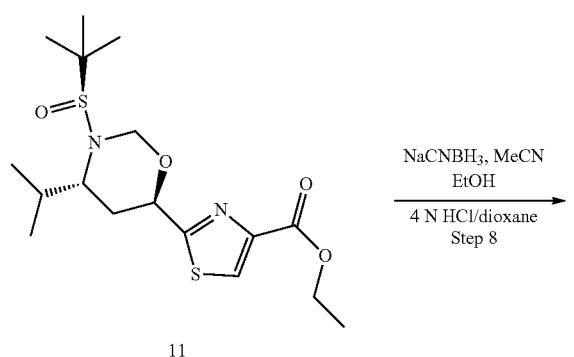
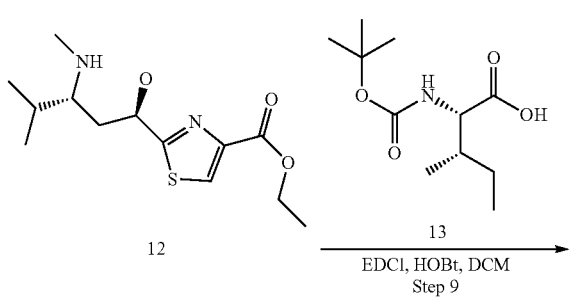
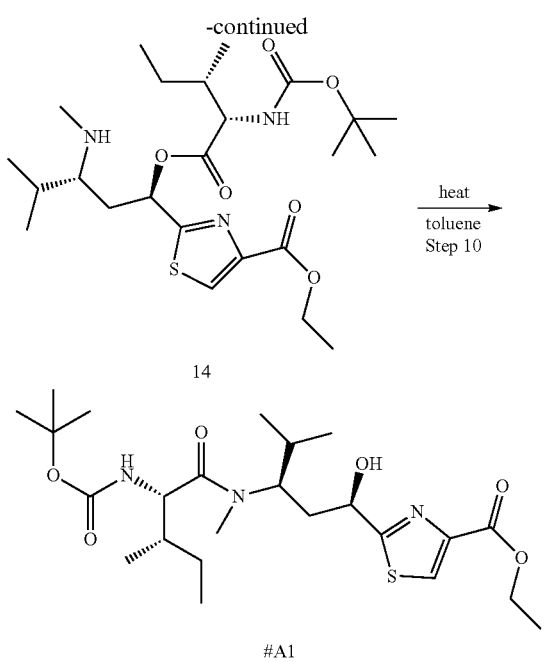

Step 1: Preparation of 2,2-diethoxyethanethioamide (2)

To a solution of diethoxyacetonitrile (1,120 g, 930 mmol) in MeOH (500 mL) was added a 17% solution of $(NH_4)_2S$ in $H_2O$ (440 mL) at rt. The mixture was stirred at rt overnight. The mixture was evaporated in vacuo to approximately 100 mL volume and filtered. The solid was washed with cooled water and dried in vacuo to afford the title compound 2 (92 g, 61%) as a white solid, which was used as such in next step.

Step 2: Preparation of ethyl 2-(diethoxymethyl)-1,3-thiazole-4-carboxylate (4)

A mixture of 2,2-diethoxyethanethioamide (2, 90 g, 552 mmol), ethyl 3-bromo-2-oxopropanoate (3,170 g, 872 mmol) and 4 Å MS (180 g) in dry EtOH (1.5 L) was refluxed overnight. The mixture was filtered and the filtrate was concentrated in vacuo. The residue was purified by silica gel chromatography (30:1 to 4:1 hexanes in EtOAc) to afford the title compound 4 (100 g, 70%) as a yellow oil.

Step 3: Preparation of ethyl 2-formylthiazole-4-carboxylate (5)

To a solution of 2-(diethoxymethyl)-1,3-thiazole-4-carboxylate (4, 70 g, 270 mmol) in DCM (70 mL) was added TFA (70 mL) at rt. The mixture was stirred at rt overnight then concentrated to dryness. The residue was dissolved in EtOAc and washed with saturated aq. $NaHCO_3$ and brine, dried over $Na_2SO_4$, and concentrated in vacuo to afford title compound 5 (41 g, 82%) as a yellow solid.

Step 4: Preparation of (S,E)-2-methyl-N-(3-methylbutan-2-ylidene)propane-2-sulfinamide (8)

A mixture of 3-methylbutan-2-one (7, 110.9 g, 1.29 mol), (S)-2-methylpropane-2-sulfinamide (6, 130 g, 1.07 mol) and $Ti(OEt)_4$ (415 g, 1.82 mol) was refluxed overnight. The mixture was cooled to rt and quenched with ice water (100 mL). The mixture was filtered through celite, the filter cake was washed with EtOAc, and the filtrate concentrated in vacuo. The residue was purified by silica gel chromatography (3:1 hexanes:EtOAc) to afford title compound 8 (163 g, 80.3%) as a slightly yellow liquid.

Step 5: Preparation of ethyl 2-[(1R,3E)-3-{[(S)-tert-butylsulfinyl]imino}-1-hydroxy-4-methylpentyl]-1,3-thiazole-4-carboxylate (9)

To a solution of (S,E)-2-methyl-N-(3-methylbutan-2-ylidene)propane-2-sulfinamide (8, 62.8 g, 332 mmol) in dry THF (1.2 L) was added LDA (186.2 mL, 372.4 mmol) at −65° C. and the mixture was stirred at −70° C. for 1 h. A 1 M solution of $TiCl(O-i-Pr)_3$ in hexane (554 mL, 554 mmol) was added and the mixture was stirred at −70° C. for 1 h. A solution of ethyl 2-formylthiazole-4-carboxylate (5, 41 g, 221.6 mmol) in THF (200 mL) was added and the mixture was stirred at −70° C. for 5 h. The reaction was quenched by addition of acetic acid (41 mL) in THF (200 mL), followed by water (100 mL). The mixture was filtered through a pad of celite, the filter cake washed with EtOAc, and the filtrate evaporated to dryness. The residue was purified by silica gel chromatography (30:1 to 3:1 hexanes: EtOAc) to afford title compound 9 (41 g, 49.5%) as a yellow oil.

Step 6: Preparation of ethyl 2-[(1R,3R)-3-{[(S)-tert-butylsulfinyl]amino}-1-hydroxy-4-methylpentyl]-1,3-thiazole-4-carboxylate (10)

To a solution of ethyl 2-[(1R,3E)-3-{[(S)-tert-butylsulfinyl]imino}-1-hydroxy-4-methylpentyl]-1,3-thiazole-4-carboxylate (9, 58 g, 155 mmol) in dry THF (1 L) was added $Ti(OEt)_4$ (70.7 g, 310 mmol) at −65° C. and the mixture was stirred at −70° C. for 20 min. Solid $NaBH_4$ (11.8 g, 310 mmol) was added in portions and the reaction was stirred at −70° C. After 3 h, the reaction was quenched with MeOH (15 mL) at −70° C., warmed to −20° C., and water (20 mL) was added. The mixture was filtered through a pad of celite, the filter cake washed with EtOAc, and the filtrate concentrated in vacuo. The residue was purified by silica gel chromatography (30:1 to 1:1 hexanes in EtOAc) to afford the title compound 10 (5.5 g, 9.1%) as a slightly yellow solid.

$^1$H NMR (400 Hz, $CDCl_3$): δ 8.10 (s, 1H), 5.48 (m, 1H), 5.20 (m, 1H), 4.44 (m, 2H), 3.46 (m, 1H), 3.32 (d, 1H), 2.29 (m, 1H), 1.91 (m, 1H), 1.71 (m, 1H), 1.44 (m, 3H), 1.28 (s, 9H), 0.94 (m, 6H); m/z: 377.1 [M+H]$^+$; 94.15% ee, Column: Chiralpak AD-H 250×4.6 mm I.D., 5 µm, Mobile phase: methanol (0.05% diethylamine) in $CO_2$ from 5% to 40%; Wavelength: 220 nm; Retention time=4.97 min.

Step 7: Preparation of ethyl 2-[(1R,3E)-3-{[(S)-tert-butylsulfinyl]imino}-1-hydroxy-4-methylpentyl]-1,3-thiazole-4-carboxylate (11)

A suspension of ethyl 2-[(1R,3R)-3-{[(S)-tert-butylsulfinyl]amino}-1-hydroxy-4-methylpentyl]-1,3-thiazole-4-carboxylate (10, 25 g, 66.5 mmol), paraformaldehyde (41.6 g, 1.3 mol) and PPTS (0.17 g, 0.67 mmol) in toluene (500 mL) was stirred at 80° C. overnight. The reaction mixture was filtered and the filtrate was concentrated under vacuum. The residue was purified by silica column chromatography (50% hexanes in EtOAc) to afford title compound 11 (11.8 g, 53%) as an oil.

Step 8: Preparation of ethyl 2-[(1R,3R)-1-hydroxy-4-methyl-3-(methylamino)pentyl]-1,3-thiazole-4-carboxylate (12)

To a solution of ethyl 2-[(1R,3E)-3-{[(S)-tert-butylsulfinyl]imino}-1-hydroxy-4-methylpentyl]-1,3-thiazole-4-carboxylate (11, 9 g, 23.2 mmol) and sodium cyanoborohydride (1.8 g, 27.8 mmol) in acetonitrile/ethanol (108 mL/12 mL) at 0° C. was added dropwise 4.0 N HCl in dioxane (30 mL, 0.12 mmol) and the solution was stirred at rt for 2 h. The reaction mixture was concentrated under vacuum and the residue was dissolved in $H_2O$ (50 mL) and extracted with EtOAc (50 mL). The aqueous phase was adjusted to pH=8 by addition of solid $NaHCO_3$ and concentrated to dryness. The residue was stirred with DCM (50 mL) and filtered. The filtrate was concentrated under vacuum to afford the title compound 12 (7.3 g, quantitative yield) as a yellow oil.

Step 9: Preparation of (1R,3R)-1-[4-(ethoxycarbonyl)-1,3-thiazol-2-yl]-4-methyl-3-(methylamino)pentyl N-(tert-butoxycarbonyl)-L-isoleucinate (14)

A solution of ethyl 2-[(1R,3R)-1-hydroxy-4-methyl-3-(methylamino)pentyl]-1,3-thiazole-4-carboxylate (12, 7.3 g, 25.52 mmol), N-(tert-butoxycarbonyl)-L-isoleucine (13, 6.5 g, 28.07 mmol), EDCl (5.4 g, 28.07 mmol) and HOBt (3.8 g, 28.07 mmol) in DCM (150 mL) was stirred at rt overnight. The reaction mixture was washed with saturated aq. $NaHCO_3$ solution and the organic phase was concentrated under vacuum. The residue was purified by silica gel chromatography (11% MeOH in DCM) to afford a residue which was dissolved in EtOAc (50 mL) and washed with saturated aq. $NaHCO_3$. The organic phase was dried over $Na_2SO_4$ and concentrated under vacuum to afford title compound 14 (6.8 g, 54%) as a yellow oil.

Step 10: Preparation of ethyl 2-[(1R,3R)-3-{[N-(tert-butoxycarbonyl)-L-isoleucyl](methyl)amino}-1-hydroxy-4-methylpentyl]-1,3-thiazole-4-carboxylate (# A1)

A solution of (1R,3R)-1-[4-(ethoxycarbonyl)-1,3-thiazol-2-yl]-4-methyl-3-(methylamino)pentyl N-(tert-butoxycarbonyl)-L-isoleucinate (14, 8 g, 16.03 mmol) in toluene (83 mL) was stirred at 90° C. overnight. The reaction mixture was concentrated under vacuum and the residue was purified by silica column chromatography (50% hexanes in EtOAc) to afford the title compound # A1 (6 g, 75%) as a white solid.

$^1$H NMR (400 MHz, $CD_3OD$): δ 8.31 (s, 1H), 6.53 (d, 1H), 4.53 (m, 1H), 4.41 (m, 4H), 3.16 (s, 3H), 2.25 (m, 1H), 1.96 (m, 4H), 1.42 (m, 15H), 1.38 (m, 2H), 1.00 (m, 12H); m/z: 522.3 [M+Na]+; 100% ee; Column: Chiralcel AD-H 150×4.6 mm I.D., 5 µm, Mobile phase: ethanol (0.05% DEA) in $CO_2$ from 5% to 40%; Wavelength: 220 nm; Retention time=5.62 min.

Preparation of methyl (2S,4R)-4-[({2-[(1R,3R)-1-(acetyloxy)-3-{[N-(tert-butoxycarbonyl)-L-isoleucyl](methyl)amino}-4-methylpentyl]-1,3-thiazol-4-yl}carbonyl)amino]-2-methyl-5-phenylpentanoate (# A2)
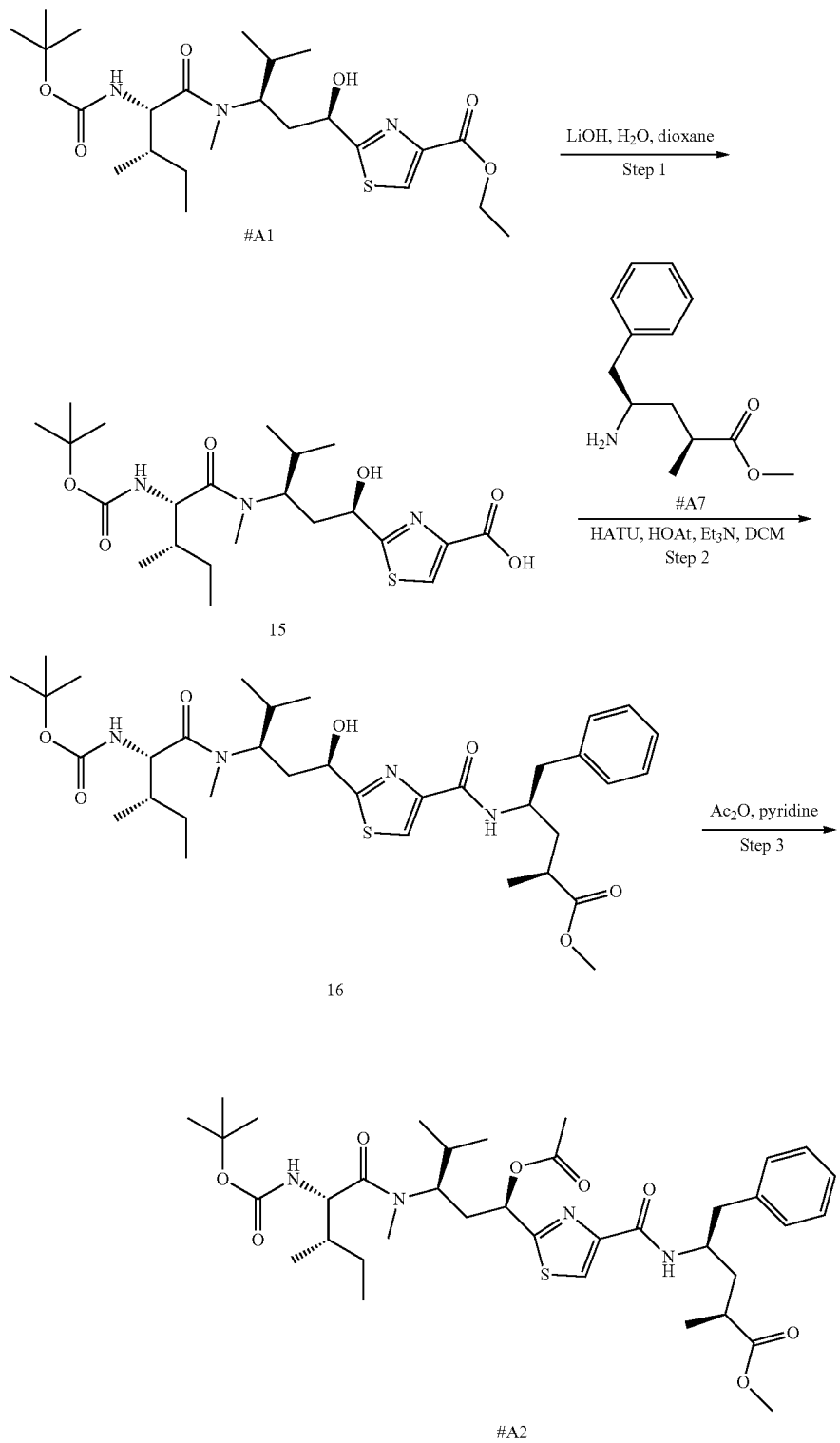

Step 1: Preparation of 2-[(1R,3R)-3-{[N-(tert-butoxycarbonyl)-L-isoleucyl](methyl)amino}-1-hydroxy-4-methylpentyl]-1,3-thiazole-4-carboxylic Acid (15)

To a solution of ethyl 2-[(1R,3R)-3-{[N-(tert-butoxycarbonyl)-L-isoleucyl](methyl)amino}-1-hydroxy-4-methylpentyl]-1,3-thiazole-4-carboxylate (# A1, 2 g, 4 mmol) in dioxane (50 mL) at 0° C. was added dropwise a solution of LiOH monohydrate (839 mg, 20 mmol) in H$_2$O (50 mL) and the solution was stirred at room temperature for 2 h. The reaction mixture was acidified to pH=1 and extracted with EtOAc The organic phase was dried over Na$_2$SO$_4$ and concentrated in vacuo to afford the title compound 15 (2.1 g, quantitative yield) as a white solid.

Step 2: Preparation of methyl (2S,4R)-4-[({2-[(1R,3R)-3-{[N-(tert-butoxycarbonyl)-L-isoleucyl](methyl)amino}-1-hydroxy-4-methylpentyl]-1,3-thiazol-4-yl}carbonyl)amino]-2-methyl-5-phenylpentanoate (16)

To a solution of 2-[(1R,3R)-3-{[N-(tert-butoxycarbonyl)-L-isoleucyl](methyl)amino}-1-hydroxy-4-methylpentyl]-1,3-thiazole-4-carboxylic acid (15, 895 mg, 1.8 mmol) and triethylamine (384 mg, 3.8 mmol) in DMF (30 mL) at 0° C. was added HOAt (258 mg, 1.9 mmol) and HATU (722 mg, 1.9 mmol). After stirring for 10 min at 0° C., methyl (2S,4R)-4-amino-2-methyl-5-phenylpentanoate hydrochloride (*Org. Biomol. Chem.* 2013, 11, 2273-2287) (490 mg, 1.9 mmol) was added and the resulting solution was stirred at rt for 3 h. The reaction mixture was diluted with H$_2$O (50 mL) and extracted with EtOAc. The organic phase was washed with brine, dried over Na$_2$SO$_4$, and concentrated under vacuum. The residue was purified by flash chromatography (7% MeOH in DCM) to afford compound 13 (1.1 g, 85%) as a yellow oil.

Step 3: Preparation methyl (2S,4R)-4-[({2-[(1R,3R)-1-(acetyloxy)-3-{[N-(tert-butoxycarbonyl)-L-isoleucyl](methyl)amino}-4-methylpentyl]-1,3-thiazol-4-yl}carbonyl)amino]-2-methyl-5-phenylpentanoate (# A2)

A solution of methyl (2S,4R)-4-[({2-[(1R,3R)-3-{[N-(tert-butoxycarbonyl)-L-isoleucyl](methyl)amino}-1-hydroxy-4-methylpentyl]-1,3-thiazol-4-yl}carbonyl)amino]-2-methyl-5-phenylpentanoate (16, 1.4 g, 2.1 mmol), Ac$_2$O (2 mL) and pyridine (10 mL) was stirred at rt overnight. The reaction mixture was concentrated under vacuum and the residue was purified by flash chromatography (30% hexanes in EtOAc) to afford the title compound # A2 (1.2 g, 80%) as a white solid.

$^1$H NMR (400 Hz, CDCl$_3$): δ 8.01 (s, 1H), 7.30 (m, 1H), 7.23 (m, 3H), 7.09 (d, 1H), 5.64 (d, 1H), 5.10 (d, 2H), 4.54 (m, 3H), 3.63 (s, 3H), 3.00 (m, 5H), 2.53 (m, 1H), 2.31 (m, 1H), 2.16 (s, 3H), 2.04 (m, 2H), 1.61 (m, 6H), 1.41 (m, 9H), 1.02 (m, 4H), 0.91 (m, 12H); m/z 739.3 [M+Na]$^+$; 98.5% ee; Column: Chiralcel AS-H 150×4.6 mm I.D., 5 μm, Mobile phase: methanol (0.05% diethylamine) in CO$_2$ from 5% to 40%; Flow rate: 2.35 mL/min; Wavelength: 220 nm; Retention time=4.65 min.

Preparation of 2-{(1R,3R)-1-(acetyloxy)-4-methyl-3-[methyl(N-{[(2R)-1-methylpiperidin-2-yl]carbonyl}-L-isoleucyl)amino]pentyl}-1,3-thiazole-4-carboxylic Acid (# A3)

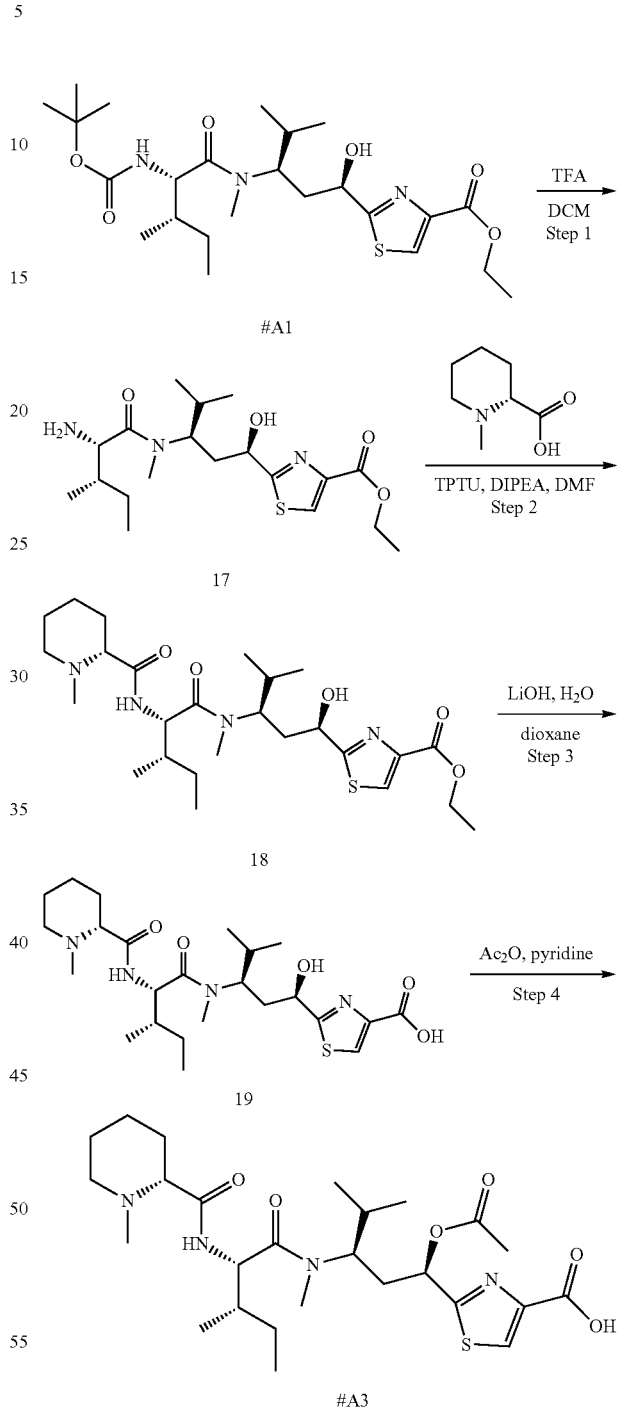

Step 1: Preparation of ethyl 2-{(1R,3R)-1-hydroxy-3-[L-isoleucyl(methyl)amino]-4-methylpentyl}-1,3-thiazole-4-carboxylate (17)

To a solution of ethyl 2-[(1R,3R)-3-{[N-(tert-butoxycarbonyl)-L-isoleucyl](methyl)amino}-1-hydroxy-4-methylpentyl]-1,3-thiazole-4-carboxylate (# A1, 5 g, 10 mmol) in DCM (100 mL) at 0° C. was added trifluroacetic acid (10 mL) dropwise and the solution was stirred at rt for 2 h. The reaction mixture was concentrated under vacuum and the residue was dissolved in EtOAc (100 mL) and basified with saturated aqueous NaHCO$_3$ (50 mL). The organic phase was washed with brine (20 mL), dried over Na$_2$SO$_4$, and concentrated under vacuum to afford the title compound 17 (3.9 g, 100%) as a gum, which was used directly in the next step.

Step 2: Preparation of ethyl 2-{(1R,3R)-1-hydroxy-4-methyl-3-[methyl(N-{[(2R)-1-methylpiperidin-2-yl]carbonyl}-L-isoleucyl)amino]pentyl}-1,3-thiazole-4-carboxylate (18)

To a solution of ethyl 2-{(1R,3R)-1-hydroxy-3-[L-isoleucyl(methyl)amino]-4-methylpentyl}-1,3-thiazole-4-carboxylate (17, 514.8 mg, 3.6 mmol) and DIPEA (1.2 g, 9 mmol) in DMF (20 mL) at 0° C. was added TPTU (1.1 g, 3.6 mmol). After stirring 15 min at 0° C., a solution of (2R)-1-methylpiperidine-2-carboxylic acid (CAS #41447-17-0) (1.2 g, 3 mmol) in DMF (5 mL) was added. The resulting solution was stirred at rt overnight and poured into H$_2$O (50 mL) and extracted with EtOAc. The organic phase was washed with saturated aqueous NaHCO$_3$ (20 mL) and brine (20 mL), dried over Na$_2$SO$_4$, and concentrated under vacuum to afford title compound 18 (1.4 g, 85%) as a yellow oil.

Step 3: Preparation of 2-{(1R,3R)-1-hydroxy-4-methyl-3-[methyl(N-{[(2R)-1-methylpiperidin-2-yl]carbonyl}-L-isoleucyl)amino]pentyl}-1,3-thiazole-4-carboxylic Acid (19)

To a solution of ethyl 2-{(1R,3R)-1-hydroxy-4-methyl-3-[methyl(N-{[(2R)-1-methylpiperidin-2-yl]carbonyl}-L-isoleucyl)amino]pentyl}-1,3-thiazole-4-carboxylate (18, 2.6 g, 4.96 mmol) in dioxane (50 mL) at 0° C. was added a solution of LiOH monohydrate (0.83 g, 19.84 mmol) in H$_2$O (50 mL). The reaction was mixture was stirred at rt for 2 h and concentrated under vacuum to yield the title compound 19, which was used in the next step without purification.

Step 4: Preparation of 2-{(1R,3R)-1-(acetyloxy)-4-methyl-3-[methyl(N-{[(2R)-1-methylpiperidin-2-yl]carbonyl}-L-isoleucyl)amino]pentyl}-1,3-thiazole-4-carboxylic Acid (# A3)

A solution of 2-{(1R,3R)-1-hydroxy-4-methyl-3-[methyl (N-{[(2R)-1-methylpiperidin-2-yl]carbonyl}-L-isoleucyl) amino]pentyl}-1,3-thiazole-4-carboxylic acid (19, 2.5 g, 4.96 mmol) in Ac$_2$O (4 mL) and pyridine (20 mL) was stirred at rt overnight. The reaction mixture was concentrated under vacuum and the residue was treated with additional pyridine (20 mL) and Ac$_2$O (4 mL) and stirred at rt for 2 h before concentration in vacuo. The residue was purified by preparative HPLC [(Column: Gemini 50×250 mm I.D., 10 μm; Mobile phase: from 10% acetonitrile in H$_2$O (0.1% NH$_3$ in H$_2$O) to 40% acetonitrile in H$_2$O (0.1% NH$_3$ in H$_2$O)] to afford title compound # A3 (1.5 g, 56%) as a white solid.

$^1$H NMR (400 MHz, DMSO-d6): δ 8.40 (s, 1H), 7.75 (d, 1H), 5.51 (d, 1H), 4.70 (m, 1H), 4.30 (br, 1H), 2.97 (s, 3H), 2.80 (m, 1H), 2.70 (m, 1H), 2.13 (m, 9H), 1.75 (m, 2H), 1.60 (m, 6H), 1.25 (m, 2H), 0.80 (m, 9H), 0.60 (d, 3H); m/z: 539.1 [M+H]$^+$; 100% ee; Column: Chiralcel OD-H 150×4.6 mm I.D., 5 μm, Mobile phase: ethanol (0.05% diethylamine) in CO$_2$ from 5% to 40%; Wavelength: 220 nm; Retention time=7.29 min.

Step 4: Preparation of 2-{(1R,3R)-1-(acetyloxy)-4-methyl-3-[methyl(N-{[(2R)-1-methylpiperidin-2-yl]carbonyl}-L-isoleucyl)amino]pentyl}-1,3-thiazole-4-carboxylic Acid (# A3)

A solution of 2-{(1R,3R)-1-hydroxy-4-methyl-3-[methyl (N-{[(2R)-1-methylpiperidin-2-yl]carbonyl}-L-isoleucyl) amino]pentyl}-1,3-thiazole-4-carboxylic acid (19, 2.5 g, 4.96 mmol) in Ac$_2$O (4 mL) and pyridine (20 mL) was stirred at rt overnight. The reaction mixture was concentrated under vacuum and the residue was treated with additional pyridine (20 mL) and Ac$_2$O (4 mL) and stirred at rt for 2 h before concentration in vacuo. The residue was purified by preparative HPLC [Column: Gemini 50×250 mm I.D, 10 μm; Mobile phase: from 10% in H$_2$O (0.1% NH$_3$ in H$_2$O) to 40% acetonitrile in H$_2$O (0.1% NH$_3$ in H$_2$O)] to afford title compound # A3 (1.5 g, 56%) as a white solid.

$^1$H NMR (400 MHz, DMSO-d6): δ 8.40 (s, 1H), 7.75 (d, 1H), 5.51 (d, 1H), 4.70 (m, 1H), 4.30 (br, 1H), 2.97 (s, 3H), 2.80 (m, 1H), 2.70 (m, 1H), 2.13 (m, 9H), 1.75 (m, 2H), 1.60 (m, 6H), 1.25 (m, 2H), 0.80 (m, 9H), 0.60 (d, 3H); m/z: 539.1 [M+H]$^+$; 100% ee; Column: Chiralcel OD-H 150×4.6 mm I.D., 5 μm, Mobile phase: ethanol (0.05% diethylamine) in CO$_2$ from 5% to 40%; Wavelength: 220 nm; Retention time=7.29 min.

Preparation of 1,2-dimethyl-D-prolyl-N-{(1R,3R)-1-[4-(ethoxycarbonyl)-1,3-thiazol-2-yl]-1-hydroxy-4-methylpentan-3-yl}-N-methyl-L-isoleucinamide (# A4)

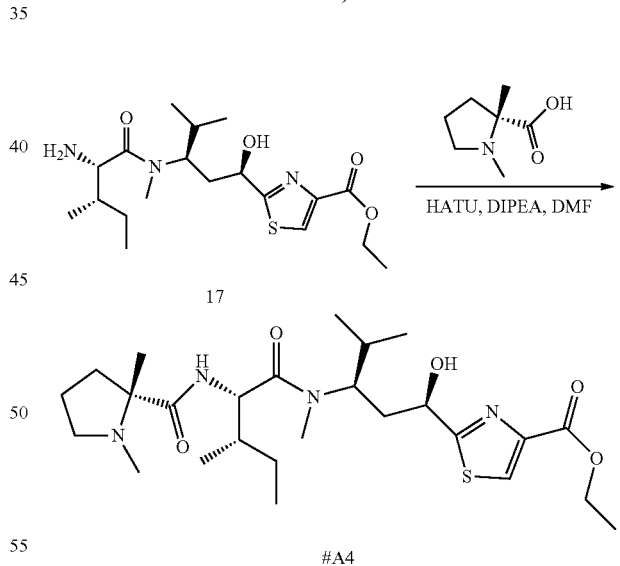

A4

Step 1: Preparation of 1,2-dimethyl-D-prolyl-N-{(1R,3R)-1-[4-(ethoxycarbonyl)-1,3-thiazol-2-yl]-1-hydroxy-4-methylpentan-3-yl}-N-methyl-L-isoleucinamide (# A4)

A solution of ethyl 2-{(1R,3R)-1-hydroxy-3-[L-isoleucyl (methyl)amino]-4-methylpentyl}-1,3-thiazole-4-carboxylate (17, 1.2 g, 3 mmol), 1,2-dimethyl-D-Proline (Doroski et al., U.S. Pat. No. 8,828,401 B2) (429 mg, 3 mmol), HATU (1.3 g, 3.3 mmol) and DIPEA (1.2 g, 9 mmol) in DMF (20 mL) was stirred at rt overnight. The reaction mixture was diluted with H$_2$O (50 mL) and extracted with EtOAc. The organic phase was washed with brine, dried over Na$_2$SO$_4$, and concentrated under vacuum. The residue was purified by silica gel chromatography (15% MeOH in DCM) to afford the title compound # A4 (0.9 g, 60%) as a yellow solid.

$^1$H NMR (400 MHz, MeOD): δ 8.32 (s, 1H), 4.71 (m, 2H), 4.42 (m, 2H), 3.20 (s, 3H), 2.74 (br, 2H), 2.25 (m, 2H), 1.98 (m, 3H), 1.56 (m, 3H), 1.38 (m, 2H), 1.03 (m, 1H), 1.00 (m, 9H); m/z: 525.1 (M+H)+; 97.4% ee; Column: Chiralcel AD-RH 150×4.6 mm I.D., 5 μm; B in A from 10% to 80%, Mobile phase A: Water with 0.07% TFA, Mobile Phase B: Acetonitrile with 0.07% TFA; Wavelength: 220 nm, Retention time=24.6 min.

Preparation of 1,2-dimethyl-D-prolyl-N-[(1R,3R)-1-(acetyloxy)-1-(4-carboxy-1,3-thiazol-2-yl)-4-methylpentan-3-yl]-N-methyl-L-isoleucinamide (# A5)

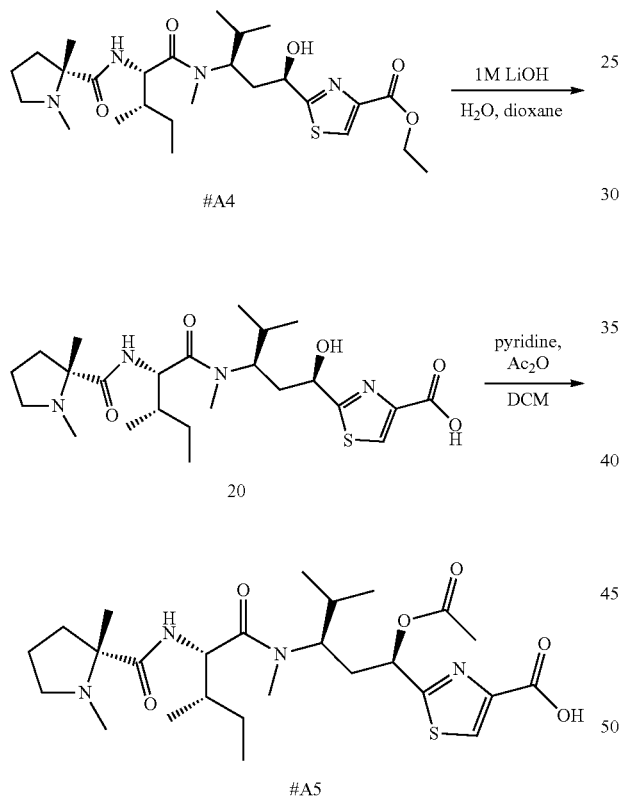

To a solution of 1,2-dimethyl-D-prolyl-N-{(1R,3R)-1-[4-(ethoxycarbonyl)-1,3-thiazol-2-yl]-1-hydroxy-4-methylpentan-3-yl}-N-methyl-L-isoleucinamide (# A4, 200 mg, 0.381 mmol) in 1,4-dioxane (2 mL) was added 1 M LiOH in water (1.1 mL) and the reaction was stirred at rt for 6 h. The reaction was quenched with HOAc (200 μL) and concentrated, and the crude residue re-dissolved in DCM (2.4 mL) and treated with pyridine (2.4 mL) and Ac$_2$O (0.5 mL). The reaction was stirred under N$_2$ for 4.5 h then concentrated to a dark oily residue which was re-dissolved in DMSO (2 mL) and purified by medium pressure reverse phase C18 chromatography (10% to 95% acetonitrile in H$_2$O over 25 minutes, each solvent containing 0.02% TFA) to afford title compound # A5 (135 mg, 66% yield). LC-MS (Protocol C): m/z 539.5 [M+H]$^+$; Retention time=0.63 min.

Preparation of (2S,4R)-4-amino-5-(4-aminophenyl)-2-methylpentanoic acid Hydrochloride (# A6) (2S,4R)-4-amino-2-methyl-5-phenylpentanoic acid Hydrochloride (# A7) methyl (2S,4R)-4-amino-2-methyl-5-phenylpentanoate Hydrochloride (# A8) and ethyl (2S,4R)-4-amino-2-methyl-5-phenylpentanoate Hydrochloride (# A9)

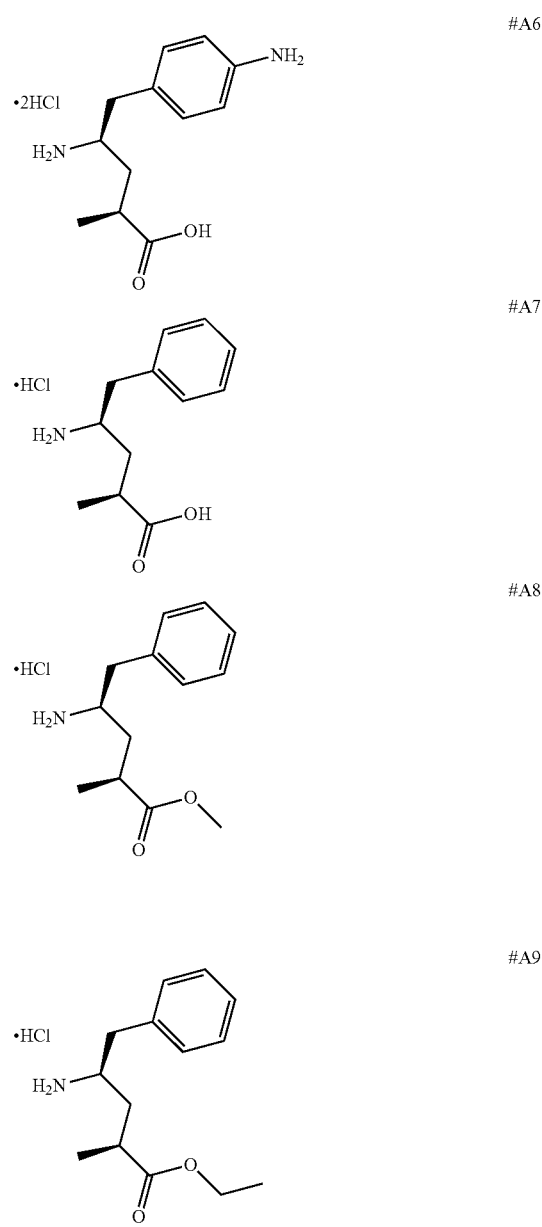

The title compound # A6 was prepared as described in Cheng et al., U.S. Pat. No. 8,394,922 B2.

The title compounds # A7, # A8, and # A9 were prepared as described in Shankar. et al., *Org. Biomol. Chem.* 2013, 11, 2273-2287.

Preparation of methyl (2S,4R)-4-{[(2-{(1R,3R)-1-(acetyloxy)-3-[L-isoleucyl(methyl)amino]-4-methylpentyl}-1,3-thiazol-4-yl)carbonyl]amino}-2-methyl-5-phenylpentanoate (# A10)

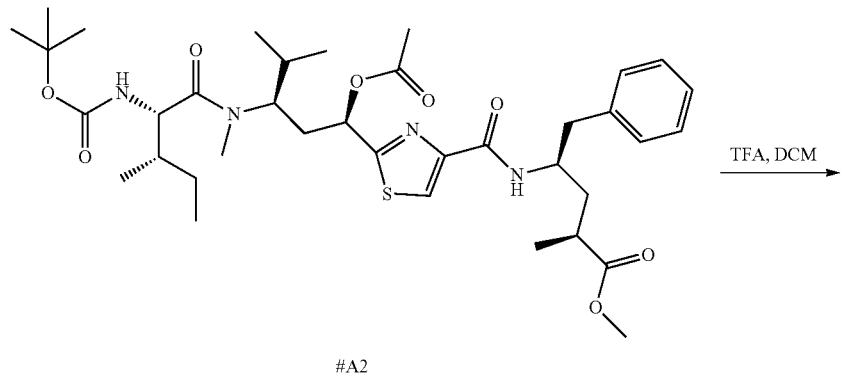

A2

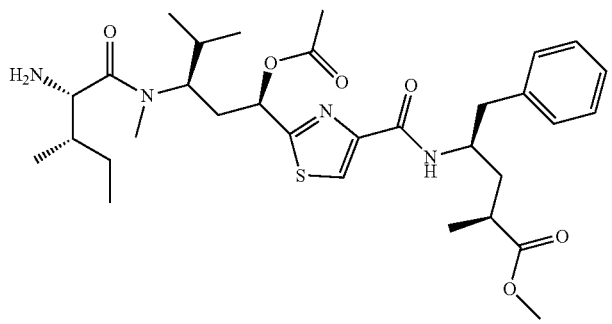

A10

To a vial containing methyl (2S,4R)-4-[({2-[(1R,3R)-1-(acetyloxy)-3-{[N-(tert-butoxycarbonyl)-L-isoleucyl](methyl)amino}-4-methylpentyl]-1,3-thiazol-4-yl}carbonyl)amino]-2-methyl-5-phenylpentanoate (# A2, 200 mg, 0.279 mmol) in DCM (20 mL) was added TFA (1.1 mL) and the reaction was stirred under an N₂ inlet at rt for 2.25 h. The reaction mixture was concentrated in vacuo, azeotroped with DCM/MeOH (1/1, 3 mL), and concentrated under high vacuum overnight to yield title compound # A10 (243 mg, quantitative yield) as a solid. The product was carried crude to following steps. LC-MS (Protocol C): m/z 617.3 [M+H]⁺; Retention time=0.72 min.

Preparation of 1,2-dimethyl-D-prolyl-N-[(1R,3R)-1-(acetylamino)-1-(4-carboxy-1,3-thiazol-2-yl)-4-methylpentan-3-yl]-N-methyl-L-isoleucinamide (# A11)

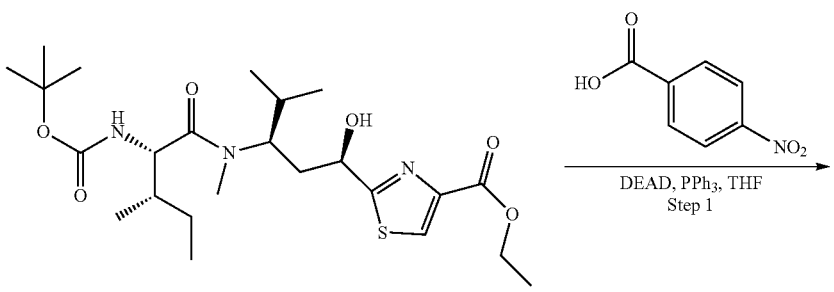

A1

-continued
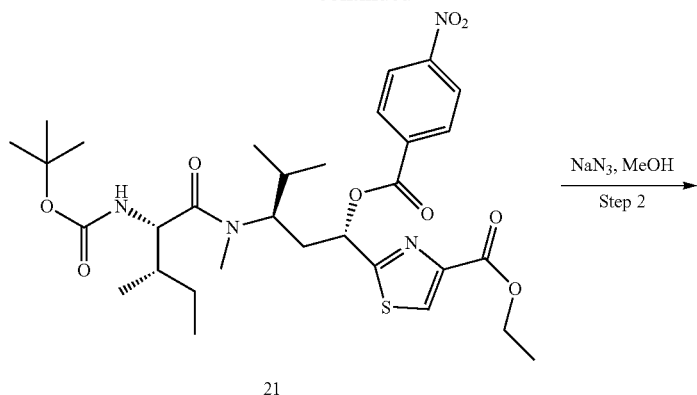
21
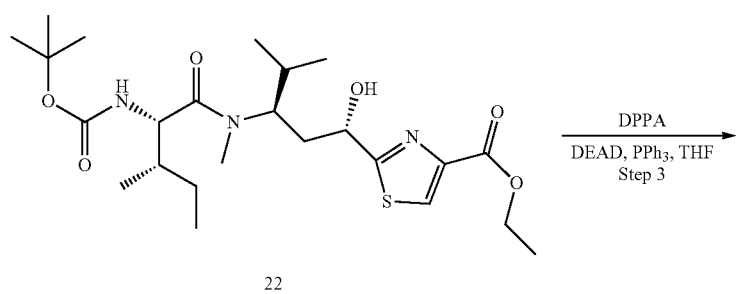
22
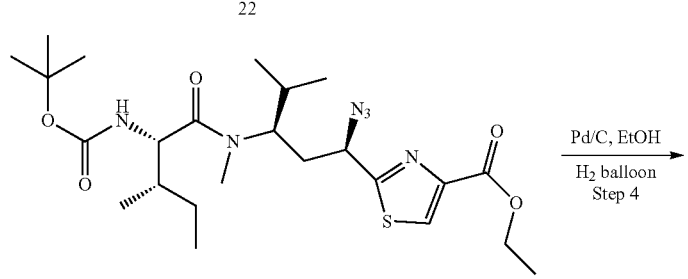
23
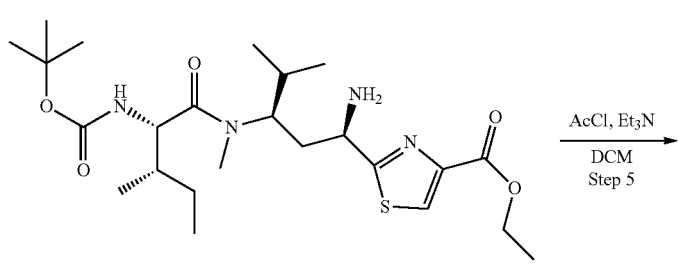
24
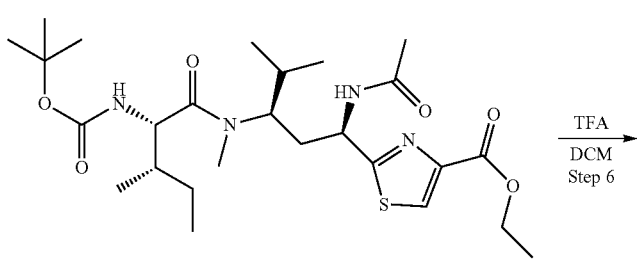
25

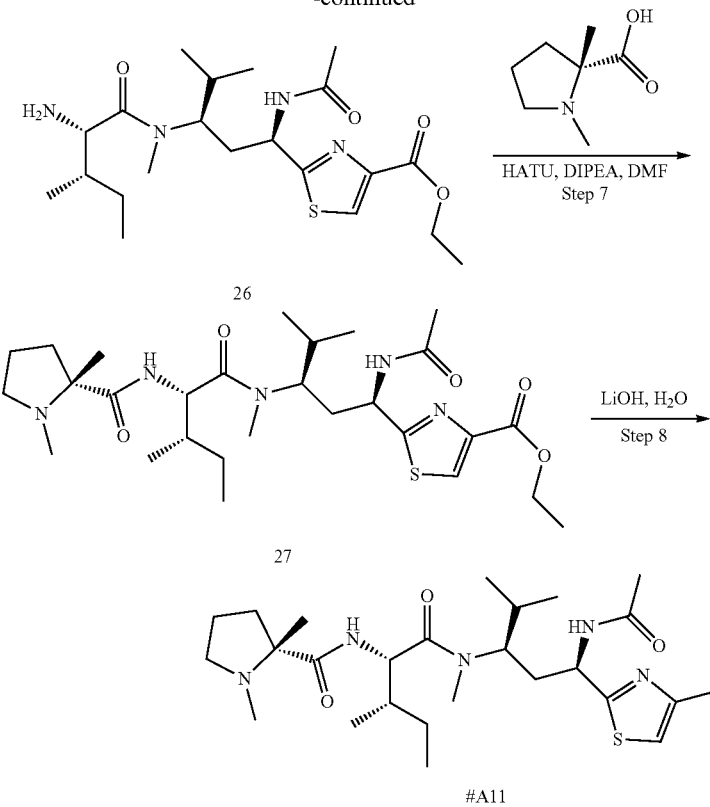

Step 1: Preparation of ethyl 2-{(1 S,3R)-3-{[N-(tert-butoxycarbonyl)-L-isoleucyl](methyl)amino}-4-methyl-1-[(4-nitrobenzoyl)oxy]pentyl}-1,3-thiazole-4-carboxylate (21)

To a solution of ethyl 2-[(1R,3R)-3-{[N-(tert-butoxycarbonyl)-L-isoleucyl](methyl)amino}-1-hydroxy-4-methylpentyl]-1,3-thiazole-4-carboxylate (# A1, 700 mg, 1.40 mmol), 4-nitrobenzoic acid (258 mg, 1.54 mmol) and triphenylphosphine (1.47 g, 5.60 mmol) in THF (20 mL) was added DIAD dropwise (976 mg, 5.60 mmol) at 0° C. and the solution was stirred at rt for 2 h. The reaction mixture was poured into H₂O (30 mL) and extracted with EtOAc (30 mL). The organic phase was dried over Na₂SO₄ and concentrated in vacuo. The residue was purified by flash silica gel chromatography (40% EtOAc in hexanes) to afford title compound 21 (700 mg, 77%) as an oil. m/z 671.1 [M+Na]⁺.

Step 2: Preparation of ethyl 2-[(1 S,3R)-3-{[N-(tert-butoxycarbonyl)-L-isoleucyl](methyl)amino}-1-hydroxy-4-methylpentyl]-1,3-thiazole-4-carboxylate (22)

A solution of ethyl 2-{(1 S,3R)-3-{[N-(tert-butoxycarbonyl)-L-isoleucyl](methyl)amino}-4-methyl-1-[(4-nitrobenzoyl)oxy]pentyl}-1,3-thiazole-4-carboxylate (21, 1.5 g, 2.312 mmol) and sodium azide (752 mg, 11.6 mmol) in MeOH (20 mL) was stirred at 30° C. overnight. The reaction mixture was poured into H₂O (20 mL) and extracted with EtOAc (20 mL). The organic phase was dried over Na₂SO₄ and concentrated in vacuo. The residue was purified by flash chromatography (40% EtOAc in hexanes) to afford title compound 22 (200 mg, 17%) as an oil.

$^1$H NMR (400 MHz, CDCl₃): δ 8.12 (s, 1H), 5.42-5.02 (m, 3H), 4.43-4.34 (m, 3H), 4.17 (m, 1H), 2.95 (m, 2H), 2.79 (m, 1H), 2.50-2.46 (m, 1H), 1.88-1.65 (m, 3H), 1.65-1.37 (m, 3H), 1.13 (m, 13H), 1.07-0.90 (m, 6H), 0.89-0.84 (m, 10); m/z: 522.1 [M+Na]⁺; 95.2% ee; Column: AS-H 250 mm×4.6 mm I.D; Mobile phase: methanol (0.05% diethylamine) in CO₂ from 5% to 40%; Wavelength: 220 nm; Retention time=2.94 min.

Step 3: Preparation of ethyl 2-[(1R,3R)-1-azido-3-{[N-(tert-butoxycarbonyl)-L-isoleucyl](methyl)amino}-4-methylpentyl]-1,3-thiazole-4-carboxylate (23)

To a solution of ethyl 2-[(1S,3R)-3-{[N-(tert-butoxycarbonyl)-L-isoleucyl](methyl)amino}-1-hydroxy-4-methylpentyl]-1,3-thiazole-4-carboxylate (22, 900 mg, 1.8 mmol), triphenyl phosphine (1.42 g, 5.40 mmol), and diphenyl phosphoryl azide (1.24 g, 4.50 mmol) in THF (50 mL) at 0° C. was added diethyl azo dicarboxylate (1.57 g, 1 mmol) and the solution was stirred at rt for 30 min. The reaction mixture was poured into H₂O (50 mL) and extracted with EtOAc (50 mL). The organic phase was concentrated under vacuum and the residue was purified by flash silica gel chromatography (30% EtOAc in hexanes) to afford title compound 23 (800 mg, 84.7%) as an oil. m/z 547.3 [M+Na]⁺.

Step 4: Preparation of ethyl 2-[(1R,3R)-1-amino-3-{[N-(tert-butoxycarbonyl)-L-isoleucyl](methyl)amino}-4-methylpentyl]-1,3-thiazole-4-carboxylate (24)

A suspension of ethyl 2-[(1R,3R)-1-azido-3-{[N-(tert-butoxycarbonyl)-L-isoleucyl](methyl)amino}-4-methylpentyl]-1,3-thiazole-4-carboxylate (23, 540 mg, 1.03 mmol) and 10% Pd—C (300 mg) in ethanol (20 mL) was stirred at rt under 40 psi $H_2$ for 2 h. The reaction mixture was filtered through a pad of celite and the filter cake was washed with EtOAc (20 mL). The combined filtrate was concentrated under vacuum to afford title compound 24 (370 mg, 72.1%) as an oil which was used without further purification.

Step 5: Preparation of ethyl 2-[(1R,3R)-1-(acetylamino)-3-{[N-(tert-butoxycarbonyl)-L-isoleucyl](methyl)amino}-4-methylpentyl]-1,3-thiazole-4-carboxylate (25)

To a solution of ethyl 2-[(1R,3R)-1-amino-3-{[N-(tert-butoxycarbonyl)-L-isoleucyl](methyl)amino}-4-methylpentyl]-1,3-thiazole-4-carboxylate (24, 370 mg, 0.742 mmol) and triethylamine (150 mg, 1.48 mmol) in DCM (5 mL) at 0° C. and was added acetyl chloride dropwise (291 mg, 3.71 mmol) and the mixture was stirred at rt for 10 min. The reaction mixture was washed with $H_2O$ (10 mL), dried over $Na_2SO_4$ and concentrated under vacuum. The residue was purified by flash chromatography (90% EtOAc in hexanes) to afford the title compound 25 (300 mg, 74.8%) as an oil. m/z 563.1 $[M+Na]^+$.

Step 6: Preparation of ethyl 2-{(1R,3R)-1-(acetylamino)-3-[L-isoleucyl(methyl)amino]-4-methylpentyl}-1,3-thiazole-4-carboxylate (26)

To a solution of ethyl 2-[(1R,3R)-1-(acetylamino)-3-{[N-(tert-butoxycarbonyl)-L-isoleucyl](methyl)amino}-4-methylpentyl]-1,3-thiazole-4-carboxylate (25, 300 mg, 1.07 mmol) in DCM (10 mL) at 0° C. was added trifluroacetic acid (1 mL) dropwise and the mixture was stirred at rt for 2 h. Additional trifluroacetic acid (1 mL) was added and the solution was stirred at rt for 0.5 h. The reaction mixture was concentrated under vacuum to afford crude compound 26 which was used directly in the next step.

Step 7: Preparation of 1,2-dimethyl-D-prolyl-N-{(1R,3R)-1-(acetylamino)-1-[4-(ethoxycarbonyl)-1,3-thiazol-2-yl]-4-methylpentan-3-yl}-N-methyl-L-isoleucinamide (27)

To a solution of ethyl 2-{(1R,3R)-1-(acetylamino)-3-[L-isoleucyl(methyl)amino]-4-methylpentyl}-1,3-thiazole-4-carboxylate (26, 216 mg, 0.56 mmol), 1,2-dimethyl-D-Proline (Doroski et al., U.S. Pat. No. 8,828,401 B2) (88.2 mg, 0.616 mmol) and DIPEA (217 mg, 1.68 mmol) in DMF (5 mL) at 0° C. was added HATU (234 mg, 0.616 mmol) and the solution was stirred at rt for 2 hrs. The reaction mixture was concentrated under vacuum to afford crude title compound 27 which was used directly in the next step.

Step 8: Preparation of 1,2-dimethyl-D-prolyl-N-[(1R,3R)-1-(acetylamino)-1-(4-carboxy-1,3-thiazol-2-yl)-4-methylpentan-3-yl]-N-methyl-L-isoleucinamide (# A11)

A solution of 1,2-dimethyl-D-prolyl-N-{(1R,3R)-1-(acetylamino)-1-[4-(ethoxycarbonyl)-1,3-thiazol-2-yl]-4-methylpentan-3-yl}-N-methyl-L-isoleucinamide (27, 316.4 mg, 0.6030 mmol) and LiOH (144 mg, 4.29 mmol) in THF (8 mL) and $H_2O$ (2 mL) was stirred at rt overnight. Additional LiOH (144 mg, 4.29 mmol) was added and stirring continued for another 24 h at rt. The reaction mixture was acidified to pH=5.0 by addition of 1.0 N aqueous HCl and the solution was directly purified by preparative HPLC (Column: YMC-Actus Triart C18, 150×30 mm I.D., 5 μm; Mobile phase: 13% acetonitrile in water (0.1% TFA) to 33% acetonitrile in water (0.1% TFA); Wavelength: 220 nm) to afford title compound # A11 (160 mg, 49%) as a white solid.

$^1$H NMR (400 MHz, DMSO-d6): δ 9.74 (br, 1H), 8.73-8.70 (m, 2H), 8.31 (s, 1H), 4.74 (m, 1H), 4.63-4.58 (m, 1H), 3.53 (m, 2H), 3.18-3.13 (m, 1H), 3.00 (s, 3H), 2.70-2.68 (m, 3H), 2.29-2.28 (m, 1H), 2.09-1.81 (m, 9H), 1.48 (m, 4H), 0.94-0.92 (m, 1H), 0.86 (m, 3H), 0.84-0.81 (m, 6H), 0.73 (m, 3H); m/z: 538.1 $[M+H]^+$; 99% ee; Column: Chiralpak AD-H 250×4.6 mm I.D., 5 μm, Mobile phase: ethanol (0.05% diethylamine) in $CO_2$ from 5% to 40%; Wavelength: 220 nm; Retention time=5.04 min.

Preparation of 2-[(6R,8R,11S)-1-[(2S)-butan-2-yl]-9-methyl-13-(7-methyl-7-azabicyclo[2.2.1]hept-1-yl)-4,10,13-trioxo-8-(propan-2-yl)-5-oxa-3,9,12-triazatridecan-6-yl]-1,3-thiazole-4-carboxylic acid (# A12)

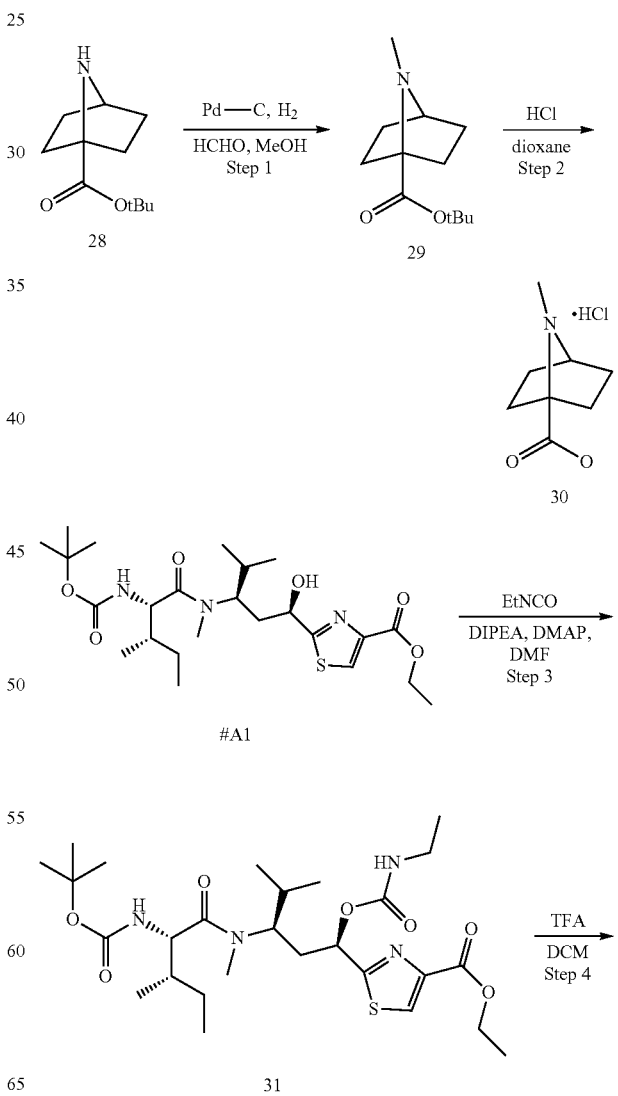

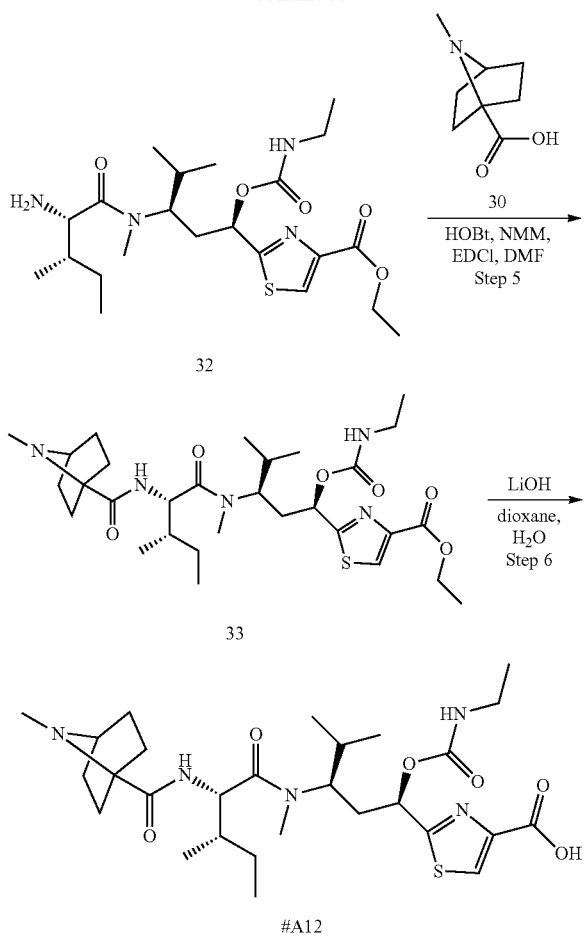

Step 1: Preparation of tert-butyl 7-methyl-7-azabicyclo[2.2.1]heptane-1-carboxylate (29)

To a solution of tert-butyl 7-azabicyclo[2.2.1]heptane-1-carboxylate (*Org. Lett.* 1999, 1, 1825) (28, 12 g, 60.827 mmol) in MeOH (60 mL) was added formaldehyde (18.26 mL, 608.273 mmol) and 10% Pd—C (3 g, 50% moisture) and the resulting reaction mixture was hydrogenated at 50 psi for 16 h. The mixture was filtered through celite and the filtrate was concentrated to afford crude compound which was purified by silica gel chromatography (40% EtOAc in hexanes) to afford title compound 29 (10.8 g, 84%) as a colorless liquid. m/z: 211.0 [M+H]$^+$.

Step 2: Preparation of 7-methyl-7-azabicyclo[2.2.1]heptane-1-carboxylic acid (30)

A solution tert-butyl 7-methyl-7-azabicyclo[2.2.1]heptane-1-carboxylate (29, 10.8 g, 51.2 mmol) in dioxane (100 mL) was added 4.0 N HCl in dioxane (100 mL) and the resulting reaction mixture was stirred at rt for 36 h. The reaction mixture was concentrated and triturated with ether to afford title compound 30 (8.5 g, 87%) as a white solid.

$^1$H NMR (400 MHz, CD$_3$OD): δ4.12 (m, 1H), 2.91 (s, 3H), 2.1-2.4 (m, 6H), 1.88-1.98 (m, 3H).

Step 3: Preparation of ethyl 2-{(1R,3R)-3-{[N-(tert-butoxycarbonyl)-L-isoleucyl](methyl)amino}-1-[(ethylcarbamoyl)oxy]-4-methylpentyl}-1,3-thiazole-4-carboxylate (31)

To a stirred solution of ethyl 2-[(1R,3R)-3-{[N-(tert-butoxycarbonyl)-L-isoleucyl](methyl)amino}-1-hydroxy-4-methylpentyl]-1,3-thiazole-4-carboxylate (# A1, 1.02 g, 2.04 mmol) and DMAP (499 mg, 4.08 mmol) in dry DMF (17.4 mL) at 0° C. was added DIPEA (2.64 g, 20.4 mmol) and ethyl isocyanate (3.63 g, 51.1 mmol) and the reaction mixture was stirred at rt for 42 h. The reaction mixture was diluted with EtOAc (50 mL), poured into H$_2$O, (100 mL) and the layers separated. The aqueous phase was extracted with EtOAc (40 mL×3) and the combined organic layers were washed with H$_2$O (50 mL×2) and brine, dried over Na$_2$SO$_4$, and concentrated under vacuum. The residue was purified by preparative HPLC (Column: Phenomenex Synergi Max-RP 250×80 mm I.D., 10 μM; Mobile phase A: H$_2$O with 0.1% TFA, Mobile Phase B: acetonitrile with 0.1% TFA; 50% to 80% B over 20 minutes, hold at 100% B for 2 minutes; Flow Rate: 80 mL/min) to give title compound 31 (750 mg, 64%) as a white solid. m/z: 593.3 [M+Na]$^+$.

Step 4: Preparation of ethyl 2-{(1R,3R)-1-[(ethylcarbamoyl)oxy]-3-[L-isoleucyl(methyl)amino]-4-methylpentyl}-1,3-thiazole-4-carboxylate (32)

To a stirred solution of ethyl 2-{(1R,3R)-3-{[N-(tert-butoxycarbonyl)-L-isoleucyl](methyl)amino}-1-[(ethylcarbamoyl)oxy]-4-methylpentyl}-1,3-thiazole-4-carboxylate (31, 750 mg, 1.31 mmol) in dry DCM (20 mL) at 0° C. was added TFA (4 mL). The reaction mixture was stirred at 0° C. for 2 h and concentrated under vacuum to give the title compound 32 (1.04 g, 97%) as a yellow gum, which was used in the next step without further purification.

Step 5: Preparation of ethyl 2-[(6R,8R,11S)-11-[(2S)-butan-2-yl]-9-methyl-13-(7-methyl-7-azabicyclo[2.2.1]hept-1-yl)-4,10,13-trioxo-8-(propan-2-yl)-5-oxa-3,9,12-triazatridecan-6-yl]-1,3-thiazole-4-carboxylate (33)

To a stirred white suspension of 7-methyl-7-azabicyclo[2.2.1]heptane-1-carboxylic acid (30, 122 mg, 0.635 mmol) in dry DMF (7 mL) at 0° C. was added EDCl (117 mg, 0.609 mmol), HOBT (85.8 mg, 0.635 mmol), and N-methyl morpholine (428 mg, 4.23 mmol) and the mixture was stirred for 1 h at rt. Ethyl 2-{(1R,3R)-1-[(ethylcarbamoyl)oxy]-3-[L-isoleucyl(methyl)amino]-4-methylpentyl}-1,3-thiazole-4-carboxylate (32, 430 mg, 0.529 mmol) was added and the reaction was stirred at rt for 24 h. H$_2$O (50 mL) was added and the reaction mixture was extracted with EtOAc (30 mL×3). The combined organic layers were washed with aq. NaHCO$_3$ and brine, dried over Na$_2$SO$_4$, and concentrated under vacuum. The residue was purified by silica gel chromatography (100%/0% to 89%/11% DCM/MeOH) to give the title compound 33 (270 mg, 84%) as a yellow oil.

Step 6: 2-[(6R,8R,11S)-11-[(2S)-butan-2-yl]-9-methyl-13-(7-methyl-7-azabicyclo[2.2.1]hept-1-yl)-4,10,13-trioxo-8-(propan-2-yl)-5-oxa-3,9,12-triazatridecan-6-yl]-1,3-thiazole-4-carboxylic Acid (# A12)

To a solution of ethyl 2-[(6R,8R,11S)-11-[(2S)-butan-2-yl]-9-methyl-13-(7-methyl-7-azabicyclo[2.2.1]hept-1-yl)-4, 10,13-trioxo-8-(propan-2-yl)-5-oxa-3,9,12-triazatridecan-6-yl]-1,3-thiazole-4-carboxylate (33, 270 mg, 0.444 mmol) in dioxane (5 mL) at 0° C. was added a solution of LiOH monohydrate (55.9 mg, 1.33 mmol) in H$_2$O (2.5 mL). The reaction mixture was stirred at rt for 1 h. The reaction mixture was adjusted to pH=5-6 with 1 N aq. HCl and concentrated under vacuum to remove dioxane. The resulting aqueous layer was purified by preparative HPLC (Column: YMC-Actus Triart C18, 150×30 mm I.D., 5 µm; Mobile phase A: H$_2$O with 0.1% TFA, Mobile phase B: acetonitrile with 0.1% TFA, 20% to 40% B over 11 minutes, hold at 100% B for 2 minutes; Flow rate: 30 mL/minute) to give title compound # A12 (200 mg, 78%) as a white solid.

$^1$H NMR (400 MHz, CDCl3): δ 8.43-8.41 (d, 1H), 8.17 (s, 1H), 5.74-5.61 (m, 1H), 5.15 (d, 1H), 4.75-4.71 (m, 1H), 4.60 (m, 1H), 4.14-4.11 (m, 1H), 3.30 (s, 2H), 3.13 (s, 3H), 2.90 (s, 2H), 2.77 (s, 1H), 2.65-2.50 (m, 1H), 2.50-2.30 (m, 3H), 2.25-1.94 (m, 5H), 1.94-1.50 (m, 5H), 1.14-0.99 (m, 5H), 0.98-0.85 (m, 13H). m/z 580.1 [M+H]$^+$; 100% ee; Column: Chiralcel OD-3 100×4.6 mm I.D., 3 µm, Mobile phase: A: CO$_2$ B:ethanol (0.05% diethylamine), Gradient: 5% to 40% B in 4.5 min, hold 40% for 2.5 min, then 5% B for 1 min; Flow rate: 2.8 mL/min; Column temperature: 40° C.

Preparation of 2-[(1R,3R)-1-[(ethylcarbamoyl)oxy]-4-methyl-3-(methyl{N-[(9-methyl-9-azabicyclo[3.3.1]non-1-yl)carbonyl]-L-isoleucyl}amino)pentyl]-1,3-thiazole-4-carboxylic Acid (# A13)

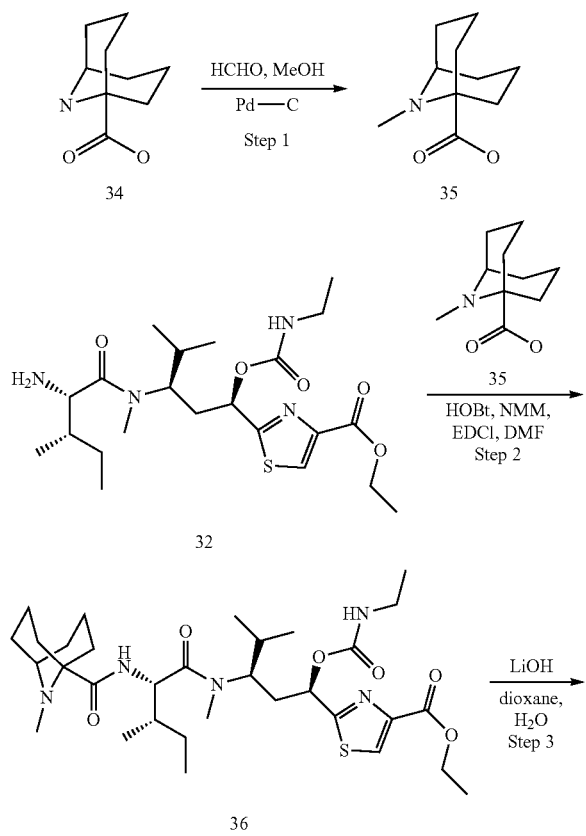

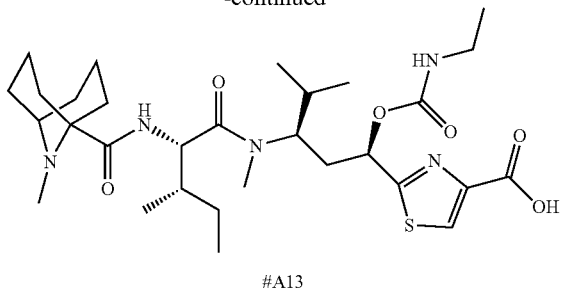

A13

Step 1: Preparation of 9-methyl-9-azabicyclo[3.3.1]nonane-1-carboxylic acid (35)

To a stirred solution of 9-azabicyclo[3.3.1]nonane-1-carboxylic acid (J. Org. Chem. 2009, 74, 5541) (34, 5 g, 29.54 mmol) in MeOH (50 ml) was added formaldehyde (5 ml) and the reaction mixture was stirred at rt for 3 h. Pd—C (1 g, 50% moisture) was added and the black suspension was hydrogenated under 30 psi for 16 h. The reaction mixture was filtered and concentrated under reduced pressure to afford the crude title compound 35. 5.4 g of crude 35 was suspended in MeOH (2.1 mL) and the suspension was heated to 60° C. The resulting solution was refrigerated for 16 h then the precipitate was removed by filtration and washed with cold MeOH (2 mL). The solid was dried under reduced pressure to afford the title compound 35 (3.3 g, 61%) as an off white solid.

Step 2: Preparation of (1R,3R)-1-[4-(ethoxymethyl)-1,3-thiazol-2-yl]-4-methyl-3-(methyl{N-[(9-methyl-9-azabicyclo[3.3.1]non-1-yl)carbonyl]-L-isoleucyl}amino)pentyl ethylcarbamate (36)

To a stirred white suspension of 9-methyl-9-azabicyclo[3.3.1]nonane-1-carboxylic acid (35, 103 mg, 0.561 mmol) in dry DMF (6 mL) at 0° C. was added EDCl (103 mg, 0.538 mmol), HOBt (75.8 mg, 0.561 mmol) and NMM (378 mg, 3.74 mmol) and the reaction mixture was stirred for 1 h at rt. A solution of ethyl 2-{(1R,3R)-1-[(ethylcarbamoyl)oxy]-3-[L-isoleucyl(methyl)amino]-4-methylpentyl}-1,3-thiazole-4-carboxylate (32, 380 mg, 0.468 mmol) in dry DMF (2 mL) was added and the reaction mixture was stirred at rt for 24 h. H$_2$O (50 mL) was added and the reaction mixture was extracted with EtOAc (30 mL×3). The combined organic layers were washed with aq. NaHCO$_3$ and brine, dried over Na$_2$SO$_4$, and concentrated under vacuum. The resulting residue was purified by silica gel chromatography (100% DCM to 88% DCM/12% MeOH) to provide the title compound 36 (300 mg, quantitative yield) as a yellow oil.

Step 3: 2-[(1R,3R)-1-[(ethylcarbamoyl)oxy]-4-methyl-3-(methyl{N-[(9-methyl-9-azabicyclo[3.3.1]non-1-yl)carbonyl]-L-isoleucyl}amino)pentyl]-1,3-thiazole-4-carboxylic Acid (# A13)

To a stirred solution of (1R,3R)-1-[4-(ethoxymethyl)-1,3-thiazol-2-yl]-4-methyl-3-(methyl{N-[(9-methyl-9-azabicyclo[3.3.1]non-1-yl)carbonyl]-L-isoleucyl}amino)pentyl ethylcarbamate (36, 300 mg, 0.472 mmol) in dioxane (6 mL) at 0° C. was added a solution of LiOH monohydrate (59.4 mg, 1.42 mmol) in H$_2$O (3 mL). The reaction mixture was stirred at rt for 1 h, the mixture adjusted to pH=5-6 with 1

N aq. HCl, and concentrated under vacuum to remove dioxane. The resulting aqueous layer was purified by preparative HPLC (Column: YMC-Actus Triart C18, 150×30 mm, 5 μm; Mobile phase A: H$_2$O with 0.1% TFA, Mobile phase B: acetonitrile with 0.1% TFA, 22% to 42% B over 11 minutes, hold at 100% B for 2 minutes; Flow rate: 30 mL/minute) to give title compound # A13 (195 mg, 68%).

$^1$H NMR (400 MHz, CDCl$_3$): δ 8.35-8.33 (d, 1H), 8.19 (s, 1H), 5.67-5.58 (m, 1H), 5.16 (d, 1H), 4.69-4.52 (m, 1H), 3.77 (s, 2H), 3.19 (s, 4H), 3.10 (s, 3H), 2.94 (s, 2H), 2.85 (s, 1H), 2.65-2.40 (m, 2H), 2.22-2.08 (m, 7H), 1.91-1.1.50 (m, 7H), 1.25-1.00 (m, 4H), 0.98-0.80 (m, 13H); m/z 608.2 [M+H]$^+$; 100% ee; Column: Chiralcel OD-3 100×4.6 mm I.D., 3 μm, Mobile phase: A: CO$_2$ B: ethanol (0.05% diethylamine), Gradient: 5% to 40% B over 4.5 min, hold at 40% for 2.5 min, then 5% B for 1 min; Flow rate: 2.8 mL/min; Column temperature: 40° C.

Preparation of [(4S)-4-amino-5-phenylpentan-2-yl]phosphonic acid (# A14)

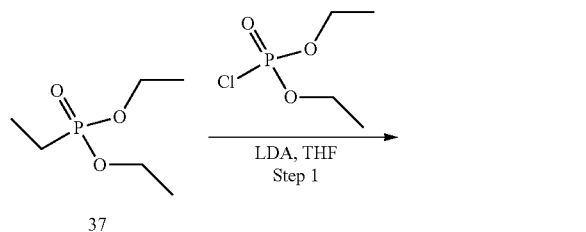

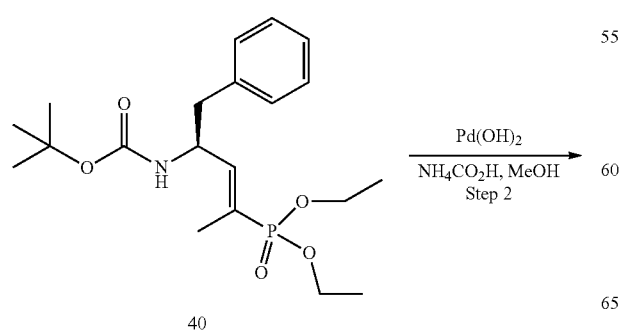

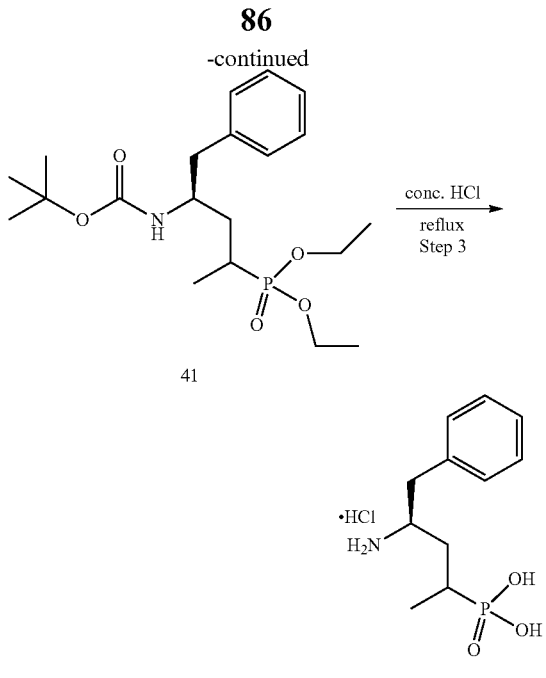

Step 1: Preparation of diethyl {(2E,4S)-4-[(tert-butoxycarbonyl)amino]-5-phenylpent-2-en-2-yl}phosphonate (40)

To a stirring solution of diisopropylamine (1.69 mL, 12.0 mmol) in THF (25 mL) at −78° C. was added n-BuLi (2.5 M in hexanes, 4.81 mL, 12.0 mmol) and the solution was stirred at −78° C. for 15 minutes. The reaction mixture was warmed to 0° C. and stirred for 15 minutes before adding of this LDA reaction mixture (6.0 mmol) dropwise to a stirring solution of diethyl ethylphosphonate (37, 0.68 g, 4.0 mmol) in THF (15 mL) at −78° C. The reaction mixture was stirred at −78° C. for 1 h and diethyl phosphorochloridate (0.692 g, 4.01 mmol) was added. The mixture was stirred at −78° C. for 45 minutes, after which time the remaining LDA solution (6.0 mmol) was added. The mixture was stirred at −78° C. for 0.5 h, 0° C. for 0.5 h, and rt for 0.5 h before re-cooling to −78° C. A solution of tert-butyl [(2S)-1-oxo-3-phenylpropan-2-yl]carbamate (39, 1.0 g, 4.01 mmol) in THF (15 mL) was added dropwise. The reaction mixture was warmed slowly to rt and stirred for 12 h, diluted with water (100 mL), and extracted with DCM (20 mL×3). The combined organic phase was washed with brine (200 mL), dried over Na$_2$SO$_4$, and concentrated. The crude product was purified by silica gel chromatography (0% to 80% EtOAc in heptanes) to give the title compound 40 (0.14 g, 9%) as a yellow gum. LC-MS (Protocol F): m/z 398.1 [M+H]$^+$; Retention time=3.18 min.

Step 2: Preparation of diethyl {(4S)-4-[(tert-butoxycarbonyl)amino]-5-phenylpentan-2-yl}phosphonate (41)

A mixture of diethyl {(2E,4S)-4-[(tert-butoxycarbonyl)amino]-5-phenylpent-2-en-2-yl}phosphonate (40, 1.40 g, 0.353 mmol), ammonium formate (6.66 g, 106 mmol), and Pd(OH)$_2$ (1.40 g) in MeOH (140 mL) was heated at reflux for 1 h. The mixture was cooled to rt, filtered through celite, and the filtrate concentrated under vacuum. The resulting residue was purified by silica gel chromatography (20% to 100% EtOAc in DCM) to give the title compound 41 (1.30 g, 92%) as a white solid, which was used without further characterization.

Step 3: Preparation of [(4S)-4-amino-5-phenylpentan-2-yl]phosphonic acid (# A14)

A suspension of diethyl {(4S)-4-[(tert-butoxycarbonyl)amino]-5-phenylpentan-2-yl}phosphonate (41, 900 mg, 2.25 mmol) in concentrated HCl (50 mL) was heated at reflux for 5 h, after which time the reaction mixture was concentrated under vacuum to give the title compound # A14 (542 mg, 86%) as a white solid.

$^1$H NMR (400 Hz, CD$_3$OD): δ 7.41 (m, 2H), 7.33 (m, 3H), 3.76 (m, 1H), 3.04-2.92 (m, 2H), 2.09-1.95 (m, 2H), 1.78-1.70 (m, 1H), 1.22 (m, 3H); m/z 244.10 [M+H]$^+$.

Preparation of diethyl [(2R,4S)-4-amino-5-(4-aminophenyl)pentan-2-yl]phosphonate (# A15) and diethyl [(2S,4S)-4-amino-5-(4-aminophenyl)pentan-2-yl]phosphonate (# A16)

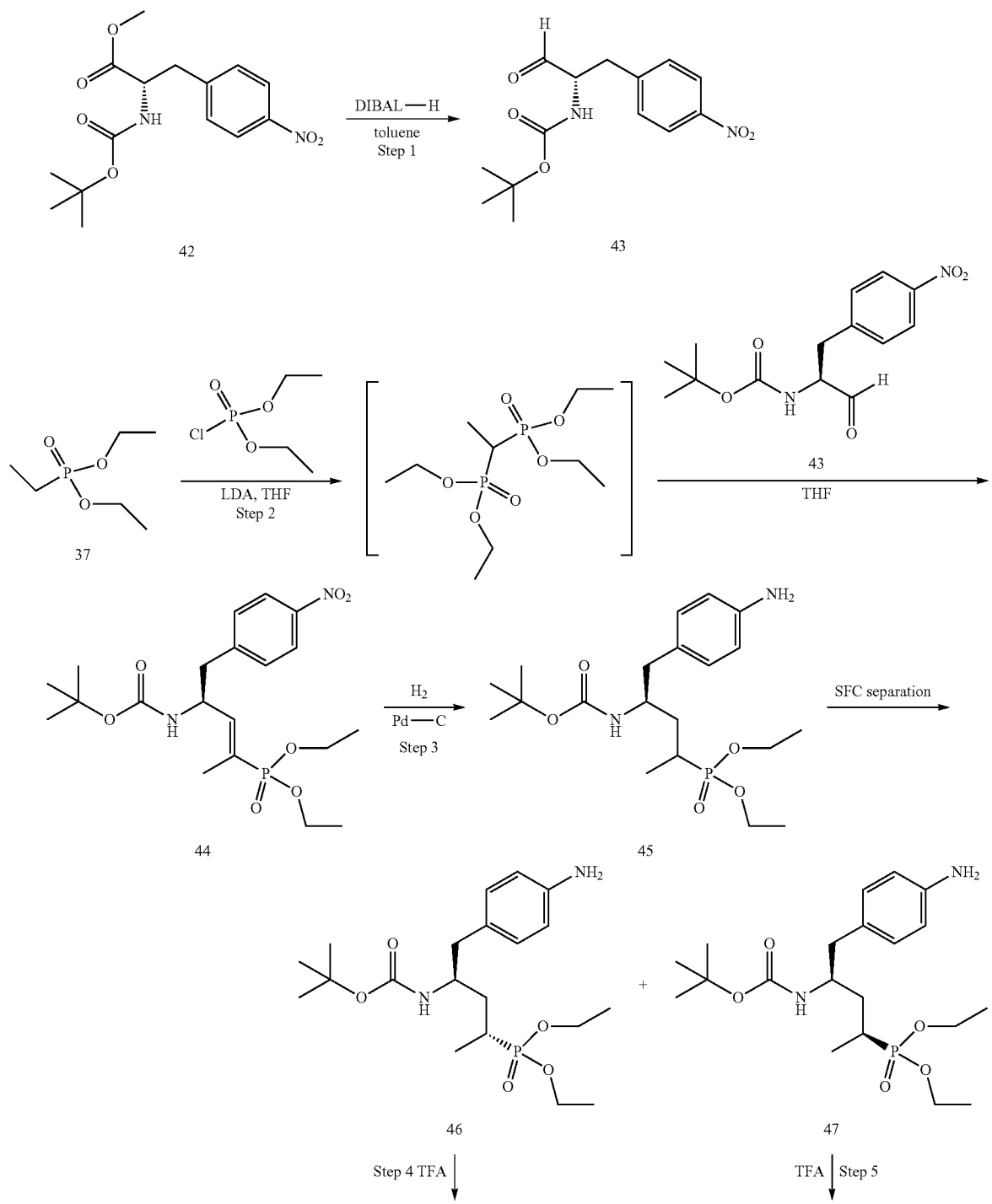

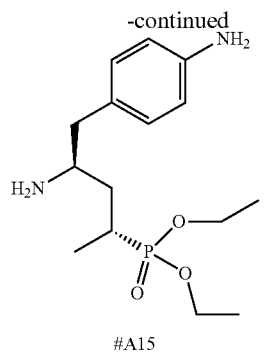

A15

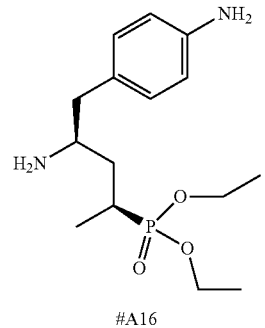

A16

Step 1: Preparation of tert-butyl [(2S)-1-(4-nitrophenyl)-3-oxopropan-2-yl]carbamate (43)

To a solution of methyl N-(tert-butoxycarbonyl)-4-nitro-L-phenylalaninate (42, 29 g, 89.0 mmol) in anhydrous toluene (600 mL) was added DIBAL-H (1 M, 178 mL, 178 mmol) dropwise at −70° C. under $N_2$. After the addition, the reaction was stirred at −70° C. for 30 min. The reaction was quenched with saturated aq. $NH_4Cl$ at −70° C. then warmed to rt and filtered. The filtrate was partitioned between EtOAc and $H_2O$ and the aqueous layer was extracted with EtOAc. The combined organic layers were washed with brine, dried over $Na_2SO_4$, and concentrated to give the title compound 43 (25 g, 95%) as yellow solid, which was used immediately in the next step.

Step 2: Preparation diethyl [(2E,4S)-4-[(tert-butoxycarbonyl)amino]-5-(4-nitrophenyl)pent-2-en-2-yl]phosphonate (44)

The title compound was prepared in 28% yield starting from ethylphosphonate (37, 28.9 mmol), diethyl phosphorochloridate (28.9 mmol), LDA (86.7 mmol), and tert-butyl (S)-(1-(4-nitrophenyl)-3-oxopropan-2-yl)carbamate (43, 28.9 mmol) using the method described above for synthesis of compound 40.

Step 3: Preparation of diethyl {(2R,4S)-5-(4-aminophenyl)-4-[(tert-butoxycarbonyl)amino]pentan-2-yl}phosphonate (46) and diethyl {(2S,4S)-5-(4-aminophenyl)-4-[(tert-butoxycarbonyl)amino]pentan-2-yl}phosphonate (47)

To a solution of tert-butyl (S,E)-(4-(diethoxyphosphoryl)-1-(4-nitrophenyl)pent-3-en-2-yl)carbamate (44, 9.62 g, 21.7 mmol) in MeOH (500 mL) was added 10% Pd—C (3.0 g) under $N_2$. The resulting mixture was heated at 30° C. while stirring under 30 psi of $H_2$ overnight. The reaction was filtered, the filtrate concentrated, and the resulting residue was purified by silica gel chromatography (10% MeOH in DCM) to give 45 as a mixture of isomers (4.3 g), which was further separated by chiral SFC (Column: ChiralPak AD, 300×50 mm I.D. 10 μm, Mobile Phase 30% B (0.1% Ammonium Hydroxide in IPA) in A:$CO_2$, flow rate 240 mL/min, Temp: 38° C. to afford title compound 46 (1.5 g) (Retention time: 6.04 min) and title compound 47 (770 mg) (Retention time: 7.08 min) as yellow oils which were used directly in the next step (Note: the stereochemical assignment at the carbon center containing phosphorous substitution is arbitrary).

Step 4: Preparation of diethyl [(2R,4S)-4-amino-5-(4-aminophenyl)pentan-2-yl]phosphonate (# A15)

To a solution of diethyl {(2R,4S)-5-(4-aminophenyl)-4-[(tert-butoxycarbonyl)amino]pentan-2-yl}phosphonate (46, 1.5 g, 3.62 mmol) in DCM (15 mL) at 0° C. was added trifluroacetic acid (9 mL) dropwise. The reaction mixture was stirred at rt for 3 h and concentrated under vacuum. The residue was purified by preparative HPLC (Column: Synergi 50×250 mm I.D., 10 μm; Mobile phase: 0% acetonitrile (0.225% TFA) in $H_2O$ to 20% acetonitrile (0.225% TFA) in $H_2O$; Wavelength: 220 nm) to give the title compound # A15 (1.45 g, quantitative yield) as a yellow solid.

$^1$H NMR (400 MHz, DMSO-d6): δ 7.88 (br, 3H), 7.14 (m, 2H), 6.93 (m, 2H), 3.96 (m, 4H), 3.52 (m, 1H), 2.85 (m, 1H), 2.72 (m, 1H), 2.08 (m, 1H), 1.82 (m, 1H), 1.56 (m, 1H) 1.20 (m, 6H), 1.02 (m, 3H). m/z 315.2 [M+H]$^+$; 100% ee; Column: Chiralpak AD-3 150×4.6 mm I.D., 3 μm, Mobile phase: methanol (0.05% diethylamine) in $CO_2$ from 5% to 40%; Wavelength: 220 nm, Retention time=4.83 min.

Step 5: Preparation of diethyl [(2S,4S)-4-amino-5-(4-aminophenyl)pentan-2-yl]phosphonate (# A16)

To a solution of diethyl {(2S,4S)-5-(4-aminophenyl)-4-[(tert-butoxycarbonyl)amino]pentan-2-yl}phosphonate (47, 0.77 g, 1.86 mmol) in DCM (10 mL) at 0° C. was added TFA (4.5 mL) dropwise. The reaction mixture was stirred at rt for 3 h and concentrated under vacuum. The residue was purified by preparative HPLC (Column: Synergi 50×250 mm I.D., 10 μm; Mobile phase: 0% acetonitrile (0.225% TFA) in $H_2O$ to 30% acetonitrile (0.225% TFA) in $H_2O$; Wavelength: 220 nm) to give title compound # A16 (0.67 g, 100%) as a yellow solid.

$^1$H NMR (400 MHz, DMSO-d6): δ 7.93 (br, 3H), 7.13 (br, 2H), 6.95 (br, 2H), 3.99 (m, 4H), 3.48 (m, 1H), 2.87 (m, 1H), 2.71 (m, 1H), 2.15 (m, 1H), 1.79 (m, 1H), 1.35 (m, 1H) 1.21 (m, 6H), 0.94 (m, 3H); m/z: 315.2 [M+H]$^+$; 97% ee; Column: Chiralpak AD-3 150×4.6 mm I.D., 3 μm; Mobile phase: methanol (0.05% diethylamine) in $CO_2$ from 5% to 40%; Wavelength: 220 nm; Retention time=5.23 min.

Preparation of 1,2-dimethyl-D-prolyl-N-{(1R,3R)-1-(4-carboxy-1,3-thiazol-2-yl)-1-[(ethylcarbamoyl)amino]-4-methylpentan-3-yl}-N-methyl-L-isoleucinamide (# A17)

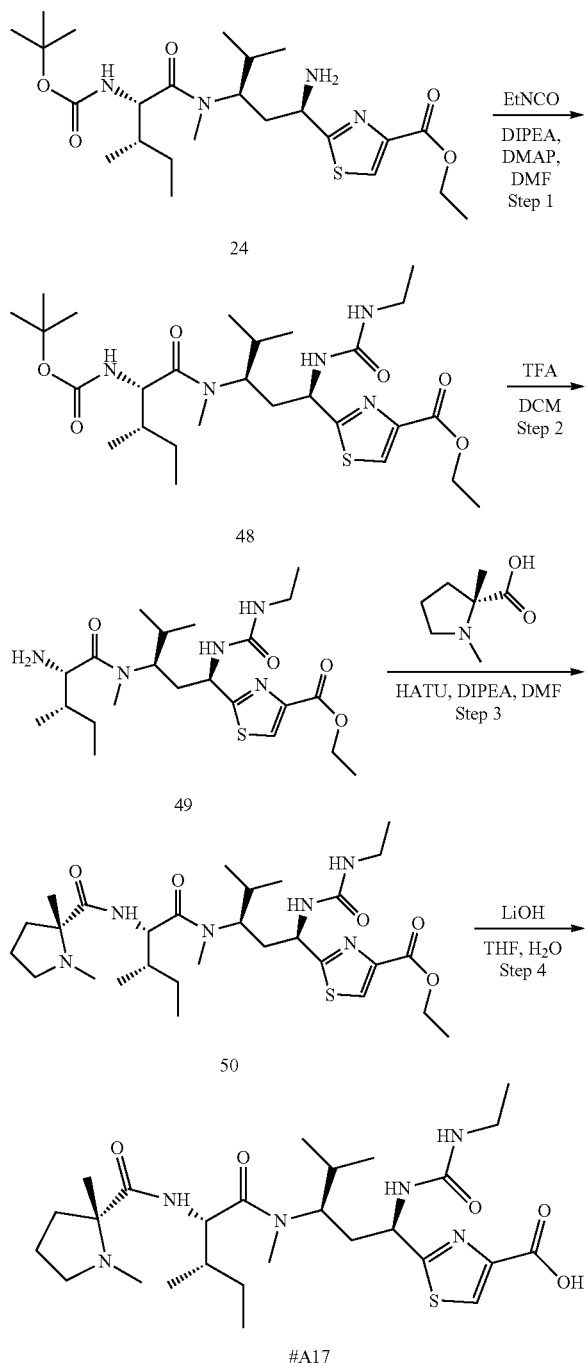

Step 1: Preparation of ethyl 2-{(1R,3R)-3-{[N-(tert-butoxycarbonyl)-L-isoleucyl](methyl)amino}-1-[(ethylcarbamoyl)amino]-4-methylpentyl}-1,3-thiazole-4-carboxylate (48)

To a stirred solution of ethyl 2-[(1R,3R)-1-amino-3-{[N-(tert-butoxycarbonyl)-L-isoleucyl](methyl)amino}-4-methylpentyl]-1,3-thiazole-4-carboxylate (24, 0.7 g, 1.40 mmol) and DMAP (343 mg, 2.81 mmol) in dry DMF (20 mL) at 0° C. was added DIPEA (1.81 g, 2.45 mL, 10 mmol) and ethyl isocyanate (2.49 g, 35.1 mmol) and the reaction mixture was stirred at 20° C. for 3 h. The reaction mixture was poured into H$_2$O (100 mL) and extracted with EtOAc (30 mL). The organic phase was dried over Na$_2$SO$_4$ and concentrated in vacuo. The residue was purified by silica gel chromatography (10% MeOH in DCM) to afford the title compound 48 (1.0 g, 125%) as a yellow oil. m/z 570.1 [M+H]$^+$ and 592 [M+Na]$^+$.

Step 2: Preparation of ethyl 2-{(1R,3R)-1-[(ethylcarbamoyl)amino]-3-[L-isoleucyl(methyl)amino]-4-methylpentyl}-1,3-thiazole-4-carboxylate (49)

To a solution of ethyl 2-{(1R,3R)-3-{[N-(tert-butoxycarbonyl)-L-isoleucyl](methyl)amino}-1-[(ethylcarbamoyl)amino]-4-methylpentyl}-1,3-thiazole-4-carboxylate (48, 1.0 g, 1.755 mmol) in DCM (20 mL) at 0° C. was added TFA (4 mL) dropwise and the solution was stirred at 15° C. for 3 h. The reaction mixture was concentrated under vacuum to afford the title compound 49 (1.1 g, quantitative yield) as a yellow oil, which was used crude in the next step. m/z 470.3 [M+H]$^+$.

Step 3: Preparation of 1,2-dimethyl-D-prolyl-N-{(1R,3R)-1-[4-(ethoxycarbonyl)-1,3-thiazol-2-yl]-1-[(ethylcarbamoyl)amino]-4-methylpentan-3-yl}-N-methyl-L-isoleucinamide (50)

To a solution of 1,2-dimethyl-D-Proline (Doroski et al., U.S. Pat. No. 8,828,401 B2) (183 mg, 1.28 mmol) and DIPEA (688 mg, 0.927 mL, 5.32 mmol) in DMF (20 mL) at 0° C. was added HATU (486 mg, 1.28 mmol) and the mixture was stirred at 15° C. for 2 h. Ethyl 2-{(1R,3R)-1-[(ethylcarbamoyl)amino]-3-[L-isoleucyl(methyl)amino]-4-methylpentyl}-1,3-thiazole-4-carboxylate (49, 500 mg, 1.06 mmol) was added and the solution was stirred at 15° C. for 15 h. The reaction mixture was concentrated in vacuo to afford the crude title compound 50 (2.0 g, quantitative yield). m/z 595.4 [M+H]$^+$ and 616.4 [M+Na]$^+$.

Step 4: Preparation of 1,2-dimethyl-D-prolyl-N-{(1R,3R)-1-(4-carboxy-1,3-thiazol-2-yl)-1-[(ethylcarbamoyl)amino]-4-methylpentan-3-yl}-N-methyl-L-isoleucinamide (# A17)

A solution of 1,2-dimethyl-D-prolyl-N-{(1R,3R)-1-[4-(ethoxycarbonyl)-1,3-thiazol-2-yl]-1-[(ethylcarbamoyl)amino]-4-methylpentan-3-yl}-N-methyl-L-isoleucinamide (50, 830 mg, 1.43 mmol) and LiOH (334 mg, 12.0 mmol) in THF (16 mL) and H$_2$O (4 mL) was stirred at 17° C. for 3 h. The solution was acidified to pH=7 by addition of 1.0 N HCl and the reaction mixture was directly purified by preparative HPLC (Column: YMC-Actus Triart C18, 150×30 mm I.D., 5 μm; Mobile Phase A: H$_2$O (0.1% TFA), Mobile Phase B: acetonitrile (0.1% TFA), 5% B to 55% B over 11 min, hold at 100% B for 2.0 min) to afford title compound # A17 (296 mg, 37%) as a solid.

$^1$H NMR (400 MHz, DMSO-d6) δ 9.73 (br. s., 1H), 8.78-8.60 (m, 1H), 8.36-8.18 (m, 1H), 6.78 (br. s., 1H), 5.97 (br. s., 1H), 4.72-4.51 (m, 2H), 3.55 (br. s., 2H), 3.24-3.09 (m, 1H), 3.08-2.91 (m, 5H), 2.75-2.65 (m, 3H), 2.36-2.20 (m, 2H), 2.12-1.75 (m, 6H), 1.57-1.38 (m, 4H), 1.17-1.02 (m, 1H), 0.98 (t, J=7.2 Hz, 3H), 0.91 (d, J=6.5 Hz, 3H), 0.88-0.80 (m, 6H), 0.76 (br. s., 2H); 100% ee; Column:

Chiralpak AS-H 250×4.6 mm I.D., 5 μm; Mobile phase: A: $CO_2$ B: ethanol (0.05% diethylamine); 5% to 40% B over 5 min, hold at 40% for 3 min then 5% B for 1.5 min; Flow rate: 2.5 mL/min; Column temp: 35° C.; Retention time=4.18 min.

Preparation of 2-Methyl-2-azabicyclo[3.1.1]heptane-1-carboxylic acid (52)

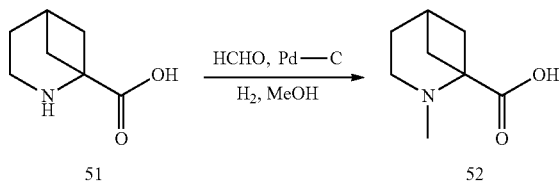

To a solution of 2-azabicyclo[3.1.1]heptane-1-carboxylic acid (*J. Org. Chem.* 2009, 74, 5541) (50, 10 g, 70.837 mmol) in MeOH (100 mL) was added formaldehyde. The resulting reaction mixture was stirred at rt for 3 h and Pd—C (5 g, 50% moisture) was added. The black suspension was hydrogenated under 40 psi $H_2$ for 16 h. The reaction mixture was filtered through celite and the filtrate was concentrated under reduced pressure to afford title compound 52 (4.6 g, 41.86%) as an off-white solid.

$^1$H NMR (400 MHz, DMSO-d6): δ 3.31 (t, 2H), 2.65 (s, 3H), 2.35-2.39 (m, 1H), 2.27-2.34 (m, 2H), 1.95-1.99 (m, 2H), 1.79-1.84 (m, 2H).

Preparation of 2-methyl-2-azabicyclo[2.1.1]hexane-1-carboxylic acid (54)

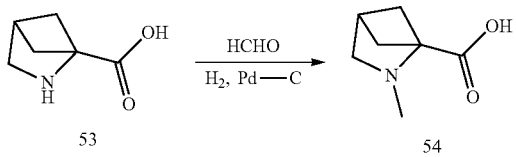

To a solution of 2-azabicyclo[2.1.1]hexane-1-carboxylic acid (Chem. Comm. 2002, 3, 250) (53, 11 g, 86.5 mmol) in MeOH (180 mL), was added formaldehyde solution (22 mL) followed by Pd—C (3.5 g) under $N_2$. The resulting reaction mixture was reacted under a 60 psi $H_2$ atmosphere for 12 h. The reaction mixture was filtered through celite, rinsing with methanol (160 mL×3). The filtrate was evaporated under reduced pressure and the residue was triturated with methanol in diethyl ether (1:1, 20 ml) to obtain compound 9 (9.85 g, 81%) as an off-white solid.

$^1$H NMR (400 MHz, $CD_3OD$): δ 3.78 (d, 1H), 3.13 (d, 1H), 2.99 (s, 3H), 2.81 (br.s, 1H), 2.36 (br.s, 2H), 1.94 (m, 1H), 1.81 (m, 1H).

Preparation of 1,2-dimethyl-D-prolyl-N-[(1 S,3R)-1-(4-carboxy-1,3-thiazol-2-yl)-1-hydroxy-4-methylpentan-3-yl]-N-methyl-L-isoleucinamide (# A18)

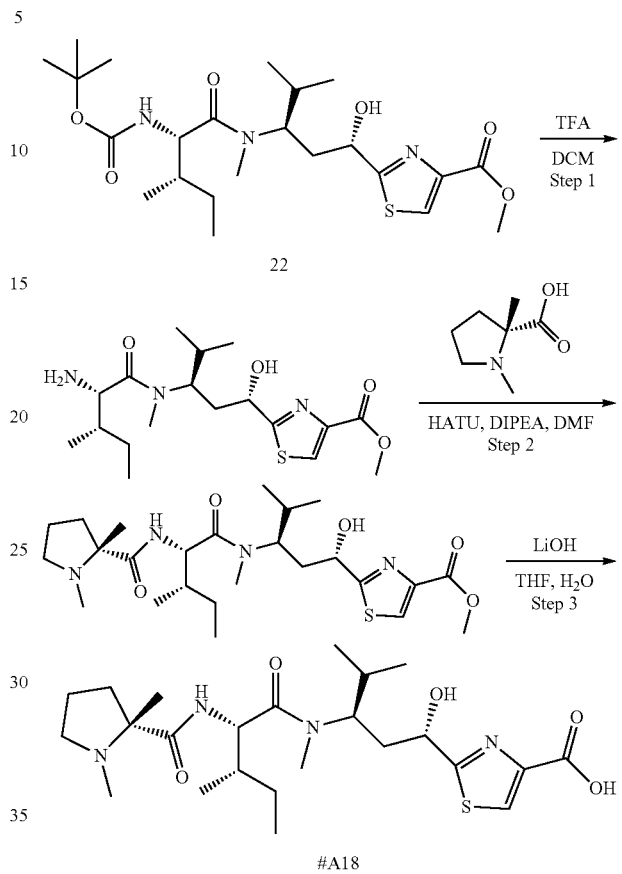

Steps 1-3: The title compound # A18 was prepared in an overall yield of 16% starting from 500 mg (1.03 mmol) of methyl 2-[(1 S,3R)-3-{[N-(tert-butoxycarbonyl)-L-isoleucyl](methyl)amino}-1-hydroxy-4-methylpentyl]-1,3-thiazole-4-carboxylate (22) using the method described for the preparation of compounds # A14 and 20.

$^1$H NMR (400 MHz, DMSO-d6): δ 9.80 (br, 1H), 8.75 (d, 1H), 8.38 (br, 1H), 4.67-4.54 (m, 2H), 4.20 (m, 1H), 3.56 (m, 2H), 3.16 (m, 1H), 2.98 (m, 3H), 2.68 (s, 3H), 2.30-1.81 (m, 8H), 1.48 (m, 4H), 1.11-0.68 (m, 12H); m/z 497.2 [M+H]$^+$; 100% ee; Column: Chiralpak AD-3 150×4.6 mm I.D., 3 μm; Mobile phase: ethanol (0.05% diethylamine) in $CO_2$ from 5% to 40%, Wavelength: 230 nm; Retention time=5.54 min.

Preparation of 1,2-dimethyl-D-prolyl-N-{(1R,3R)-1-(4-carboxy-1,3-thiazol-2-yl)-1-[(ethylcarbamoyl)oxy]-4-methylpentan-3-yl}-N-methyl-L-isoleucinamide (# A19)

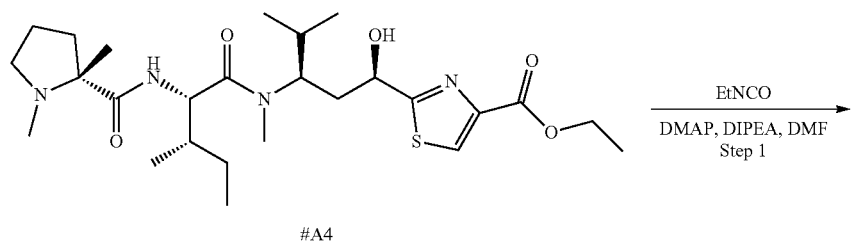

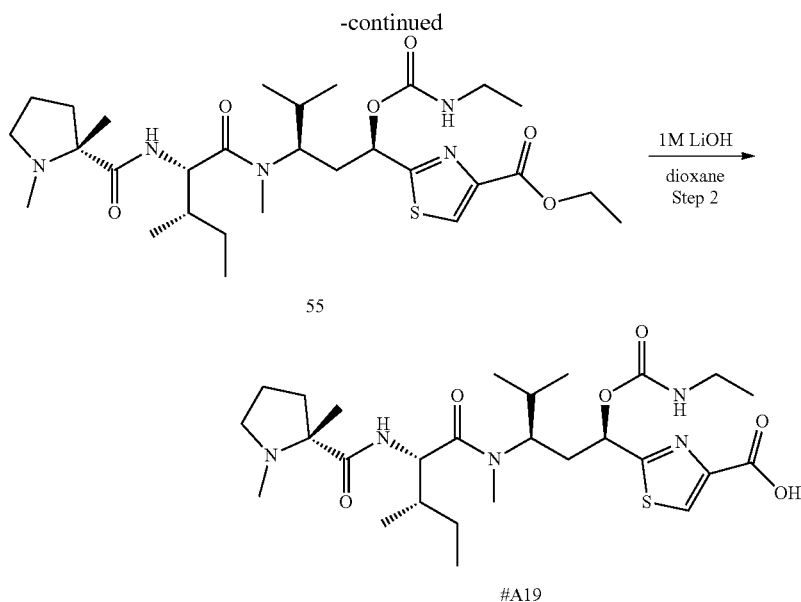

Step 1: Preparation of 1,2-dimethyl-D-prolyl-N-{(1R,3R)-1-[4-(ethoxycarbonyl)-1,3-thiazol-2-yl]-1-[(ethylcarbamoyl)oxy]-4-methylpentan-3-yl}-N-methyl-L-isoleucinamide (55)

To a vial containing 1,2-dimethyl-D-prolyl-N-{(1R,3R)-1-[4-(ethoxycarbonyl)-1,3-thiazol-2-yl]-1-hydroxy-4-methylpentan-3-yl}-N-methyl-L-isoleucinamide (# A4, 85 mg, 0.162 mmol) and DMAP (36 mg, 0.300 mmol) was added DMF (1.2 mL) and ethyl isocyanate (580 μL, 7.25 mmol). The reaction was stirred in a capped vial at rt for 22.5 h then the reaction was concentrated and the residue was purified by medium pressure reverse phase C18 chromatography (10% to 95% acetonitrile in $H_2O$ over 25 minutes, each solvent containing 0.02% TFA) to provide title compound 55 (69 mg, 84%) as a glassy yellow solid. LC-MS (Protocol C): m/z 596.7 [M+H]$^+$, retention time=0.72 min.

Step 2: Preparation of 1,2-dimethyl-D-prolyl-N-{(1R,3R)-1-(4-carboxy-1,3-thiazol-2-yl)-1-[(ethylcarbamoyl)oxy]-4-methylpentan-3-yl}-N-methyl-L-isoleucinamide (# A19)

To a vial containing 1,2-dimethyl-D-prolyl-N-{(1R,3R)-1-[4-(ethoxycarbonyl)-1,3-thiazol-2-yl]-1-[(ethylcarbamoyl)oxy]-4-methylpentan-3-yl}-N-methyl-L-isoleucinamide (55, 66 mg, 0.110 mmol) in 1,4-dioxane (5.5 mL) was added 1 M LiOH in water (330 μL) and the reaction was stirred at rt for 6 h then quenched with HOAc (60 μL) and concentrated. The crude residue was purified by medium pressure reverse phase C18 chromatography (10% to 95% acetonitrile in $H_2O$ over 25 minutes, each solvent containing 0.02% TFA) to provide the title compound # A19 (53 mg, 84% yield) as a glassy solid. LC-MS (Protocol C): m/z 568.6 [M+H]$^+$; Retention time=0.63 min.

Preparation of N-(tert-butoxycarbonyl)-N-methyl-D-valyl-N-[(1R,3R)-1-(acetyloxy)-1-(4-carboxy-1,3-thiazol-2-yl)-4-methylpentan-3-yl]-N-methyl-L-isoleucinamide (# A20)

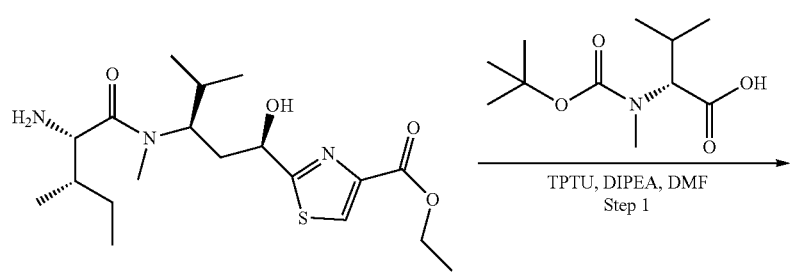

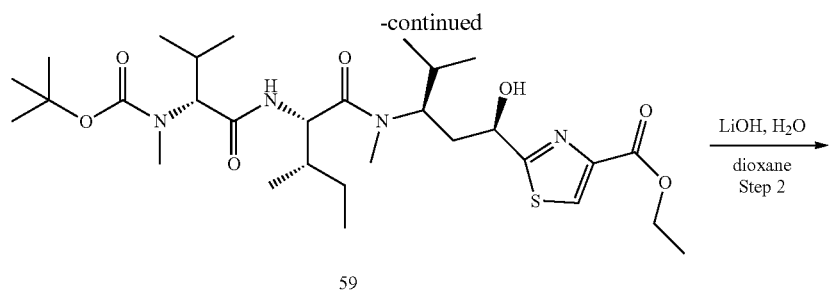

59

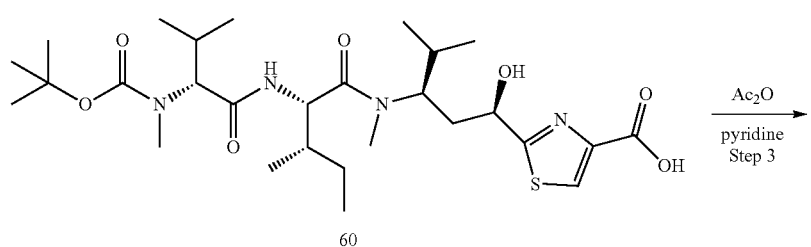

60

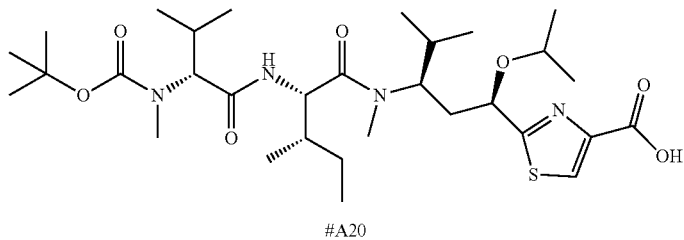

A20

Step 1: Preparation of N-(tert-butoxycarbonyl)-N-methyl-D-valyl-N-{(1R,3R)-1-[4-(ethoxycarbonyl)-1,3-thiazol-2-yl]-1-hydroxy-4-methylpentan-3-yl}-N-methyl-L-isoleucinamide (59)

To a solution of N-(tert-butoxycarbonyl)-N-methyl-D-valine (1.2 g, 5.11 mmol) and DIPEA (1.6 g, 12.78 mmol) in DMF (20 mL) at 0° C. was added TPTU (1.5 g, 5.11 mmol). After stirring 15 min at 0° C. ethyl 2-{(1R,3R)-1-hydroxy-3-[L-isoleucyl(methyl)amino]-4-methylpentyl}-1,3-thiazole-4-carboxylate (17, 1.7 g, 4.26 mmol) in DMF (5 mL) was added dropwise and the resulting solution was stirred at rt overnight. The reaction mixture was poured into H$_2$O (50 mL) and the solution was extracted with EtOAc (30 mL×2). The organic phase was washed with saturated aqueous NaHCO$_3$ (20 mL) and brine (20 mL), dried over Na$_2$SO$_4$, and concentrated in vacuo to afford crude title compound 59 (2.8 g, quantitative yield) as a yellow oil, which was used without further purification.

Step 2: Preparation of N-(tert-butoxycarbonyl)-N-methyl-D-valyl-N-[(1R,3R)-1-(4-carboxy-1,3-thiazol-2-yl)-1-hydroxy-4-methylpentan-3-yl]-N-methyl-L-isoleucinamide (60)

The title compound was prepared in 93% yield from N-(tert-butoxycarbonyl)-N-methyl-D-valyl-N-{(1R,3R)-1-[4-(ethoxycarbonyl)-1,3-thiazol-2-yl]-1-hydroxy-4-methylpentan-3-yl}-N-methyl-L-isoleucinamide (59, 7.4 mmol) and LiOH monohydrate (29.6 mmol) using the procedure described above for compound 19.

Step 3: Preparation of N-(tert-butoxycarbonyl)-N-methyl-D-valyl-N-[(1R,3R)-1-(acetyloxy)-1-(4-carboxy-1,3-thiazol-2-yl)-4-methylpentan-3-yl]-N-methyl-L-isoleucinamide (# A20)

The title compound was prepared in 60% yield from N-(tert-butoxycarbonyl)-N-methyl-D-valyl-N-[(1R,3R)-1-(4-carboxy-1,3-thiazol-2-yl)-1-hydroxy-4-methylpentan-3-yl]-N-methyl-L-isoleucinamide (60, 6.84 mmol) and acetic anhydride (8 mL) and pyridine (40 mL) using the procedure described above for compound # A3.

$^1$H NMR (400 MHz, DMSO-d6): δ 8.34 (d, 1H), 7.99 (d, 1H), 5.52 (d, 1H), 4.60 (m, 1H), 4.40 (m, 1H), 4.26 (m, 1H), 4.04 (m, 1H), 2.97 (m, 3H), 2.69 (m, 3H), 2.19 (m, 6H), 1.87 (m, 1H), 1.71 (m, 1H), 1.47 (m, 10H), 1.10 (m, 1H), 0.91 (m, 16H), 0.62 (m, 3H); m/z 649.1 [M+Na]$^+$; Column: Chiralcel AD-H 150×4.6 mm I.D., 5 μm; Mobile phase: ethanol (0.05% diethylamine) in CO$_2$ from 5% to 40%, Wavelength: 220 nm; Retention time=2.71 min.

Preparation of ethyl 2-{(1R,3R)-3-[(N-{[(2R)-1,2-dimethylpiperidin-2-yl]carbonyl}-L-isoleucyl)(methyl)amino]-1-hydroxy-4-methylpentyl}-1,3-thiazole-4-carboxylate (# A21) and ethyl 2-{(1R,3R)-3-[(N-{[(2S)-1,2-dimethylpiperidin-2-yl]carbonyl}-L-isoleucyl)(methyl)amino]-1-hydroxy-4-methylpentyl}-1,3-thiazole-4-carboxylate (# A22)

containing 0.2% NH$_4$OH; Flow Rate 80 mL/min) to afford title compounds # A21 and # A22.

Title compound # A21 (arbitrarily assigned as the R-piperidine diastereomer):

95.6% ee; Chiral SFC Column: Chiral Tech AD-H 250 mm×4.6 mm 5 µm, Mobile Phase A: CO$_2$, Mobile Phase B:

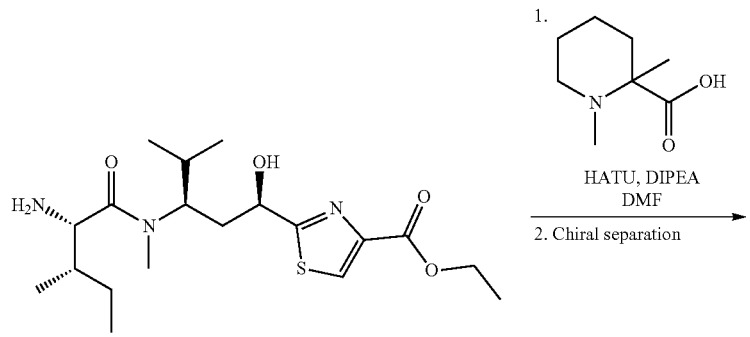

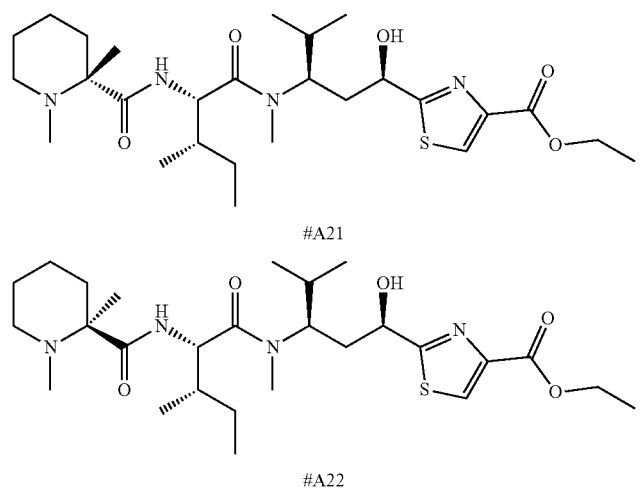

To a vial containing 1,2-dimethylpiperidine-2-carboxylic acid (141 mg, 0.900 mmol) and HATU (461 mg, 1.2 mmol) was added DCM (1 mL), DMF (10 mL), and DIPEA (844 µL, 4.80 mmol). The reaction was stirred for 1.75 h at rt then added to a vial containing ethyl 2-{(1R,3R)-1-hydroxy-3-[L-isoleucyl(methyl)amino]-4-methylpentyl}-1,3-thiazole-4-carboxylate (17, 308 mg, 0.6 mmol). Additional DMF (1.5 mL) was added and reaction was stirred at rt for 18 h. The reaction was concentrated and purified by medium pressure reverse phase C18 chromatography (10% to 95% acetonitrile in H$_2$O over 25 minutes, each solvent containing 0.02% TFA) to provide 372 mg of a mixture of # A21 and # A22 (25). The mixture was prepped further by chiral SFC (Column: Chiral Tech AD-H 500 mm×21.2 mm I.D., 5 µm; Mobile Phase A: 92.5% CO$_2$, Mobile Phase B: 7.5% ethanol ethanol containing 0.2% NH$_4$OH; 5% B over 1.0 minute then 60% B over 8.5 minutes and 5% B over 1.5 minutes; Retention time=4.49 min.

LC-MS (Protocol C): m/z 539.5 [M+H]$^+$; Retention time=0.65 min.

Title compound # A22 (arbitrarily assigned as the S-piperidine diastereomer): 97.6% ee: Chiral SFC: Column: Chiral Tech AD-H 250 mm×4.6 mm 5 µm, Mobile Phase A: CO$_2$, Mobile Phase B: ethanol containing 0.2% NH$_4$OH; 5% B over 1.0 minute to 60% B over 8 minutes and 5% B over 1.5 minutes; Retention time=4.71 min.

LC-MS (Protocol C): m/z 539.5 [M+Na]$^+$; Retention time=0.67 min.

Preparation of 2-{(1R,3R)-1-(acetyloxy)-3-[(N-{[(2S)-1,2-dimethylpiperidin-2-yl]carbonyl}-L-isoleucyl)(methyl)amino]-4-methylpentyl}-1,3-thiazole-4-carboxylic Acid (# A23)

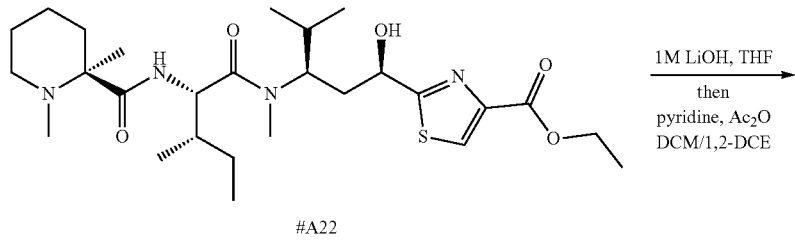

A22

1M LiOH, THF
then
pyridine, Ac$_2$O
DCM/1,2-DCE

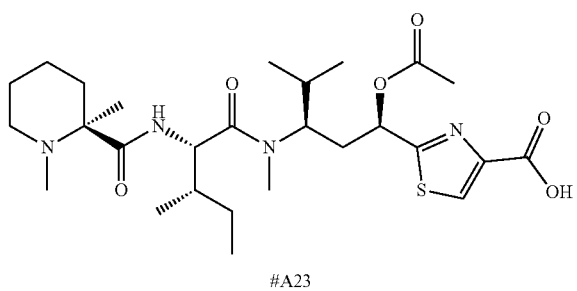

A23

The target was prepared in near quantitative yield from ethyl 2-{(1R,3R)-3-[(N-{[(2S)-1,2-dimethylpiperidin-2-yl]carbonyl}-L-isoleucyl)(methyl)amino]-1-hydroxy-4-methylpentyl}-1,3-thiazole-4-carboxylate (# A22, 0.089 mmol) using the method described above for compound # A5. LC-MS (Protocol C): m/z 553.3 [M+H]$^+$; Retention time=0.67 minutes.

Preparation of 2-{(1R,3R)-3-[(N-{[(2R)-1,2-dimethylpiperidin-2-yl]carbonyl}-L-isoleucyl)(methyl)amino]-1-[(ethylcarbamoyl)oxy]-4-methylpentyl}-1,3-thiazole-4-carboxylic acid (# A24) and 2-{(1R,3R)-3-[(N-{[(2S)-1,2-dimethylpiperidin-2-yl]carbonyl}-L-isoleucyl)(methyl)amino]-1-[(ethylcarbamoyl)oxy]-4-methylpentyl}-1,3-thiazole-4-carboxylic acid (# A25)

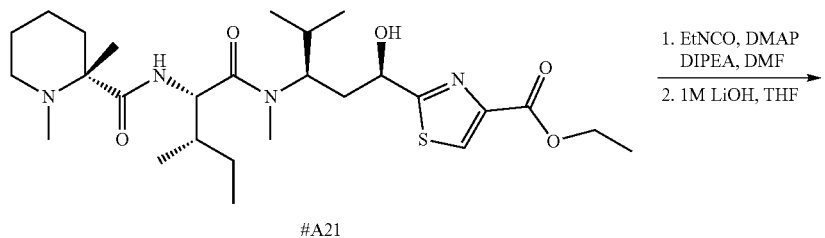

A21

1. EtNCO, DMAP
   DIPEA, DMF
2. 1M LiOH, THF

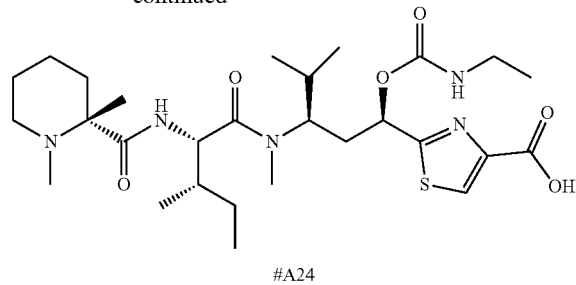

A24

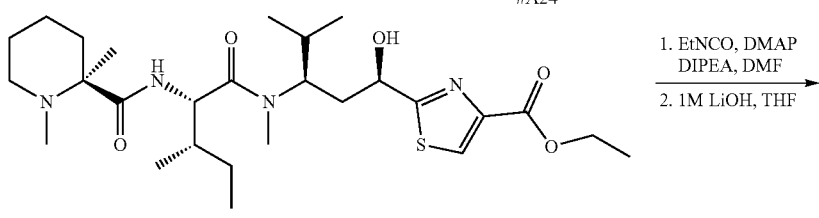

A22

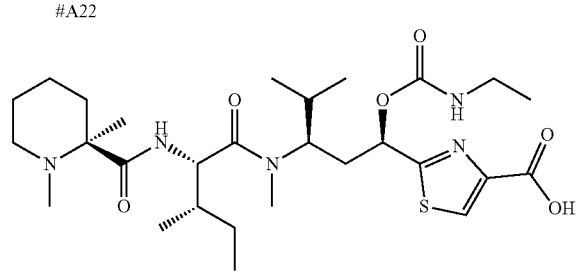

A25

The title compounds # A24 and # A25 were prepared in yields of 61% and 72% from ethyl 2-{(1R,3R)-3-[(N-{[(2R)-1,2-dimethylpiperidin-2-yl]carbonyl}-L-isoleucyl)(methyl)amino]-1-hydroxy-4-methylpentyl}-1,3-thiazole-4-carboxylate (# A21, 0.11 mmol) and ethyl 2-{(1R,3R)-3-[(N-{[(2S)-1,2-dimethylpiperidin-2-yl]carbonyl}-L-isoleucyl)(methyl)amino]-1-hydroxy-4-methylpentyl}-1,3-thiazole-4-carboxylate (# A22, 0.1 mmol), respectively, using the method described above for # A19.

A24: LC-MS (Protocol C): m/z 582.3 [M+H]⁺; Retention time=0.66 min.

A25: LC-MS (Protocol C): m/z 582.5 [M+H]⁺; Retention time=0.62 min.

Preparation of 1-[5-(4-acetylphenoxy)pentyl]-1H-pyrrole-2,5-dione (# A26)

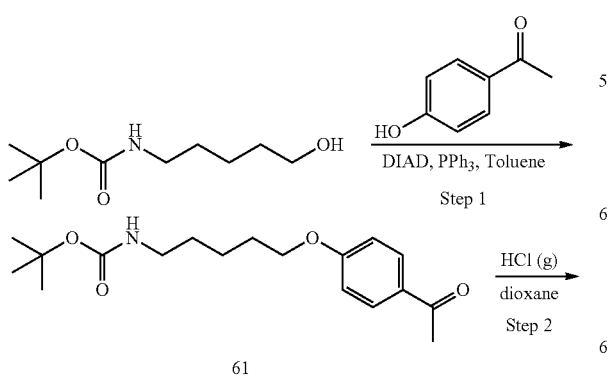

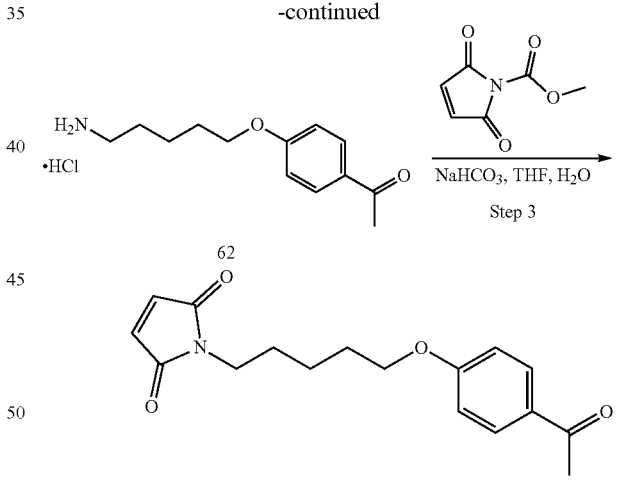

A26

Step 1: Preparation of tert-butyl [5-(4-acetylphenoxy)pentyl]carbamate (61)

To the mixture of tert-butyl (5-hydroxypentyl)carbamate (5 g, 24.6 mmol) and 1-(4-hydroxyphenyl)ethanone (3.35 g, 24.6 mmol) and triphenylphosphine (7.24 g, 27.1 mmol.) in anhydrous toluene (50 mL) was added DIAD (5.48 g, 27.1 mmol) dropwise at 0 to 10° C. under N₂. After the addition, the solution was stirred at rt for 1 h. The mixture was diluted with EtOAc and washed with aq. NH₄Cl and brine. The organic layers were dried over Na₂SO₄ and concentrated under vacuum. The residue was purified by silica gel chromatography (5% to 15% EtOAc in hexanes) to afford title compound 61 (4.55 g, 58%) as a colorless oil.

Step 2: Preparation of 1-{4-[(5-aminopentyl)oxy]phenyl}ethanone hydrochloride (62)

To a solution of tert-butyl [5-(4-acetylphenoxy)pentyl]carbamate (61, 4.55 g, 14.17 mol) in dioxane (50 mL) was added 4 M HCl in dioxane (50 mL) at 0-10° C., and the reaction was stirred at rt for 3 h. The precipitated solid was collected by filtration and washed with DCM. The solid was dried under reduced pressure to give title compound 62 (2.57 g, 70%) as a white solid.

Step 3: Preparation of 1-[5-(4-acetylphenoxy)pentyl]-1H-pyrrole-2,5-dione (# A26)

To a solution of 1-{4-[(5-aminopentyl)oxy]phenyl}ethanone hydrochloride (62, 2.57 g, 10.0 mmol) in THF (70 mL) was added aq. $K_2CO_3$ (40 mL) at 0-10° C. Methyl 2,5-dioxo-2,5-dihydro-1H-pyrrole-1-carboxylate (1.86 g, 12.0 mmol) was added and the reaction mixture was stirred at rt for 1 hour and extracted with EtOAc (50 mL×3). The combined organic layers were washed with brine, dried over $Na_2SO_4$, and concentrated under vacuum. The residue was purified by silica gel chromatography (5% to 10% EtOAc in hexanes) to afford the target compound # A26 (2.51 g, 84%) as a white solid.

$^1$H NMR (400 MHz, $CDCl_3$): δ 7.92 (d, 2H), 6.91 (d, 2H), 6.70 (s, 2H), 4.01 (m, 2H), 3.56 (m, 2H), 2.54 (s, 3H), 1.84 (m, 2H), 1.69 (m, 2H), 1.48 (m, 2H); m/z 302.1 $[M+H]^+$.

Preparation of 1,2-dimethyl-D-prolyl-N-{(1R,3R)-1-(4-carboxy-1,3-thiazol-2-yl)-4-methyl-1-[(methylcarbamoyl)oxy]pentan-3-yl}-N-methyl-L-isoleucinamide (# A27)

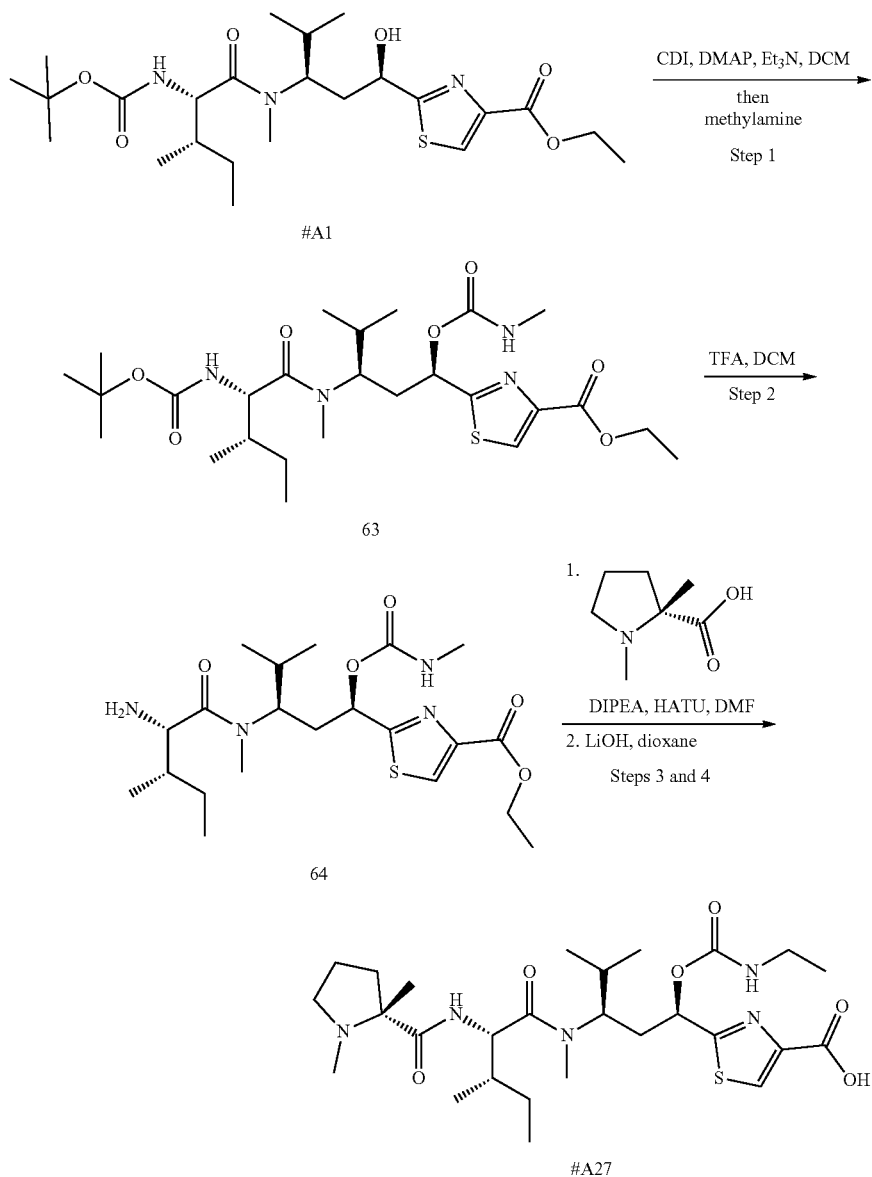

Step 1: Preparation of ethyl 2-{(1R,3R)-3-{[N-(tert-butoxycarbonyl)-L-isoleucyl](methyl)amino}-4-methyl-1-[(methylcarbamoyl)oxy]pentyl}-1,3-thiazole-4-carboxylate (63)

To a vial containing ethyl 2-[(1R,3R)-3-{[N-(tert-butoxycarbonyl)-L-isoleucyl](methyl)amino}-1-hydroxy-4-methylpentyl]-1,3-thiazole-4-carboxylate (# A1, 60 mg, 0.120 mmol) was added DMAP (44 mg, 0.360 mg) and CDI (40 mg, 0.240 mmol) followed by DCM (2 mL). Et₃N (84 μL, 0.600 mmol) was added and the reaction was stirred under N₂ at rt for 20 h. Methylamine (0.9 mL, 2 M in THF) was added and the reaction was stirred at rt for 30 h, concentrated, and the residue purified by reverse phase chromatography (10% to 95% acetonitrile in H₂O over 25 minutes, each solvent containing 0.02% TFA) to afford title compound 63 (64 mg, 95%) as a colorless gum. LC-MS (Protocol C): m/z 579.3 [M+Na]⁺; Retention time=1.0 min.

Step 2: Preparation of ethyl 2-{(1R,3R)-3-[L-isoleucyl(methyl)amino]-4-methyl-1-[(methylcarbamoyl)oxy]pentyl}-1,3-thiazole-4-carboxylate (64)

To a solution of ethyl 2-{(1R,3R)-3-{[N-(tert-butoxycarbonyl)-L-isoleucyl](methyl)amino}-4-methyl-1-[(methylcarbamoyl)oxy]pentyl}-1,3-thiazole-4-carboxylate (63, 64 mg, 0.114 mmol) in DCM (7 mL) and TFA (0.4 mL) and the reaction was stirred at rt under N₂. After 3 h the reaction was concentrated in vacuo and azeotroped with MeOH/acetonitrile (1/1) to afford the title compound as a colorless gum (quantitative yield), which was used crude in the next step. LC-MS (Protocol C): m/z 457.3 [M+Na]⁺; Retention time=0.60 min.

Steps 3 and 4: Preparation of 1,2-dimethyl-D-prolyl-N-{(1R,3R)-1-(4-carboxy-1,3-thiazol-2-yl)-4-methyl-1-[(methylcarbamoyl)oxy]pentan-3-yl}-N-methyl-L-isoleucinamide (# A27)

The title compound was prepared in 65% yield from ethyl 2-{(1R,3R)-3-[L-isoleucyl(methyl)amino]-4-methyl-1-[(methylcarbamoyl)oxy]pentyl}-1,3-thiazole-4-carboxylate (64, 0.179 mmol) and 1,2-dimethyl-D-Proline (Doroski et al., U.S. Pat. No. 8,828,401 B2) (0.215 mmol) using the method described above for compound # A11. LC-MS (Protocol C): m/z 554.6 [M+H]⁺; Retention time=0.61 min.

Preparation of 1,2-dimethyl-D-prolyl-N-{(1R,3R)-1-(4-carboxy-1,3-thiazol-2-yl)-1-[(dimethylcarbamoyl)oxy]-4-methylpentan-3-yl}-N-methyl-L-isoleucinamide (# A28)

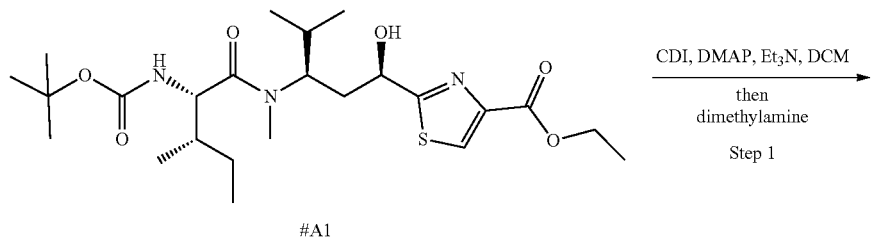

A1

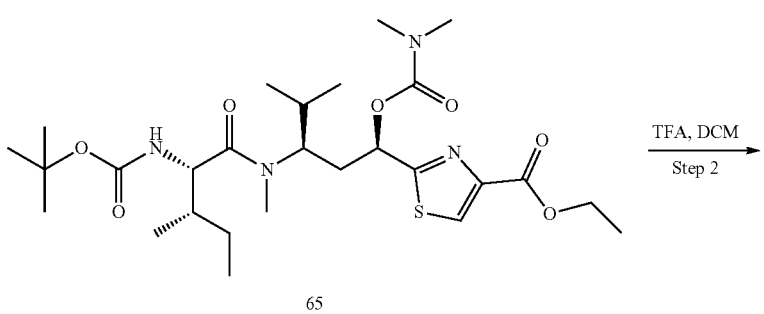

65

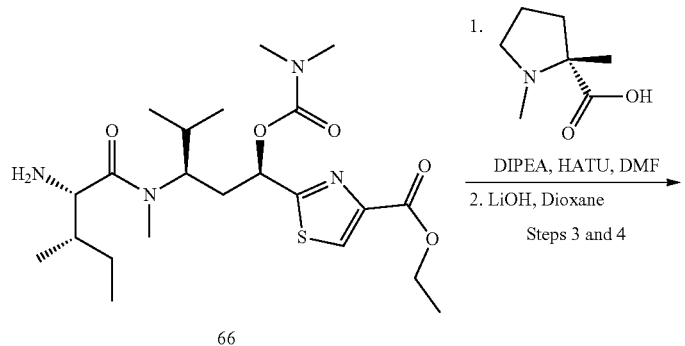

66

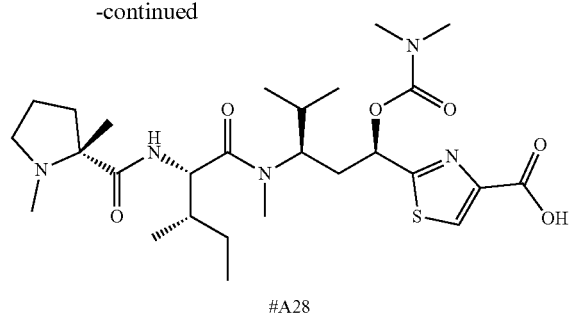

A28

Step 1: Preparation of ethyl 2-{(1R,3R)-3-{[N-(tert-butoxycarbonyl)-L-isoleucyl](methyl)amino}-1-[(dimethylcarbamoyl)oxy]-4-methylpentyl}-1,3-thiazole-4-carboxylate (65)

The title compound 65 was prepared in 97% yield from ethyl 2-[(1R,3R)-3-{[N-(tert-butoxycarbonyl)-L-isoleucyl](methyl)amino}-1-hydroxy-4-methylpentyl]-1,3-thiazole-4-carboxylate (# A1, 0.144 mmol), CDI (0.272 mmol) and N,N-dimethylamine (1.1 mL, 2 M in THF) using the method described above for compound 63. LC-MS (Protocol C): m/z 593.6 [M+Na]$^+$; Retention time=1.01 min.

Step 2: Preparation of ethyl 2-{(1R,3R)-1-[(dimethylcarbamoyl)oxy]-3-[L-isoleucyl(methyl)amino]-4-methylpentyl}-1,3-thiazole-4-carboxylate (66)

The title compound 66 was prepared in quantitative yield from ethyl 2-{(1R,3R)-3-{[N-(tert-butoxycarbonyl)-L-isoleucyl](methyl)amino}-1-[(dimethylcarbamoyl)oxy]-4-methylpentyl}-1,3-thiazole-4-carboxylate (79, 0.131 mmol) and TFA (0.5 mL) using the method described above for compound 64. LC-MS (Protocol C): m/z 471.3 [M+H]$^+$; Retention time=1.01 min.

Steps 3 and 4: Preparation of 1,2-dimethyl-D-prolyl-N-{(1R,3R)-1-(4-carboxy-1,3-thiazol-2-yl)-1-[(dimethylcarbamoyl)oxy]-4-methylpentan-3-yl}-N-methyl-L-isoleucinamide (# A28)

The title compound was prepared in 75% overall yield starting from ethyl 2-{(1R,3R)-1-[(dimethylcarbamoyl)oxy]-3-[L-isoleucyl(methyl)amino]-4-methylpentyl}-1,3-thiazole-4-carboxylate (66, 0.083 mmol) and 1,2-dimethyl-D-Proline, (Doroski et al, U.S. Pat. No. 8,828,401 B2) (0.100 mmol) using the method described above for compound # A11. LC-MS (Protocol C): m/z 568.7 [M+H]$^+$; Retention time=1.01 min.

Preparation of 4-[(2S)-2-amino-2-(1,3-thiazol-2-yl)ethyl]aniline hydrochloric Acid Salt (# A29)

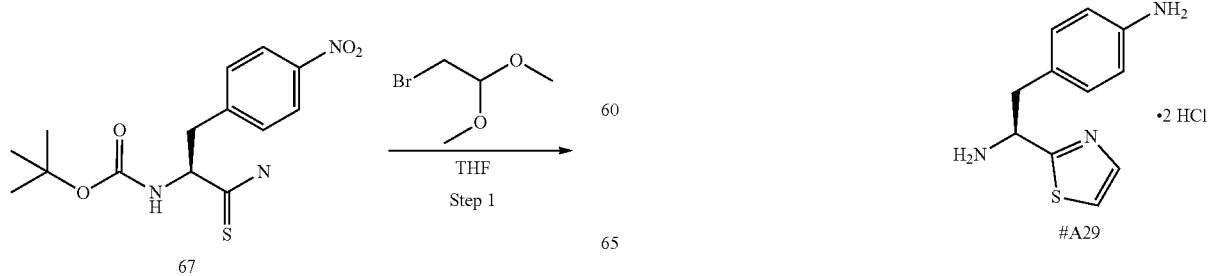

A29

Step 1. Preparation of tert-butyl [(2S)-1-amino-3-(4-nitrophenyl)-1-thioxopropan-2-yl]carbamate (68) and tert-butyl [(2R)-1-amino-3-(4-nitrophenyl)-1-thioxopropan-2-yl]carbamate (69)

To a solution of tert-butyl [(2S)-1-amino-3-(4-nitrophenyl)-1-thioxopropan-2-yl]carbamate (US Patent 2014, 0249100 A1) (67, 1.2 g, 3.69 mmol) in anhydrous THF (37 mL) was added 2-bromo-1,1-dimethoxyethane (3.12 g, 18.44 mmol). After the addition, the reaction mixture was heated at reflux for 3 h with stirring. The reaction mixture was concentrated to dryness and purified by flash silica gel chromatography (5% to 25% EtOAc in petroleum ether) to afford a mixture of title compounds 68 and 69. The mixture was separated via SFC (Column: ChiralCel OJ-H, 250×30 mm I.D., 5 μm; Mobile phase A: $CO_2$; Mobile phase B: ethanol; Gradient: 30% B; 60 mL/min, 100 bar back pressure, 38° C.; Wavelength: 220 nm) to afford pure 68 (200 mg, 16%, Retention time=4.76 min.) and 69 (Retention time=4.45 min.) as yellow solids.

Step 2. Preparation of tert-butyl [(1S)-2-(4-aminophenyl)-1-(1,3-thiazol-2-yl)ethyl]carbamate (70)

To a solution of tert-butyl [(2S)-1-amino-3-(4-nitrophenyl)-1-thioxopropan-2-yl]carbamate (68, 300 mg, 0.859 mmol) in MeOH (15 mL) was added Zn powder (335 mg, 5.15 mmol). The reaction mixture was degassed and bubbled with $N_2$ for 10 min. To the above suspension was added ammonium formate (541 mg, 8.59 mmol) at 0° C. in one portion. The reaction mixture was stirred at rt for 2 h under $N_2$, filtered, and the filter cake washed with MeOH. The combined organic phase was concentrated, the residue partitioned between EtOAc and brine, and the aqueous layer extracted with EtOAc. The combined organic layers were washed with brine, dried over $Na_2SO_4$, and concentrated to a crude product, which was purified via flash silica gel chromatography (1% to 40% EtOAc in petroleum ether) to afford the title compound 70 (215 mg, 78%) as a yellow solid.

Step 3. Preparation of 4-[(2S)-2-amino-2-(1,3-thiazol-2-yl)ethyl]aniline hydrochloric Acid Salt (# A29)

To a solution of tert-butyl [(1S)-2-(4-aminophenyl)-1-(1,3-thiazol-2-yl)ethyl]carbamate (70, 215 mg, 0.673 mmol) in 1,4-dioxane (4 mL) was added 4 N HCl in dioxane (4 mL) at 0° C. After the addition, the reaction mixture was warmed to rt and stirred for 2 h. The reaction mixture was stirred at 20° C. overnight then filtered and the filter cake washed with MTBE, diluted with MeOH, and concentrated under high vacuum. The resulting crude residue was dissolved in $H_2O$ and lyophilized to afford the title compound # A29 (128.5 mg, 75%) as a yellow solid.

$^1$H NMR (400 MHz, DMSO-d6): δ 10.46 (br, 2H), 9.02 (s, 3H), 7.88 (s, 1H), 7.87 (s, 1H), 7.31 (d, 2H), 7.27 (d, 2H), 5.08 (m, 1H), 3.51 (m, 1H), 3.27 (m, 1H); LC-MS (Protocol B): m/z 220.1 [M+H]$^+$; Retention time=0.16 min; 100% ee; Column: Chiralcel OZ-3 150×4.6 mm I.D., 3 μm; Mobile phase: 5% to 40% EtOH (0.05% diethylamine) in $CO_2$ over 12 minutes; Wavelength: 220 nm; Retention time=5.7 min.

Preparation of pentafluorophenyl 2-{(1R,3R)-1-(acetyloxy)-4-methyl-3-[methyl(N-{[(2R)-1-methylpiperidin-2-yl]carbonyl}-L-isoleucyl)amino]pentyl}-1,3-thiazole-4-carboxylate (# A30)

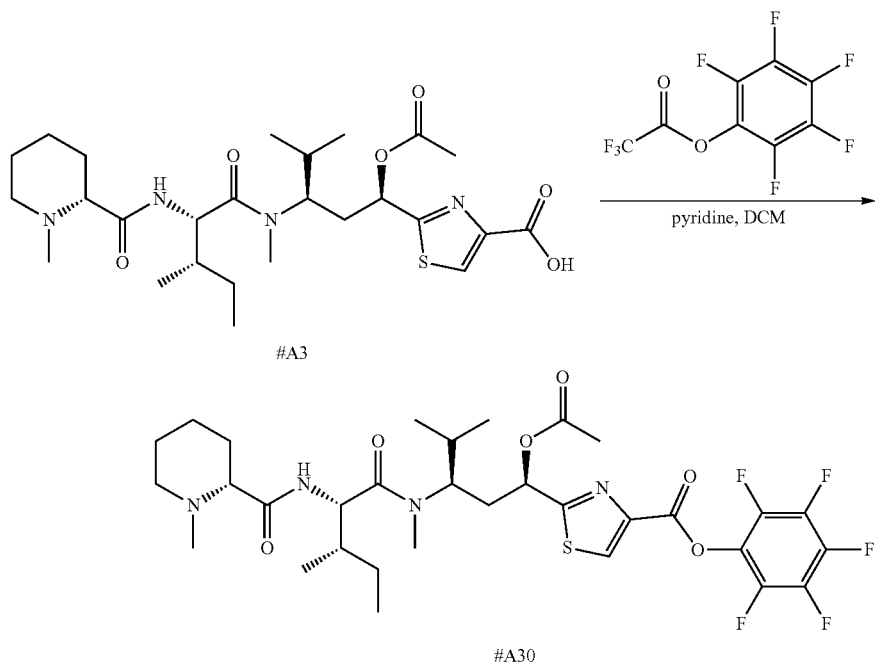

To a vial containing 2-{(1R,3R)-1-(acetyloxy)-4-methyl-3-[methyl(N-{[(2R)-1-methylpiperidin-2-yl]carbonyl}-L-isoleucyl)amino]pentyl}-1,3-thiazole-4-carboxylic acid (# A3, 150 mg, 0.153 mmol) was added DCM (1.0 mL) and pyridine (25 μL, 0.306 mmol) followed by pentafluorophenyl trifluoroacetate (53 μL, 0.306 mmol) and the reaction was stirred for 1 h at rt. The reaction was concentrated to a thick oil and was purified by silica gel chromatography (0% to 100% EtOAc in heptanes). The purified product was azeotroped with heptane/DCM (1/1) to provide the title compound # A30 (106 mg, 98% yield) as a white solid. LC-MS (Protocol C): m/z 705.1 [M+H]⁺; Retention time=0.89 min.

Preparation of 1,2-dimethyl-D-prolyl-N-[(1R,3R)-1-(acetyloxy)-4-methyl-1-{4-[(pentafluorophenoxy)carbonyl]-1,3-thiazol-2-yl}pentan-3-yl]-N-methyl-L-isoleucinamide (# A31)

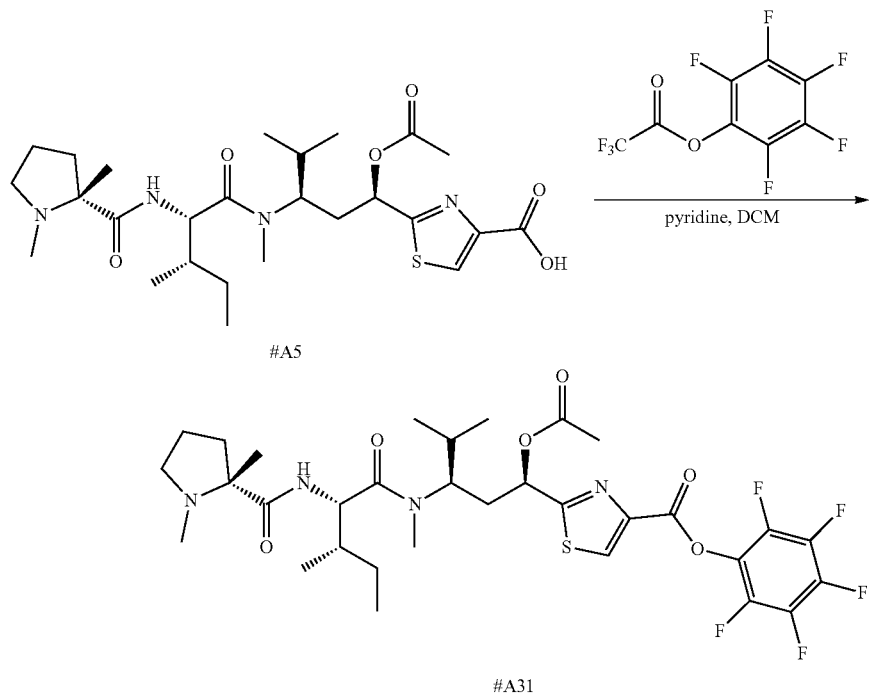

To a vial containing 1,2-dimethyl-D-prolyl-N-[(1R,3R)-1-(acetyloxy)-1-(4-carboxy-1,3-thiazol-2-yl)-4-methylpentan-3-yl]-N-methyl-L-isoleucinamide (# A5, 256 mg, 0.475 mmol) was added DCM (10 mL) and pyridine (130 μL, 0.950 mmol). The reaction was cooled to 0° C. under N₂ and pentafluorophenyl trifluoroacetate (167 μL, 0.950 mmol) was added. After ~5 minutes, the ice bath was removed and the reaction was stirred under N₂ for 3.5 h, concentrated, re-dissolved in DCM (3 mL), and purified by flash silica gel chromatography (0% to 60% MeOH in DCM) to provide the title compound # A31 (283 mg, 85% yield) as a white solid. LC-MS (Protocol B): m/z 705.5 [M+H]⁺; Retention time=1.64 min.

Preparation of 1,2-dimethyl-D-prolyl-N-[(1R,3R)-1-[(ethylcarbamoyl)oxy]-4-methyl-1-{4-[(pentafluorophenoxy)carbonyl]-1,3-thiazol-2-yl}pentan-3-yl]-N-methyl-L-isoleucinamide (# A32)

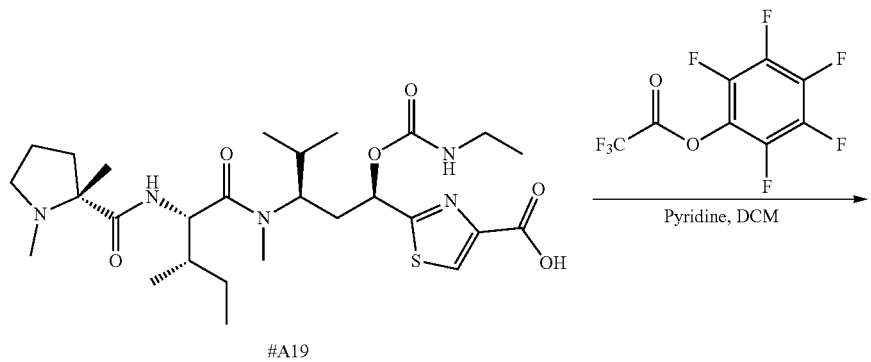

-continued

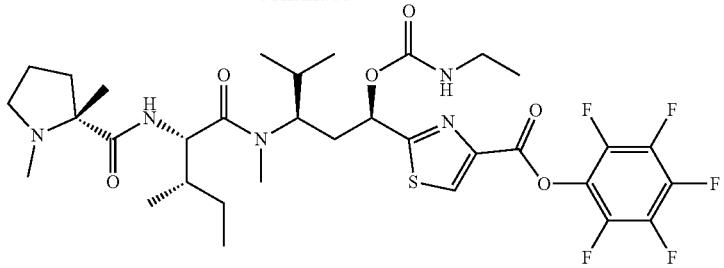

A32

The title compound was prepared in 58% yield from 1,2-dimethyl-D-prolyl-N-{(1R,3R)-1-(4-carboxy-1,3-thiazol-2-yl)-1-[(ethylcarbamoyl)oxy]-4-methylpentan-3-yl}-N-methyl-L-isoleucinamide (# A19, 0.093 mmol) and pentafluorophenyl trifluoroacetate (0.231 mmol) using the method described above for compound # A31. LC-MS (Protocol C): m/z 734.7 [M+H]$^+$; Retention time=0.88 min.

Preparation of 1,2-dimethyl-D-prolyl-N-[(1R,3R)-1-[(ethylcarbamoyl)amino]-4-methyl-1-{4-[(pentafluorophenoxy)carbonyl]-1,3-thiazol-2-yl}pentan-3-yl]-N-methyl-L-isoleucinamide (# A33)

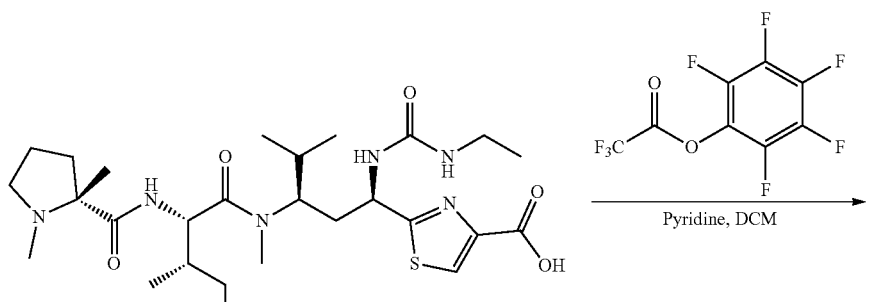

A17

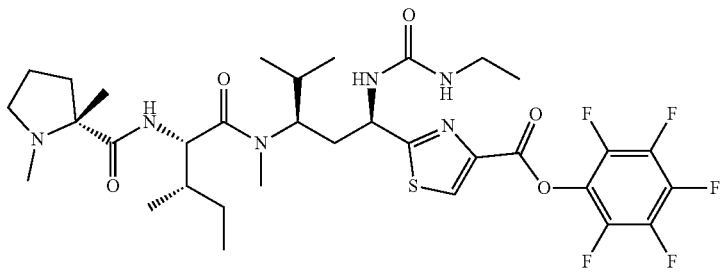

A33

The title compound was prepared in 94% yield from 1,2-dimethyl-D-prolyl-N-{(1R,3R)-1-(4-carboxy-1,3-thiazol-2-yl)-1-[(ethylcarbamoyl)amino]-4-methylpentan-3-yl}-N-methyl-L-isoleucinamide (# A17, 0.110 mmol) and pentafluorophenyl trifluoroacetate (0.220 mmol) using the method described above for compound # A31. LC-MS (Protocol C): m/z 733.2 [M+H]$^+$; Retention time=0.82 min.

The Following PFP Esters were Prepared in Yields Ranging from 50-90% from the Corresponding Acids Using the Method Described Above for # A31:

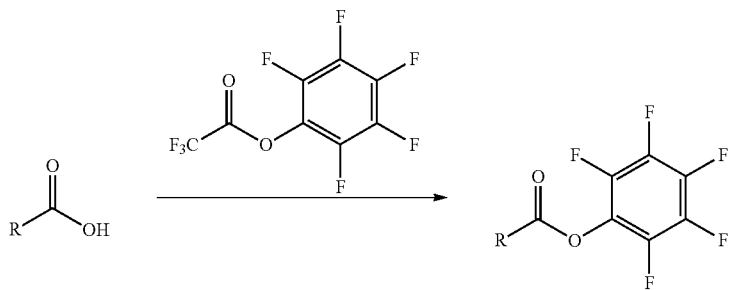
| Example | Starting Acid | Product | LCMS Protocol/RT | m/z (M + H)+ |
|---|---|---|---|---|
| #A34 | #A11 | | Protocol B 1.42 min | 704.7 |
| #A35 | #A12 | | Protocol C 0.88 min | 747.4 |
| #A36 | #A13 | | Protocol C 0.88 min | 774.3 |
| #A37 | #A23 | | Protocol C 0.83 min | 719.5 |
| #A38 | #A24 | | Protocol C 0.83 min | 748.5 |

-continued
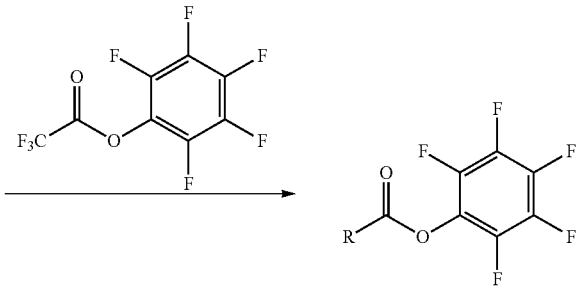
| Example | Starting Acid | Product | LCMS Protocol/RT | m/z (M + H)+ |
|---|---|---|---|---|
| #A39 | #A25 | 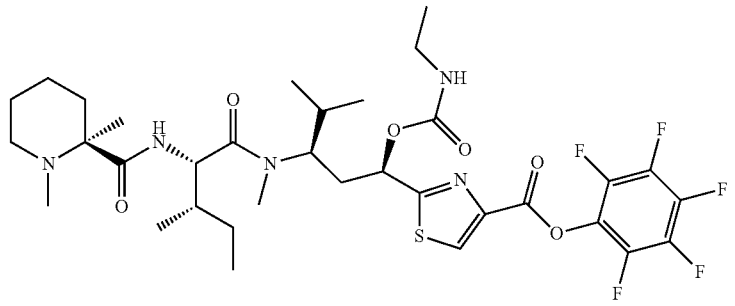 [SMILES: CCNC(=O)O[C@H](C[C@H](C(C)C)N(C)C(=O)[C@@H](NC(=O)[C@]1(C)CCCCN1C)[C@@H](C)CC)c1nc(C(=O)Oc2c(F)c(F)c(F)c(F)c2F)cs1] | Protocol C 0.83 min | 748.5 |
| #A40 | #A27 | 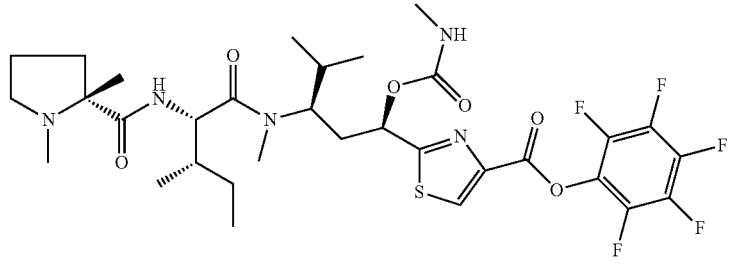 [SMILES: CC[C@H](C)[C@H](NC(=O)[C@@]1(C)CCCN1C)C(=O)N(C)[C@H](C[C@@H](OC(=O)NC)c1nc(C(=O)Oc2c(F)c(F)c(F)c(F)c2F)cs1)C(C)C] | Protocol C 0.80 min | 720.7 |
| #A41 | #A28 | 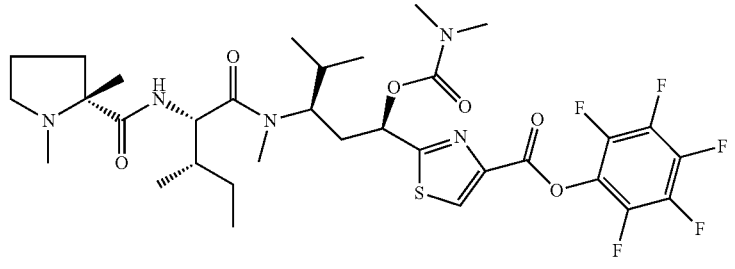 [SMILES: CC[C@H](C)[C@H](NC(=O)[C@@]1(C)CCCN1C)C(=O)N(C)[C@H](C[C@@H](OC(=O)N(C)C)c1nc(C(=O)Oc2c(F)c(F)c(F)c(F)c2F)cs1)C(C)C] | Protocol C 0.83 min | 734.3 |
| #A42 | #A20 | 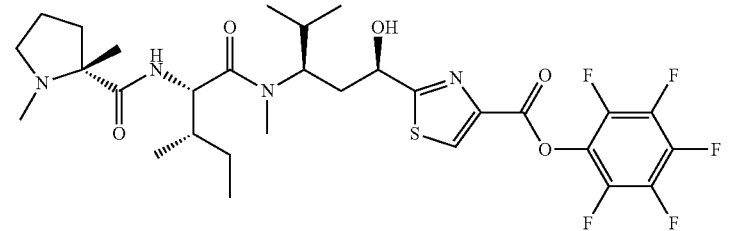 [SMILES: CC[C@H](C)[C@H](NC(=O)[C@@]1(C)CCCN1C)C(=O)N(C)[C@H](C[C@@H](O)c1nc(C(=O)Oc2c(F)c(F)c(F)c(F)c2F)cs1)C(C)C] | Protocol C 0.90 min | 663.7 |

-continued

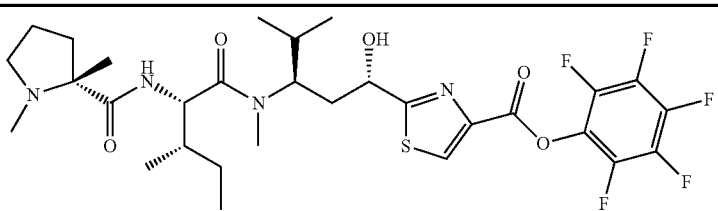

| Example | Starting Acid | Product | LCMS Protocol/RT | m/z (M + H)+ |
|---|---|---|---|---|
| #A43 | #A18 | | Protocol C 0.84 min | 663.1 |

Preparation of methyl (2S,4R)-4-{[(2-{(1R,3R)-1-(acetyloxy)-3-[(N-{[1-(dimethylamino)cyclopentyl]carbonyl}-L-isoleucyl)(methyl)amino]-4-methylpentyl}-1,3-thiazol-4-yl)carbonyl]amino}-2-methyl-5-phenylpentanoate (# B1)

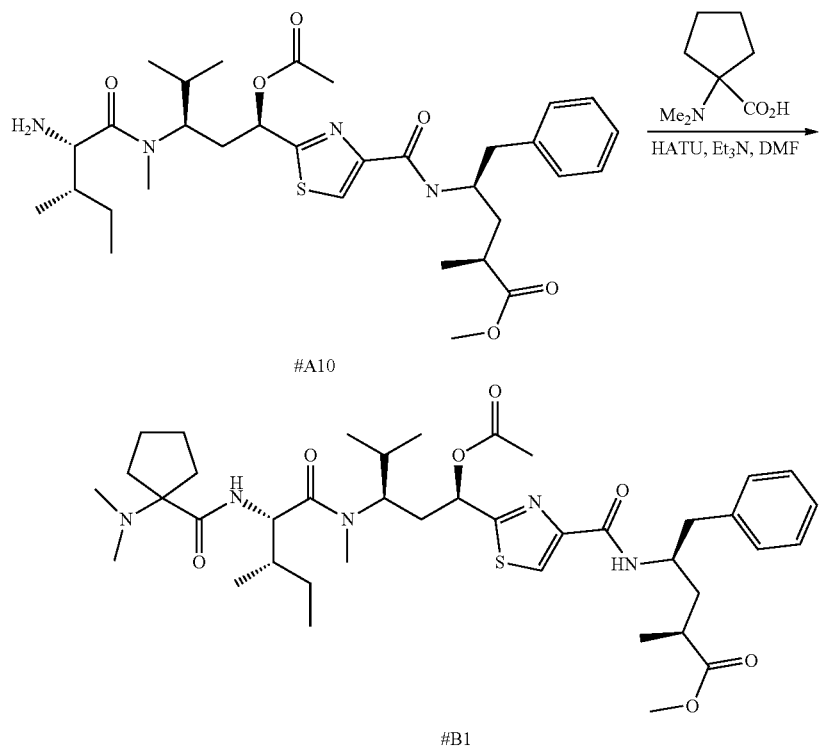

To a solution of 1-(dimethylamino)cyclopentane-1-carboxylic acid (CAS 933690-12-1) (4.1 mg, 0.02 mmol) in DMF (0.25 mL) was added HATU (9.5 mg, 0.025 mmol) and DIPEA (0.011 mL, 0.063 mmol) and the mixture was stirred for 15 min. A solution of methyl (2S,4R)-4-{[(2-{(1R,3R)-1-(acetyloxy)-3-[L-isoleucyl(methyl)amino]-4-methylpentyl}-1,3-thiazol-4-yl)carbonyl]amino}-2-methyl-5-phenylpentanoate (# A10, 14.0 mg, 0.021 mmol) in DMF (0.25 mL) was added and the mixture was stirred at rt overnight, concentrated in vacuo, and the residue purified by reverse phase chromatography (Table 1) to afford the title compound # B1 as its trifluoroacetate salt (13.0 mg, 76%).

Preparation of 1,2-dimethyl-L-prolyl-N-[(1R,3R)-1-(acetyloxy)-1-(4-{[(2R,4S)-5-methoxy-4-methyl-5-oxo-1-phenylpentan-2-yl]carbamoyl}-1,3-thiazol-2-yl)-4-methylpentan-3-yl]-N-methyl-L-isoleucinamide (# B2)

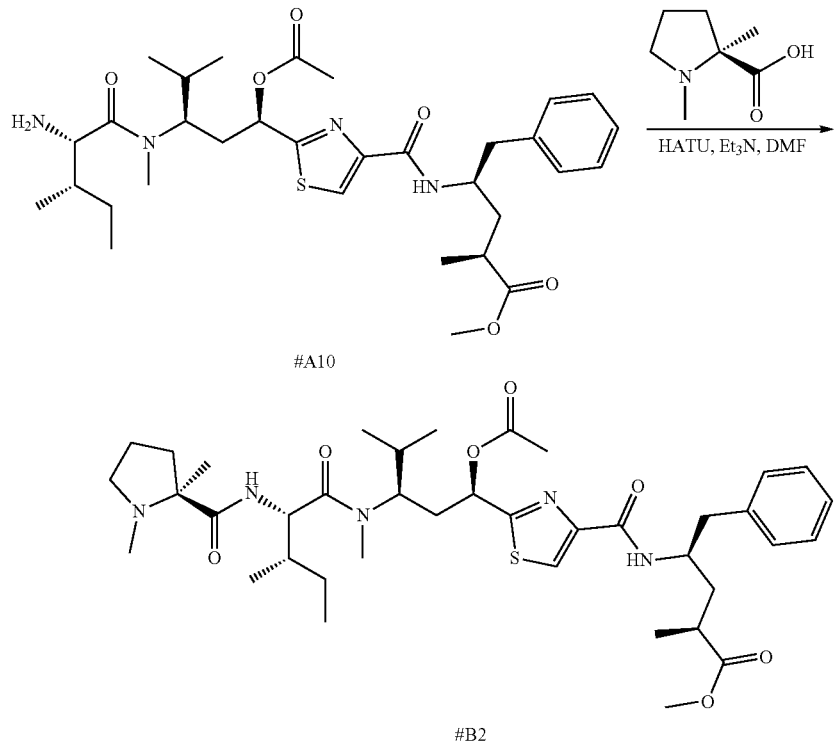

To a solution of 1,2-dimethyl-L-Proline (Doroski et al., U.S. Pat. No. 8,828,401 B2) (4.4 mg, 0.03 mmol) in DMF (0.25 mL) was added HATU (14.5 mg, 0.037 mmol) and DIPEA (0.016 mL, 0.093 mmol) and the mixture was stirred for 15 min. A solution of methyl (2S,4R)-4-{[(2-{(1R,3R)-1-(acetyloxy)-3-[L-isoleucyl(methyl)amino]-4-methylpentyl}-1,3-thiazol-4-yl)carbonyl]amino}-2-methyl-5-phenylpentanoate (# A10, 20.0 mg, 0.031 mmol) in DMF (0.25 mL) was added and the mixture was stirred at rt overnight, concentrated in vacuo, and the residue purified by reverse phase chromatography (Table 1) to afford the title compound # B2 as its trifluoroacetate salt (8.6 mg, 30%).

Preparation of N-[(1R,3R)-1-(acetyloxy)-4-methyl-1-(4-{[(2S)-1-phenyl-4-phosphonopentan-2-yl]carbamoyl}-1,3-thiazol-2-yl)pentan-3-yl]-N-methyl-N~2~-{[(2R)-1-methylpiperidin-2-yl]carbonyl}-L-isoleucinamide (# B3)

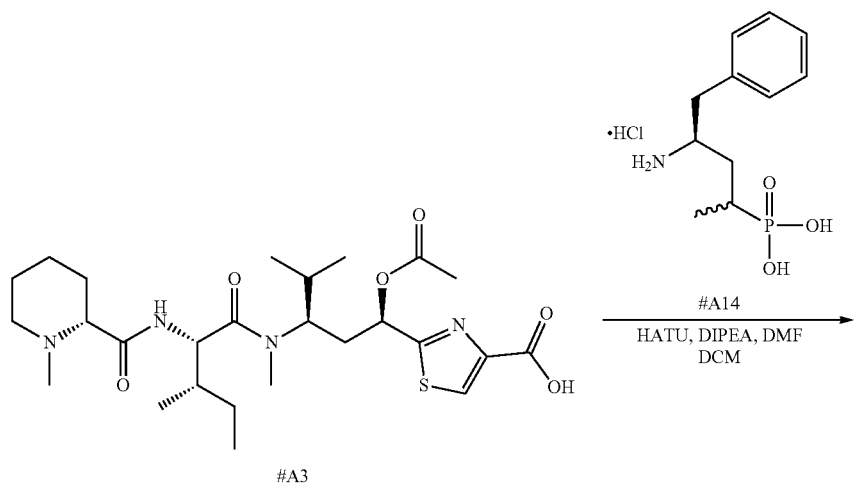

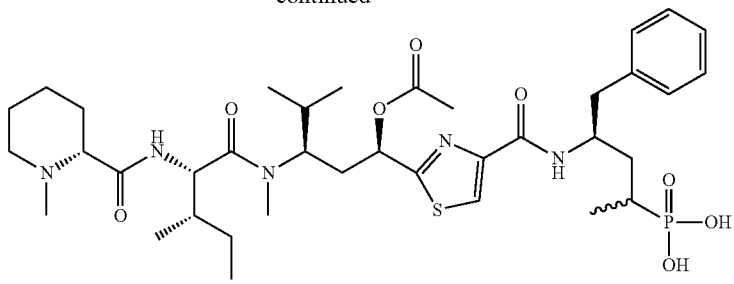
B3

To a vial containing 2-{(1R,3R)-1-(acetyloxy)-4-methyl-3-[methyl(N-{[(2R)-1-methylpiperidin-2-yl]carbonyl}-L-isoleucyl)amino]pentyl}-1,3-thiazole-4-carboxylic acid (# A3, 35 mg, 0.054 mmol) and HATU (21.2 mg, 0.054 mmol) was added DCM (1 mL), DMF (0.1 mL), and DIPEA (48 µL, 0.270 mmol). The reaction was stirred for 5 minutes then added to a stirring solution of [(4S)-4-amino-5-phenylpentan-2-yl]phosphonic acid (# A14, 21.0 mg, 0.075 mmol) in DCM (1 mL) and DMF (0.1 mL). After stirring for 0.5 h at rt, the reaction was quenched by addition of H₂O (1 mL) containing several drops of TFA. The reaction was purified by preparative HPLC (Table 1) to afford title compound # B3 (2.9 mg, 6.1%) as its TFA salt. LC-MS (Protocol D) m/z 765.4 [M+H]⁺; Retention time=7.09 min.

Preparation of 3-{2-[(2-{(1R,3R)-1-(acetyloxy)-4-methyl-3-[methyl(N-{[(2R)-1-methylpiperidin-2-yl]carbonyl}-L-isoleucyl)amino]pentyl}-1,3-thiazol-4-yl)carbonyl]-1-benzylhydrazinyl}-2-methylpropanoic Acid (# B4)

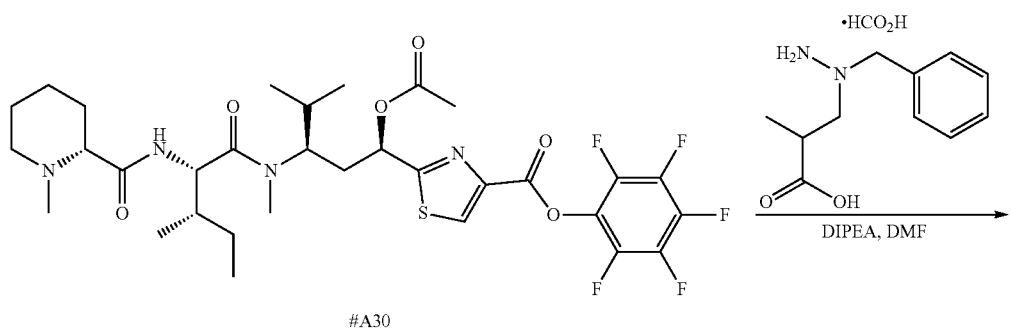

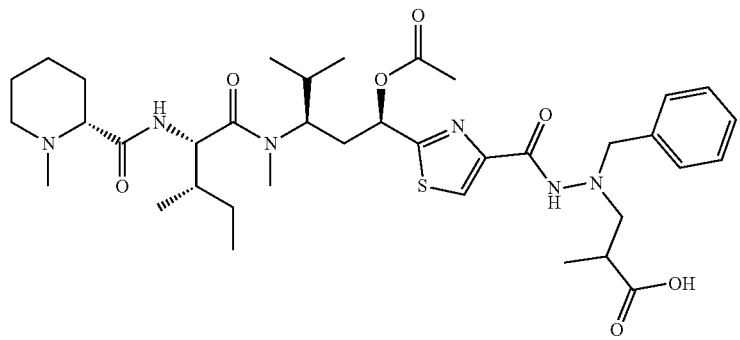
B4

A solution of 3-(1-benzylhydrazinyl)-2-methylpropanoic acid (Great Britain Patent GB1260939) (3.2 mg, 0.014 mmol) in DMF (1 mL) and DIPEA (300 µL) was added pentafluorophenyl 2-{(1R,3R)-1-(acetyloxy)-4-methyl-3-[methyl(N-{[(2R)-1-methylpiperidin-2-yl]carbonyl}-L-isoleucyl)amino]pentyl}-1,3-thiazole-4-carboxylate (# A30, 10 mg, 0.014 mmol) and the reaction was stirred at rt for 14 h. The reaction was concentrated and purified by reverse phase chromatography (Table 1) to afford title compound # B4 (1.3 mg, 12%) as a gum.

Preparation of 1,2-dimethyl-D-prolyl-N-[(1R,3R)-1-(acetyloxy)-1-(4-{[(2R,4S)-5-methoxy-4-methyl-5-oxo-1-phenylpentan-2-yl]carbamoyl}-1,3-thiazol-2-yl)-4-methylpentan-3-yl]-N-methyl-L-isoleucinamide (# B5)

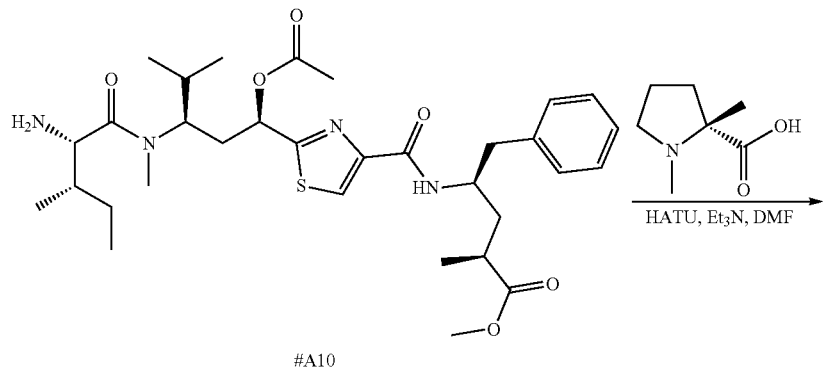

A10

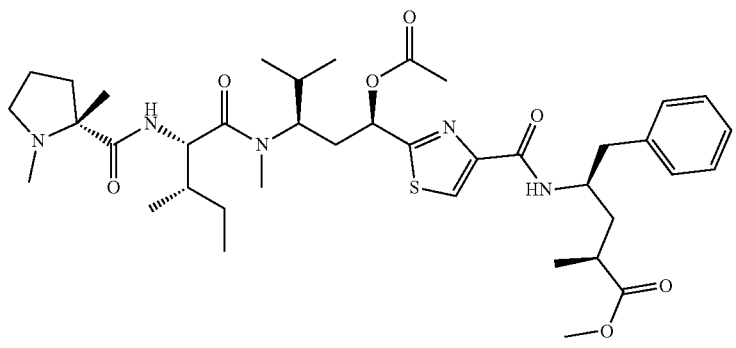

B5

The title compound was prepared in 22% yield from 1,2-dimethyl-L-Proline (Doroski et al., U.S. Pat. No. 8,828,401 B2) (2.49 mg, 0.02 mmol) and methyl (2S,4R)-4-{[(2-{(1R,3R)-1-(acetyloxy)-3-[L-isoleucyl(methyl)amino]-4-methylpentyl}-1,3-thiazol-4-yl)carbonyl]amino}-2-methyl-5-phenylpentanoate (# A10, 13.0 mg, 0.02 mmol) using the method described above for compound # B2. LC-MS (Protocol D): m/z 742.4 [M+H]$^+$; Retention time=7.99 min.

Preparation of 2-methyl-D-prolyl-N-[(1R,3R)-1-(acetyloxy)-1-(4-{[(2R,4S)-5-methoxy-4-methyl-5-oxo-1-phenylpentan-2-yl]carbamoyl}-1,3-thiazol-2-yl)-4-methylpentan-3-yl]-N-methyl-L-isoleucinamide (# B6)

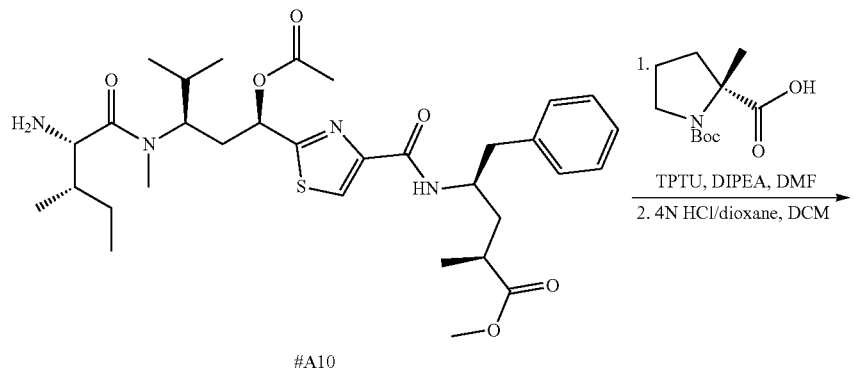
A10

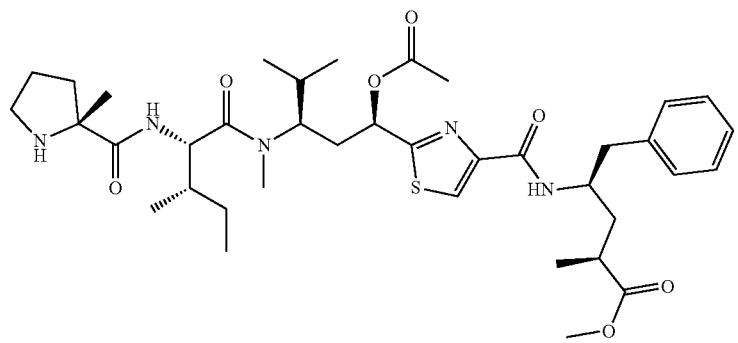
B6

To a solution of 1-(tert-butoxycarbonyl)-2-methyl-D-proline (4.6 mg, 0.02 mmol) in DMF (0.25 mL) was added DIPEA (0.011 mL, 0.06 mmol) and TPTU (7.1 mg, 0.024 mmol). The reaction was stirred for 15 minutes and methyl (2S,4R)-4-{[(2-{(1R,3R)-1-(acetyloxy)-3-[L-isoleucyl(methyl)amino]-4-methylpentyl}-1,3-thiazol-4-yl)carbonyl]amino}-2-methyl-5-phenylpentanoate (#A10, 13.1 mg, 0.02 mmol) was added and the reaction was stirred at rt for 18 h. The reaction was quenched with water (1.5 mL) and extracted with EtOAc (3×2.5 mL). The combined organic layers were loaded onto a SPE cartridge charged with sodium sulfate and concentrated in vacuo. The yellow oil was dissolved into DCM (0.5 mL) and 4 N HCl in dioxane (0.5 mL) was added. The reaction was stirred at rt for 80 minutes then concentrated under vacuum. Purification by reverse phase chromatography (Table 1) afforded # B6 (5 mg, 34%) as the TFA salt.

Preparation of 1,2-dimethyl-D-prolyl-N-[(1R,3R)-1-(acetyloxy)-1-(4-{[(2R,4S)-5-ethoxy-4-methyl-5-oxo-1-phenylpentan-2-yl]carbamoyl}-1,3-thiazol-2-yl)-4-methylpentan-3-yl]-N-methyl-L-isoleucinamide (# B7)
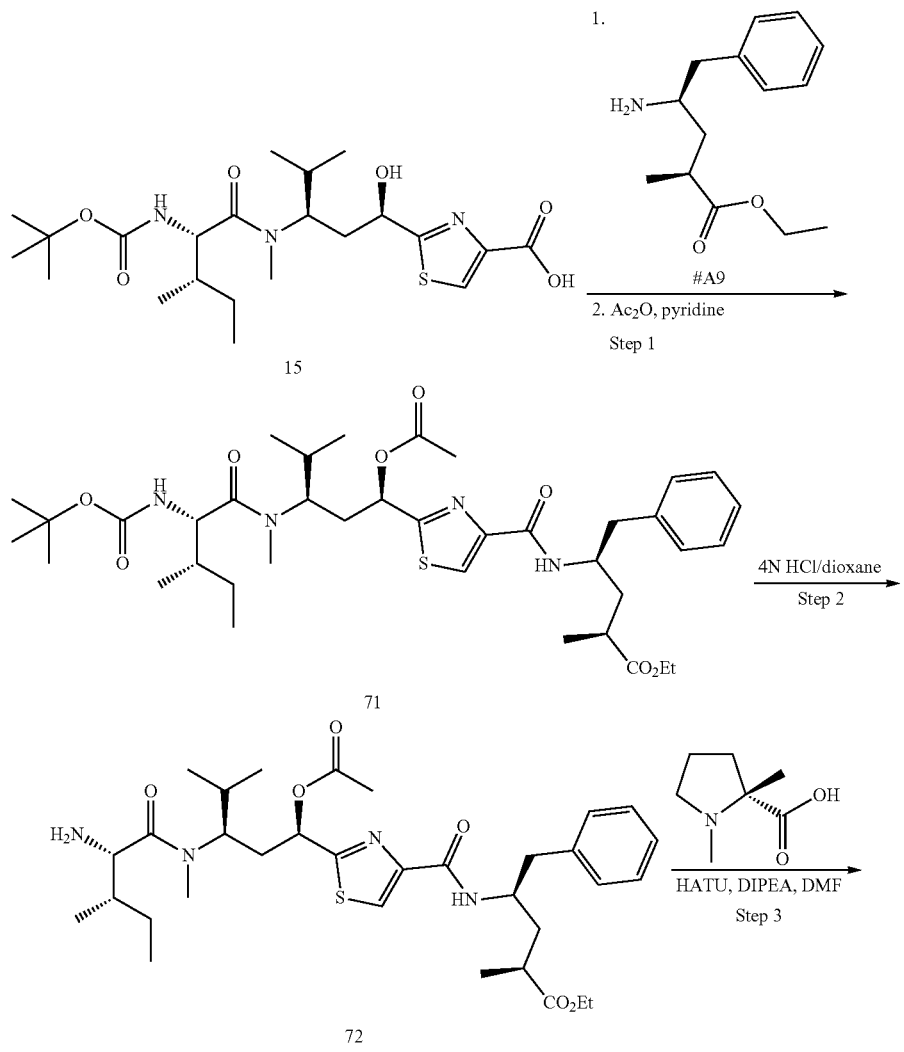
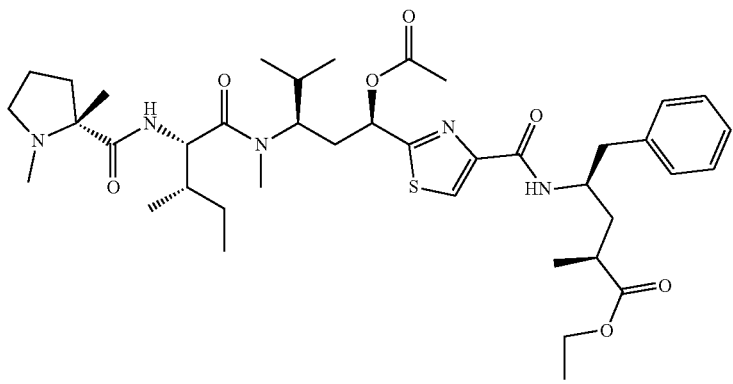

Step 1: Preparation of ethyl (2S,4R)-4-[({2-[(1R, 3R)-1-(acetyloxy)-3-{[N-(tert-butoxycarbonyl)-L-isoleucyl](methyl)amino}-4-methylpentyl]-1,3-thiazol-4-yl}carbonyl)amino]-2-methyl-5-phenylpentanoate (71)

The title compound was prepared in 85% yield starting from 2-[(1R,3R)-3-{[N-(tert-butoxycarbonyl)-L-isoleucyl](methyl)amino}-1-hydroxy-4-methylpentyl]-1,3-thiazole-4-carboxylic acid (15, 0.195 mmol) and ethyl (2S,4R)-4-amino-2-methyl-5-phenylpentanoate (# A9, 0.215 mmol) using the two-step method described above for compound # A2. LC-MS (Protocol B): m/z 753 [M+Na]$^+$; Retention time=2.34 min.

Step 2: Preparation of ethyl (2R,4S)-4-{[(2-{(1R, 3S)-1-(acetyloxy)-3-[L-alloisoleucyl(methyl)amino]-4-methylpentyl}-1,3-thiazol-4-yl)carbonyl]amino}-2-methyl-5-phenylpentanoate (72)

A solution of ethyl (2S,4R)-4-[({2-[(1R,3R)-1-(acetyloxy)-3-{[N-(tert-butoxycarbonyl)-L-isoleucyl](methyl)amino}-4-methylpentyl]-1,3-thiazol-4-yl}carbonyl)amino]-2-methyl-5-phenylpentanoate (71, 0.12 g, 0.164 mmol) in DCM (2.0 mL) was treated with 4.0 N HCl in dioxane (2.0 mL) and the mixture stirred at rt for 6 h. The reaction was evaporated to dryness and the residue azeotroped with EtOAc (2×5 mL) to give the title compound 72 (0.11 g, quantitative yield) as a hygroscopic solid. LC-MS (Protocol B): m/z 631.9 [M+H]$^+$; Retention time=1.32 min.

Step 3: Preparation of 1,2-dimethyl-D-prolyl-N-[(1R,3R)-1-(acetyloxy)-1-(4-{[(2R,4S)-5-ethoxy-4-methyl-5-oxo-1-phenylpentan-2-yl]carbamoyl}-1,3-thiazol-2-yl)-4-methylpentan-3-yl]-N-methyl-L-isoleucinamide (# B7)

The title compound was prepared in 7.7% yield from ethyl (2R,4S)-4-{[(2-{(1R,3S)-1-(acetyloxy)-3-[L-alloisoleucyl(methyl)amino]-4-methylpentyl}-1,3-thiazol-4-yl)carbonyl]amino}-2-methyl-5-phenylpentanoate (72, 0.163 mmol) and 1,2-dimethyl-L-Proline (Doroski et al., U.S. Pat. No. 8,828,401 B2) (0.163 mmol) using the method described above for compound # B2.

Preparation of 1,2-dimethyl-D-prolyl-N-[(1R,3R)-1-(acetyloxy)-1-(4-{[(2R,4S)-4-carboxy-1-phenylpentan-2-yl]carbamoyl}-1,3-thiazol-2-yl)-4-methylpentan-3-yl]-N-methyl-L-isoleucinamide (# B8)

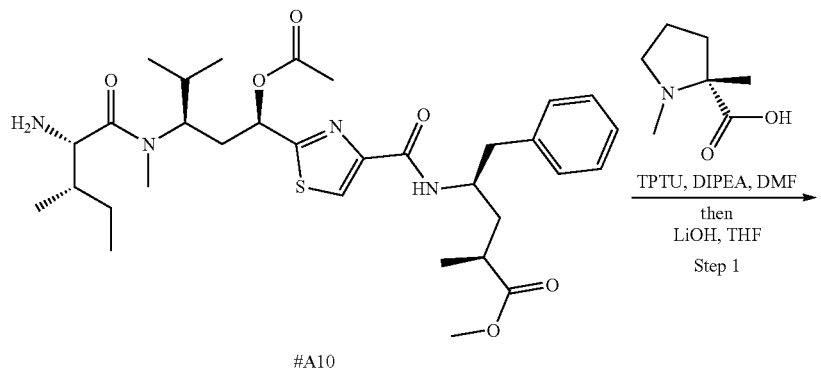

A10

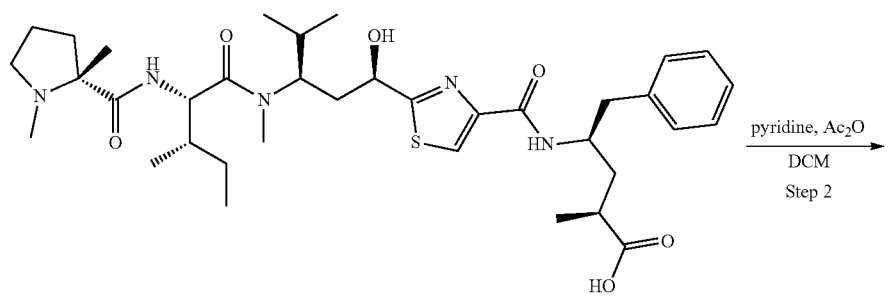

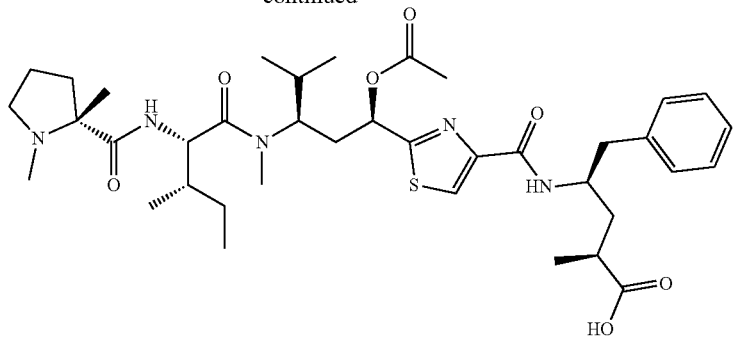

B8

Step 1. Synthesis of 1,2-dimethyl-D-prolyl-N-[(1R,3R)-1-(4-{[(2R,4S)-4-carboxy-1-phenylpentan-2-yl]carbamoyl}-1,3-thiazol-2-yl)-1-hydroxy-4-methylpentan-3-yl]-N-methyl-L-isoleucinamide (73)

To a slurry of 1,2-dimethyl-D-proline (20 mg, 0.14 mmol) in DMF (0.4 mL) was added DIPEA (0.417 mL, 0.417 mmol) followed by TPTU (51.1 mg, 0.167 mmol). The reaction was stirred for minutes and a solution of methyl (2S,4R)-4-{[(2-{(1R,3R)-1-(acetyloxy)-3-[L-isoleucyl(methyl)amino]-4-methylpentyl}-1,3-thiazol-4-yl)carbonyl]amino}-2-methyl-5-phenylpentanoate (#A10, 90.8 mg, 0.14 mmol) in DMF (0.25 mL) was added. The reaction was stirred at rt for 18 h then quenched with water (1.5 mL) and extracted with EtOAc (3×2.5 mL). The combined organics were dried with sodium sulfate, filtered, and concentrated in vacuo. The oil was slurried into THF (6 mL) and a solution of LiOH (17 mg) in H$_2$O (2 mL) was added. The resulting reaction mixture was stirred at rt for 72 h. The reaction was concentrated in vacuo and the crude residue purified by medium pressure reverse phase C18 chromatography (10% to 80% acetonitrile in H$_2$O, each solvent containing 0.02% TFA) to provide a foam which was re-dissolved in DCM and precipitated with hexanes, affording title compound 73 (91 mg, 81%). LC-MS (Protocol C): m/z 686.8 [M+Na]$^+$; Retention time=0.7 min.

Step 2. Synthesis of 1,2-dimethyl-D-prolyl-N-[(1R,3R)-1-(acetyloxy)-1-(4-{[(2R,4S)-4-carboxy-1-phenylpentan-2-yl]carbamoyl}-1,3-thiazol-2-yl)-4-methylpentan-3-yl]-N-methyl-L-isoleucinamide (# B8)

To a solution of 1,2-dimethyl-D-prolyl-N-[(1R,3R)-1-(4-{[(2R,4S)-4-carboxy-1-phenylpentan-2-yl]carbamoyl}-1,3-thiazol-2-yl)-1-hydroxy-4-methylpentan-3-yl]-N-methyl-L-isoleucinamide (73, 90 mg, 0.11 mmol) in DCM (1 mL) was added pyridine (1 mL) and acetic anhydride (0.1 mL) and the reaction was stirred at rt for 2 h. Additional acetic anhydride (0.1 mL) was added and the reaction stirred at rt for 18 h. The reaction was concentrated in vacuo and the crude residue purified by medium pressure reverse phase chromatography (Table 1) to provide a foam, which was further dissolved in DCM and precipitated with hexanes, affording the title compound # B8 (74 mg, 90%).

Preparation of 1,2-dimethyl-D-prolyl-N-[(1R,3R)-1-(acetyloxy)-1-(4-{[(2R,4S)-1-(4-aminophenyl)-4-carboxypentan-2-yl]carbamoyl}-1,3-thiazol-2-yl)-4-methylpentan-3-yl]-N-methyl-L-isoleucinamide (# B9)

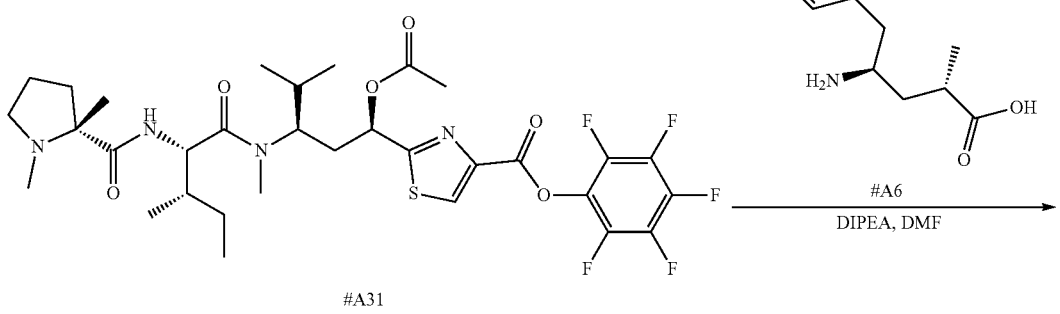

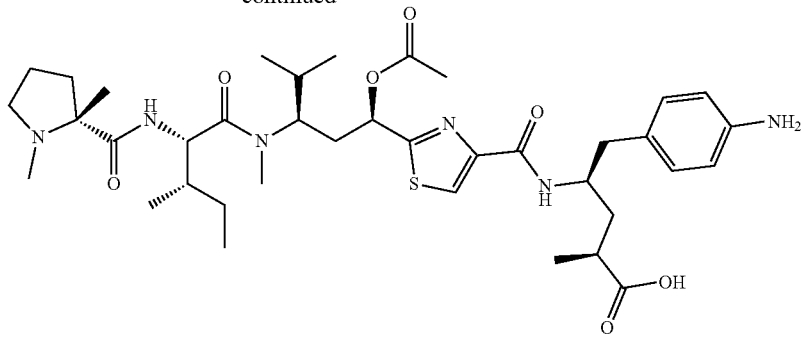

B9

To a vial containing 1,2-dimethyl-D-prolyl-N-[(1R,3R)-1-(acetyloxy)-4-methyl-1-{4-[(pentafluorophenoxy)carbonyl]-1,3-thiazol-2-yl}pentan-3-yl]-N-methyl-L-isoleucinamide (# A31, 135 mg, 0.192 mmol) and (2S,4R)-4-amino-5-(4-aminophenyl)-2-methylpentanoic acid Hydrochloride (# A6, 57 mg, 0.192 mmol) was added DMF (7.3 mL) and DIPEA (270 μL, 1.54 mmol) and the reaction was stirred at rt in a capped vial. After stirring for 17 h at rt, the reaction was concentrated to a crude residue which was re-dissolved in DMSO (2 mL) and purified by reverse phase chromatography (Table 1) to afford title compound # B9 (115 mg, 80%). LC-MS (Protocol C): m/z 743.8 [M+H]$^+$; Retention time=0.63 min.

Preparation of (1R,3R)-1-(4-{[(2S,4R)-1-(4-aminophenyl)-4-(diethoxyphosphoryl)pentan-2-yl]carbamoyl}-1,3-thiazol-2-yl)-4-methyl-3-[methyl(N-{[(2R)-1-methylpiperidin-2-yl]carbonyl}-L-isoleucyl)amino]pentyl Acetate (# B10)

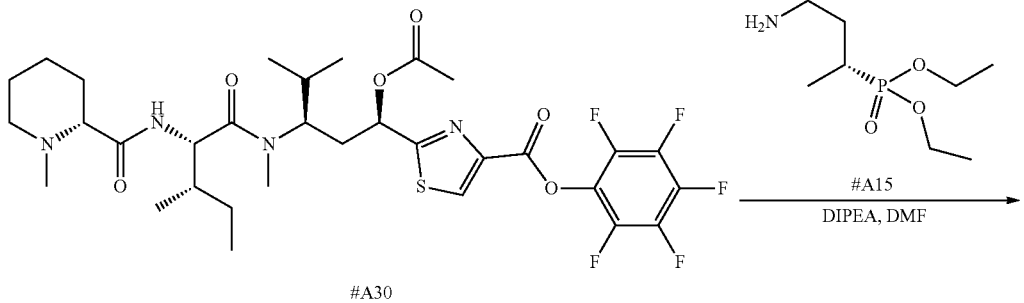

A30 → #A15, DIPEA, DMF

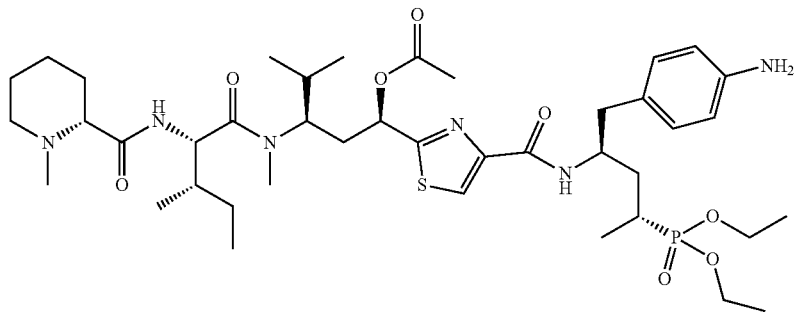

B10

To a vial containing pentafluorophenyl 2-{(1R,3R)-1-(acetyloxy)-4-methyl-3-[methyl(N-{[(2R)-1-methylpiperidin-2-yl]carbonyl}-L-isoleucyl)amino]pentyl}-1,3-thiazole-4-carboxylate (# A30, 25 mg, 0.035 mmol) and diethyl [(2R,4S)-4-amino-5-(4-aminophenyl)pentan-2-yl]phosphonate (# A15, 15 mg, 0.035 mmol) was added DMF (1.5 mL) and DIPEA (49 µL, 0.280 mmol) and the reaction was stirred at rt in a capped vial. After stirring for 4 h at rt, the reaction was concentrated and the residue was purified by reverse phase chromatography (Table 1) to afford the title compound # B10 (11.4 mg, 39%).

Preparation of (1R,3R)-1-(4-{[(2S,4S)-1-(4-aminophenyl)-4-(diethoxyphosphoryl)pentan-2-yl]carbamoyl}-1,3-thiazol-2-yl)-4-methyl-3-[methyl(N-{[(2R)-1-methylpiperidin-2-yl]carbonyl}-L-isoleucyl)amino]pentyl Acetate (# B11)

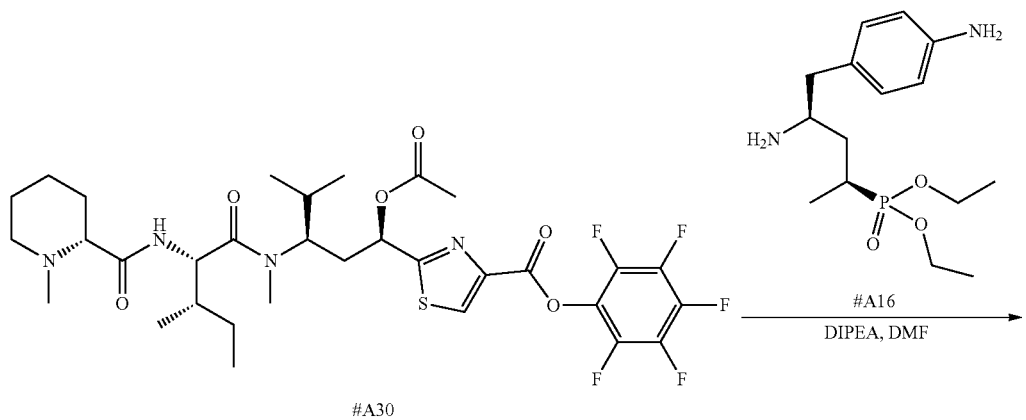

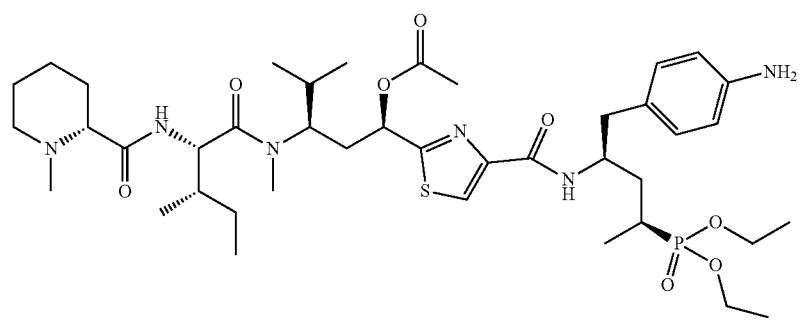

B11

To a vial containing pentafluorophenyl 2-{(1R,3R)-1-(acetyloxy)-4-methyl-3-[methyl(N-{[(2R)-1-methylpiperidin-2-yl]carbonyl}-L-isoleucyl)amino]pentyl}-1,3-thiazole-4-carboxylate (# A30, 25 mg, 0.035 mmol) and diethyl [(2S,4S)-4-amino-5-(4-aminophenyl)pentan-2-yl]phosphonate (# A16, 15 mg, 0.035 mmol) was added DMF (1.5 mL) and DIPEA (49 µL, 0.280 mmol) and the reaction was stirred at rt in a capped vial. After stirring for 4 h at rt, the reaction was concentrated and the residue was purified by reverse phase chromatography (Table 1) to afford the title compound # B11 (8.9 mg, 30%).

Preparation of N-methyl-D-valyl-N-[(1R,3R)-1-(acetyloxy)-1-(4-{[(2R,4S)-4-carboxy-1-phenylpentan-2-yl]carbamoyl}-1,3-thiazol-2-yl)-4-methylpentan-3-yl]-N-methyl-L-isoleucinamide (# B12)
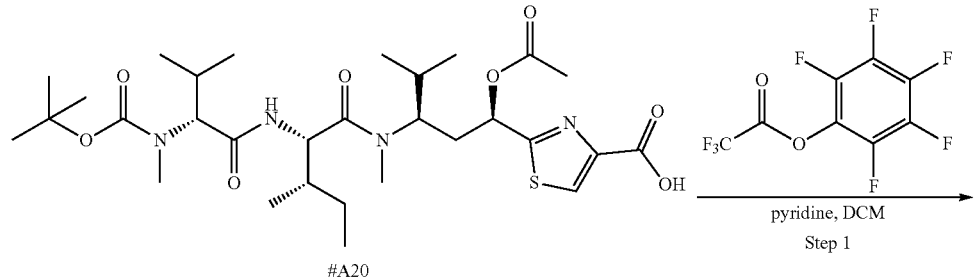
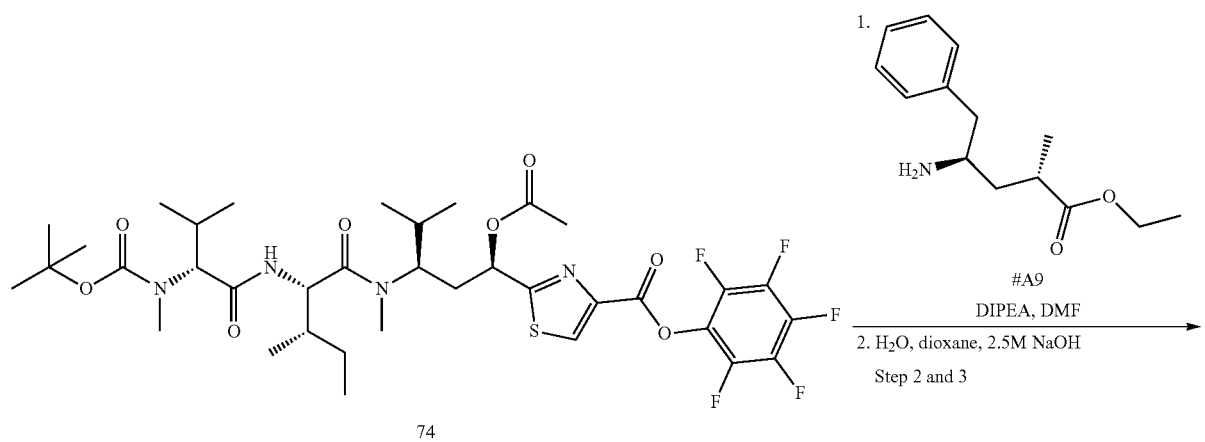
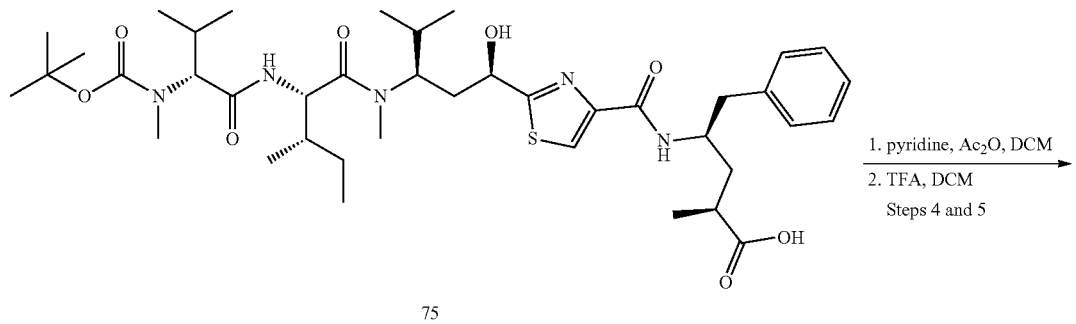
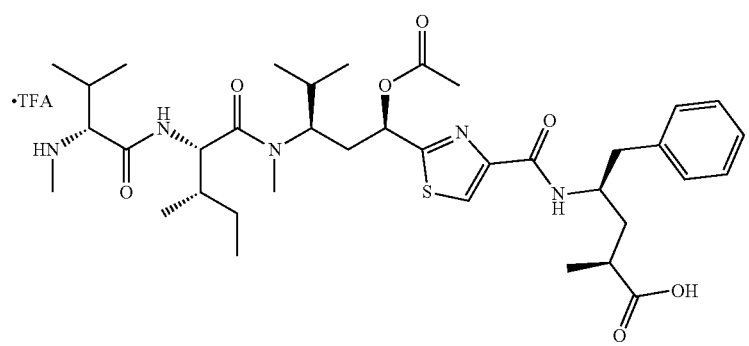

Step 1: Preparation of N-(tert-butoxycarbonyl)-N-methyl-D-valyl-N-[(1R,3R)-1-(acetyloxy)-4-methyl-1-{4-[(pentafluorophenoxy)carbonyl]-1,3-thiazol-2-yl}pentan-3-yl]-N-methyl-L-isoleucinamide (74)

The title compound 74 was prepared in 86% yield from N-(tert-butoxycarbonyl)-N-methyl-D-valyl-N-[(1R,3R)-1-(acetyloxy)-1-(4-carboxy-1,3-thiazol-2-yl)-4-methylpentan-3-yl]-N-methyl-L-isoleucinamide (# A20, 0.319 mmol) and pentafluorophenyl trifluoroacetate (0.957 mmol) using the method described above for compound # A31. LC-MS (Protocol C): m/z 815.3 [M+Na]+; Retention time=1.20 min.

Steps 2 and Step 3: Preparation of N-(tert-butoxycarbonyl)-N-methyl-D-valyl-N-[(1R,3R)-1-(acetyloxy)-1-(4-{[(2R,4S)-4-carboxy-1-phenylpentan-2-yl]carbamoyl}-1,3-thiazol-2-yl)-4-methylpentan-3-yl]-N-methyl-L-isoleucinamide (75)

To a vial containing N-(tert-butoxycarbonyl)-N-methyl-D-valyl-N-[(1R,3R)-1-(acetyloxy)-4-methyl-1-{4-[(pentafluorophenoxy)carbonyl]-1,3-thiazol-2-yl}pentan-3-yl]-N-methyl-L-isoleucinamide (74,143 mg, 0.180 mmol) and ethyl (2S,4R)-4-amino-2-methyl-5-phenylpentanoate hydrochloride (# A9, 21 mg, 0.091 mmol) was added DMF (7 mL) and DIPEA (129 µL, 0.731 mmol) and the reaction was stirred under $N_2$ for 16 h at rt. The reaction was concentrated and the residue was purified by silica gel chromatography (0% to 60% EtOAc in heptane over 20 minutes, then hold at 60% EtOAc for 6 minutes) to afford N-(tert-butoxycarbonyl)-N-methyl-D-valyl-N-[(1R,3R)-1-(4-{[(2R,4S)-5-ethoxy-4-methyl-5-oxo-1-phenylpentan-2-yl]carbamoyl}-1,3-thiazol-2-yl)-1-hydroxy-4-methylpentan-3-yl]-N-methyl-L-isoleucinamide (65 mg, 43%), which was re-dissolved in 1,4-dioxane (6 mL) and $H_2O$ (0.8 mL). 2.5 M aq. NaOH (0.8 mL) was added and the reaction was heated at 75° C. for 21 h. The reaction was cooled to rt, concentrated to remove dioxane, then acidified to pH=3 with aqueous citric acid. The resulting suspension was extracted with EtOAc (3×) then the combined organic layers were washed with brine, dried over $Na_2SO_4$, filtered, and concentrated to provide title compound 75 (37 mg, 100%) as a slightly yellow gum. LC-MS (Protocol B): m/z 774.4 [M+H]+; Retention time=2.24 min.

Steps 4 and 5: Preparation of N-methyl-D-valyl-N-[(1R,3R)-1-(acetyloxy)-1-(4-{[(2R,4S)-4-carboxy-1-phenylpentan-2-yl]carbamoyl}-1,3-thiazol-2-yl)-4-methylpentan-3-yl]-N-methyl-L-isoleucinamide (# B12)

To a solution of crude N-(tert-butoxycarbonyl)-N-methyl-D-valyl-N-[(1R,3R)-1-(acetyloxy)-1-(4-{[(2R,4S)-4-carboxy-1-phenylpentan-2-yl]carbamoyl}-1,3-thiazol-2-yl)-4-methylpentan-3-yl]-N-methyl-L-isoleucinamide (75, 37.0 mg, 0.05 mmol) in DCM/pyridine (1/1, 3.12 mL) was added acetic anhydride (112 µL). The reaction was stirred at rt for 7 h then concentrated and the residue purified by silica gel chromatography (0% to 10% MeOH in DCM over 6 minutes, then hold at 10% for 3 minutes) to yield a crude residue which was immediately dissolved in DCM (1.8 mL). TFA (90 µL) was added and the reaction was stirred at rt for 2.25 h. The reaction mixture was concentrated and the residue purified by reverse phase chromatography (Table 1) to afford the target compound # B12 (13.7 mg, 72%).

Preparation of methyl (2S,4R)-4-[({2-[(1R,3R)-1-(acetyloxy)-4-methyl-3-{methyl[(2S,3S)-3-methyl-2-{[(7-methyl-7-azabicyclo[2.2.1]hept-1-yl)carbonyl]amino}pentanoyl]amino}pentyl]-1,3-thiazol-4-yl}carbonyl)amino]-2-methyl-5-phenylpentanoate (# B13)

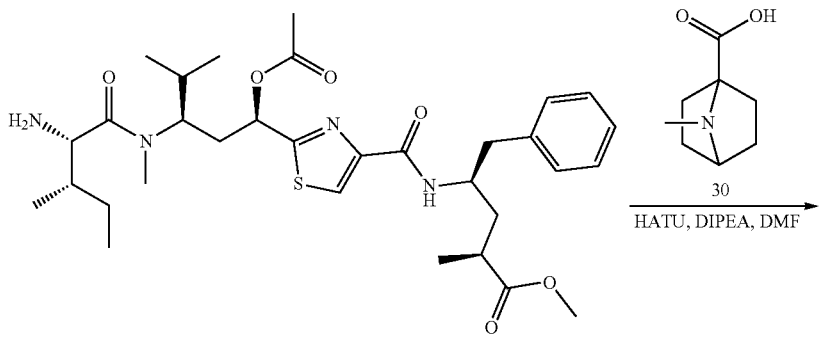

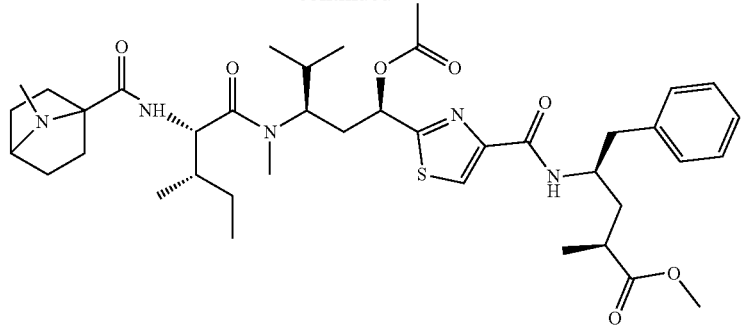

B13

To a vial containing 7-methyl-7-azabicyclo[2.2.1]heptane-1-carboxylic acid (30, 7.3 mg, 0.038 mmol) and HATU (14.6 mg, 0.038 mmol) was added DMF (0.5 mL) and DIPEA (28 μL, 0.160 mmol). The reaction was stirred in a capped vial for 0.5 h and a solution of methyl (2S,4R)-4-{[(2-{(1R,3R)-1-(acetyloxy)-3-[L-isoleucyl(methyl)amino]-4-methylpentyl}-1,3-thiazol-4-yl)carbonyl]amino}-2-methyl-5-phenylpentanoate (# A10, 20 mg, 0.032 mmol) in DMF (0.4 mL) was added. After stirring for ~18 h at rt, the reaction was concentrated and the residue was purified by reverse phase chromatography (Table 1) to afford the title compound # B13 (14.5 mg, 60%).

Preparation of methyl (2S,4R)-4-[({2-[(1R,3R)-1-(acetyloxy)-4-methyl-3-(methyl{N-[(2-methyl-2-azabicyclo[3.1.1]hept-1-yl)carbonyl]-L-isoleucyl}amino)pentyl]-1,3-thiazol-4-yl}carbonyl)amino]-2-methyl-5-phenylpentanoate (# B14)

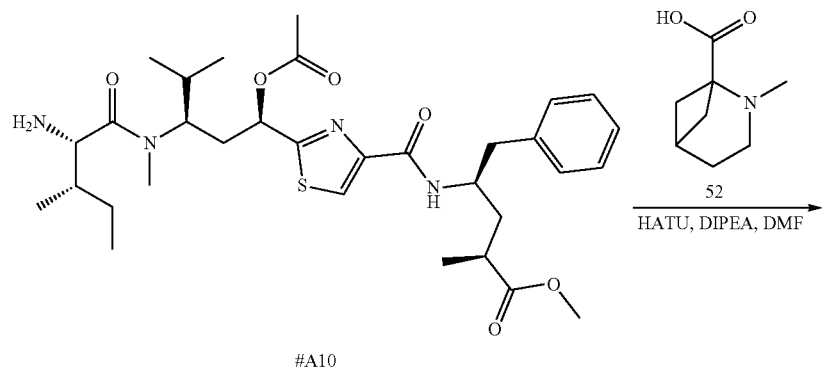

A10

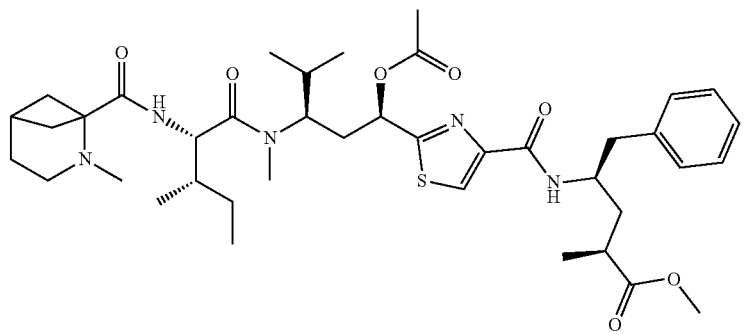

B14

The title compound was prepared in 65% yield from methyl (2S,4R)-4-{[(2-{(1R,3R)-1-(acetyloxy)-3-[L-iso-leucyl(methyl)amino]-4-methylpentyl}-1,3-thiazol-4-yl)carbonyl]amino}-2-methyl-5-phenylpentanoate (# A10, 20 mg, 0.032 mmol) and 2-Methyl-2-azabicyclo[3.1.1]heptane-1-carboxylic acid (52, 0.038 mmol) using the method described above for example # B13.

Preparation of 1,2-dimethyl-D-prolyl-N-[(1R,3R)-1-(4-{[(2R,4S)-4-carboxy-1-phenylpentan-2-yl]carbamoyl}-1,3-thiazol-2-yl)-1-hydroxy-4-methylpentan-3-yl]-N-methyl-L-isoleucinamide (# B15)

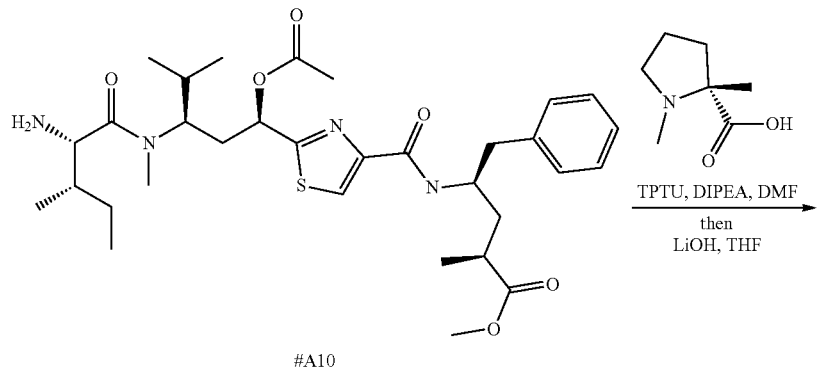

A10

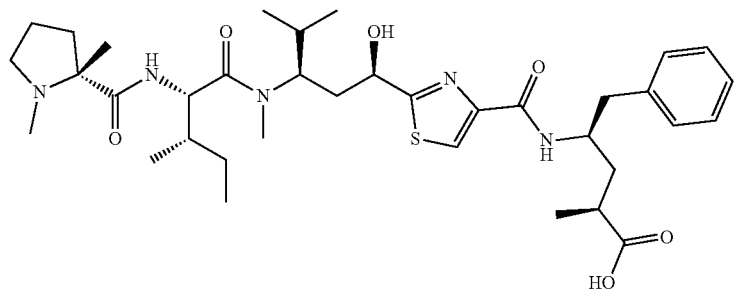

B15

To a solution of (R)-1,2-dimethylpyrrolidine-2-carboxylic acid (Doroski et al., U.S. Pat. No. 8,828,401 B2) (20 mg, 0.14 mmol) in DMF (0.4 mL) was added DIPEA (0.417 mL, 0.417 mmol), followed by TPTU (51.1 mg, 0.167 mmol). The reaction was stirred for 15 minutes and a solution of methyl (2S,4R)-4-(2-((1R,3R)-1-acetoxy-3-((2S,3S)-2-amino-N,3-dimethylpentanamide)-4-methylpentyl)thiazole-4-carboxamido)-2-methyl-5-phenylpentanoate (# A10, 90.8 mg, 0.14 mmol) in DMF (0.25 mL) was added. The reaction was stirred at rt for 18 h then quenched with water (1.5 mL) and extracted with ethyl acetate (3×2.5 mL). The combined organic layers were dried with sodium sulfate, filtered, and concentrated in vacuo. The resulting oil was slurried into THF (6 mL) and a solution of LiOH (17 mg) in H$_2$O was added. The resulting mixture was stirred at rt for 72 h, concentrated in vacuo, and purified by reverse phase chromatography (Table 1) to afford title compound # B15 (90 mg, 81%).

Preparation of methyl (2S,4R)-4-[({2-[(1R,3R)-1-(acetyloxy)-4-methyl-3-(methyl{N-[(9-methyl-9-azabicyclo[3.3.1]non-1-yl)carbonyl]-L-isoleucyl}amino)pentyl]-1,3-thiazol-4-yl}carbonyl)amino]-2-methyl-5-phenylpentanoate (# B16)

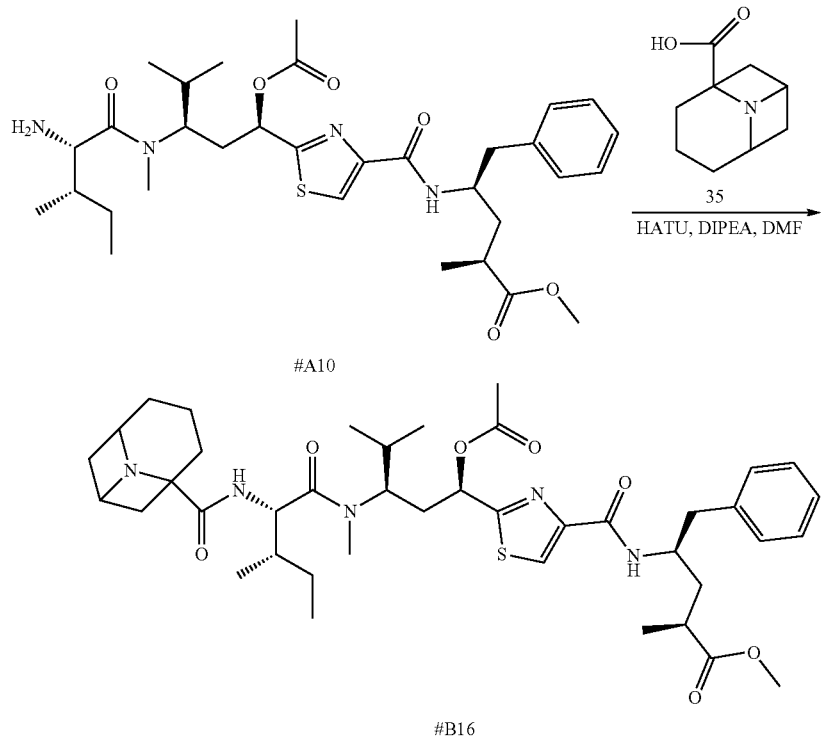

The title compound was prepared in 65% yield from methyl (2S,4R)-4-{[(2-{(1R,3R)-1-(acetyloxy)-3-[L-isoleucyl(methyl)amino]-4-methylpentyl}-1,3-thiazol-4-yl)carbonyl]amino}-2-methyl-5-phenylpentanoate (# A10, 20 mg, 0.032 mmol) and 9-methyl-9-azabicyclo[3.3.1]nonane-1-carboxylic acid (35, 0.038 mmol) using the method described above for example # B13.

Preparation of methyl (2S,4R)-4-[({2-[(1R,3R)-1-(acetyloxy)-4-methyl-3-(methyl{N-[(2-methyl-2-azabicyclo[2.1.1]hex-1-yl)carbonyl]-L-isoleucyl}amino)pentyl]-1,3-thiazol-4-yl}carbonyl)amino]-2-methyl-5-phenylpentanoate (# B17)

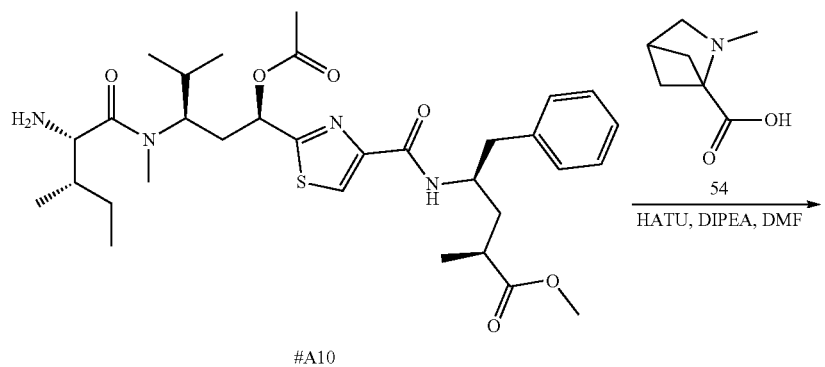

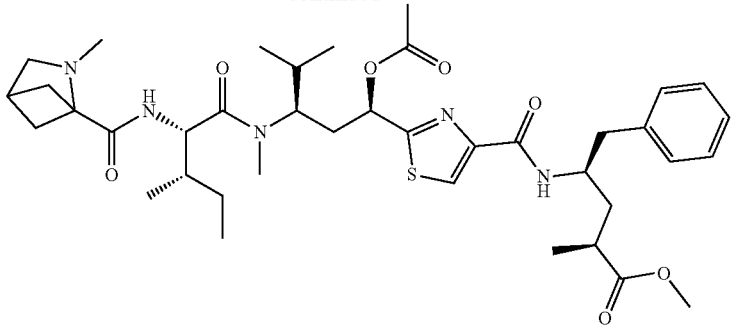

B17

The title compound was prepared in 67% yield from methyl (2S,4R)-4-{[(2-{(1R,3R)-1-(acetyloxy)-3-[L-isoleucyl(methyl)amino]-4-methylpentyl}-1,3-thiazol-4-yl)carbonyl]amino}-2-methyl-5-phenylpentanoate (# A10, 20 mg, 0.032 mmol) and 2-methyl-2-azabicyclo[2.1.1]hexane-1-carboxylic acid (54, 0.038 mmol) using the method described above for example # B13.

Preparation of 1,2-dimethyl-D-prolyl-N-[(1R,3R)-1-(acetylamino)-1-(4-{[(2R,4S)-5-ethoxy-4-methyl-5-oxo-1-phenylpentan-2-yl]carbamoyl}-1,3-thiazol-2-yl)-4-methylpentan-3-yl]-N-methyl-L-isoleucinamide (# B18)

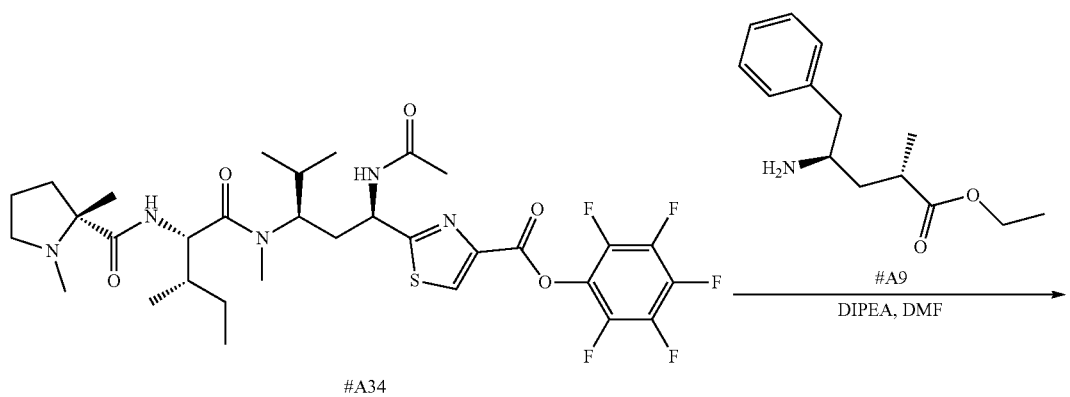

A34  →  #A9, DIPEA, DMF

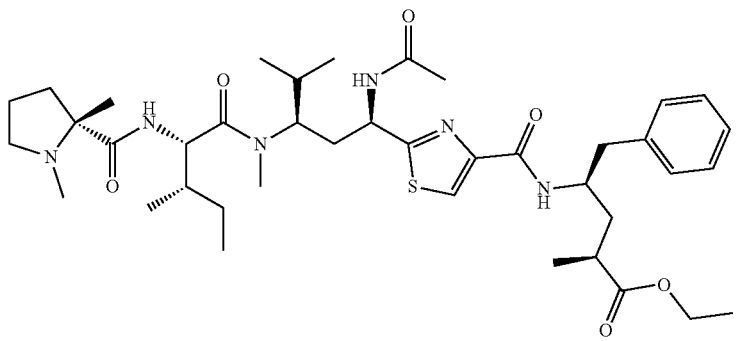

B18

To a vial containing 1,2-dimethyl-D-prolyl-N-[(1R,3R)-1-(acetylamino)-4-methyl-1-{4-[(pentafluorophenoxy)carbonyl]-1,3-thiazol-2-yl}pentan-3-yl]-N-methyl-L-isoleucinamide (# A34, 10 mg, 0.014 mmol) in DMF (0.5 mL) was added DIPEA (0.015 mL, 0.085 mmol) followed by ethyl (2S,4R)-4-amino-2-methyl-5-phenylpentanoate hydrochloride (# A9, 4.0 mg, 0.016 mmol). The reaction was stirred at rt for 1 h then concentrated via genevac. The residue was purified by reverse phase chromatography (Table 1) to afford target compound # B18 (5.4 mg, 49%).

Preparation of 1,2-dimethyl-D-prolyl-N-[(1R,3R)-1-(acetylamino)-1-(4-{[(2R,4S)-4-carboxy-1-phenylpentan-2-yl]carbamoyl}-1,3-thiazol-2-yl)-4-methylpentan-3-yl]-N-methyl-L-isoleucinamide (# B19)

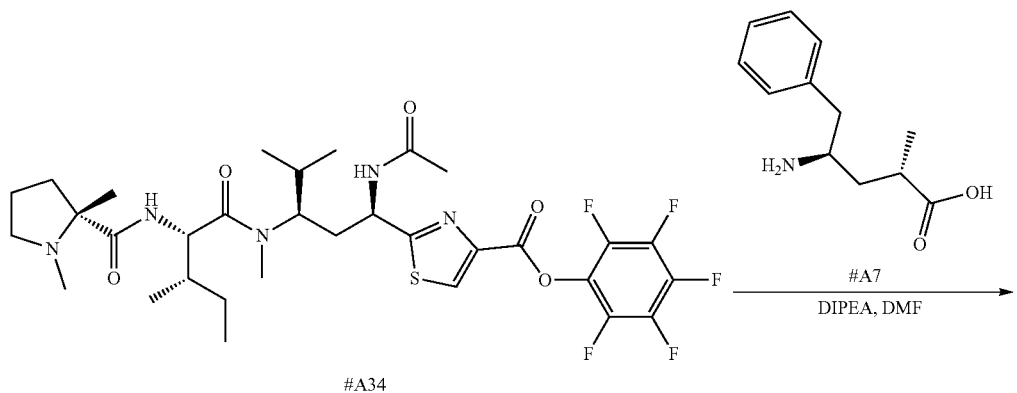

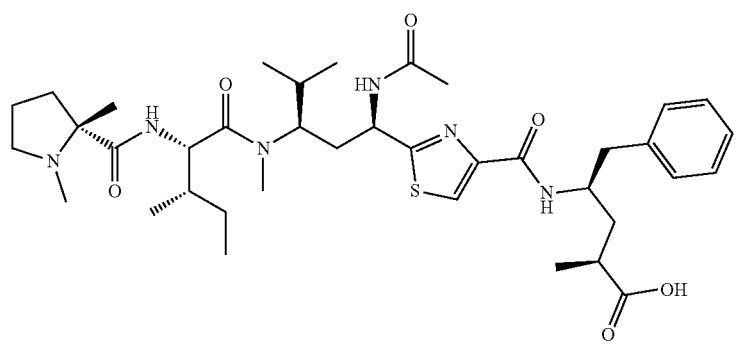

To a vial containing 1,2-dimethyl-D-prolyl-N-[(1R,3R)-1-(acetylamino)-4-methyl-1-{4-[(pentafluorophenoxy)carbonyl]-1,3-thiazol-2-yl}pentan-3-yl]-N-methyl-L-isoleucinamide (# A34, 10 mg, 0.014 mmol) in DMF (0.5 mL) was added DIPEA (0.015 mL, 0.085 mmol) followed by (2S,4R)-4-amino-2-methyl-5-phenylpentanoic acid (# A7, 3.46 mg, 0.014 mmol). The reaction was stirred at rt for 1 h and concentrated via genevac. The residue was purified by reverse phase chromatography (Table 1) to afford target compound # B19 (4.6 mg, 46%).

Preparation of 1,2-dimethyl-D-prolyl-N-[(1R,3R)-1-(acetylamino)-1-(4-{[(2R,4S)-5-methoxy-4-methyl-5-oxo-1-phenylpentan-2-yl]carbamoyl}-1,3-thiazol-2-yl)-4-methylpentan-3-yl]-N-methyl-L-isoleucinamide (# B20)

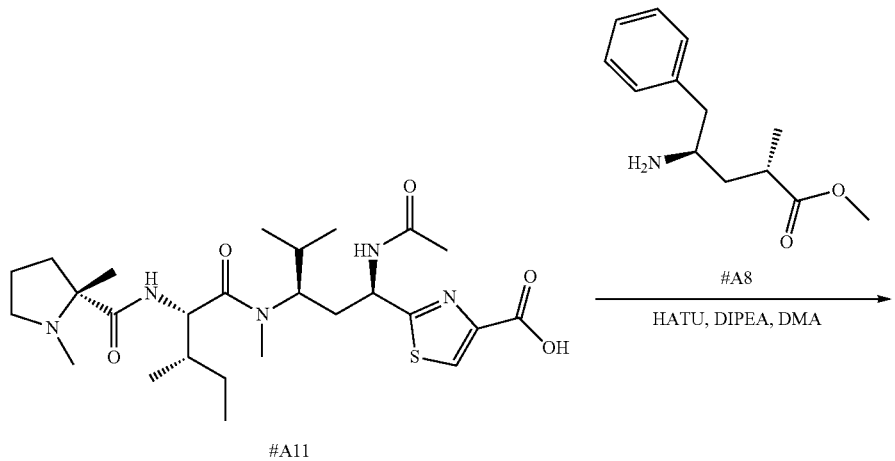

To a vial containing a solution of 1,2-dimethyl-D-prolyl-N-[(1R,3R)-1-(acetylamino)-1-(4-carboxy-1,3-thiazol-2-yl)-4-methylpentan-3-yl]-N-methyl-L-isoleucinamide (# A11, 17 mg, 0.026 mmol) in DMA (0.5 mL) was added DIPEA (0.014 mL, 0.078 mmol) and HATU (10.2 mg, 0.026 mmol), followed by methyl (2S,4R)-4-amino-2-methyl-5-phenylpentanoate hydrochloride (# A8, 5.7 mg, 0.026 mmol). The reaction was stirred at rt for 1 h then concentrated via genevac. The residue was purified by reverse phase chromatography (Table 1) to afford the target compound # B20 (11.4 mg, 60%).

Preparation of Examples # B21-# B33

These compounds were prepared in 15-80% yields by reaction of the respective PFP esters (1.0 eq) with the amine nucleophile (1-1.5 eq) in DMF in the presence of DIPEA (10 eq) using the method describe above for example # B19.

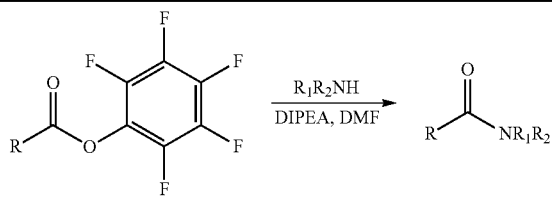
| Example | Starting PFP Ester | Amine Nucleophile | Product | IUPAC Name | Yield* |
|---|---|---|---|---|---|
| #B21 | #A32 | #A6 | | 1,2-dimethyl-D-prolyl-N-{(1R,3R)-1-(4-{[(2R,4S)-1-(4-aminophenyl)-4-carboxypentan-2-yl]carbamoyl}-1,3-thiazol-2-yl)-1-[(ethylcarbamoyl)oxy]-4-methylpentan-3-yl}-N-methyl-L-isoleucinamide | 30% |
| #B22 | #A32 | | | 1,2-dimethyl-D-prolyl-N-{(1R,3R)-1-[(ethylcarbamoyl)oxy]-1-(4-{[(2S)-3-hydroxy-1-methoxy-1-oxobutan-2-yl]carbamoyl}-1,3-thiazol-2-yl)- | 76% |

-continued
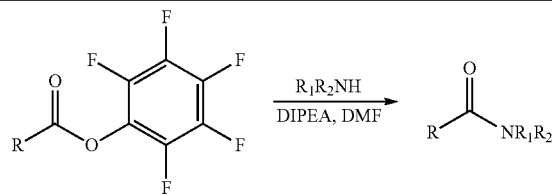
| Example | Starting PFP Ester | Amine Nucleophile | Product | IUPAC Name | Yield* |
|---|---|---|---|---|---|
| | | | | 4-methyl-pentan-3-yl]-N-methyl-L-iso-leucin-amide | |
| #B23 | #A37 | #A6 | | (2S,4R)-4-{[(2-{(1R,3R)-1-(acetyl-oxy)-3-[(N-{[(2S)-1,2-di-methyl-piper-idin-2-yl]car-bonyl}-L-iso-leucyl)(methyl)amino]-4-methyl-pentyl}-1,3-thiazol-4-yl)car-bonyl]amino}-5-(4-amino-phenyl)-2-methyl-pen-tanoic acid | 18% |
| #B24 | #A38 | #A6 | | (2S,4R)-5-(4-amino-phenyl)-4-{[(2-{(1R,3R)-3-[(N-{[(2R)-1,2-di-methyl-piper-idin-2-yl]car- | 32% |

-continued

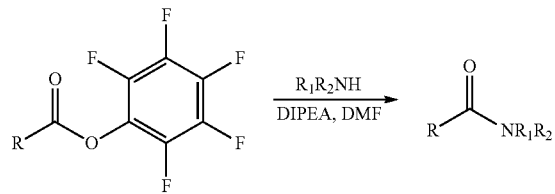

| Example | Starting PFP Ester | Amine Nucleophile | Product | IUPAC Name | Yield* |
|---|---|---|---|---|---|
| | | | | bonyl}-L-isoleucyl)(methyl)amino]-1-[(ethylcarbamoyl)oxy]-4-methylpentyl}-1,3-thiazol-4-yl)carbonyl]amino}-2-methyl pentanoic acid | |
| #B25 | #A39 | #A6 | | (2S,4R)-5-(4-aminophenyl)-4-{[(2-{(1R,3R)-3-[(N-{[(2S)-1,2-dimethylpiperidin-2-yl]carbonyl}-L-isoleucyl)(methyl)amino]-1-[(ethylcarbamoyl)oxy]-4-methylpentyl}-1,3-thiazol-4-yl)carbonyl]amino}-2-methyl pentanoic acid | 33% |

-continued
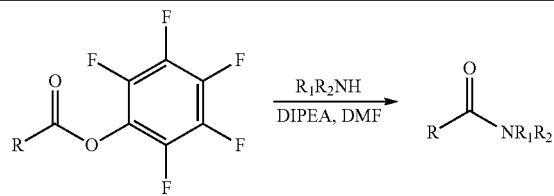
| Example | Starting PFP Ester | Amine Nucleophile | Product | IUPAC Name | Yield* |
|---|---|---|---|---|---|
| #B26 | #A35 | #A6 | | (2S,4R)-5-(4-aminophenyl)-4-{[(2-[(6R,8R,11S)-11-[(2S)-butan-2-yl]-9-methyl-13-(7-methyl-7-azabicyclo[2.2.1]hept-1-yl)-4,10,13-trioxo-8-(propan-2-yl)-5-oxa-3,9,12-triazatridecan-6-yl]-1,3-thiazol-4-yl}carbonyl)amino]-2-methylpentanoic acid | 48% |
| #B27 | #A36 | #A6 | | (2S,4R)-5-(4-aminophenyl)-4-{[(2-{(1R,3R)-1-[(ethylcarbamoyl)oxy]-4-methyl-3-(methyl{N-[(9-methyl-9-azabicyclo[3.3.1]non-1- | 32% |

-continued
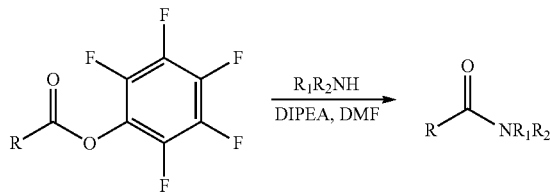
| Example | Starting PFP Ester | Amine Nucleophile | Product | IUPAC Name | Yield* |
|---|---|---|---|---|---|
| | | | | yl)carbonyl]-L-isoleucyl}amino)pentyl]-1,3-thiazol-4-yl}carbonyl)amino]-2-methylpentanoic acid | |
| #B28 | #A34 | #A6 | | 1,2-dimethyl-D-prolyl-N-[(1R,3R)-1-(acetylamino)-1-(4-{[(2R,4S)-1-(4-aminophenyl)-4-carboxypentan-2-yl]carbamoyl}-1,3-thiazol-2-yl)-4-methylpentan-3-yl]-N-methyl-L-isoleucinamide | 70% |

-continued
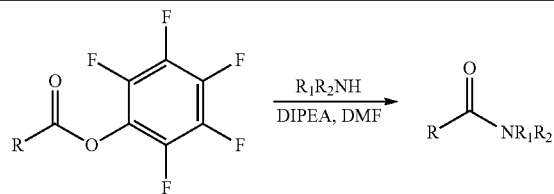
| Example | Starting PFP Ester | Amine Nucleophile | Product | IUPAC Name | Yield* |
|---|---|---|---|---|---|
| #B29 | #A33 | #A6 | 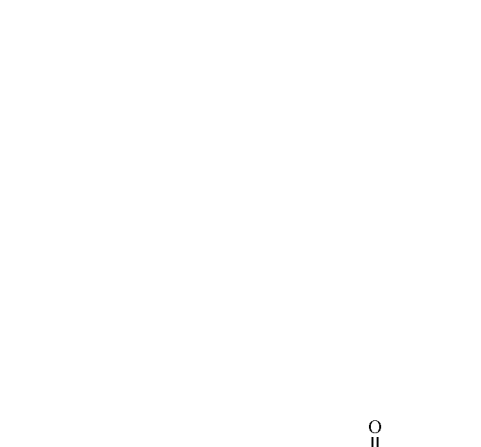 | 1,2-dimethyl-D-prolyl-N-{(1R,3R)-1-(4-{[(2R,4S)-1-(4-aminophenyl)-4-carboxypentan-2-yl]carbamoyl}-1,3-thiazol-2-yl)-1-[(ethylcarbamoyl)amino]-4-methylpentan-3-yl}-N-methyl-L-isoleucinamide | 76% |
| #B30 | #A40 | #A6 | 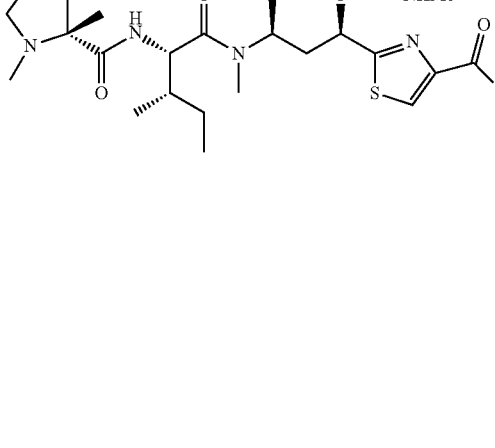 | 1,2-dimethyl-D-prolyl-N-{(1R,3R)-1-(4-{[(2R,4S)-1-(4-aminophenyl)-4-carboxypentan-2-yl]carbamoyl}-1,3-thiazol-2-yl)-4-methyl-1-[(methyl- | 67% |

-continued
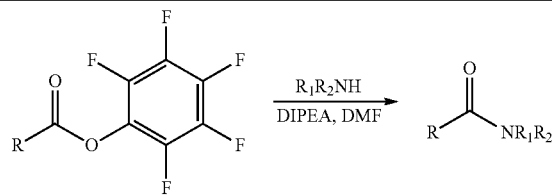
| Example | Starting PFP Ester | Amine Nucleophile | Product | IUPAC Name | Yield* |
|---|---|---|---|---|---|
| | | | | carbamoyl)oxy]pentan-3-yl}-N-methyl-L-isoleucinamide | |
| #B31 | #A41 | #A6 | | 1,2-dimethyl-D-prolyl-N-{(1R,3R)-1-(4-{[(2R,4S)-1-(4-aminophenyl)-4-carboxypentan-2-yl]carbamoyl}-1,3-thiazol-2-yl)-1-[(dimethylcarbamoyl)oxy]-4-methylpentan-3-yl}-N-methyl-L-isoleucinamide | 35% |
| #B32 | #A42 | #A6 | | 1,2-dimethyl-D-prolyl-N-{(1R,3R)-1-(4-{[(2R,4S)-1-(4-aminophenyl)-4-carboxypentan- | 55% |

-continued
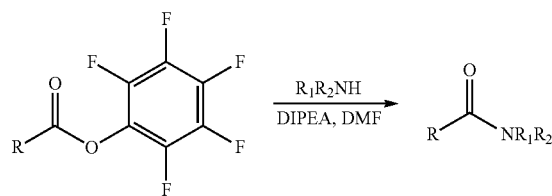
| Example | Starting PFP Ester | Amine Nucleophile | Product | IUPAC Name | Yield* |
|---|---|---|---|---|---|
| | | | | 2-yl]carbamoyl}-1,3-thiazol-2-yl)-1-hydroxy-4-methylpentan-3-yl]-N-methyl-L-isoleucinamide | |
| #B33 | #A43 | #A6 | | 1,2-dimethyl-D-prolyl-N-{(1S,3R)-1-(4-{[(2R,4S)-1-(4-aminophenyl)-4-carboxypentan-2-yl]carbamoyl}-1,3-thiazol-2-yl)-1-hydroxy-4-methylpentan-3-yl]-N-methyl-L-isoleucinamide | 37% |
*See Table 1 for purification details Preparation of N,N,-2-trimethylalanyl-N-[(1R,3R)-1-(acetyloxy)-1-(4-{[(2R,4S)-5-methoxy-4-methyl-5-oxo-1-phenylpentan-2-yl]carbamoyl}-1,3-thiazol-2-yl)-4-methylpentan-3-yl]-N-methyl-L-isoleucinamide (# B34)

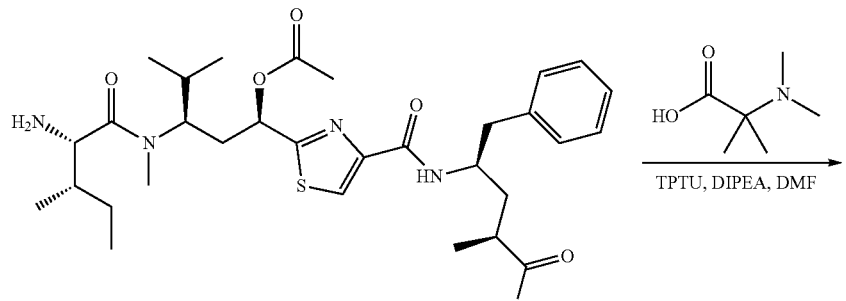

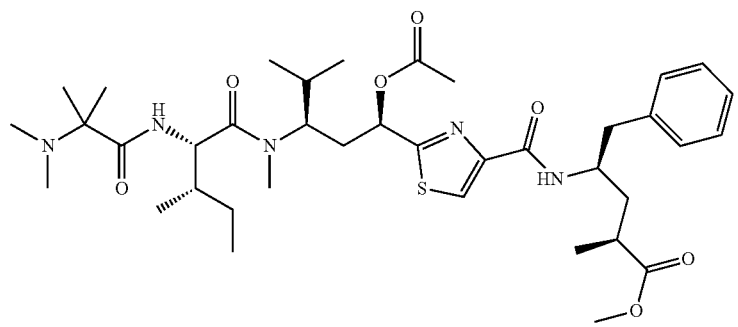

To a vial containing 2-(dimethylamino)-2-methylpropanoic acid (2.6 mg, 0.02 mmol) was added a solution of TPTU (5.9 mg, 0.02 mmol) in DMF (0.25 mL) followed by DIPEA (0.010 mL, 0.06 mmol). The reaction was stirred for 15 minutes and a solution of methyl (2S,4R)-4-{[(2-{(1R,3R)-1-(acetyloxy)-3-[L-isoleucyl(methyl)amino]-4-methylpentyl}-1,3-thiazol-4-yl)carbonyl]amino}-2-methyl-5-phenylpentanoate (# A10, 13.1 mg, 0.02 mmol) in DMF (0.25 mL) was added. The reaction was stirred at rt for 18 h then quenched with H₂O (1.5 mL) and extracted with EtOAc (3×2.5 mL). The combined organic extracts were loaded onto a SPE cartridge charged with sodium sulfate and concentrated via genevac. The residue was purified by reverse phase chromatography (Table 1) to afford the title compound # B34 (8.4 mg, 58%).

Preparation of 2-methylalanyl-N-[(1R,3R)-1-(acetyloxy)-1-(4-{[(2R,4S)-5-methoxy-4-methyl-5-oxo-1-phenylpentan-2-yl]carbamoyl}-1,3-thiazol-2-yl)-4-methylpentan-3-yl]-N-methyl-L-isoleucinamide (# B35)

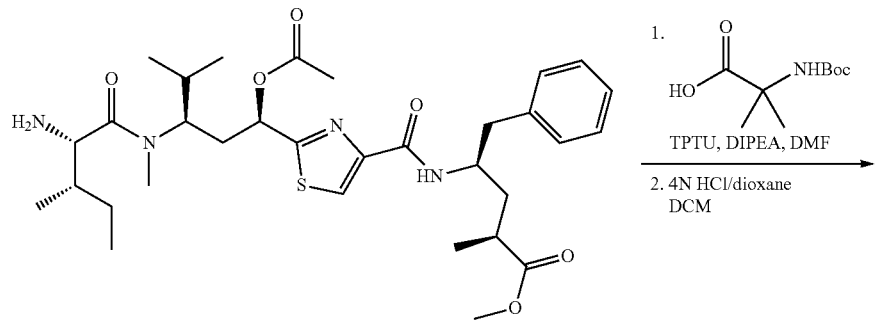

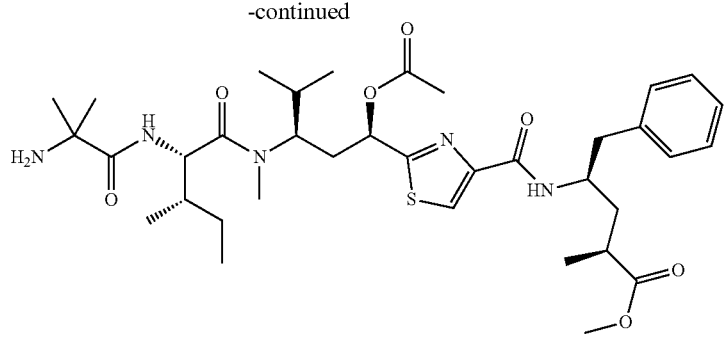

B35

To a vial containing 2-((tert-butoxycarbonyl)amino)-2-methylpropanoic acid (4.0 mg, 0.02 mmol) was added a solution of TPTU (5.9 mg, 0.02 mmol) in DMF (0.25 mL) followed by DIPEA (0.010 mL, 0.06 mmol). The reaction was stirred for 15 minutes and a solution of methyl (2S, 4R)-4-{[(2-{(1R,3R)-1-(acetyloxy)-3-[L-isoleucyl(methyl)amino]-4-methylpentyl}-1,3-thiazol-4-yl)carbonyl]amino}-2-methyl-5-phenylpentanoate (# A10, 13.1 mg, 0.02 mmol) in DMF (0.25 mL) was added. The reaction was stirred at rt for 18 h then quenched with $H_2O$ (1.5 mL) and extracted with EtOAc (3×2.5 mL). The combined organic extracts were loaded onto a SPE cartridge charged with sodium sulfate and concentrated via genevac. The residue was dissolved into DCM (1.0 mL) and 4 N HCl in dioxane (1.0 mL) was added. The reaction was stirred at rt for 1 h and solvent removed via genevac. Purification by reverse phase chromatography (Table 1) afforded the title compound # B35 (4.3 mg, 31%).

TABLE 1

Preparative Gradient and Analytical Data for Examples #B1-#B35

| Example | Prep. Method | Prep. Gradient | Analytical Protocol | Ret. Time | m/z [M + H]$^+$ | $^1$H NMR (400 MHz, DMSO-d6) |
|---|---|---|---|---|---|---|
| #B1 | F | 85.0% $H_2O$/15.0% acetonitrile linear to 0% $H_2O$/100% acetonitrile in 8.5 min, HOLD at 0% $H_2O$/100% acetonitrile to 10.0 min. Flow: 25 mL/min. | A | 2.89 | 756.3 | |
| #B2 | E | 80.0% $H_2O$/20.0% acetonitrile linear to 40% $H_2O$/60% acetonitrile in 8.5 min to 0% $H_2O$/100% acetonitrile to 9.0 min, HOLD at 0% $H_2O$/100% acetonitrile from 9.0 to 10.0 min. Flow 25 mL/min | A | 2.8 | 742.3 | |
| #B3 | | HPLC (Method B) | D | 7.09 | 765.4 | |
| #B4 | E | 90.0% $H_2O$/10.0% acetonitrile linear to 0% $H_2O$/100% acetonitrile in 10.5 min, HOLD at 0% $H_2O$/100% acetonitrile to 12.0 min. Flow: 25mL/min. | A | 2.87 | 729.4 | |
| #B5 | — | HPLC (Method B) | D | 7.99 | 742.4 | |
| #B6 | E | 80.0% $H_2O$/20.0% acetonitrile linear to 40% $H_2O$/60% acetonitrile in 8.5 min to 0% $H_2O$/100% acetonitrile to 9.0 min, HOLD at 0% $H_2O$/100% Acetonitrile from 9.0 to 10.0 min. Flow: 25 mL/min. | A | 2.8 | 728.4 | |
| #B7 | — | HPLC (Method B) | D | 7.62 | 757.4 | |
| #B8 | — | Medium pressure reverse phase C18 chromatography (Gradient: 10% to 80% acetonitrile in water with 0.02% TFA in each phase) | C | 0.77 | 728.8 | |

TABLE 1-continued

Preparative Gradient and Analytical Data for Examples #B1-#B35

| Example | Prep. Method | Prep. Gradient | Analytical Protocol | Ret. Time | m/z [M + H]+ | $^1$H NMR (400 MHz, DMSO-d6) |
|---|---|---|---|---|---|---|
| #B9 | — | Medium pressure reverse phase C18 chromatography (Gradient: 10% to 95% acetonitrile in water with 0.02% TFA in each phase) | C | 0.63 | 743.8 | δ 8.12 (m), 7.90 (d, 1H, J = 9.2 Hz), 7.25 (m), 7.12 (m), 7.00 (m), 6.97 (m), 6.68 (m), 5.54 (m), 4.57 (m), 4.08 (m), 3.53 (m), 3.56 (m), 3.10 (m), 2.94 (s), 2.70 (m), 2.63 (m), 2.50 (m), 2.27 (m), 2.05 (s), 2.03 (m), 1.78 (m), 1.50 (m), 1.41 (s), 1.21 (m), 1.05 (m), 1.00 (d, J = 7.2 Hz), 0.90 (m), 0.79 (m), 0.66 (d, J = 6.4 Hz) |
| #B10 | E | 90.0% H$_2$O/10.0% acetonitrile linear to 50% H$_2$O/50% acetonitrile in 8.5 min to 0% H$_2$O/100% acetonitrile to 9.0 min, HOLD at 0% H$_2$O/100% acetonitrile from 9.0 to 10.0 min. Flow: 25 mL/min. | A | 1.99 | 418.3* | |
| #B11 | E | 90.0% H$_2$O/10.0% acetonitrile linear to 50% H$_2$O/50% acetonitrile in 8.5 min to 0% H$_2$O/100% acetonitrile to 9.0 min, HOLD at 0% H$_2$O/100% acetonitrile from 9.0 to 10.0 min. Flow: 25 mL/min. | A | 1.97 | 835.4 | |
| #B12 | E | 90.0% H$_2$O/10.0% acetonitrile linear to 40% H$_2$O/60% acetonitrile in 8.5 min to 0% H$_2$O/100% acetonitrile to 9.0 min, HOLD at 0% H$_2$O/100% acetonitrile from 9.0 to 10.0 min. Flow: 25 mL/min. | A | 2.62 | 716.5 | |
| #B13 | E | 95.0% H$_2$O/5.0% acetonitrile linear to 0% H$_2$O/100% acetonitrile in 8.5 min, HOLD at 0% H$_2$O/100% acetonitrile to 10.0 min. Flow: 25 mL/min. | A | 2.8 | 754.5 | |
| #B14 | E | 95.0% H$_2$O/5.0% acetonitrile linear to 0% H$_2$O/100% acetonitrile in 8.5 min, HOLD at 0% H$_2$O/100% acetonitrile to 10.0 min. Flow: 25 mL/min. | A | 2.82 | 754.5 | |
| #B15 | E | 85.0% H$_2$O/15.0% acetonitrile linear to 50% H$_2$O/50% acetonitrile in 8.5 min to 0% H$_2$O/100% acetonitrile to 9.0 min, HOLD at 0% H$_2$O/100% acetonitrile from 9.0 to 10.0 min. Flow: 25 mL/min. | A | 2.53 | 686.5 | |
| #B16 | E | 95.0% H$_2$O 5.0% acetonitrile linear to 0% H$_2$O/100% acetonitrile in 8.5 min, HOLD at 0% | A | 2.91 | 782.5 | |

TABLE 1-continued

Preparative Gradient and Analytical Data for Examples #B1-#B35

| Example | Prep. Method | Prep. Gradient | Analytical Protocol | Ret. Time | m/z [M + H]+ | 1H NMR (400 MHz, DMSO-d6) |
|---|---|---|---|---|---|---|
| | | H2O/100% acetonitrile to 10.0 min. Flow: 25 mL/min. | | | | |
| #B17 | E | 95.0% H2O/5.0% acetonitrile linear to 0% H2O/100% acetonitrile in 8.5 min, HOLD at 0% H2O/100% acetonitrile to 10.0 min. Flow: 25 mL/min. | A | 2.77 | 740.5 | |
| #B18 | E | 95.0% H2O/5.0% acetonitrile linear to 50% H2O/50% acetonitrile in 10.5 min to 0% H2O/ 100% acetonitrile to 11.0 min, HOLD at 0% H2O/100% acetonitrile from 11.0 to 12.0 min. Flow: 25 mL/min. | A | 1.73 | 755.4 | |
| #B19 | E | 95.0% H2O/5.0% acetonitrile linear to 60% H2O/40% acetonitrile in 10.5 min to 0% H2O/ 100% acetonitrile to 11.0 min, HOLD at 0% H2O/100% acetonitrile from 11.0 to 12.0 min. Flow: 25 mL/min. | A | 1.76 | 727.4 | |
| #B20 | E | 95.0% H2O/5.0% acetonitrile linear to 40% H2O/60% acetonitrile in 10.5 min to 0% H2O/100% acetonitrile to 11.0 min, HOLD at 0% H2O/100% acetonitrile from 11.0 to 12.0 min. Flow: 25 mL/min. | A | 2.5 | 741.7 | |
| #B21 | E | 95.0% H2O/5.0% acetonitrile linear to 50% H2O/50% acetonitrile in 8.5 min to 0% H2O/100% acetonitrile to 9.0 min, HOLD at 0% H2O/100% acetonitrile from 9.0 to 10.0 min. Flow: 25 mL/min. | A | 1.75 | 772.5 | |
| #B22 | E | 80.0% H2O/20.0% acetonitrile linear to 60% H2O/40% acetonitrile in 8.5 min to 0% H2O/100% acetonitrile to 9.0 min, HOLD at 0% H2O/100% acetonitrile from 9.0 to 10.0 min. Flow: 25 mL/min. | A | 2.2 | 683.7 | |
| #B23 | E | 90.0% H2O/10.0% acetonitrile linear to 65% H2O/35% acetonitrile in 10.5 min to 0% H2O/100% acetonitrile to 11.0 min, HOLD at 0% H2O/100% acetonitrile from 11.0 to 12.0 min. Flow: 25 mL/min. | A | 1.83 | 757.6 | |
| #B24 | E | 85.0% H2O/15.0% acetonitrile linear to 60% H2O/40% acetonitrile in 10.5 min to 0% H2O/100% acetonitrile to 11.0 min, HOLD at 0% H2O/100% acetonitrile from 11.0 to 12.0 min. Flow: 25 mL/min. | A | 1.87 | 786.6 | |
| #B25 | E | 85.0% H2O/15.0% acetonitrile linear to 60% | A | 1.86 | 786.6 | |

TABLE 1-continued

Preparative Gradient and Analytical Data for Examples #B1-#B35

| Example | Prep. Method | Prep. Gradient | Analytical Protocol | Ret. Time | m/z [M + H]+ | 1H NMR (400 MHz, DMSO-d6) |
|---|---|---|---|---|---|---|
| | | H₂O/40% acetonitrile in 10.5 min to 0% H₂O/100% acetonitrile to 11.0 min, HOLD at 0% H₂O/100% acetonitrile from 11.0 to 12.0 min. Flow: 25 mL/min. | | | | |
| #B26 | E | 85.0% H₂O/15.0% acetonitrile linear to 70% H₂O/30% acetonitrile in 10.5 min to 0% H₂O/100% acetonitrile to 11.0 min, HOLD at 0% H₂O/100% acetonitrile from 11.0 to 12.0 min. Flow: 25 mL/min. | A | 1.9 | 784.7 | |
| #B27 | E | 85.0% H₂O/15.0% acetonitrile linear to 70% H₂O/30% acetonitrile in 10.5 min to 0% H₂O/100% acetonitrile to 11.0 min, HOLD at 0% H₂O/100% acetonitrile from 11.0 to 12.0 min. Flow: 25 mL/min. | A | 2 | 812.7 | |
| #B28 | E | 95.0% H₂O/5.0% acetonitrile linear to 50% H₂O/50% acetonitrile in 8.5 min to 0% H₂O/100% acetonitrile to 9.0 min, HOLD at 0% H₂O/100% acetonitrile from 9.0 to 10.0 min. Flow: 25 mL/min. | A | 1.82 | 742.7 | |
| #B29 | E | 85.0% H₂O/15.0% acetonitrile linear to 60% H₂O/40% acetonitrile in 8.5 min to 0% H₂O/100% acetonitrile to 9.0 min, HOLD at 0% H₂O/100% acetonitrile from 9.0 to 10.0 min. Flow: 25 mL/min. | A | 1.91 | 771.5 | |
| #B30 | E | 90.0% H₂O/10.0% acetonitrile linear to 40% H₂O/60% acetonitrile in 8.5 min to 0% H₂O/100% acetonitrile to 9.0 min, HOLD at 0% H₂O/100% acetonitrile from 9.0 to 10.0 min. Flow: 25 mL/min. | A | 1.9 | 379.9* | |
| #B31 | E | 95.0% H₂O/5.0% acetonitrile linear to 50% H₂O/50% acetonitrile in 8.5 min to 0% H₂O/100% acetonitrile to 9.0 min, HOLD at 0% H₂O/100% acetonitrile from 9.0 to 10.0 min. Flow: 25 mL/min. | A | 2 | 772.5 | |
| #B32 | — | HPLC (Method B) | D | 5.89 | 702.4 | |
| #B33 | F | 85.0% H₂O/15.0% acetonitrile linear to 50% H₂O/50% acetonitrile in 8.5 min to 0% H₂O/100% acetonitrile to 9.0 min, HOLD at 0% H₂O/100% acetonitrile from 9.0 to 10.0 min. Flow: 25 mL/min. | E | 1.73 | 701.6 | |

TABLE 1-continued

Preparative Gradient and Analytical Data for Examples #B1-#B35

| Example | Prep. Method | Prep. Gradient | Analytical Protocol | Ret. Time | m/z [M + H]+ | 1H NMR (400 MHz, DMSO-d6) |
|---|---|---|---|---|---|---|
| #B34 | E | 85.0% H2O/15.0% acetonitrile linear to 0% H2O/100% acetonitrile in 8.5 min, HOLD at 0% H2O/100% acetonitrile to 10.0 min. Flow: 25 mL/min | A | 2.8 | 730.5 | |
| #B35 | E | 85.0% H2O/15.0% acetonitrile linear to 0% H2O/100% acetonitrile in 8.5 min, HOLD at 0% H2O/100% acetonitrile to 10.0 min. Flow: 25 mL/min. | A | 2.7 | 702.4 | |

General Method for Coupling of Pentafluoro Ester (# A30) with Amine Nucleophiles in a Parallel Format.

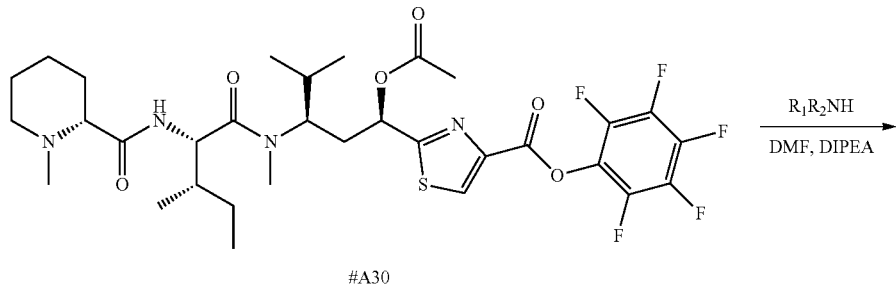

A30

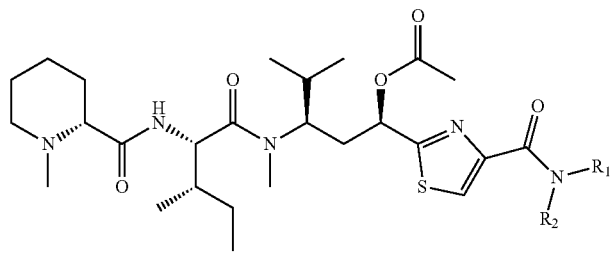

B36-#B41

To a vial containing PFP ester # A30 (1 eq) and the amine (1 eq) was added DMF (1.5 mL) and DIPEA (49 uL, 0.280 mmol) and the reaction was stirred at rt in a capped vial. After stirring for 4 h at rt, the reaction was concentrated to a crude gummy residue which was re-dissolved in DMSO (0.9 mL) and purified by preparative HPLC (Method A) to provide the target compound.

TABLE 2

Prep and QC Data for Analogs #B36 to #B41

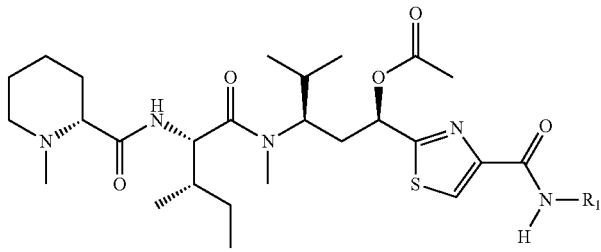

| Example Number | R₁ | Starting Amine (R₁NH₂) | Source of R₁NH₂ | Amount made; Yield | Mass spectrum: LC-MS or HPLC observed m/z [M + H]⁺ and retention time (Protocol A) | IUPAC Name |
|---|---|---|---|---|---|---|
| #B36 | 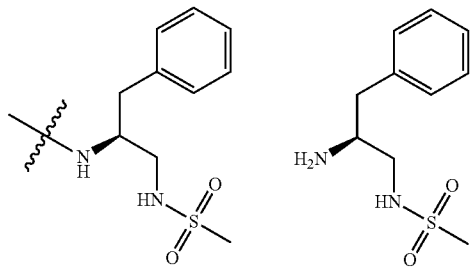 | | WO 974 6553 | 3.0 mg; 29% | 749.4; 2.51 minutes | (1R,3R)-4-methyl-3-[methyl(N-{[(2R)-1-methylpiperidin-2-yl]carbonyl}-L-isoleucyl)amino]-1-[4-({(2S)-1-[(methylsulfonyl)amino]-3-phenylpropan-2-yl}carbamoyl)-1,3-thiazol-2-yl]pentyl acetate |
| #B37 | 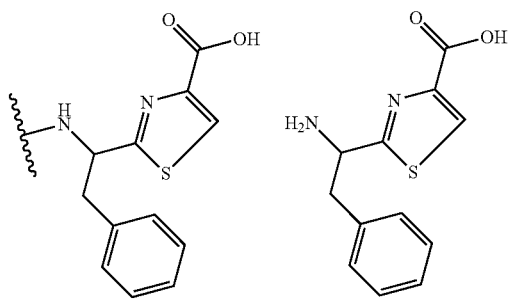 | | Org. Lett. 2006, 8, 2417-2420 | 1.8 mg; 17% | 769.4; 2.53 minutes | 2-(1-{[(2-{(1R,3R)-1-(acetyloxy)-4-methyl-3-[methyl(N-{[(2R)-1-methylpiperidin-2-yl]carbonyl}-L-isoleucyl)amino]pentyl}-1,3-thiazol-4-yl)carbonyl]amino}-2-phenylethyl)-1,3-thiazole-4-carboxylic acid |
| #B38 | 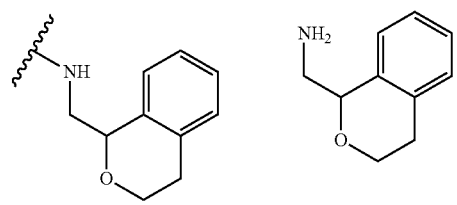 | | CAS: 19158-90-8 | 2.5 mg; 26% | 684.4; 2.67 minutes | (1R,3R)-1-{4-[(3,4-dihydro-1H-isochromen-1-ylmethyl)carbamoyl]-1,3-thiazol-2-yl}-4-methyl-3-[methyl(N-{[(2R)-1-methylpiperidin-2-yl]carbonyl}-L-isoleucyl)amino]pentyl acetate |

TABLE 2-continued

Prep and QC Data for Analogs #B36 to #B41

| Example Number | R₁ | Starting Amine (R₁NH₂) | Source of R₁NH₂ | Amount made; Yield | Mass spectrum: LC-MS or HPLC observed m/z $[M + H]^+$ and retention time (Protocol A) | IUPAC Name |
|---|---|---|---|---|---|---|
| #B39 | | | CAS: 672310-08-6 | 3.9 mg; 36% | 781.5; 2.74 minutes | ethyl 5-[(1S)-1-{[(2-{(1R,3R)-1-(acetyloxy)-4-methyl-3-[methyl(N-{[(2R)-1-methylpiperidin-2-yl]carbonyl}-L-isoleucyl)amino]pentyl}-1,3-thiazol-4-yl)carbonyl]amino}-2-phenylethyl]-1,3-oxazole-4-carboxylate |
| #B40 | | | Org. Biomol. Chem. 2012, 10, 7618-7627 | 2.0 mg; 21% | 371.3*; 2.15 minutes | (1R,3R)-4-methyl-3-[methyl(N-{[(2R)-1-methylpiperidin-2-yl]carbonyl}-L-isoleucyl)amino]-1-[4-({(2S)-1-(morpholin-4-yl)-3-phenylpropan-2-yl]carbamoyl}-1,3-thiazol-2-yl)pentyl acetate |
| #B41 | | | | 6.1 mg; 66% | 659.4; 2.14 minutes | (1R,3R)-4-methyl-3-[methyl(N-{[(2R)-1-methylpiperidin-2-yl]carbonyl}-L-isoleucyl)amino]-1-[4-{[2-(2-oxopyridin-1(2H)-yl)ethyl]carbamoyl}-1,3-thiazol-2-yl)pentyl acetate |

*$[M + 2H]^{2+}$

General Method for Coupling of Pentafluoro Ester (# A31) with Amine Nucleophiles in a Parallel Format.

PFP ester # A31 (1.0 eq) was reacted with the amine nucleophile (1-1.5 eq) in DMF in the presence of DIPEA (5 eq), stirring at rt for 18-24 h. Reactions were concentrated to dryness and purified by reverse phase chromatography (Protocol A).

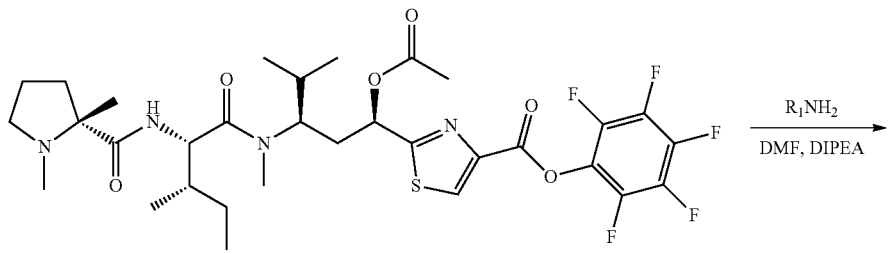

A31

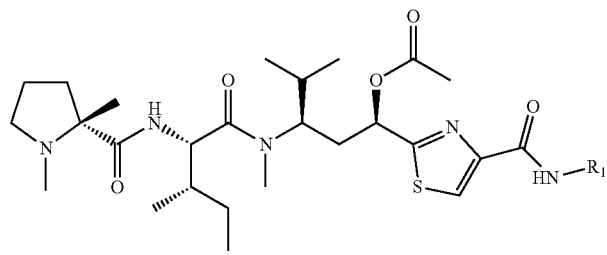

B42-#B80

TABLE 3

Prep and QC Data for Analogs #B42-#B80

| Example Number | R₁ | Starting Amine | Source of amine | Amount made; Yield | Mass spectrum: LC-MS or HPLC observed m/z; [M + H]⁺ and Retention time (Protocol A) | IUPAC Name |
|---|---|---|---|---|---|---|
| #B42 | (pyrazolylethyl-NH group) | H₂N-CH₂CH₂-(3,5-dimethylpyrazol-1-yl) | CAS: 62821-88-9 | 6.7 mg; 48% | 660.4; 2.15 minutes | 1,2-dimethyl-D-prolyl-N-[(1R,3R)-1-(acetyloxy)-1-(4-{[2-(3,5-dimethyl-1H-pyrazol-1-yl)ethyl]carbamoyl}-1,3-thiazol-2-yl)-4-methylpentan-3-yl]-N-methyl-L-isoleucinamide |

TABLE 3-continued

Prep and QC Data for Analogs #B42-#B80

| Example Number | R₁ | Starting Amine | Source of amine | Amount made; Yield | Mass spectrum: LC-MS or HPLC observed m/z; [M + H]⁺ and Retention time (Protocol A) | IUPAC Name |
|---|---|---|---|---|---|---|
| #B43 | | | CAS: 7663-77-6 | 5.9 mg; 42% | 663.3; 2.21 minutes | 1,2-dimethyl-D-prolyl-N-[(1R,3R)-1-(acetyloxy)-4-methyl-1-(4-{[3-(2-oxopyrrolidin-1-yl)propyl]carbamoyl}-1,3-thiazol-2-yl)pentan-3-yl]-N-methyl-L-isoleucinamide |
| #B44 | | | CAS: 350046-24-1 | 6.3 mg; 42% | 697.4; 2.38 minutes | 1,2-dimethyl-D-prolyl-N-[(1R,3R)-1-(acetyloxy)-4-methyl-1-(4-{[2-(1-oxo-1,3-dihydro-2H-isoindol-2-yl)ethyl]carbamoyl}-1,3-thiazol-2-yl)pentan-3-yl]-N-methyl-L-isoleucinamide |
| #B45 | | | CAS: 17027-51-9 | 6.6 mg; 44% | 718.3; 3.1 minutes | 1,2-dimethyl-D-prolyl-N-[(1R,3R)-1-(acetyloxy)-1-(4-{[2-(biphenyl- |

TABLE 3-continued

Prep and QC Data for Analogs #B42-#B80

| Example Number | R₁ | Starting Amine | Source of amine | Amount made; Yield | Mass spectrum: LC-MS or HPLC observed m/z; [M + H]⁺ and Retention time (Protocol A) | IUPAC Name |
|---|---|---|---|---|---|---|
| | | | | | | 4-yl)ethyl]carbamoyl}-1,3-thiazol-2-yl)-4-methylpentan-3-yl]-N-methyl-L-isoleucinamide |
| #B46 | 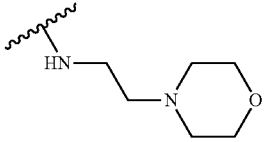 [SMILES: *NCCN1CCOCC1] | 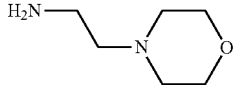 | CAS: 2038-03-1 | 6.5 mg; 46% | 651.4; 1.8 minutes | 1,2-dimethyl-D-prolyl-N-[(1R,3R)-1-(acetyloxy)-4-methyl-1-(4-{[2-(morpholin-4-yl)ethyl]carbamoyl}-1,3-thiazol-2-yl)pentan-3-yl]-N-isomethyl-L-leucinamide |
| #B47 | 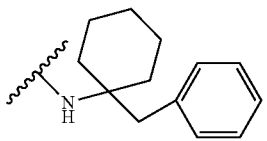 [SMILES: *NC1(Cc2ccccc2)CCCCC1] | 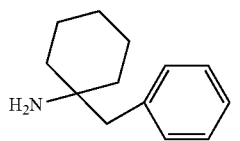 [SMILES: NC1(Cc2ccccc2)CCCCC1] | CAS: 19165-94-7 | 6.2 mg; 41% | 710.5; 3.2 minutes | 1,2-dimethyl-D-prolyl-N-[(1R,3R)-1-(acetyloxy)-1-{4-[(1-benzylcyclohexyl)carbamoyl]-1,3-thiazol-2-yl}-4-methylpentan-3-yl]-N-methyl-L-isoleucinamide |

TABLE 3-continued

Prep and QC Data for Analogs #B42-#B80

| Example Number | R₁ | Starting Amine | Source of amine | Amount made; Yield | Mass spectrum: LC-MS or HPLC observed m/z; [M + H]⁺ and Retention time (Protocol A) | IUPAC Name |
|---|---|---|---|---|---|---|
| #B48 | (structure: -NH-CH₂CH₂-imidazole) | (structure: H₂N-CH₂CH₂-imidazole) | CAS: 5739-10-6 | 7.2 mg; 55% | 316.7*  1.8 minutes | 1,2-dimethyl-D-prolyl-N-[(1R,3R)-1-(acetyloxy)-1-{4-{[2-(1H-imidazol-1-yl)ethyl]carbamoyl}-1,3-thiazol-2-yl}-4-methylpentan-3-yl]-N-methyl-L-isoleucinamide |
| #B49 | (structure: -NH-CH₂CH₂-cyclohexyl) | (structure: H₂N-CH₂CH₂-cyclohexyl) | CAS: 4442-85-7 | 5.7 mg; 41% | 648.4; 3.1 minutes | 1,2-dimethyl-D-prolyl-N-[(1R,3R)-1-(acetyloxy)-1-{4-[(2-cyclohexylethyl)carbamoyl]-1,3-thiazol-2-yl}-4-methylpentan-3-yl]-N-methyl-L-isoleucinamide |
| #B50 | (structure: HO-CH₂-CH(NH-)-CH₂-phenyl) | (structure: HO-CH₂-CH(NH₂)-CH₂-phenyl) | CAS: 16088-07-6 | 5.4 mg; 38% | 672.3; 2.5 minutes | 1,2-dimethyl-D-prolyl-N-[(1R,3R)-1-(acetyloxy)-1-{4-[(1-hydroxy-3-phenylpropan-2-yl) |

TABLE 3-continued

Prep and QC Data for Analogs #B42-#B80

| Example Number | R₁ | Starting Amine | Source of amine | Amount made; Yield | Mass spectrum: LC-MS or HPLC observed m/z; [M + H]⁺ and Retention time (Protocol A) | IUPAC Name |
|---|---|---|---|---|---|---|
| | | | | | | carbamoyl]-1,3-thiazol-2-yl}-4-methylpentan-3-yl]-N-methyl-L-isoleucinamide |
| #B51 | | | CAS: 139163-87-4; Tetrahedron Lett. 2004, 45, 5477-5479 | 9.2 mg; 61% | 730.4; 2.6 minutes | 1,2-dimethyl-D-prolyl-N-[(1R,3R)-1-(acetyloxy)-1-(4-{[(2S,3R)-3-hydroxy-4-methoxy-4-oxo-1-phenylbutan-2-yl]carbamoyl}-1,3-thiazol-2-yl)-4-methylpentan-3-yl]-N-methyl-L-isoleucinamide |
| #B52 | | | CAS: 41049-53-0 | 8.4 mg; 60% | 654.4; 2.7 minutes | 1,2-dimethyl-D-prolyl-N-[(1R,3R)-1-(acetyloxy)-4-methyl-1-{4-[(1-phenylcyclopropyl)carbamoyl]-1,3-thiazol-2-yl}pentan-3-yl]-N- |

TABLE 3-continued

Prep and QC Data for Analogs #B42-#B80

| Example Number | R₁ | Starting Amine | Source of amine | Amount made; Yield | Mass spectrum: LC-MS or HPLC observed m/z; [M + H]⁺ and Retention time (Protocol A) | IUPAC Name |
|---|---|---|---|---|---|---|
| | | | | | | methyl-L-isoleucin-amide |
| #B53 | 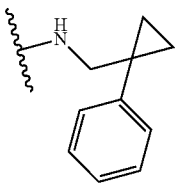 [SMILES: *NCC1(c2ccccc2)CC1] | 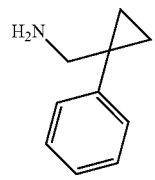 | CAS: 935-42-2 | 8.6 mg; 61% | 668.4; 2.8 minutes | 1,2-dimethyl-D-prolyl-N-[(1R,3R)-1-(acetyl-oxy)-4-methyl-1-(4-{[(1-phenyl-cyclo-propyl)methyl]carba-moyl}-1,3-thiazol-2-yl}pentan-3-yl]-N-methyl-L-isoleucin-amide |
| #B54 | 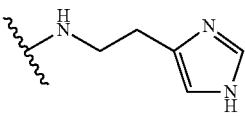 [SMILES: *NCCc1c[nH]cn1] | 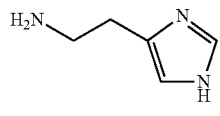 | CAS: 51-45-6 | 10.3 mg; 78% | 316.8* 1.8 minutes | 1,2-dimethyl-D-prolyl-N-[(1R,3R)-1-(acetyl-oxy)-1-(4-{[2-(1H-imidazol-4-yl)ethyl]carba-moyl}-1,3-thiazol-2-yl)-4-methyl-pentan-3-yl]-N-methyl-L-isoleucin-amide |

TABLE 3-continued

Prep and QC Data for Analogs #B42-#B80

| Example Number | R₁ | Starting Amine | Source of amine | Amount made; Yield | Mass spectrum: LC-MS or HPLC observed m/z; [M + H]⁺ and Retention time (Protocol A) | IUPAC Name |
|---|---|---|---|---|---|---|
| #B55 | 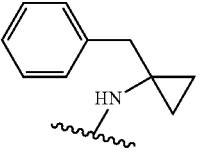 [SMILES: *NC1(Cc2ccccc2)CC1] | 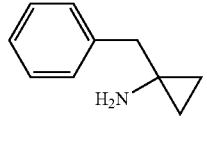 | CAS: 27067-03-4 | 8.8 mg; 63% | 668.4; 2.8 minutes | 1,2-dimethyl-D-prolyl-N-[(1R,3R)-1-{4-[(1-benzyl-cyclopropyl)carbamoyl]-1,3-thiazol-2-yl}-4-methylpentan-3-yl]-N-methyl-L-isoleucinamide |
| #B56 | 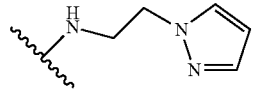 [SMILES: *NCCn1cccn1] | 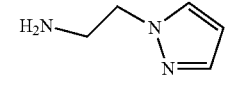 | CAS: 101395-71-5 | 9.7 mg; 75% | 632.4; 2.3 minutes | 1,2-dimethyl-D-prolyl-N-[(1R,3R)-1-(acetyloxy)-4-methyl-1-(4-{[2-(1H-pyrazol-1-yl)ethyl]carbamoyl}-1,3-thiazol-2-yl)pentan-3-yl]-N-methyl-L-isoleucinamide |
| #B57 | 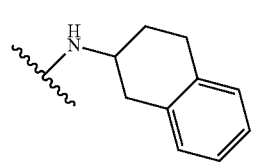 [SMILES: *NC1CCc2ccccc2C1] | 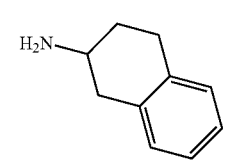 | CAS: 2954-50-9 | 7.7 mg; 55% | 668.5; 2.9 minutes | 1,2-dimethyl-D-prolyl-N-{(1R,3R)-1-(acetyloxy)-4-methyl-1-[4-(1,2,3,4-tetrhydronaphthalen-2-ylcarbamoyl)-1,3- |

TABLE 3-continued

Prep and QC Data for Analogs #B42-#B80

| Example Number | R₁ | Starting Amine | Source of amine | Amount made; Yield | Mass spectrum: LC-MS or HPLC observed m/z; [M + H]⁺ and Retention time (Protocol A) | IUPAC Name |
|---|---|---|---|---|---|---|
| | | | | | | thiazol-2-yl)pentan-3-yl}-N-methyl-L-isoleucinamide |
| #B58 | (structure) | (structure) | WO 974 6553 | 8.5 mg; 53% | 749.5; 2.5 minutes | 1,2-dimethyl-D-prolyl-N-{(1R,3R)-1-(acetyloxy)-4-methyl-1-[4-({(2S)-1-[(methylsulphonyl)amino]-3-phenylpropan-2-yl}carbamoyl)-1,3-thiazol-2-yl]pentan-3-yl}-N-methyl-L-isoleucinamide |
| #B59 | (structure) | (structure) | CAS: 61-54-1 | 4.6 mg; 33% | 681.5; 2.7 minutes | 1,2-dimethyl-D-prolyl-N-[(1R,3R)-1-(acetyloxy)-1-(4-{[2-(1H-indol-3-yl)ethyl]carbamoyl}-1,3-thiazol-2-yl)-4-methylpentan-3-yl]-N-methyl-L-isoleucinamide |

TABLE 3-continued

Prep and QC Data for Analogs #B42-#B80

| Example Number | R₁ | Starting Amine | Source of amine | Amount made; Yield | Mass spectrum: LC-MS or HPLC observed m/z; [M + H]⁺ and Retention time (Protocol A) | IUPAC Name |
|---|---|---|---|---|---|---|
| #B60 | 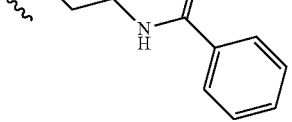 | 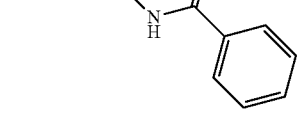 | CAS: 1009-17-2 | 9.7 mg; 69% | 685.6; 2.4 minutes | 1,2-dimethyl-D-prolyl-N-[(1R,3R)-1-(acetyloxy)-1-(4-{[2-(benzoylamino)ethyl]carbamoyl}-1,3-thiazol-2-yl)-4-methylpentan-3-yl]-N-methyl-L-isoleucinamide |
| #B61 | 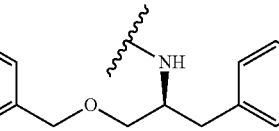 | 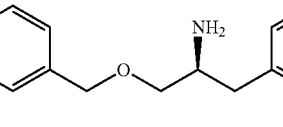 | CAS: 83053-86-5; Can. J. Chem. 1982, 60, 1836-41 | 9.5 mg; 59% | 762.5; 3.1 minutes | 1,2-dimethyl-D-prolyl-N-[(1R,3R)-1-(acetyloxy)-1-(4-{[(2S)-1-(benzyloxy)-3-phenylpropan-2-yl]carbamoyl}-1,3-thiazol-2-yl)-4-methylpentan-3-yl]-N-methyl-L-isoleucinamide |
| #B62 | 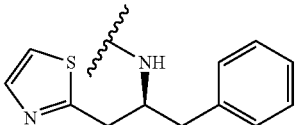 | 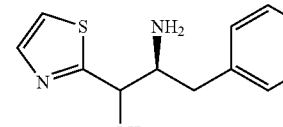 | CAS: 1383049-19-1; J. Org. Chem. 1990, 55, 1439-46 | 10.3 mg; 64% | 755.3; 2.6 minutes | 1,2-dimethyl-D-prolyl-N-[(1R,3R)-1-(acetyloxy)-1-(4-{[(2S)-1-hydroxy- |

TABLE 3-continued

Prep and QC Data for Analogs #B42-#B80

| Example Number | R₁ | Starting Amine | Source of amine | Amount made; Yield | Mass spectrum: LC-MS or HPLC observed m/z; [M + H]⁺ and Retention time (Protocol A) | IUPAC Name |
|---|---|---|---|---|---|---|
| | | | | | | 3-phenyl-1-(1,3-thiazol-2-yl)propan-2-yl]carbamoyl}-1,3-thiazol-2-yl)-4-methylpentan-3-yl]-N-methyl-L-isoleucinamide |
| #B63 | 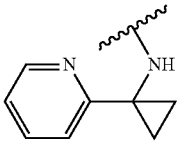 [SMILES: *NC1(c2ccccn2)CC1] | 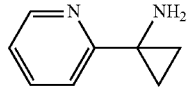 | CAS: 503417-37-6 | 9.1 mg; 65% | 655.3; 1.9 minutes | 1,2-dimethyl-D-prolyl-N-[(1R,3R)-4-(acetyloxy)-4-methyl-1-(4-{[1-(pyridin-2-yl)cyclopropyl]carbamoyl}-1,3-thiazol-2-yl)pentan-3-yl]-N-methyl-L-isoleucinamide |
| #B64 | 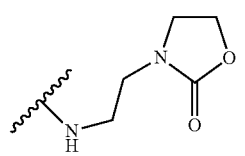 [SMILES: *NCCN1CCOC1=O] | 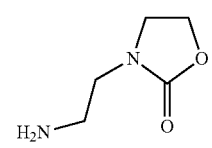 | CAS: 141778-93-0 | 9.2 mg; 66% | 651.3; 2.1 minutes | 1,2-dimethyl-D-prolyl-N-[(1R,3R)-1-(acetyloxy)-4-methyl-1-(4-{[2-(2-oxo-1,3-oxazolidin-3-yl)ethyl]carbamoyl}-1,3-thiazol-2- |

TABLE 3-continued

Prep and QC Data for Analogs #B42-#B80

| Example Number | R₁ | Starting Amine | Source of amine | Amount made; Yield | Mass spectrum: LC-MS or HPLC observed m/z; [M + H]⁺ and Retention time (Protocol A) | IUPAC Name |
|---|---|---|---|---|---|---|
| | | | | | | yl) pentan-3-yl]-N-methyl-L-isoleucinamide |
| #B65 | [structure: NH-CH₂-C(phenyl)(1-methylpiperidin-4-yl)] | [structure: 4-phenyl-1-methylpiperidin-4-yl-methanamine] | CAS: 1859-37-6 | 11.8 mg; 79% | 725.4; 2.1 minutes | 1,2-dimethyl-D-prolyl-N-[(1R,3R)-1-(acetyloxy)-4-methyl-1-(4-{[(1-methyl-4-phenyl-piperidin-4-yl)methyl]carbamoyl}-1,3-thiazol-2-yl)pentan-3-yl]-N-methyl-L-isoleucinamide |
| #B66 | [structure: NH-CH(CH₂Ph)-aryl-N(CH₃)₂] | [structure: 1-[4-(dimethylamino)phenyl]-2-phenylethan-1-amine] | CAS: 208654-85-7; J. Org. Chem. 1998, 63, 2824-2828 | 12.2 mg; 76% | 761.4; 2.3 minutes | 1,2-dimethyl-D-prolyl-N-{(1R,3R)-1-(acetyloxy)-1-[4-({1-[4-(dimethylamino)phenyl]-2-phenylethyl}carbamoyl)-1,3-thiazol-2-yl]-4-methylpentan-3-yl}-N-methyl-L-isoleucinamide |

TABLE 3-continued

Prep and QC Data for Analogs #B42-#B80

| Example Number | R₁ | Starting Amine | Source of amine | Amount made; Yield | Mass spectrum: LC-MS or HPLC observed m/z; [M + H]⁺ and Retention time (Protocol A) | IUPAC Name |
|---|---|---|---|---|---|---|
| #B67 | (diphenylmethyl)-NH- structure | diphenylmethylamine (NH₂) | CAS: 91-00-9 | 9.5 mg; 63% | 704.4; 3.0 minutes | 1,2-dimethyl-D-prolyl-N-[(1R,3R)-1-(acetyl-oxy)-1-{4-[(diphenyl-methyl)carba-moyl]-1,3-thiazol-2-yl}-4-methyl-pentan-3-yl]-N-methyl-L-isoleucin-amide |
| #B68 | -NH-CH₂CH₂-(pyrazin-2-yl) | H₂N-CH₂CH₂-(pyrazine) | CAS: 5321-59-5 | 10.4 mg; 74% | 644.6; 2.2 minutes | 1,2-dimethyl-D-prolyl-N-{(1R,3R)-1-(acetyl-oxy)-4-methyl-1-(4-{[2-(pyrazin-2-yl)ethyl]carba-moyl}-1,3-thiazol-2-yl)pentan-3-yl]-N-methyl-L-isoleucin-amide |
| #B69 | -NH-CH₂-(isochroman) | H₂N-CH₂-(isochroman) | CAS: 19158-90-8 | 9.6 mg; 69% | 684.7; 2.7 minutes | 1,2-dimethyl-D-prolyl-N-[(1R,3R)-1-(acetyl-oxy)-1-{4-[(3,4-dihydro-1H-iso-chromen-1- |

TABLE 3-continued

Prep and QC Data for Analogs #B42-#B80

| Example Number | R₁ | Starting Amine | Source of amine | Amount made; Yield | Mass spectrum: LC-MS or HPLC observed m/z; [M + H]⁺ and Retention time (Protocol A) | IUPAC Name |
|---|---|---|---|---|---|---|
| | | | | | | ylmethyl)carbamoyl]-1,3-thiazol-2-yl}-4-methylpentan-3-yl}-N-methyl-L-isoleucinamide |
| #B70 | | | CAS: 4735-50-6 | 9.2 mg; 61% | 692.5; 3.0 minutes | 1,2-dimethyl-D-prolyl-N-[(1R,3R)-1-(acetyloxy)-4-methyl-1-(4-{[2-(naphthalen-1-yl)ethyl]carbamoyl}-1,3-thiazol-2-yl)pentan-3-yl]-N-methyl-L-isoleucinamide |
| #B71 | | | CAS: 856973-36-9 | 11.2 mg; 80% | 644.4; 2.2 minutes | 1,2-dimethyl-D-prolyl-N-[(1R,3R)-1-(acetyloxy)-4-methyl-1-(4-{[2-(pyrimidin-5-yl)ethyl]carbamoyl}-1,3-thiazol-2-yl)pentan-3-yl]-N-methyl-L-isoleucinamide |

TABLE 3-continued

Prep and QC Data for Analogs #B42-#B80

| Example Number | R₁ | Starting Amine | Source of amine | Amount made; Yield | Mass spectrum: LC-MS or HPLC observed m/z; [M + H]⁺ and Retention time (Protocol A) | IUPAC Name |
|---|---|---|---|---|---|---|
| #B72 | 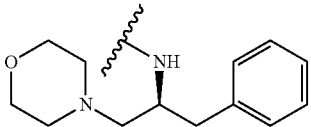 [SMILES: *N[C@@H](Cc1ccccc1)CN1CCOCC1] | 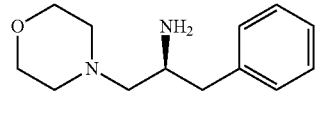 [SMILES: N[C@@H](Cc1ccccc1)CN1CCOCC1] | Org. Biomol. Chem. 2012, 10, 7618-7627 | 13.2 mg; 83% | 741.5; 2.2 minutes | 1,2-dimethyl-D-prolyl-N-[(1R,3R)-1-(acetyl-oxy)-4-methyl-1-(4-{[(2S)-1-(mor-pholin-4-yl)-3-phenyl-propan-2-yl]carba-moyl}-1,3-thiazol-2-yl)pentan-3-yl]-N-methyl-L-isoleucin-amide |
| #B73 | 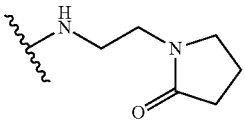 [SMILES: *NCCN1CCCC1=O] | 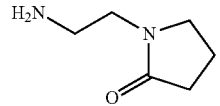 | CAS: 24935-08-8 | 9.2 mg; 66% | 649.5; 2.1 minutes | 1,2-dimethyl-D-prolyl-N-[(1R,3R)-1-(acetyl-oxy)-4-methyl-1-(4-{[2-(2-oxo-pyrroli-din-1-yl)ethyl]carba-moyl}-1,3-thiazol-2-yl)pentan-3-yl]-N-methyl-L-isoleucin-amide |

TABLE 3-continued

Prep and QC Data for Analogs #B42-#B80

| Example Number | R₁ | Starting Amine | Source of amine | Amount made; Yield | Mass spectrum: LC-MS or HPLC observed m/z; [M + H]⁺ and Retention time (Protocol A) | IUPAC Name |
|---|---|---|---|---|---|---|
| #B74 | | | CAS: 25611-78-3 | 10 mg; 67% | 718.5; 3.0 minutes | 1,2-dimethyl-D-prolyl-N-[(1R,3R)-1-(acetyloxy)-1-{4-[(1,2-diphenylethyl)carbamoyl]-1,3-thiazol-2-yl}-4-methylpentan-3-yl]-N-methyl-L-isoleucinamide |
| #B75 | | | U.S. Pat. No. US 7332515 | 7.6 mg; 48% | 781.5; 2.8 minutes | 1,2-dimethyl-D-prolyl-N-{(1R,3R)-1-(acetyloxy)-1-[4-({(1S)-1-[4-(ethoxycarbonyl)-1,3-oxazol-5-yl]-2-phenylethyl}carbamoyl)-1,3-thiazol-2-yl]-4-methylpentan-3-yl}-N-methyl-L-isoleucinamide |
| #B76 | | | CAS: 7728-74-7 | 9.7 mg; 69% | 325.3; 2.3 minutes | 1,2-dimethyl-D-prolyl-N-[(1R,3R)-1-(acetyloxy)- |

TABLE 3-continued

Prep and QC Data for Analogs #B42-#B80

| Example Number | R₁ | Starting Amine | Source of amine | Amount made; Yield | Mass spectrum: LC-MS or HPLC observed m/z; [M + H]⁺ and Retention time (Protocol A) | IUPAC Name |
|---|---|---|---|---|---|---|
| | | | | | | 4-methyl-1-(4-{[2-(1,3-thiazol-4-yl)ethyl]carbamoyl}-1,3-thiazol-2-yl)pentan-3-yl]-N-methyl-L-isoleucinamide |
| #B77 | (pyrazolyl-ethyl-NH structure) | (pyrazolyl-ethyl-NH₂ structure) | CAS: 796845-58-4 | 2.2 mg; 16% | 323.8*; 2.2 minutes | 1,2-dimethyl-D-prolyl-N-[(1R,3R)-1-(acetyloxy)-4-methyl-1-(4-{[2-(1-methyl-1H-pyrazol-4-yl)ethyl]carbamoyl}-1,3-thiazol-2-yl)pentan-3-yl]-N-methyl-L-isoleucinamide |
| #B78 | (thiazolyl-benzyl-NH structure) | (thiazolyl-benzyl-NH₂ structure) | CAS: 130199-65-4 | 10.1 mg; 67% | 725.3; 2.7 minutes | 1,2-dimethyl-D-prolyl-N-[(1R,3R)-1-(acetyloxy)-4-methyl-1-(4-{[(1S)-2-phenyl-1-(1,3-thiazol-2-yl)ethyl]carbamoyl}-1,3- |

TABLE 3-continued

Prep and QC Data for Analogs #B42-#B80

| Example Number | R₁ | Starting Amine | Source of amine | Amount made; Yield | Mass spectrum: LC-MS or HPLC observed m/z; [M + H]⁺ and Retention time (Protocol A) | IUPAC Name |
|---|---|---|---|---|---|---|
| | | | | | | thiazol-2-yl)pentan-3-yl]-N-methyl-L-isoleucinamide |
| #B79 | [structure: NH-CH2CH2-benzotriazole] | [structure: H2N-CH2CH2-benzotriazole] | CAS: 26861-65-4 | 9.2 mg; 66% | 683.3; 2.4 minutes; | 1,2-dimethyl-D-prolyl-N-[(1R,3R)-1-(acetyloxy)-1-(4-{[2-(1H-benzotriazol-1-yl)ethyl]carbamoyl}-1,3-thiazol-2-yl)-4-methylpentan-3-yl]-N-methyl-L-isoleucinamide |
| #B80 | [structure: NH-CH(thiazolyl)-CH2-C6H4-NH2] | [structure: NH2-CH(thiazolyl)-CH2-C6H4-NH2] | Synthesis provided herein (#A29) | 10.6 mg; 66% | 370.8; 2.4 minutes | 1,2-dimethyl-D-prolyl-N-[(1R,3R)-1-(acetyloxy)-1-(4-{[(1S)-2-(4-aminophenyl)-1-(1,3-thiazol-2-yl)ethyl]carbamoyl}-1,3-thiazol-2-yl)-4-methylpentan- |

TABLE 3-continued

Prep and QC Data for Analogs #B42-#B80

| Example Number | R₁ | Starting Amine | Source of amine | Amount made; Yield | Mass spectrum: LC-MS or HPLC observed m/z; [M + H]⁺ and Retention time (Protocol A) | IUPAC Name |
|---|---|---|---|---|---|---|
| | | | | | | 3-yl]-N-methyl-L-isoleucinamide |

*[M + 2 H]²⁺

Preparation of Linker Payloads (# LP)

Preparation of 1,2-dimethyl-D-prolyl-N-{(1R,3R)-1-(acetyloxy)-1-[4-({(2R,4S)-4-carboxy-1-[4-({N-[6-(2,5-dioxo-2,5-dihydro-1H-pyrrol-1-yl)hexanoyl]glycyl}amino)phenyl]pentan-2-yl}carbamoyl)-1,3-thiazol-2-yl]-4-methyl pentan-3-yl}-N-methyl-L-isoleucinamide (# LP 1)

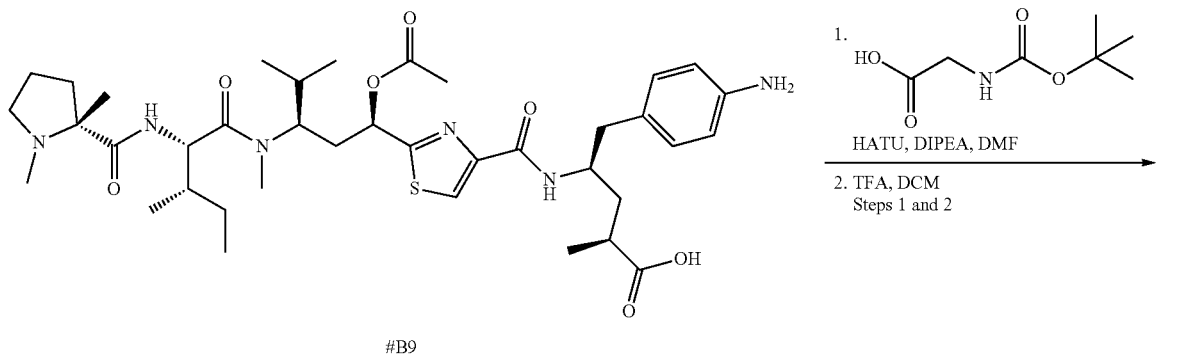

B9

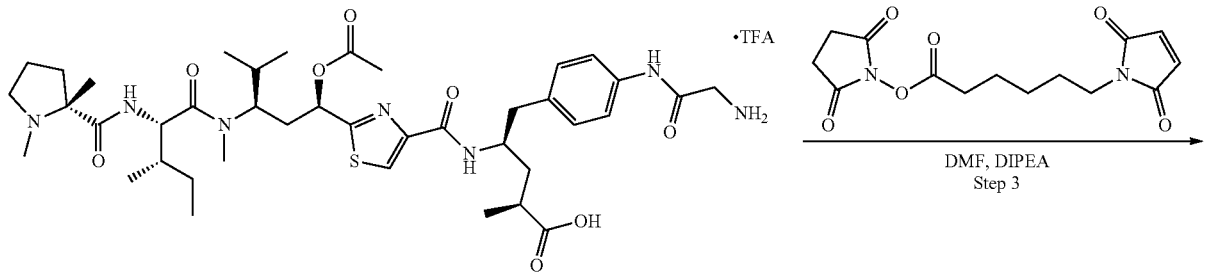

76

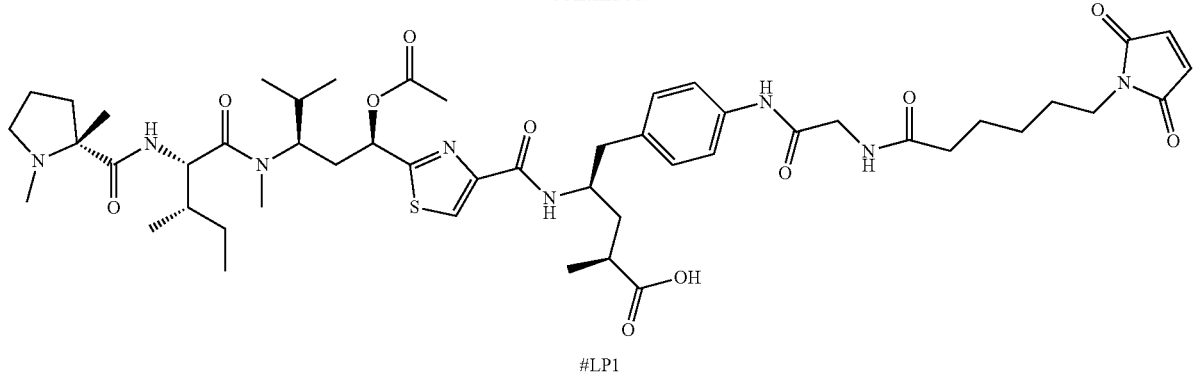

LP1

Step 1: Preparation of 1,2-dimethyl-D-prolyl-N-[(1R,3R)-1-(acetyloxy)-1-(4-{[(2R,4S)-1-(4-{[N-(tert-butoxycarbonyl)glycyl]amino}phenyl)-4-carboxypentan-2-yl]carbamoyl}-1,3-thiazol-2-yl)-4-methylpentan-3-yl]-N-methyl-L-isoleucinamide To a vial containing N-Boc glycine (166 mg, 0.948 mmol) and HATU (364 mg, 0.948 mmol) was added DMF (2 mL), and DIPEA (417 µL, 2.37 mmol). The reaction was stirred under N$_2$ for 0.5 h then added by syringe to a vial containing 1,2-dimethyl-D-prolyl-N-[(1R,3R)-1-(acetyloxy)-1-(4-{[(2R,4S)-1-(4-aminophenyl)-4-carboxypentan-2-yl]carbamoyl}-1,3-thiazol-2-yl)-4-methylpentan-3-yl]-N-methyl-L-isoleucinamide (# B9, 203 mg, 0.237 mmol), further diluting with DMF (1.2 mL). After stirring for 2.5 h at rt the reaction was concentrated and the residue re-dissolved in DMSO (~2 mL) and H$_2$O (~1 mL, containing 0.02% TFA) and purified by medium pressure C18 chromatography (10% acetonitrile/90% H$_2$O for 5 minutes, then 10% acetonitrile to 95% acetonitrile in H$_2$O over 18 minutes, each solvent containing 0.02% TFA) to yield the title compound (73 mg, 35%) as a white solid. LC-MS (Protocol C): m/z 900.4 [M+H]$^+$; Retention time=0.84 min.

Step 2: Preparation of 1,2-dimethyl-D-prolyl-N-{(1R,3R)-1-(acetyloxy)-1-[4-({(2R,4S)-4-carboxy-1-[4-(glycylamino)phenyl]pentan-2-yl}carbamoyl)-1,3-thiazol-2-yl]-4-methylpentan-3-yl}-N-methyl-L-isoleucinamide TFA Salt (76)

To a vial containing 1,2-dimethyl-D-prolyl-N-[(1R,3R)-1-(acetyloxy)-1-(4-{[(2R,4S)-1-(4-{[N-(tert-butoxycarbonyl)glycyl]amino}phenyl)-4-carboxypentan-2-yl]carbamoyl}-1,3-thiazol-2-yl)-4-methylpentan-3-yl]-N-methyl-L-isoleucinamide (35 mg, 0.039 mmol) was added DCM (1 mL) and TFA (350 µL) and the reaction was stirred at rt under N$_2$. After 3 h the reaction was concentrated in vacuo and dried under high vacuum to afford the title compound (45 mg, quantitative yield) as a gummy residue, which was used crude in the next step. LC-MS (Protocol C): m/z 800.4 [M+H]$^+$; Retention time=0.68 min.

Step 3: Preparation of 1,2-dimethyl-D-prolyl-N-{(1R,3R)-1-(acetyloxy)-1-[4-({(2R,4S)-4-carboxy-1-[4-({N-[6-(2,5-dioxo-2,5-dihydro-1H-pyrrol-1-yl)hexanoyl]glycyl}amino)phenyl]pentan-2-yl}carbamoyl)-1,3-thiazol-2-yl]-4-methyl pentan-3-yl}-N-methyl-L-isoleucinamide (# LP1)

To a vial containing 1,2-dimethyl-D-prolyl-N-{(1R,3R)-1-(acetyloxy)-1-[4-({(2R,4S)-4-carboxy-1-[4-(glycylamino)phenyl]pentan-2-yl}carbamoyl)-1,3-thiazol-2-yl]-4-methylpentan-3-yl}-N-methyl-L-isoleucinamide TFA salt (76, 79 mg, 0.099 mmol) was added 1-{6-[(2,5-dioxopyrrolidin-1-yl)oxy]-6-oxohexyl}-1H-pyrrole-2,5-dione (31 mg, 0.101 mmol) and DMF (2.6 mL). DIPEA (52 µL, 0.296 mmol) was added and the reaction was stirred at rt in a capped vial for 1.5 h. An additional (10 mg, 0.048 mmol) of 1-{6-[(2,5-dioxopyrrolidin-1-yl)oxy]-6-oxohexyl}-1H-pyrrole-2,5-dione and DIPEA (14 µL, 0.081 mmol) was added and the reaction stirred at rt for 2 h. The reaction was concentrated and purified by reverse phase chromatography (Method B) to provide the title compound # LP1 (35 mg, 26%) as a white solid. HPLC (Protocol D) m/z 993.4[M+H]$^+$; Retention time=7.02 min.

Preparation of 1,2-dimethyl-D-prolyl-N-[(1R,3R)-1-(acetyloxy)-1-(4-{[(2R,4S)-4-carboxy-1-{4-[({[4-({N-[6-(2,5-dioxo-2,5-dihydro-1H-pyrrol-1-yl)hexanoyl]-L-valyl-N~5~carbamoyl-L-ornithyl}amino)benzyl]oxy}carbonyl)amino]phenyl}pentan-2-yl]carbamoyl}-1,3-thiazol-2-yl)-4-methylpentan-3-yl]-N-methyl-L-isoleucinamide (# LP2)

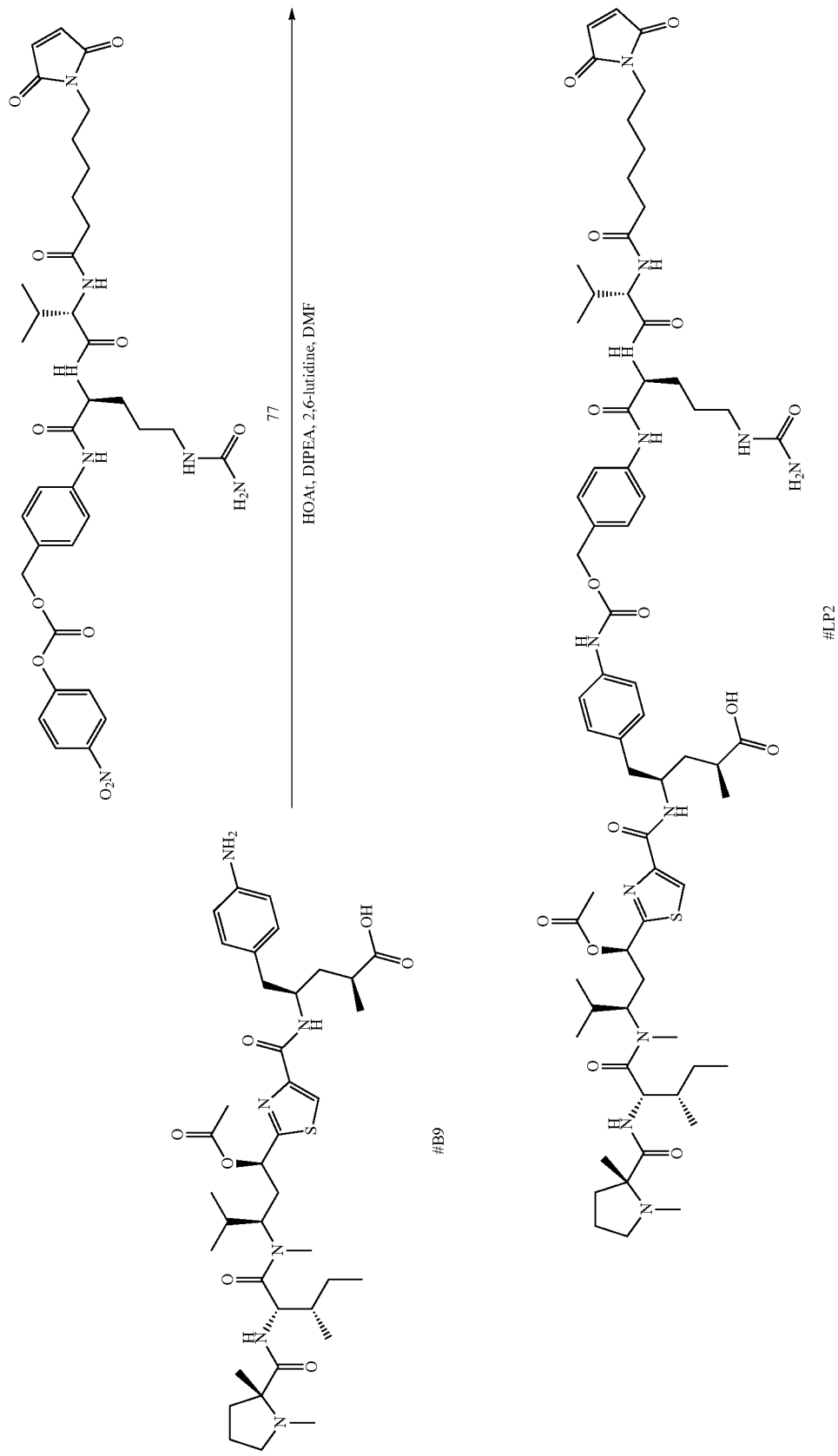

To a vial containing 1,2-dimethyl-D-prolyl-N-[(1R,3R)-1-(acetyloxy)-1-(4-{[(2R,4S)-1-(4-aminophenyl)-4-carboxypentan-2-yl]carbamoyl}-1,3-thiazol-2-yl)-4-methylpentan-3-yl]-N-methyl-L-isoleucinamide (# B9, 16 mg, 0.019 mmol), HOAt (10.3 mg, 0.076 mmol), and N-[6-(2,5-dioxo-2,5-dihydro-1H-pyrrol-1-yl)hexanoyl]-L-valyl-N~5~-carbamoyl-N-[4-({[(4-nitrophenoxy)carbonyl]oxy}methyl)phenyl]-L-ornithinamide (Eur. Pat. Appl. 1994, EP624377) (77, 27 mg, 0.037 mmol) in DMF (2 mL) was added DIPEA (13 µL, 0.076 mmol) and 2,6-lutidine (9 µL, 0.076 mmol) and the reaction was stirred at rt in a capped vial for 15.5 h at rt. The reaction was placed under $N_2$ and heated in an oil bath at 50° C. for 6.5 h, refrigerated overnight, and heated for an additional 24 h at 50° C. The reaction was concentrated to a yellow oil and purified by reverse phase chromatography (Method B) to afford the title compound # LP2 (1.6 mg, 6%) in 87% purity. HPLC (Protocol D) m/z 1342.6 [M+H]$^+$; Retention time=7.26 min.

Preparation of 1,2-dimethyl-D-prolyl-N-{(1R,3R)-1-(acetyloxy)-1-[4-({(2R,4S)-4-carboxy-1-[4-({N-[6-(2,5-dioxo-2,5-dihydro-1H-pyrrol-1-yl)hexanoyl]-L-valyl-L-alanyl}amino)phenyl]pentan-2-yl}carbamoyl)-1,3-thiazol-2-yl]-4-methylpentan-3-yl}-N-methyl-L-isoleucinamide (# LP3)

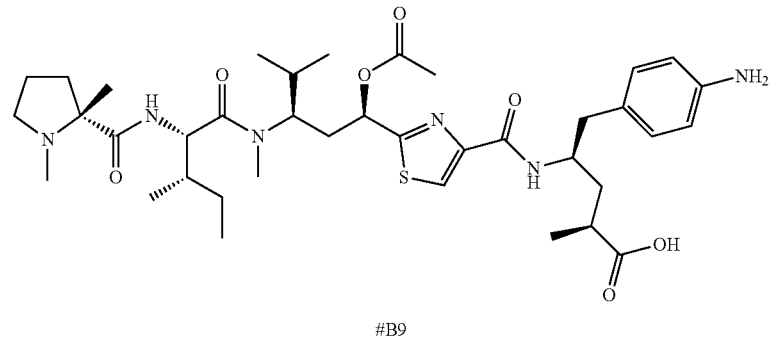

B9

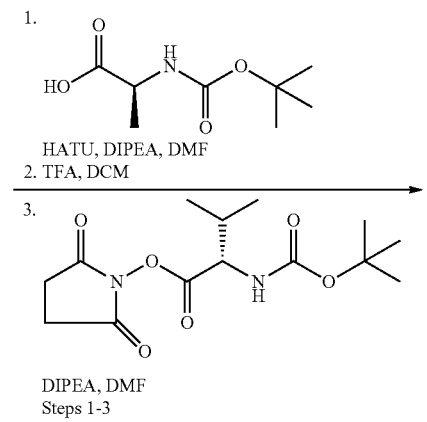

HATU, DIPEA, DMF
2. TFA, DCM

3.

DIPEA, DMF
Steps 1-3

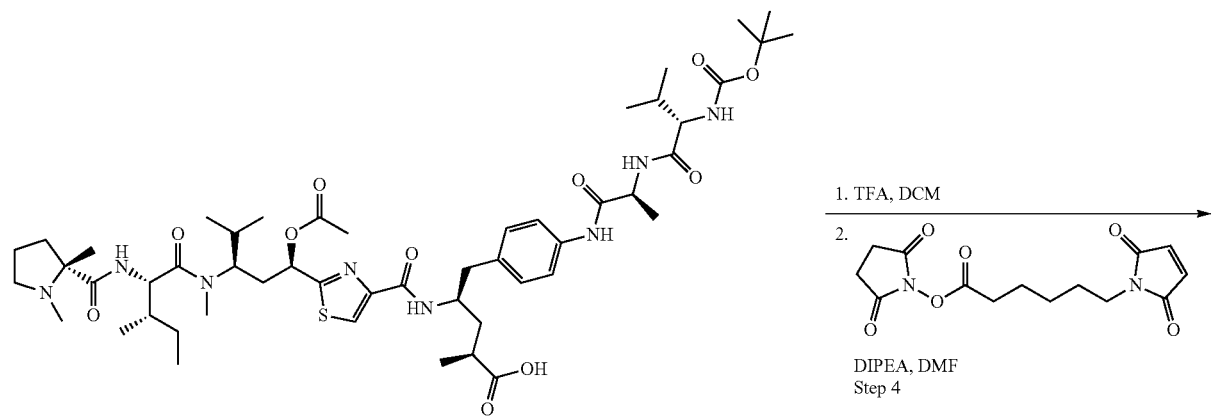

1. TFA, DCM
2.

DIPEA, DMF
Step 4

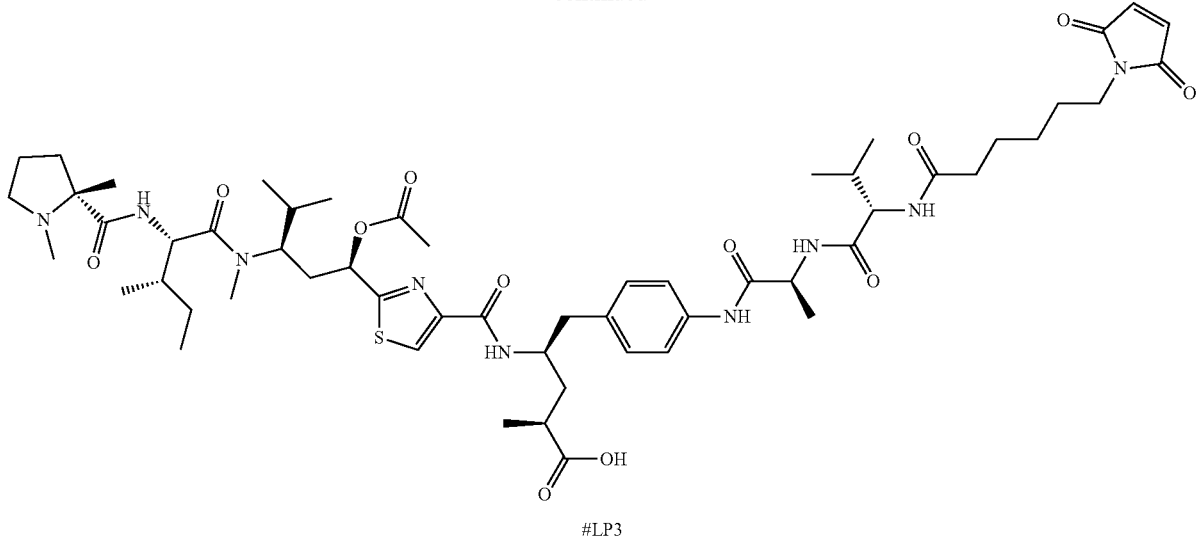

LP3

Step 1: Preparation of 1,2-dimethyl-D-prolyl-N-[(1R,3R)-1-(acetyloxy)-1-(4-{[(2R,4S)-1-(4-{[N-(tert-butoxycarbonyl)-L-alanyl]amino)}phenyl)-4-carboxypentan-2-yl]carbamoyl}-1,3-thiazol-2-yl)-4-methylpentan-3-yl]-N-methyl-L-isoleucinamide To a vial containing N-Boc L-Alanine (5 mg, 0.026 mmol) and HATU (9 mg, 0.024 mmol) was added DMF (0.9 mL) and DIPEA (21 µL, 0.120 mmol). The reaction was stirred under $N_2$ for 0.75 h then a solution of 1,2-dimethyl-D-prolyl-N-[(1R,3R)-1-(acetyloxy)-1-(4-{[(2R,4S)-1-(4-aminophenyl)-4-carboxypentan-2-yl]carbamoyl}-1,3-thiazol-2-yl)-4-methylpentan-3-yl]-N-methyl-L-isoleucinamide (# B9, 21 mg, 0.024 mmol) in DMF (2 mL) was added. The reaction was stirred at rt for 17 h and 0.192 mmol of HATU-activated N-Boc L-alanine (prepared by stirring HATU (74 mg, 0.192 mmol), N-Boc L-Alanine (36 mg, 0.192 mmol), and DIPEA (85 µl, 0.480 mmol) in 0.6 mL DMF for 30 minutes) was added in two equal aliquots over the course of 24 h. After stirring for a total of 40 h at rt, the reaction was concentrated and the residue re-dissolved in DMSO (1.5 mL) and purified by medium pressure C18 chromatography (10% to 95% acetonitrile in $H_2O$ over 25 minutes, each solvent containing 0.02% TFA) to yield the title compound (8 mg, 40%) as a white solid. LC-MS (Protocol C): m/z 914.4 $[M+H]^+$; Retention time=0.85 min.

Step 2. Preparation of 1,2-dimethyl-D-prolyl-N-{(1R,3R)-1-(acetyloxy)-1-[4-({(2R,4S)-1-[4-(L-alanylamino)phenyl]-4-carboxypentan-2-yl}carbamoyl)-1,3-thiazol-2-yl]-4-methylpentan-3-yl}-N-methyl-L-isoleucinamide TFA Salt To a vial containing 1,2-dimethyl-D-prolyl-N-[(1R,3R)-1-(acetyloxy)-1-(4-{[(2R,4S)-1-(4-{[N-(tert-butoxycarbonyl)-L-alanyl]amino}phenyl)-4-carboxypentan-2-yl]carbamoyl}-1,3-thiazol-2-yl)-4-methylpentan-3-yl]-N-methyl-L-isoleucinamide (8 mg, 0.009 mmol) was added DCM (0.9 mL) and TFA (80 µL) and the reaction was stirred at rt under $N_2$. After 3 h the reaction was concentrated in vacuo and dried under high vacuum to afford the title compound (10 mg, quantitative yield) as a gummy residue, which was used crude in the next step. LC-MS (Protocol C): m/z 814.6 $[M+H]^+$; Retention time=0.58 min.

Step 3: Preparation of 1,2-dimethyl-D-prolyl-N-[(1R,3R)-1-(acetyloxy)-1-(4-{[(2R,4S)-1-(4-{[N-(tert-butoxycarbonyl)-L-valyl-L-alanyl]amino}phenyl)-4-carboxypentan-2-yl]carbamoyl}-1,3-thiazol-2-yl)-4-methylpentan-3-yl]-N-methyl-L-isoleucinamide (78)

To a vial containing 1,2-dimethyl-D-prolyl-N-{(1R,3R)-1-(acetyloxy)-1-[4-({(2R,4S)-1-[4-(L-alanylamino)phenyl]-4-carboxypentan-2-yl}carbamoyl)-1,3-thiazol-2-yl]-4-methylpentan-3-yl}-N-methyl-L-isoleucinamide TFA salt (8.2 mg, 0.010 mmol) was added a solution of L-Valine N-Hydroxy succinimide (3.5 mg, 0.011 mmol) in DMF (700 µL), followed by DIPEA (14 µL, 0.080 mmol) and additional DMF (100 µL). The reaction was stirred at rt for 4 h, concentrated, and purified by preparative HPLC (Method H) to afford the target compound 78 (5.8 mg, 57%) as a colorless solid. LC-MS (Protocol C): m/z 1013.8 $[M+H]^+$; Retention time=0.82 min.

Step 4: Preparation of 1,2-dimethyl-D-prolyl-N-{(1R,3R)-1-(acetyloxy)-1-[4-({(2R,4S)-4-carboxy-1-[4-({N-[6-(2,5-dioxo-2,5-dihydro-1H-pyrrol-1-yl)hexanoyl]-L-valyl-L-alanyl}amino)phenyl]pentan-2-yl}carbamoyl)-1,3-thiazol-2-yl]-4-methylpentan-3-yl}-N-methyl-L-isoleucinamide (# LP3)

To a vial containing 1,2-dimethyl-D-prolyl-N-[(1R,3R)-1-(acetyloxy)-1-(4-{[(2R,4S)-1-(4-{[N-(tert-butoxycarbonyl)-L-valyl-L-alanyl]amino}phenyl)-4-carboxypentan-2-yl]carbamoyl}-1,3-thiazol-2-yl)-4-methylpentan-3-yl]-N-methyl-L-isoleucinamide (78, 5.8 mg, 0.006 mmol) was added DCM (0.5 mL) and TFA (30 µL) and the reaction was stirred at rt under $N_2$. After 3 h the reaction was concentrated in vacuo and dried under high vacuum to afford 1,2-dimethyl-D-prolyl-N-[(1R,3R)-1-(acetyloxy)-1-(4-{[(2R,4S)-4-carboxy-1-{4-[(L-valyl-L-alanyl)amino]phenyl}pentan-2-yl]carbamoyl}-1,3-thiazol-2-yl)-4-methylpentan-3-yl]-N-methyl-L-isoleucinamide as a gummy residue, which was treated immediately with 1-{6-

[(2,5-dioxopyrrolidin-1-yl)oxy]-6-oxohexyl}-1H-pyrrole-2,5-dione (3.5 mg, 0.011 mmol) in DMF (0.9 mL). To this reaction mixture was added DIPEA (11 µl, 0.064 mmol) and the reaction was stirred at rt in a capped vial for 5 h. The reaction was concentrated and the residue purified by reverse phase chromatography (Method B) to provide title compound # LP3 (3.4 mg, 38%) as a white solid. HPLC (Protocol D) m/z 1107.5 [M+H]$^+$; Retention time=7.16 min.

Preparation of 1,2-dimethyl-D-prolyl-N-[(1R,3R)-1-(acetyloxy)-1-(4-{[(2R,4S)-5-{(2Z)-2-[1-(4-{[5-(2,5-dioxo-2,5-dihydro-1H-pyrrol-1-yl)pentyl]oxy}phenyl)ethylidene]hydrazinyl}-4-methyl-5-oxo-1-phenylpentan-2-yl]carbamoyl}-1,3-thiazol-2-yl)-4-methylpentan-3-yl]-N-methyl-L-isoleucinamide (# LP4)

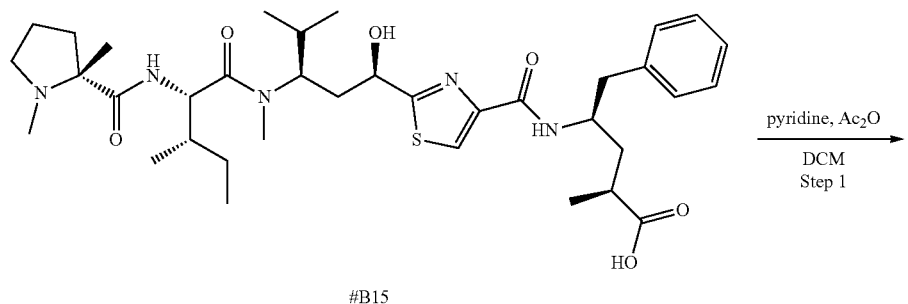

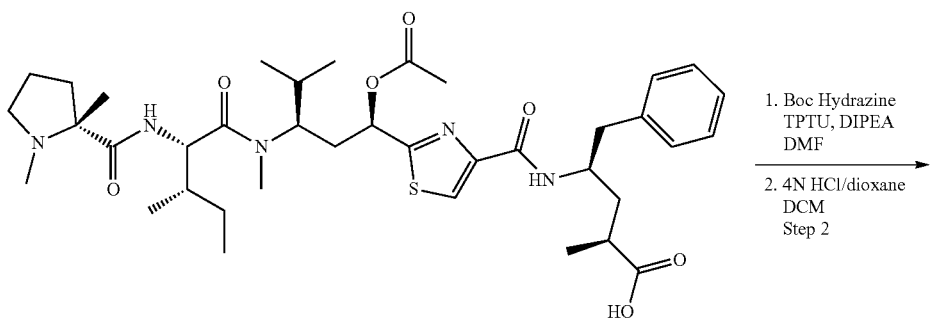

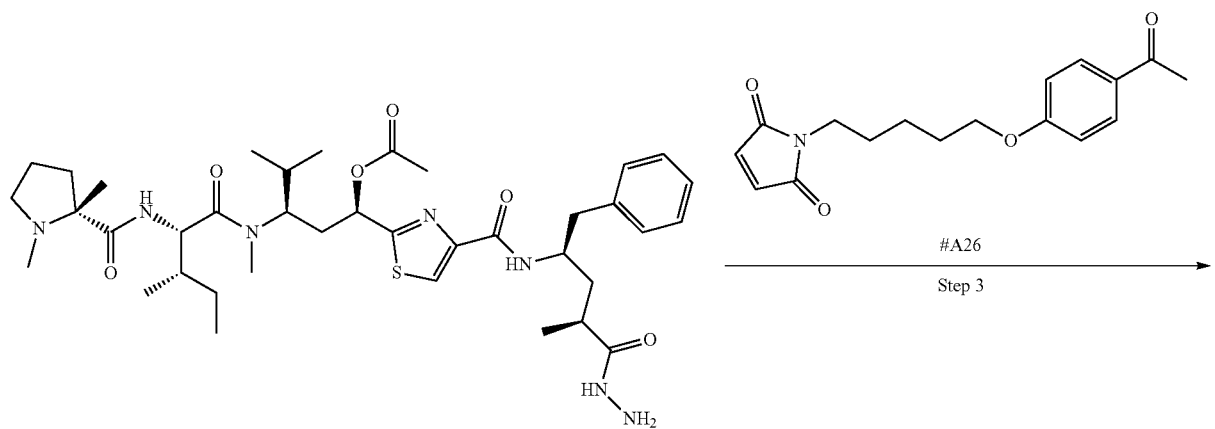

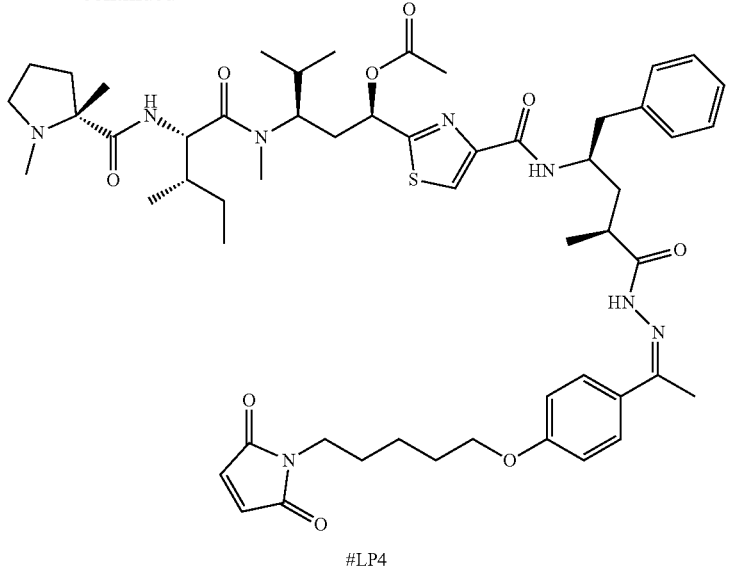

LP4

Step 1: Synthesis of 1,2-dimethyl-D-prolyl-N-[(1R,3R)-1-(acetyloxy)-1-(4-{[(2R,4S)-4-carboxy-1-phenylpentan-2-yl]carbamoyl}-1,3-thiazol-2-yl)-4-methylpentan-3-yl]-N-methyl-L-isoleucinamide (79)

To a solution of 1,2-dimethyl-D-prolyl-N-[(1R,3R)-1-(4-{[(2R,4S)-4-carboxy-1-phenylpentan-2-yl]carbamoyl}-1,3-thiazol-2-yl)-1-hydroxy-4-methylpentan-3-yl]-N-methyl-L-isoleucinamide (# B15, 90 mg, 0.11 mmol) in DCM (1 mL) was added pyridine (1 mL) and acetic anhydride (0.1 mL). The reaction was stirred at rt for 2 h then additional acetic anhydride (0.1 mL) was added and the reaction stirred at rt for 18 h. The reaction was concentrated in vacuo and the crude residue purified by medium pressure reverse phase C18 chromatography (10% to 80% acetonitrile in water, 0.02% TFA in each phase). The resulting foam was re-dissolved in DCM and precipitated with hexanes to afford title compound 79 (74 mg, 90%). LC-MS (Protocol B): m/z 728.8 [M+H]$^+$; Retention time=0.77 min.

Step 2: Synthesis of 1,2-dimethyl-D-prolyl-N-[(1R,3R)-1-(acetyloxy)-1-(4-{[(2R,4S)-5-hydrazinyl-4-methyl-5-oxo-1-phenylpentan-2-yl]carbamoyl}-1,3-thiazol-2-yl)-4-methylpentan-3-yl]-N-methyl-L-isoleucinamide (80)

To a vial containing 1,2-dimethyl-D-prolyl-N-[(1R,3R)-1-(acetyloxy)-1-(4-{[(2R,4S)-4-carboxy-1-phenylpentan-2-yl]carbamoyl}-1,3-thiazol-2-yl)-4-methylpentan-3-yl]-N-methyl-L-isoleucinamide (79, 38 mg, 0.052 mmol) dissolved in DMF (0.4 mL), was added TPTU (19 mg, 0.62 mmol) and DIPEA (0.156 mL, 0.156 mmol). The reaction was stirred for 15 minutes and tert-butyl hydrazinecarboxylate (7 mg, 0.52 mmol) was added. The reaction was stirred at rt for 72 h then quenched with H$_2$O (1.5 mL) and extracted with EtOAc (4×2.5 mL). The combined organic extracts were dried over sodium sulfate, filtered, and concentrated in vacuo. The crude oil was dissolved in DCM (1.0 mL) and 4 N HCl in dioxane (1.0 mL) was added. The reaction mixture was stirred at rt for 15 minutes, solvent removed in vacuo, and the crude residue purified by medium pressure reverse phase C18 chromatography (10% to 85% acetonitrile in water, 0.02% TFA in each phase). The resulting foam was re-dissolved in DCM and precipitated with hexanes to afford title compound 80 (31 mg, 83%). LC-MS (Protocol D): m/z 743.4 [M+H]$^+$; Retention time=6.49 min.

Step 3: Synthesis of 1,2-dimethyl-D-prolyl-N-[(1R,3R)-1-(acetyloxy)-1-(4-{[(2R,4S)-5-{(2Z)-2-[1-(4-{[5-(2,5-dioxo-2,5-dihydro-1H-pyrrol-1-yl)pentyl]oxy}phenyl)ethylidene]hydrazinyl}-4-methyl-5-oxo-1-phenylpentan-2-yl]carbamoyl}-1,3-thiazol-2-yl)-4-methylpentan-3-yl]-N-methyl-L-isoleucinamide (# LP4)

To a vial containing 1,2-dimethyl-D-prolyl-N-[(1R,3R)-1-(acetyloxy)-1-(4-{[(2R,4S)-5-hydrazinyl-4-methyl-5-oxo-1-phenylpentan-2-yl]carbamoyl}-1,3-thiazol-2-yl)-4-methylpentan-3-yl]-N-methyl-L-isoleucinamide (80, 21 mg, 0.028 mmol) in ethanol (1.4 mL) was added 1-[5-(4-acetylphenoxy)pentyl]-1H-pyrrole-2,5-dione (# A26, 8.4 mg, 0.028 mmol) and glacial acetic acid (0.027 mL, 0.476 mmol). The reaction mixture was stirred at rt for 18 h then concentrated in vacuo and azeotroped with 1/1 DCM/heptane to provide a crude solid. The solid was purified by reverse phase chromatography (Method C) to afford the title compound # LP4 (5.8 mg, 20%). LC-MS (Protocol D): m/z 1025.4 [M+H]$^+$; Retention time=7.98 min.

Preparation of 1,2-dimethyl-D-prolyl-N-{(1R,3R)-1-[4-({(2R,4S)-4-carboxy-1-[4-({N-[6-(2,5-dioxo-2,5-dihydro-1H-pyrrol-1-yl)hexanoyl]glycyl}amino)phenyl]pentan-2-yl}carbamoyl)-1,3-thiazol-2-yl]-1-hydroxy-4-methylpentan-3-yl}-N-methyl-L-isoleucinamide (# LP5)

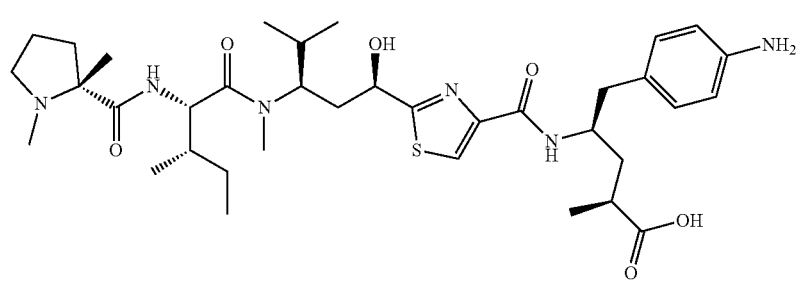

B32

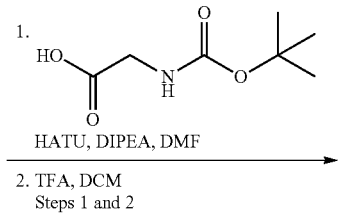

1. HATU, DIPEA, DMF
2. TFA, DCM
Steps 1 and 2

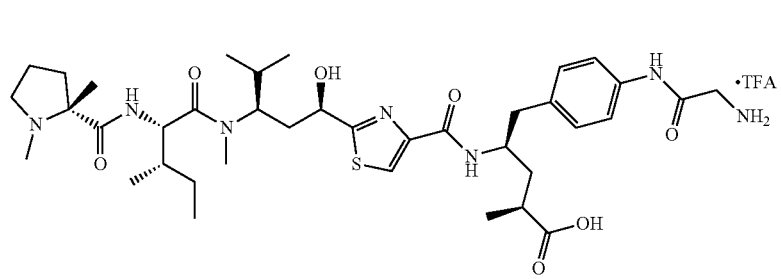

81

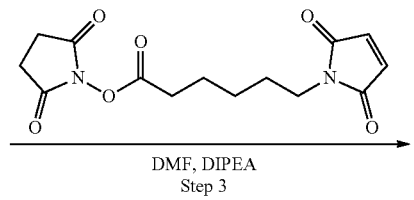

DMF, DIPEA
Step 3

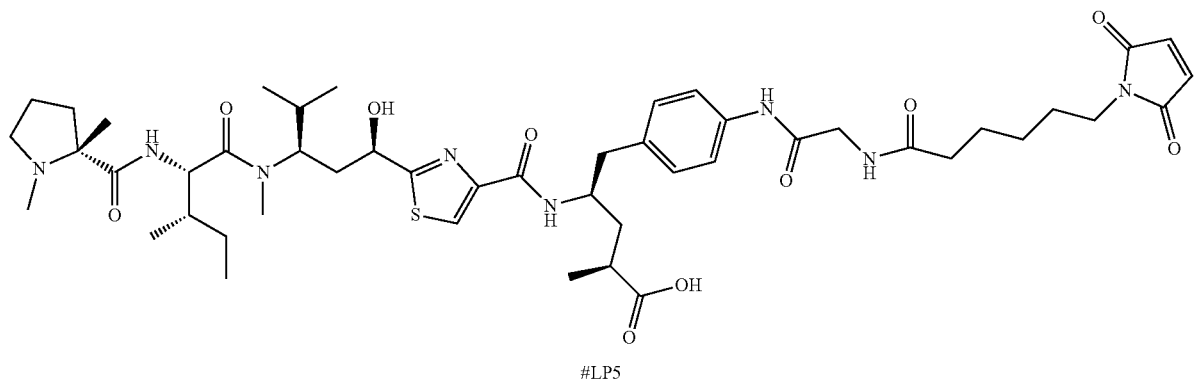

LP5

Step 1: Preparation of 1,2-dimethyl-D-prolyl-N-[(1R,3R)-1-(4-{[(2R,4S)-1-(4-{[N-(tert-butoxycarbonyl)glycyl]amino}phenyl)-4-carboxypentan-2-yl]carbamoyl}-1,3-thiazol-2-yl)-1-hydroxy-4-methylpentan-3-yl]-N-methyl-L-isoleucin Amide To a vial containing N-Boc glycine (8 mg, 0.045 mmol) and HATU (17 mg, 0.045 mmol) was added DMF (1.5 mL) and DIPEA (54 μL, 0.31 mmol). The reaction was stirred in a capped vial for 0.5 h then added by syringe to a vial containing a solution of 1,2-dimethyl-D-prolyl-N-[(1R,3R)-1-(4-{[(2R,4S)-1-(4-aminophenyl)-4-carboxypentan-2-yl]carbamoyl}-1,3-thiazol-2-yl)-1-hydroxy-4-methylpentan-3-yl]-N-methyl-L-isoleucinamide (# B32, 21 mg, 0.026 mmol) in DMF (1 mL). After stirring for 24 h at rt, an additional 0.003 mmol of HATU-activated N-Boc glycine (prepared by stirring HATU (10 mg, 0.003 mmol), N-Boc glycine (6 mg, 0.034 mmol) and DIPEA (36 μl, 0.207 mmol) in 0.5 mL DMF for 30 minutes) was added and the reaction mixture was stirred for 24 h. The reaction was concentrated to a crude gummy residue which was re-dissolved in DMSO (~2 mL) and purified by medium pressure C18 chromatography (10% to 95% acetonitrile in H₂O over 25 minutes, each solvent containing 0.02% TFA) to afford the title compound (7 mg, 20%). LC-MS (Protocol C): m/z 858.5 [M+H]⁺; Retention time=0.71 min.

Step 2: Preparation of 1,2-dimethyl-D-prolyl-N-{(1R,3R)-1-[4-({(2R,4S)-4-carboxy-1-[4-(glycylamino)phenyl]pentan-2-yl}carbamoyl)-1,3-thiazol-2-yl]-1-hydroxy-4-methylpentan-3-yl}-N-methyl-L-isoleucinamide TFA Salt (81)

To a vial containing 1,2-dimethyl-D-prolyl-N-[(1R,3R)-1-(4-{[(2R,4S)-1-(4-{[N-(tert-butoxycarbonyl)glycyl]amino}phenyl)-4-carboxypentan-2-yl]carbamoyl}-1,3-thiazol-2-yl)-1-hydroxy-4-methylpentan-3-yl]-N-methyl-L-isoleucinamide (7 mg, 0.007 mmol) was added DCM (200 μL) and TFA (80 μL) and the reaction was stirred at rt under N$_2$. After 3 h the reaction was concentrated under high vacuum to afford the title compound 81 (9.5 mg, quantitative yield) as a gummy residue, which was used crude in the next step.

Step 3: Preparation of 1,2-dimethyl-D-prolyl-N-{(1R,3R)-1-[4-({(2R,4S)-4-carboxy-1-[4-({N-[6-(2,5-dioxo-2,5-dihydro-1H-pyrrol-1-yl)hexanoyl]glycyl}amino)phenyl]pentan-2-yl}carbamoyl)-1,3-thiazol-2-yl]-1-hydroxy-4-methylpentan-3-yl}-N-methyl-L-isoleucinamide (# LP5)

To a vial containing 1,2-dimethyl-D-prolyl-N-{(1R,3R)-1-[4-({(2R,4S)-4-carboxy-1-[4-(glycylamino)phenyl]pentan-2-yl}carbamoyl)-1,3-thiazol-2-yl]-1-hydroxy-4-methylpentan-3-yl}-N-methyl-L-isoleucinamide TFA salt (81, 9.2 mg, 0.012 mmol) was added 1-{6-[(2,5-dioxopyrrolidin-1-yl)oxy]-6-oxohexyl}-1H-pyrrole-2,5-dione (3.6 mg, 0.012 mmol) and DMF (0.7 mL). DIPEA (20 μL, 0.110 mmol) was added and the reaction was stirred at rt in a capped vial for 17.5 h. The reaction was concentrated to a brown gummy residue and purified by reverse phase chromatography (Method D) to provide target compound # LP5 (3 mg, 26%) as a white solid. HPLC (Protocol D) m/z 951.5 [M+H]$^+$; Retention time=6.70 min.

Preparation of 1,2-dimethyl-D-prolyl-N-{(1R,3R)-1-[4-({(2R,4S)-4-carboxy-1-[4-({N-[6-(2,5-dioxo-2,5-dihydro-1H-pyrrol-1-yl)hexanoyl]glycyl}amino)phenyl]pentan-2-yl}carbamoyl)-1,3-thiazol-2-yl]-1-[(ethylcarbamoyl)oxy]-4-methylpentan-3-yl}-N-methyl-L-isoleucinamide (# LP6)

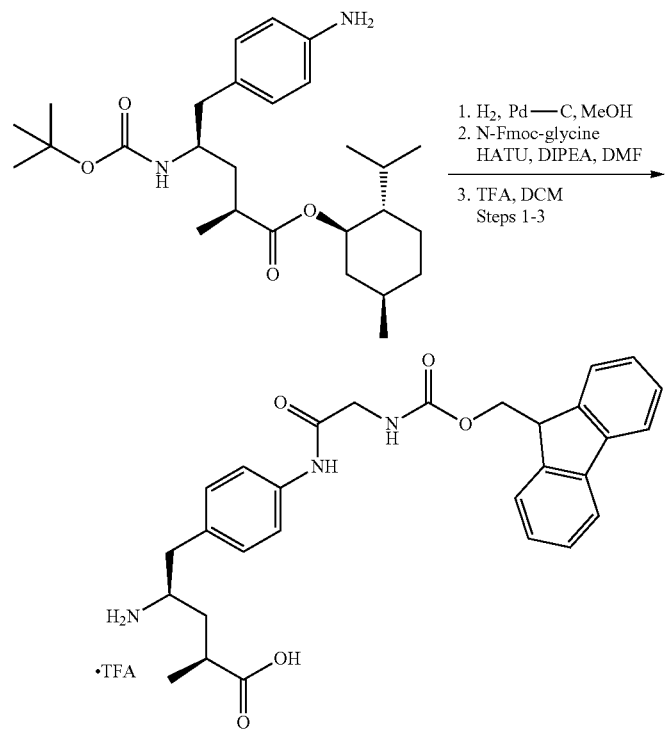

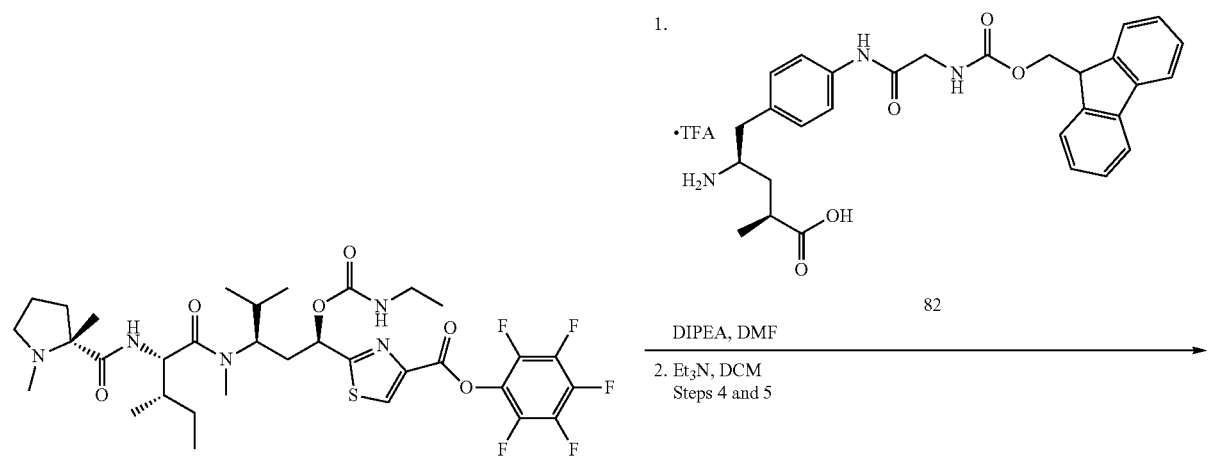

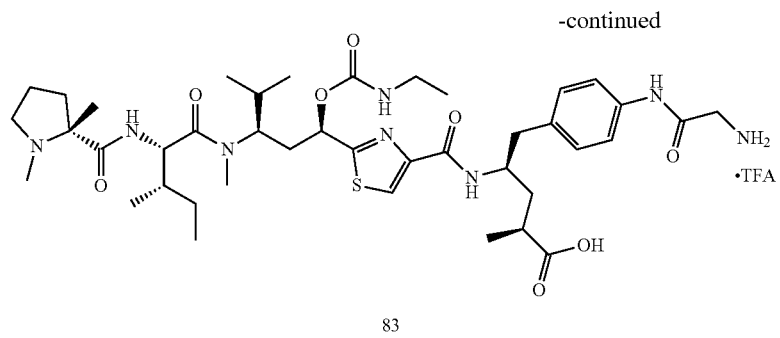
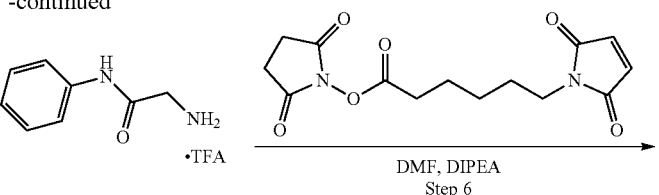

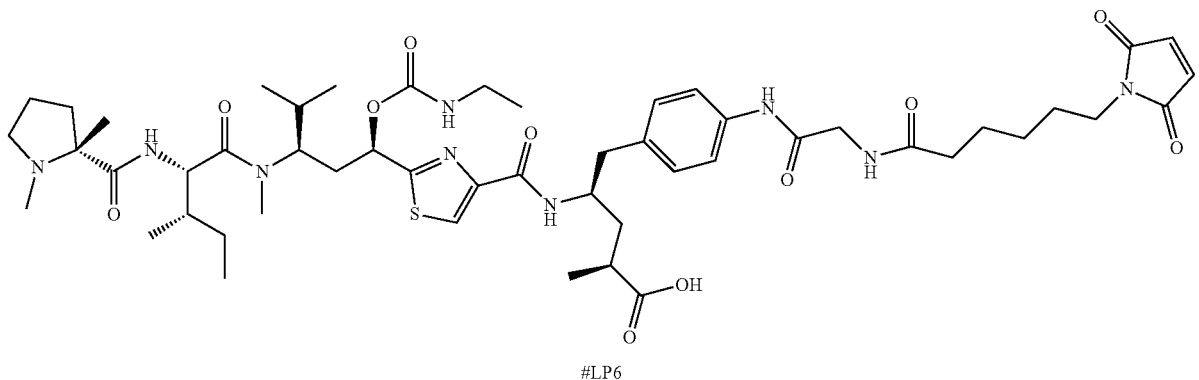 [SMILES: CCNC(=O)O[C@H](C[C@H](C(C)C)N(C)C(=O)[C@@H](NC(=O)[C@@]1(C)CCCN1C)[C@@H](C)CC)c1nc(C(=O)N[C@@H](Cc2ccc(NC(=O)CNC(=O)CCCCCN3C(=O)C=CC3=O)cc2)C[C@H](C)C(=O)O)cs1]

LP6

Step 1: Preparation of (1R,2S,5R)-5-methyl-2-(propan-2-yl)cyclohexyl (2S,4R)-5-(4-aminophenyl)-4-[(tert-butoxycarbonyl)amino]-2-methylpentanoate A solution of (1R,2S,5R)-5-methyl-2-(propan-2-yl)cyclohexyl (2S,4R)-4-[(tert-butoxycarbonyl)amino]-2-methyl-5-(4-nitrophenyl)pentanoate (800 mg, 1.63 mmol) and Pd—C (500 mg) in MeOH (30 mL) was stirred under 40 psi $H_2$ at it overnight. The reaction mixture was filtered through a pad of celite and the filtrate was concentrated in vacuo to afford the title compound (750 mg, quantitative yield) as a yellow oil. LC-MS: m/z 483.2 [M+Na]+; Retention time=0.883 min.

Step 2: Preparation of (2S,4R)-4-amino-5-[4-({N-[(9H-fluoren-9-ylmethoxy)carbonyl]glycyl}amino)phenyl]-2-methylpentanoic Acid To a solution of (1R,2S,5R)-5-methyl-2-(propan-2-yl)cyclohexyl (2S,4R)-5-(4-aminophenyl)-4-[(tert-butoxycarbonyl)amino]-2-methylpentanoate (700 mg, 1.52 mmol), N-Fmoc glycine (497 mg, 1.67 mmol), and DIPEA (295 mg, 2.28 mmol) in DMF (20 mL) at 0° C. was added HATU (636 mg, 1.67 mmol) and the solution was stirred at rt for 2 h. The reaction mixture was poured into $H_2O$ and extracted with EtOAc. The organic phase was washed with brine, dried over $Na_2SO_4$, and concentrated in vacuo. The residue was purified by flash silica gel chromatography (100% EtOAc to 10% MeOH/90% DCM) to afford the target compound (900 mg, 80%) as a yellow oil.

Step 3: Preparation of (2S,4R)-4-amino-5-[4-({N-[(9H-fluoren-9-ylmethoxy)carbonyl]glycyl}amino)phenyl]-2-methylpentanoic Acid TFA Salt (82)

A solution of (2S,4R)-4-amino-5-[4-({N-[(9H-fluoren-9-ylmethoxy)carbonyl]glycyl}amino)phenyl]-2-methylpentanoic acid (1.0 g, 1.351 mmol) in TFA (10 mL) was refluxed at 110° C. for 1 h. The reaction mixture was stirred at 130° C. for 15 min under microwave conditions. The reaction mixture was concentrated in vacuo to a crude oil which was purified by preparative HPLC (Column: Synergi 250 mm×50 mm I.D., 10 μm; Mobile phase: 25% acetonitrile in $H_2O$ (0.1% TFA) to 55% acetonitrile in $H_2O$ (0.1% TFA) over 30 minutes) to afford the title compound 82 (330 mg, 49%) as a white solid.

$^1$H NMR (400 MHz, DMSO-d6): δ 10.01 (br, 1H), 7.92-7.82 (m, 5H), 7.74-7.73 (m, 2H), 7.58-7.56 (m, 3H), 7.43-7.41 (m, 2H), 7.36-7.34 (m, 2H), 7.19-7.17 (m, 2H), 4.32-4.20 (m, 3H), 3.80-3.73 (m, 2H), 2.89-2.73 (m, 1H), 1.86-1.81 (m, 1H), 1.01 (d, 3H). m/z 502.3 [M+H]+; 92% ee: Column: Chiralcel CD-PH 150×4.6 mm I.D., 5 μm, Mobile phase: 10% to 80% acetonitrile (0.1% TFA) in $H_2O$ (0.1% TFA); Wavelength: 254 nm; Retention time=15.6 min.

Step 4: Preparation of 1,2-dimethyl-D-prolyl-N-{(1R,3R)-1-[4-({(2R,4S)-4-carboxy-1-[4-({N-[(9H-fluoren-9-ylmethoxy)carbonyl]glycyl}amino)phenyl]pentan-2-yl}carbamoyl)-1,3-thiazol-2-yl]-1-[(ethylcarbamoyl)oxy]-4-methylpentan-3-yl}-N-methyl-L-isoleucinamide To a vial containing PFP ester # A32 (20 mg, 0.027 mmol) and (2S,4R)-4-amino-5-[4-({N-[(9H-fluoren-9-ylmethoxy)carbonyl]glycyl}amino)phenyl]-2-methylpentanoic acid TFA salt (82, 17 mg, 0.027 mmol) was added DMF (1.5 mL) and DIPEA (33 μL, 0.189 mmol) and the reaction was stirred in a capped vial at rt. After stirring for 16 h at rt, the reaction was concentrated to a gummy residue which was re-dissolved in DMSO (~1.5 mL) and acetonitrile/$H_2O$ (0.5 mL, 1/1, each containing 0.02% TFA), and purified by medium pressure C18 chromatography (10% to 95% acetonitrile in $H_2O$ over 25 minutes, each solvent containing 0.02% TFA)

243 to afford the target compound (19 mg, 67%) as a colorless solid. LC-MS (Protocol C): m/z 1051.6 [M+H]+; Retention time=0.83 min.

Step 5: Preparation of 1,2-dimethyl-D-prolyl-N-{(1R,3R)-1-[4-({(2R,4S)-4-carboxy-1-[4-(glycy-lamino)phenyl]pentan-2-yl}carbamoyl)-1,3-thiazol-2-yl]-1-[(ethylcarbamoyl)oxy]-4-methylpentan-3-yl}-N-methyl-L-isoleucinamide TFA Salt (83)

To a vial containing 1,2-dimethyl-D-prolyl-N-{(1R,3R)-1-[4-({(2R,4S)-4-carboxy-1-[4-({N-[(9H-fluoren-9-yl-methoxy)carbonyl]glycyl}amino)phenyl]pentan-2-yl}carbamoyl)-1,3-thiazol-2-yl]-1-[(ethylcarbamoyl)oxy]-4-methylpentan-3-yl}-N-methyl-L-isoleucinamide (19 mg, 0.018 mmol) was added DCM (1 mL) and N,N-diethylamine (30 μL, 0.290 mmol) and the resulting reaction was stirred at rt in a closed vial for 3 h, after which time additional N,N-diethylamine (130 μL) was added in 3 aliquots over the course of 4 hours. After stirring for a total of 7 h at rt, the reaction was concentrated in vacuo, the residue re-dissolved in DMSO (~1.5 mL) and acetonitrile/H2O (0.5 mL, 1/1, each solvent containing 0.02% TFA), and purified by medium pressure C18 chromatography (10% to 95% acetonitrile in H2O over 25 minutes, each solvent containing 0.02% TFA) to afford title compound 83 (10 mg, 62%) as a colorless solid. LC-MS (Protocol C): m/z 829.4 [M+H]+; Retention time=0.61 min.

244

Step 6: Preparation of 1,2-dimethyl-D-prolyl-N-{(1R,3R)-1-[4-({(2R,4S)-4-carboxy-1-[4-({N-[6-(2,5-dioxo-2,5-dihydro-1H-pyrrol-1-yl)hexanoyl]glycyl}amino)phenyl]pentan-2-yl}carbamoyl)-1,3-thiazol-2-yl]-1-[(ethylcarbamoyl)oxy]-4-methylpentan-3-yl}-N-methyl-L-isoleucinamide (# LP6)

To a vial containing 1,2-dimethyl-D-prolyl-N-{(1R,3R)-1-[4-({(2R,4S)-4-carboxy-1-[4-(glycylamino)phenyl]pentan-2-yl}carbamoyl)-1,3-thiazol-2-yl]-1-[(ethylcarbamoyl)oxy]-4-methylpentan-3-yl}-N-methyl-L-isoleucinamide TFA salt (83, 10 mg, 0.011 mmol) was added 1-{6-[(2,5-dioxopyrrolidin-1-yl)oxy]-6-oxohexyl}-1H-pyrrole-2,5-dione (3 mg, 0.010 mmol) and DMF (1.2 mL). DIPEA (17 μL, 0.099 mmol) was added and the reaction was stirred at rt in a closed vial for 17 h. The reaction was concentrated and the resulting residue purified by reverse phase chromatography (Method D) to provide the target compound # LP6 (5.8 mg, 52%) as a colorless solid. HPLC (Protocol D) m/z 1022.8 [M+H]+; Retention time=6.92 min.

Preparation of ethyl (2S,4R)-4-{[(2-{(1R,3R)-1-(acetyloxy)-4-methyl-3-[methyl(N-{[(2R)-1-methyl-piperidin-2-yl]carbonyl}-L-isoleucyl)amino]pentyl}-1,3-thiazol-4-yl)carbonyl]amino}-2-methyl-5-{4-[(pyridin-2-yldisulfanyl)methyl]phenyl}pentanoate (# LP7)

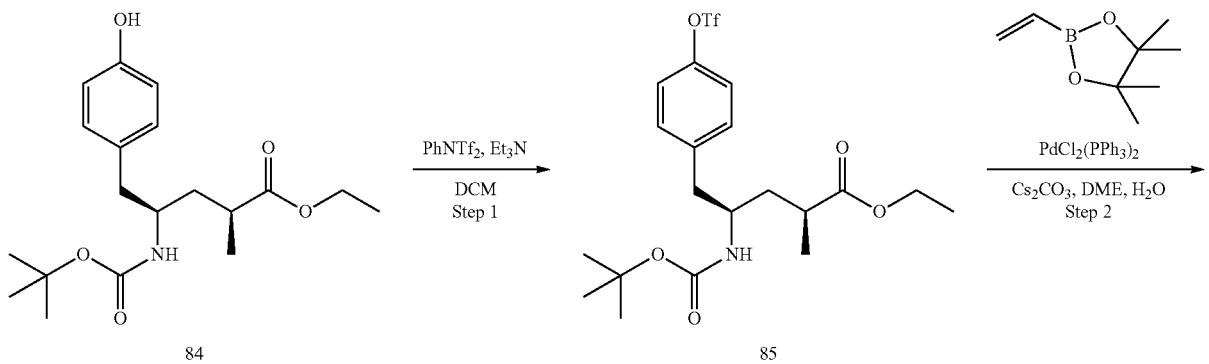

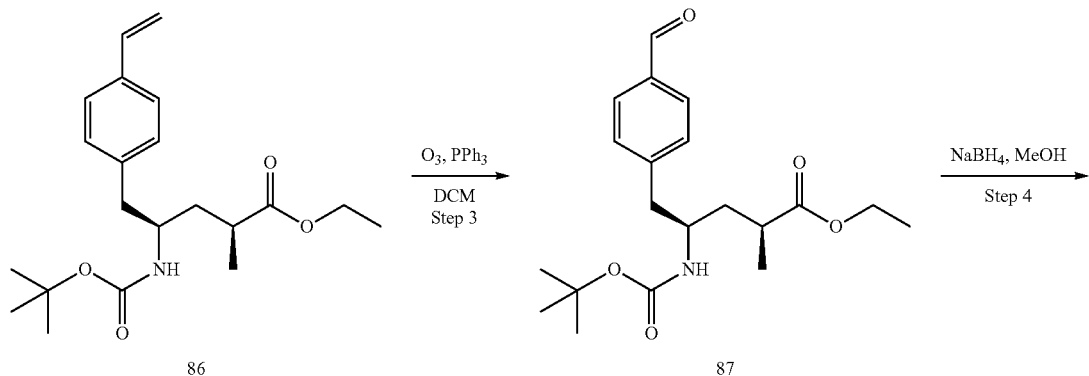

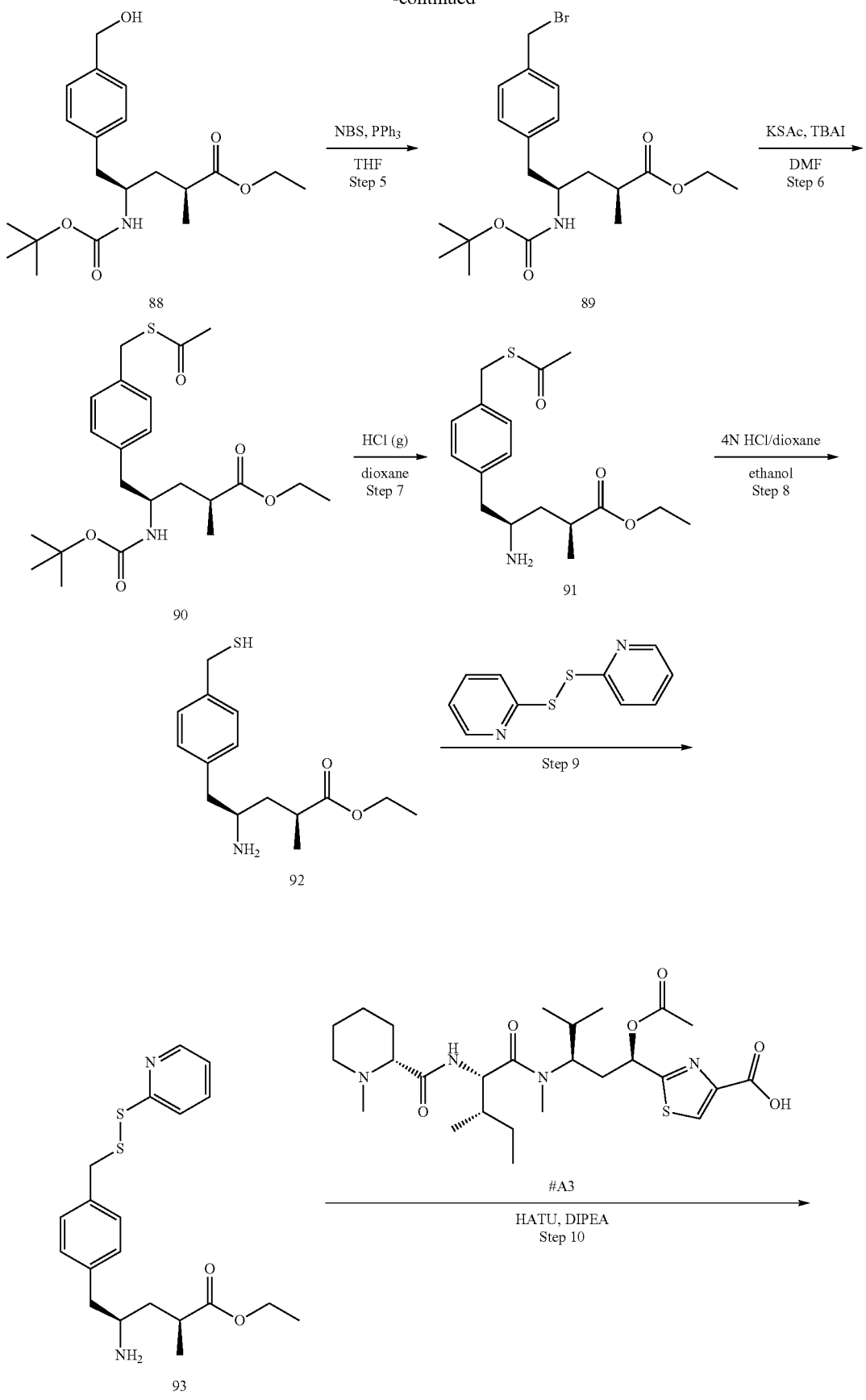

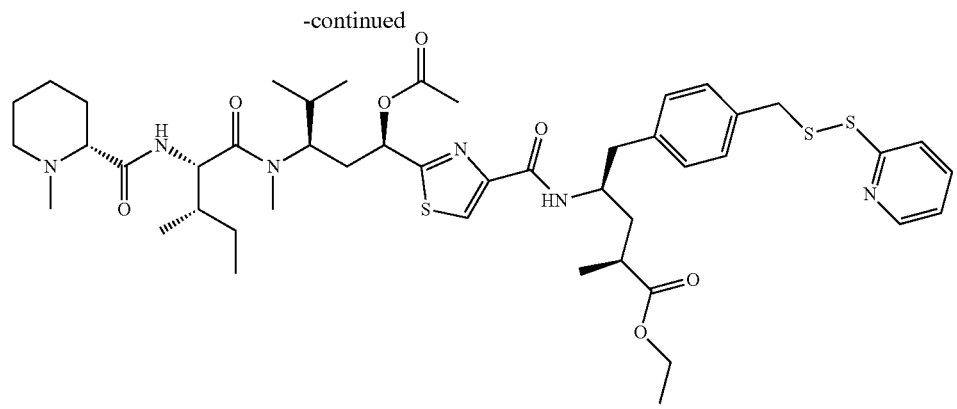

LP7

Step 1: Preparation of ethyl (2S,4R)-4-[(tert-butoxycarbonyl)amino]-2-methyl-5-(4-{[(trifluoromethyl)sulfonyl]oxy}phenyl)pentanoate (85)

A solution of ethyl (2S,4R)-4-[(tert-butoxycarbonyl)amino]-5-(4-hydroxyphenyl)-2-methylpentanoate (*Org. Lett.* 2009, 11, 5567) (84, 12 g, 27.2 mmol), 1,1,1-trifluoro-N-phenyl-N-[(trifluoromethyl)sulfonyl]methanesulfonamide (30.2 g, 81.6 mmol), and Et$_3$N (9.1 g, 89.8 mmol) in DCM (200 mL) was stirred at rt overnight. The reaction mixture was washed with satd. aqueous NaHCO$_3$ (200 mL) and brine (200 mL) and concentrated in vacuo. The residue was purified by silica column chromatography (30/1 to 20/1 hexanes/EtOAc) to afford title compound 85 (14 g, 88%) as a yellow oil.

Step 2: Preparation of ethyl (2S,4R)-4-[(tert-butoxycarbonyl)amino]-5-(4-ethenylphenyl)-2-methylpentanoate (86)

A solution of ethyl (2S,4R)-4-[(tert-butoxycarbonyl)amino]-2-methyl-5-(4-{[(trifluoromethyl)sulfonyl]oxy}phenyl)pentanoate (85, 14 g, 29 mmol), 2-ethenyl-4,4,5,5-tetramethyl-1,3,2-dioxaborolane (8.9 g, 58 mmol), Pd(PPh$_3$)$_2$Cl$_2$ (2.0 g, 2.9 mmol), and Cs$_2$CO$_3$ (28.4 g, 87 mmol) in DME (210 mL) and H$_2$O (105 mL) was stirred at 80° C. overnight under N$_2$. The reaction mixture was poured into H$_2$O (200 mL) and extracted with EtOAc (100 mL×2). The organic phase was concentrated under vacuum and the residue was purified by silica gel chromatography (30/1 to 10/1 hexanes/EtOAc) to afford title compound 86 (7.2 g, 68%) as an oil.

Step 3: Preparation of ethyl (2S,4R)-4-[(tert-butoxycarbonyl)amino]-5-(4-formylphenyl)-2-methylpentanoate (87)

A solution of ethyl (2S,4R)-4-[(tert-butoxycarbonyl)amino]-5-(4-ethenylphenyl)-2-methylpentanoate (86, 16 g, 16.6 mmol) in DCM (120 mL) at −60° C. was treated with oxygen saturated with ozone (O$_3$) until the reaction solution turned blue. N$_2$ was then bubbled through the reaction mixture until disappearance of the blue color was observed. PPh$_3$ (8.7 g, 33.2 mmol) was added in batches and the resulting solution was stirred at rt overnight before immediate use in the next step.

Step 4: Preparation of ethyl (2S,4R)-4-[(tert-butoxycarbonyl)amino]-5-[4-(hydroxymethyl)phenyl]-2-methylpentanoate (88)

To the solution of ethyl (2S,4R)-4-[(tert-butoxycarbonyl)amino]-5-(4-formylphenyl)-2-methylpentanoate (87) from Step 3 was added methanol (50 mL) and NaBH$_4$ (16.6 mmol) at −20° C. After stirring at this temperature for 20 min, the reaction was quenched by addition of H$_2$O (50 mL) and extracted with DCM (50 mL×2). The organic phase was dried over Na$_2$SO$_4$ and concentrated under vacuum. The residue was purified by flash silica gel chromatography (37% EtOAc in hexanes) to afford the title compound 88 (6 g, 100%) as an oil.

Step 5: Preparation of ethyl (2S,4R)-5-[4-(bromomethyl)phenyl]-4-[(tert-butoxycarbonyl)amino]-2-methylpentanoate (89)

To a solution of ethyl (2S,4R)-4-[(tert-butoxycarbonyl)amino]-5-[4-(hydroxymethyl)phenyl]-2-methylpentanoate (88, 6.0 g, 16.4 mmol) in THF (120 mL) was added PPh$_3$ (12.8 g, 49.2 mmol) followed by NBS (8.8 g, 49.2 mmol) at 0° C. The solution was warmed to rt and stirred for 0.5 h. The reaction mixture was poured into H$_2$O (300 mL) and extracted with EtOAc (50 mL×2). The organic phase was dried over Na$_2$SO$_4$ and concentrated under vacuum. The residue was purified by flash silica gel chromatography (18% EtOAc in hexanes) to afford the title compound 89 (5.9 g, 84%) as a colorless liquid.

Step 6: Preparation of ethyl (2S,4R)-5-{4-[(acetylsulfanyl)methyl]phenyl}-4-[(tert-butoxycarbonyl)amino]-2-methylpentanoate (90)

To a solution of ethyl (2S,4R)-5-[4-(bromomethyl)phenyl]-4-[(tert-butoxycarbonyl)amino]-2-methylpentanoate (89, 5.9 g, 13.8 mmol) and TBAI (516.6 mg, 1.4 mmol) in DMF (60 mL) was added Potassium thioacetate (1.7 g, 15.2 mmol) at 0° C. and the suspension was stirred at rt overnight. The reaction mixture was poured into H$_2$O (120 mL) and extracted with EtOAc (100 mL). The organic phase washed with brine (50 mL×2), dried over Na$_2$SO$_4$, and concentrated under vacuum. The residue was purified by flash silica gel chromatography (30% EtOAc in petroleum ether) to afford the title compound 90 (5.5 g, 95%) as a yellow oil which was further purified by Chiral SFC (Column: ChiralPak AD, 300×50 mm I.D. 10 μm, Mobile Phase 15% B (0.1%

Ammonium Hydroxide in IPA) in A:$CO_2$, flow rate 220 mL/min, Temp: 38° C.) to yield 90 in >95% ee.

Step 7: Preparation of ethyl (2S,4R)-5-{4-[(acetyl-sulfanyl)methyl]phenyl}-4-amino-2-methylpentanoate (91)

To a solution of ethyl (2S,4R)-5-{4-[(acetylsulfanyl)methyl]phenyl}-4-[(tert-butoxycarbonyl)amino]-2-methylpentanoate (90, 1.6 g, 3.8 mmol) in EtOAc (15 mL) was added 4.0 M HCl in dioxane (15 mL) dropwise at 0° C. After the addition, the solution was stirred at rt for 3 h and the reaction mixture was concentrated under vacuum to afford title compound 91 (1.2 g, 86%) as a white solid.

$^1$H NMR (400 Hz, DMSO-d6): δ 8.30 (s, 3H), 7.25 (d, 2H), 7.19 (d, 2H), 4.09 (s, 2H), 3.96 (m, 2H), 3.30 (m, 1H), 3.04 (m, 1H), 2.74 (m, 2H), 2.34 (s, 3H), 1.77 (m, 1H), 1.74 (m, 1H), 1.09 (m, 6H). m/z 324.0 [M+H]$^+$; 100% ee; Column: Chiralcel AD-H 150×4.6 mm I.D., 5 µm; Mobile phase: ethanol (0.05% diethylamine) in $CO_2$ from 5% to 40%, Wavelength: 220 nm; Retention time=5.41 min.

Step 8: Preparation of ethyl (2S,4R)-4-amino-2-methyl-5-[4-(sulfanylmethyl)phenyl]pentanoate (92)

To a solution of ethyl (2S,4R)-5-{4-[(acetylsulfanyl)methyl]phenyl}-4-amino-2-methylpentanoate (91, 300 mg, 0.834 mmol) in ethanol (1 mL) was added 4 N HCl in dioxane (2.0 mL) and the reaction was heated at 35° C. for 18 h. The reaction was concentrated under vacuum to give crude title compound 92, which was used directly in the following step.

Step 9: Synthesis of ethyl (2S,4R)-4-amino-2-methyl-5-{4-[(pyridin-2-yldisulfanyl)methyl]phenyl}pentanoate (93)

To a solution of ethyl (2S,4R)-4-amino-2-methyl-5-[4-(sulfanylmethyl)phenyl]pentanoate (92, 265 mg, 0.834 mmol) in ethanol (2 mL) was added 2,2'-disulfanediyldipyridine (184 mg. 0834 mmol) and the mixture was stirred at rt for 2 h. The solvent was removed in vacuo and the crude residue purified by medium pressure reverse phase C18 chromatography (0% to 80% acetonitrile in $H_2O$, each solvent containing 0.02% TFA). The resulting oil was further purified by reverse phase chromatography (Method G) to afford the title compound 93 (130 mg, 31%). LC-MS (Protocol B): m/z 391.4 [M+H]$^+$; Retention time=1.01 min.

Step 10: Preparation of ethyl (2S,4R)-4-{[(2-{(1R,3R)-1-(acetyloxy)-4-methyl-3-[methyl(N-{[(2R)-1-methylpiperidin-2-yl]carbonyl}-L-isoleucyl)amino]pentyl}-1,3-thiazol-4-yl)carbonyl]amino}-2-methyl-5-{4-[(pyridin-2-yldisulfanyl)methyl]phenyl}pentanoate (# LP7)

The title compound was prepared in 30% yield [(purification by HPLC (Method B)] from 2-{(1R,3R)-1-(acetyloxy)-4-methyl-3-[methyl(N-{[(2R)-1-methylpiperidin-2-yl]carbonyl}-L-isoleucyl)amino]pentyl}-1,3-thiazole-4-carboxylic acid (# A3, 0.278 mmol) and ethyl (2S,4R)-4-amino-2-methyl-5-{4-[(pyridin-2-yldisulfanyl)methyl]phenyl}pentanoate (93, 0.253 mmol) using the method described above for compound # B1. LC-MS (Protocol D): m/z 911.5 [M+H]$^+$; Retention time=7.97 min.

General Method for Preparation, Purification and Analysis of ADCs

Method A: Conjugation of Commercial HERCEPTIN Antibody with Linker Payload Via Internal Disulfides A solution of commercially available HERCEPTIN antibody (~15 mg/mL) was prepared in 50 mM phosphate buffered saline (pH 7.0) containing 50 mM EDTA. Tris(2-carboxyethyl)phosphine hydrochloride (TCEP) was added (~2.0 molar equivalents) as a 5 mM solution in distilled water. The resulting solution was heated to 37° C. for 1 h. Upon cooling, the reaction was treated with appropriate volumes PBS and dimethyl acetamide (DMA) to bring the resulting solution to ~5 mg/mL in PBS containing ~10% DMA (vol/vol). The appropriate linker payload was added as a 10 mM stock in DMA (~7 eq) and the reaction was allowed to stand or was gently agitated at room temperature. After 70 minutes, the reaction was buffer exchanged into PBS using GE PD-10 Sephadex G25 columns per the manufacturer's instructions. The resulting material was concentrated slightly (by ultrafiltration) and purified by size-exclusion chromatography on a Superdex200 column. The monomeric fractions were concentrated and filter sterilized to give the final ADC.

Method B: Site-Specific Conjugation of Linker-Payloads to a Trastuzumab Antibody Containing Engineered Cysteine Residues A solution of trastuzumab containing incorporating an engineered cyststeine residue (Kabat numbering, see WO2013093809) was prepared in 50 mM phosphate buffer, pH 7.4. PBS, EDTA (0.5 M stock), and TCEP (0.5 M stock) were added such that the final protein concentration was ~10 mg/mL, the final EDTA concentration was ~20 mM, and the final TCEP concentration was approximately ~6.6 mM (100 molar eq.). The reaction was allowed to stand at rt for 2-48 h and then buffer exchanged into PBS using GE PD-10 Sephadex G25 columns per the manufacturer's instructions. Alternative methods such as diafiltration or dialysis are also useful in particular circumstances. The resulting solution was treated with approximately 50 equivalents of dehydroascorbate (50 mM stock in 1:1 EtOH/water). The antibody was allowed to stand at 4° C. overnight and subsequently buffer exchanged into PBS using GE PD-10 Sephadex G25 columns per the manufacturer's instructions. Again, alternative methods such as diafiltration or dialysis are also useful in particular circumstances.

The antibody thus prepared was diluted to ~2.5 mg/mL in PBS containing 10% DMA (vol/vol) and treated with the appropriate linker-payload (10 molar eq.) as a 10 mM stock solution in DMA. After 2 h at rt, the mixture was buffer exchanged into PBS (per above) and purified by size-exclusion chromatography on a Superdex 200 column. The monomeric fractions were concentrated and filter sterilized to give the final ADC.

Method C: Enzyme Mediated Conjugation to Antibody Carrying Reactive Glutamine Residues:

Therapeutic antibody carrying transglutamine enzyme-reactive glutamine residues is dialyzed into Dulbecco's Phosphate Buffered Saline (DPBS, Lonza). The transglutaminase mediated conjugation is carried by mixing 0.5-5.0 mg/mL transglutaminase reactive glutamine containing antibody in 25 mM Tris Buffer pH 8.0, 150 mM NaCl, 0.31 mM reduced glutathione with 5.0-20.0-fold molar excess of amino alkyl linker carrying payload (5-10 mM in dimethylacetamide (DMA) or dimethyl sulfoxide (DMSO)) and 2% w/v transglutaminase (Ajinomot Activa TI). The reaction is then incubated from 4-16 h at room temperature. The reaction mixture is subsequently buffer exchanged into DPBS (pH7.4) using GE Healthcare Sephadex G-25 M buffer exchange columns per manufacturer's instructions. Crude material is purified by size exclusion chromatography (SEC) using a GE AKTA Explorer system with a GE Superdex 200 column and DPBS (pH7.4) eluent. The pooled monomer fraction from AKTA is then concentrated if required. The ADC is further characterized via size exclusion chromatography (SEC) for purity and liquid chromatography electrospray ionization tandem mass spectrometry (LC-ESI MS) to calculate drug-antibody ratio (loading). The protein concentration is determined via UV spectrophotometer.

General Analytical Methods for Conjugation Examples

LC-MS (Method ADC1): Column=Waters BEH300-C4, 2.1×100 mm (P/N=186004496); Instrument=Acquity UPLC with an SQD2 mass spec detector; Flow rate=0.7 mL/min; Temperature=80° C.; Buffer A=water+0.1% formic acid; Buffer B=acetonitrile+0.1% formic acid. The gradient runs from 3% B to 95% B over 2 minutes, holds at 95% B for 0.75 min, and then re-equilibrates at 3% B. The sample is reduced with TCEP or DTT immediately prior to injection. The eluate is monitored by LCMS (400-2000 daltons) and the protein peak is deconvoluted using MaxEnt1. DAR is reported as a weight average loading as has been previously described.

SEC (Method ADC2): Column: Superdex200 (5/150 GL); Mobile phase: Phosphate buffered saline containing 2% acetonitrile, pH 7.4; Flow rate=0.25 mL/min; Temperature=ambient; Instrument: Agilent 1100 HPLC.

HIC (Method ADC3): Column: TSKGel Butyl NPR, 4.6 mm×3.5 cm (P/N=S0557-835); Buffer A=1.5 M ammonium sulfate containing 10 mM phosphate, pH 7; Buffer B=10 mM phosphate, pH 7+20% isopropyl alcohol; Flow rate=0.8 mL/min; Temperature=ambient; Gradient=0% B to 100% B over 12 minutes, hold at 100% B for 2 minutes, then re-equilibrate at 100% A; Instrument: Agilent 1100 HPLC.

TABLE 4

Structure of ADC and Payload Linkers used to prepare them

| ADC# | Structure | LP used for synthesis |
|---|---|---|
| ADC#1 | 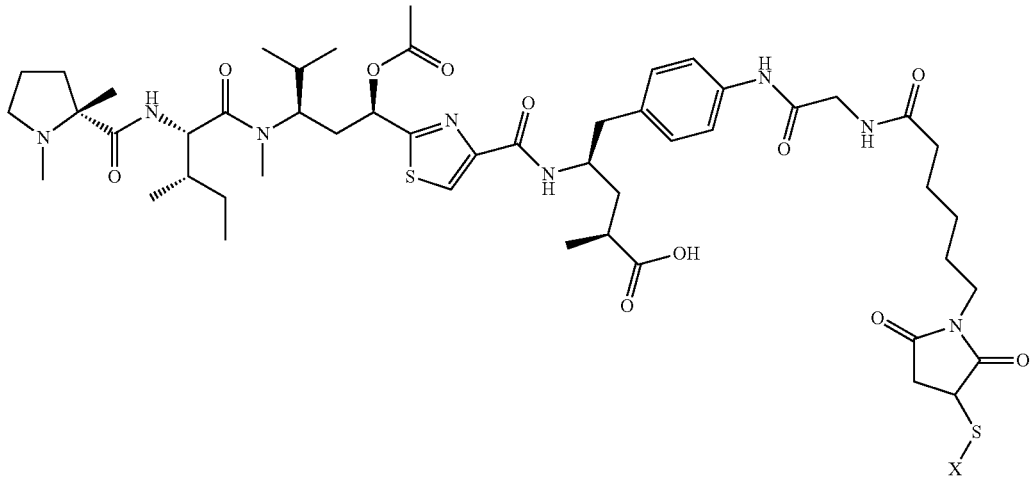 | LP#1 |

TABLE 4-continued

Structure of ADC and Payload Linkers used to prepare them

| ADC# | Structure | LP used for synthesis |
|---|---|---|
| ADC#2 | 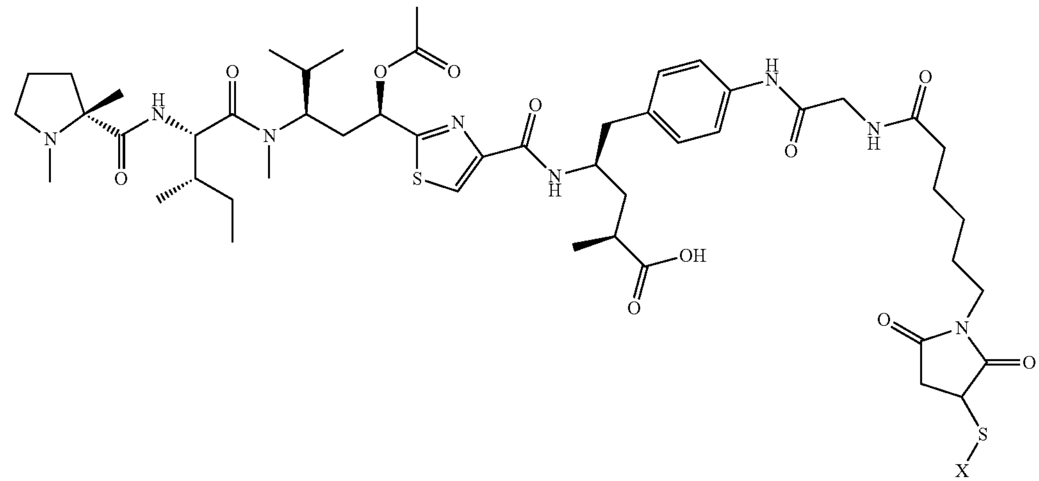 | LP#1 |
| ADC#3 | 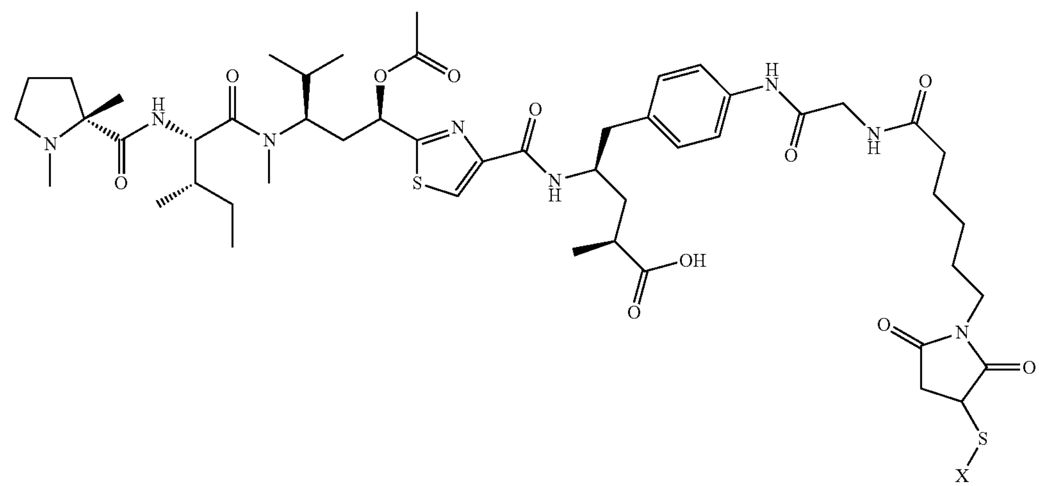 | LP#1 |
| ADC#4 | 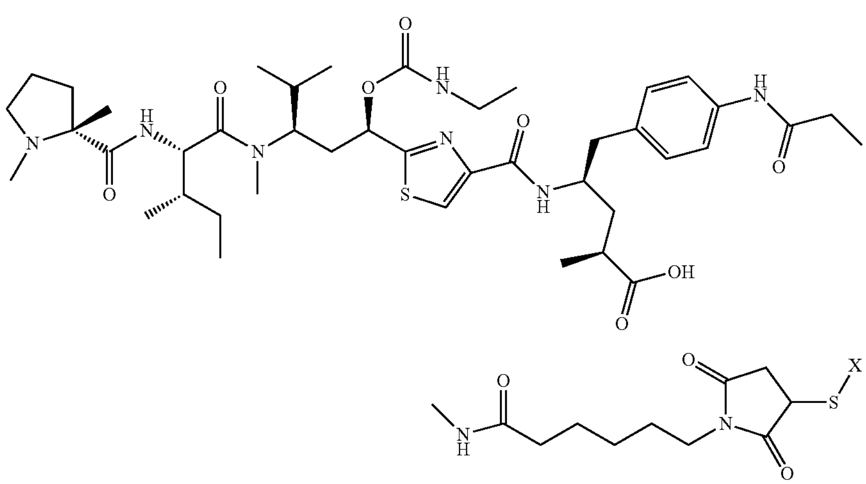 | LP#6 |

TABLE 4-continued

Structure of ADC and Payload Linkers used to prepare them

| ADC# | Structure | LP used for synthesis |
|---|---|---|
| ADC#5 | 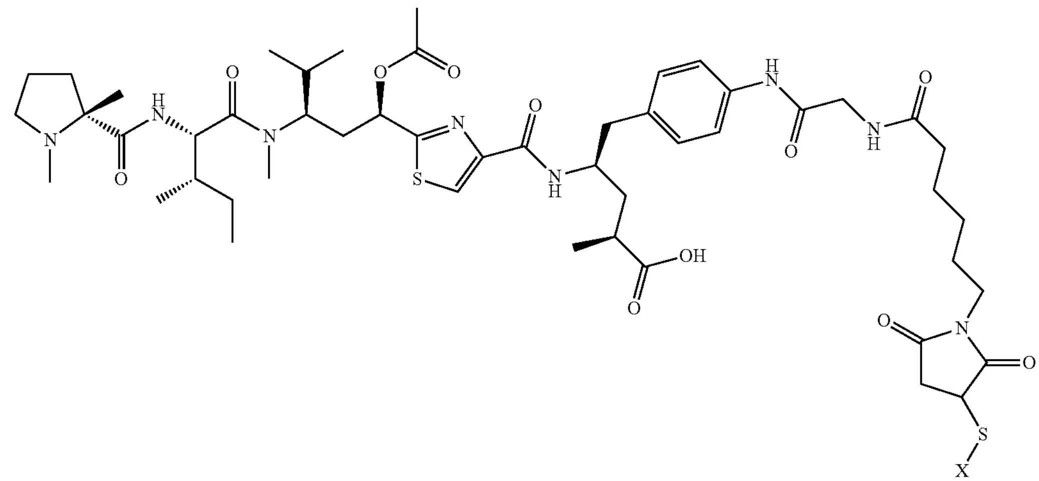 | LP#1 |
| ADC#6 | 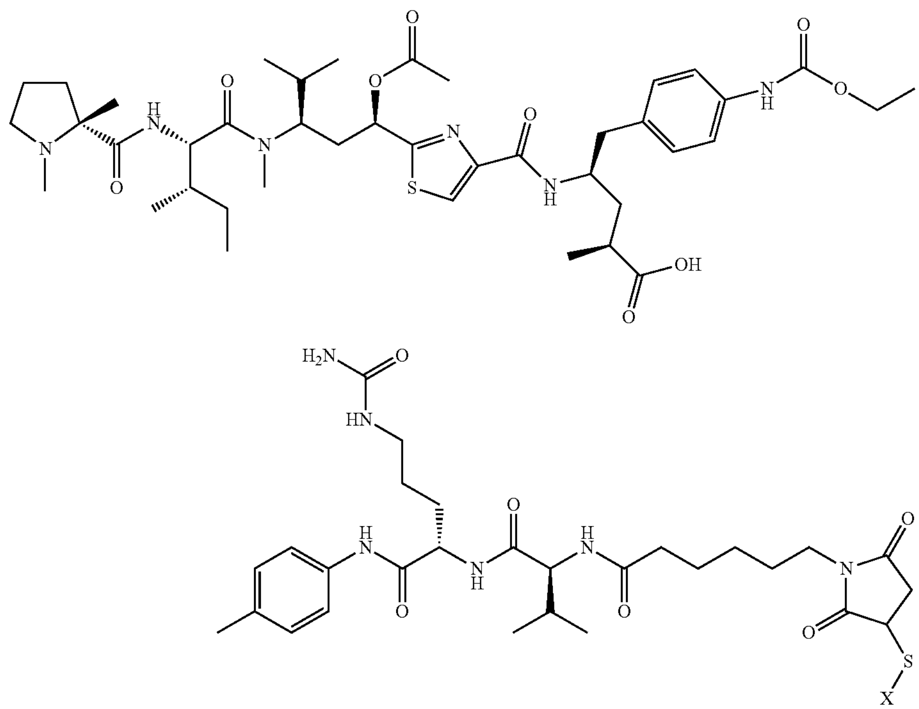 | LP#2 |

TABLE 4-continued
Structure of ADC and Payload Linkers used to prepare them
| ADC# | Structure | LP used for synthesis |
|---|---|---|
| ADC#7 | 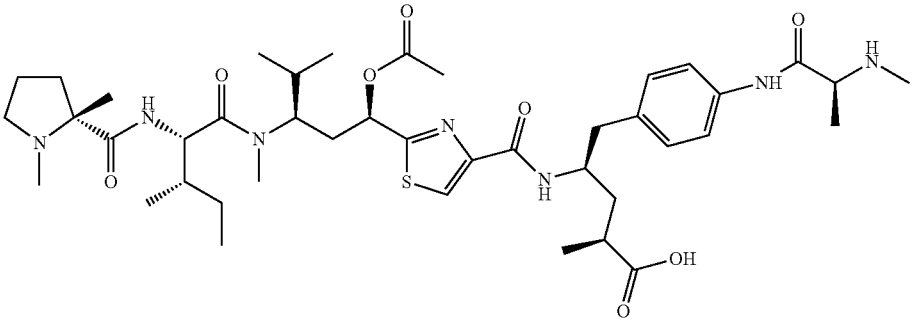 | LP#3 |
| ADC#8 | 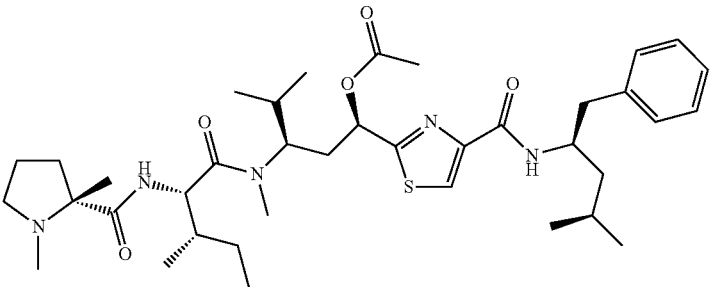 | LP#4 |

TABLE 4-continued

Structure of ADC and Payload Linkers used to prepare them

| ADC# | Structure | LP used for synthesis |
|---|---|---|
| ADC#9 | 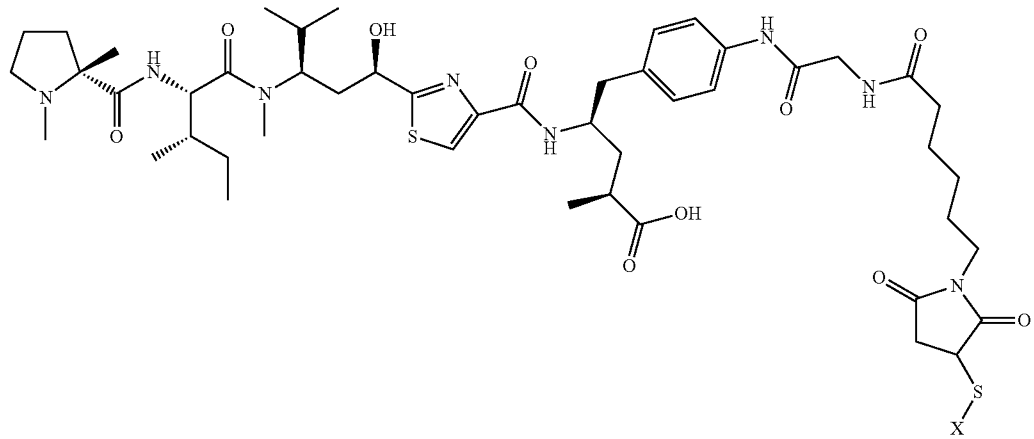 | LP#5 |
| ADC#10 | 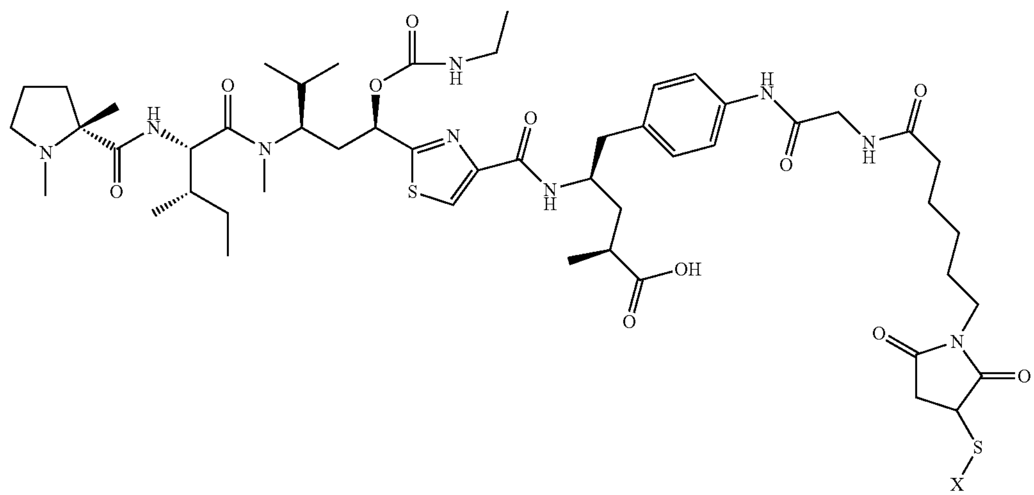 | LP#6 |
| ADC#11 | 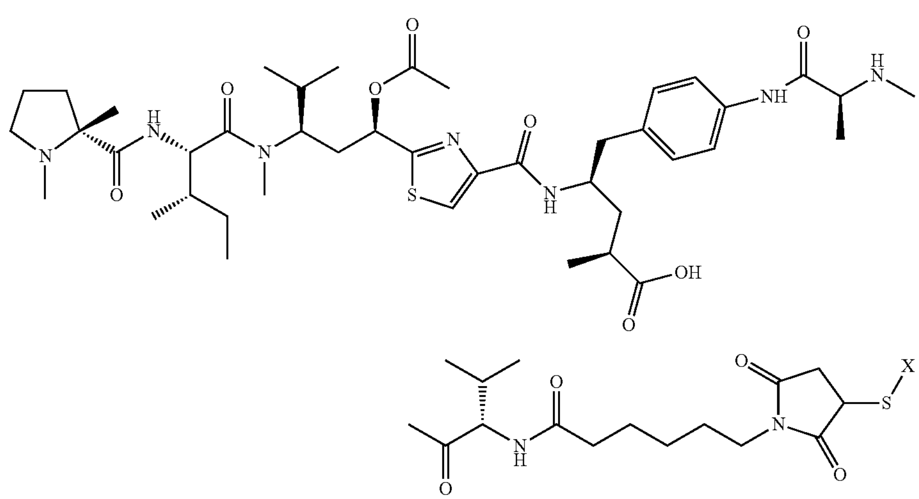 | LP#3 |

TABLE 4-continued
Structure of ADC and Payload Linkers used to prepare them
| ADC# | Structure | LP used for synthesis |
|---|---|---|
| ADC#12 | 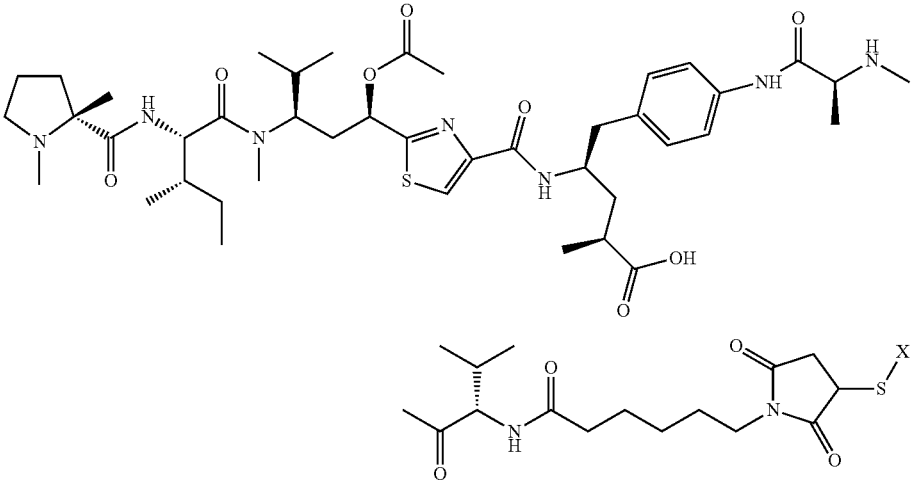 | LP#3 |
| ADC#13 | 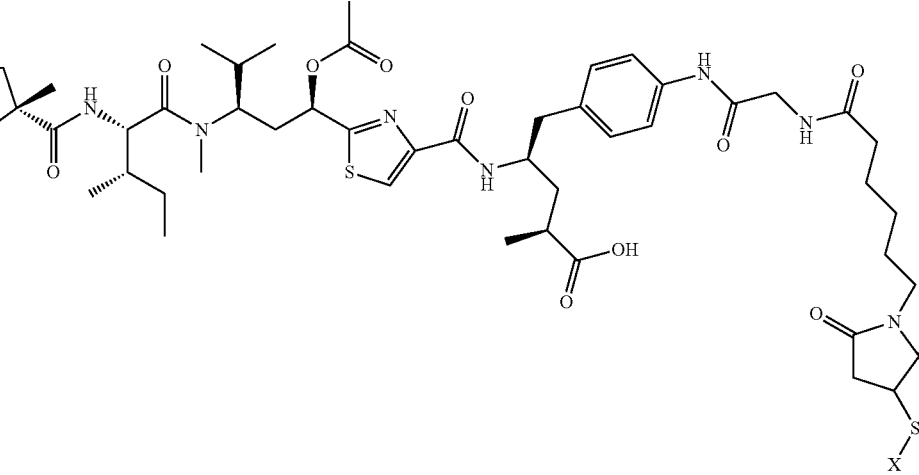 | LP#1 |
| ADC#14 | 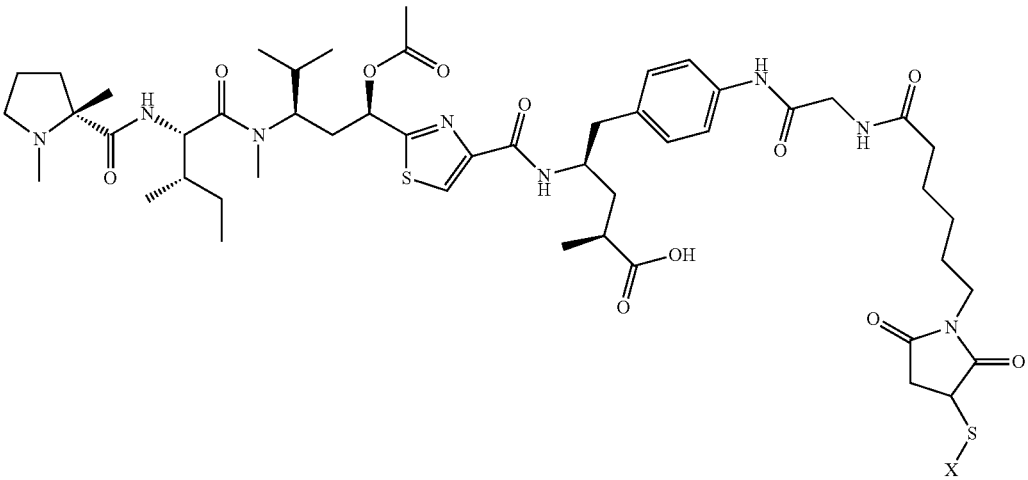 | LP#1 |

263                                                                 264

TABLE 4-continued

Structure of ADC and Payload Linkers used to prepare them

| ADC# | Structure | LP used for synthesis |
|---|---|---|
| ADC#15 | 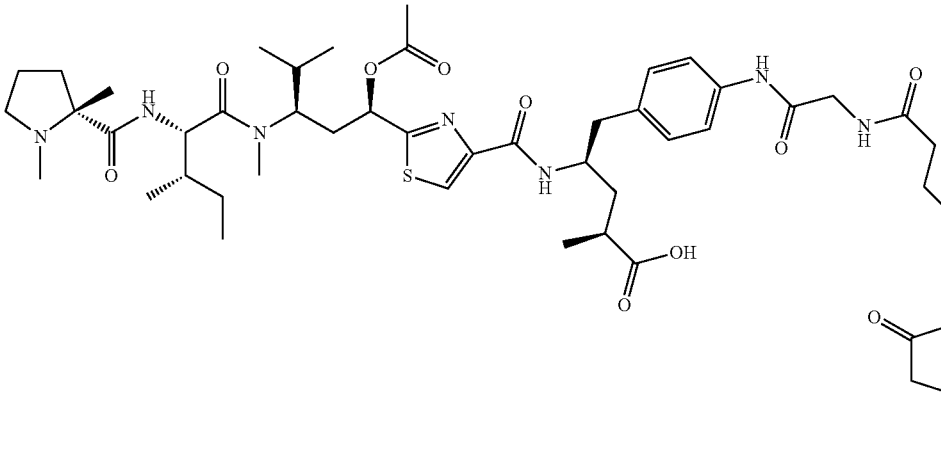 | LP#1 |
| ADC#16 | 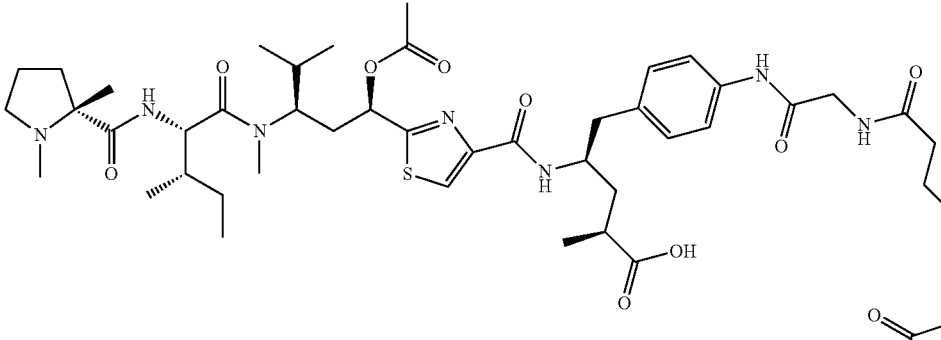 | LP#1 |

TABLE 5

General Method for Preparation of ADCs

| ADC# | General Method for preparation | Antibody used/ Conjugating Amino acid | Linker-payload used | Theoretical MW (increase) |
|---|---|---|---|---|
| ADC#1 | A | Tras | LP#1 | 993 |
| ADC#2 | B | Tras-C392 | LP#1 | 993 |
| ADC#3 | B | Tras-C334 | LP#1 | 993 |
| ADC#4 | A | Tras | LP#6 | 1022 |
| ADC#5 | B | Tras-C114 | LP#1 | 993 |
| ADC#6 | B | Tras-C114 | LP#2 | 1341 |
| ADC#7 | B | Tras-C114 | LP#3 | 1105 |
| ADC#8 | B | Tras-C114 | LP#4 | 1025 |
| ADC#9 | B | Tras-C114 | LP#5 | 950 |
| ADC#10 | B | Tras-C114 | LP#6 | 1022 |

TABLE 5-continued

General Method for Preparation of ADCs

| ADC# | General Method for preparation | Antibody used/ Conjugating Amino acid | Linker-payload used | Theoretical MW (increase) |
|---|---|---|---|---|
| ADC#11 | B | Tras-C334 | LP#3 | 1105 |
| ADC#12 | B | Tras-C392 | LP#3 | 1105 |
| ADC#13 | B | Tras-C347 | LP#1 | 993 |
| ADC#14 | B | Tras-C443 | LP#1 | 993 |
| ADC#15 | B | Tras-C388 | LP#1 | 993 |
| ADC#16 | B | Tras-kappa-C183 | LP#1 | 993 |

TABLE 6

Analytical Characterization of ADCs

| ADC# | Isolated yield | HPLC-HIC retention time | Observed Δ mass for the Heavy Chain (HC) portion | Drug per Antibody ratio (DAR) (LC/MS Method) | Drug per Antibody ratio (DAR) (HIC Method) |
|---|---|---|---|---|---|
| ADC#1 | 79% | 5.43 | 994 | 4.4 | NA |
| ADC#2 | 75% | 5.54 | 993 | 2.0 | 2.0 |
| ADC#3 | 52% | 5.19 | 993 | 2.0 | 2.0 |
| ADC#4 | 58% | 5.91 | 1022 | 4.0 | NA |
| ADC#5 | 68% | NA | 992 | 2.0 | NA |
| ADC#6 | 100% | NA | 1342 | 2.0 | NA |
| ADC#7 | 34% | NA | 1108 | 2.0 | NA |
| ADC#8 | 73% | NA | 1026 | 2.0 | NA |
| ADC#9 | 54% | 5.61 | 951 | 1.9 | 1.9 |
| ADC#10 | 52% | 5.71 | 1024 | 1.9 | 1.8 |
| ADC#11 | 66% | 5.25 | 1102 | 2.0 | 2.0 |
| ADC#12 | 68% | 5.54 | 1106 | 2.0 | 2.0 |
| ADC#13 | 36% | 5.96 | 993 | 2.0 | 2.0 |
| ADC#14 | 50% | 6.64 | 996 | 2.1 | 2.0 |
| ADC#15 | 48% | 5.95 | 994 | 2.0 | 2.0 |
| ADC#16 | 64% | 5.38 | 993 | 2.0 | 2.0 |

Synthesis of BODIPY-labeled *vinca* peptide probe {N-(5-{2-[(3,5-dimethyl-1H-pyrrol-2-yl-kappaN)methylidene]-2H-pyrrol-5-yl-kappaN}pentanoyl)-N-methyl-L-valyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamidato}(difluoro)boron (# B81)

To a vial containing 4,4-DIFLUORO-5,7-DIMETHYL-4-BORA-3A,4A-DIAZA-S-INDACENE-3-PENTANOIC ACID (93, 3.2 mg, 0.01 mmol) in DCM (0.4 mL) and DMF (0.1 mL) was added DIPEA (1 drop) and HATU (3.9 mg, 0.01 mmol). The mixture was stirred for 0.5 h and transferred to a vial containing Monomethyl Auristatin-F (CAS 745017-94-1) (7.3 mg, 0.01 mmol). The reaction was stirred at rt overnight, concentrated in vacuo, and the residue purified by reverse phase HPLC (Method B) to give the title compound # B81 (5.9 mg, 63%) as a white solid. LC-MS (Protocol D): m/z 1034.6; Retention time=7.80 and 8.01 min.

Tubulin Peptide-Binding Site Competition Assay

Tubulin binding potency was measured for payloads or cysteine-capped linker-payloads using a fluorescence polarization (FP) competition assay. The binding of a BODIPY-labeled vinca peptide probe (# B31) to a tubulin/RB3-stathmin-like-domain (RB3-SLD-tdm) complex generates a high FP signal, which can be decreased when mixing with test compounds that compete with the FP probe. The order of addition for the reagents in the FP assay was designed to pre-mix the FP probe with various concentrations of the test compound before mixing them with the tubulin/RB3-SLD-dm complex. The final assay concentrations of the probe, tubulin and RB3-SLD-dm were 3, 6, and 100 nM, respectively. $IC_{50}$ for each test compound is obtained by fitting the dose-dependent FP signal change using GraphPad Prism version 5 software (La Jolla, Calif.) while $K_i$ is converted from the $IC_{50}$ using the equations described previously (Nikolovska-Coleska et al., 2004). The FP signals were measured on an Infinite M1000 (Tecan, San Jose, Calif.) using ProxiPlate-384 F Plus, Black (Perkin-Elmer, Waltham, Mass., Cat #6008260) with 15 µL of solution per well.

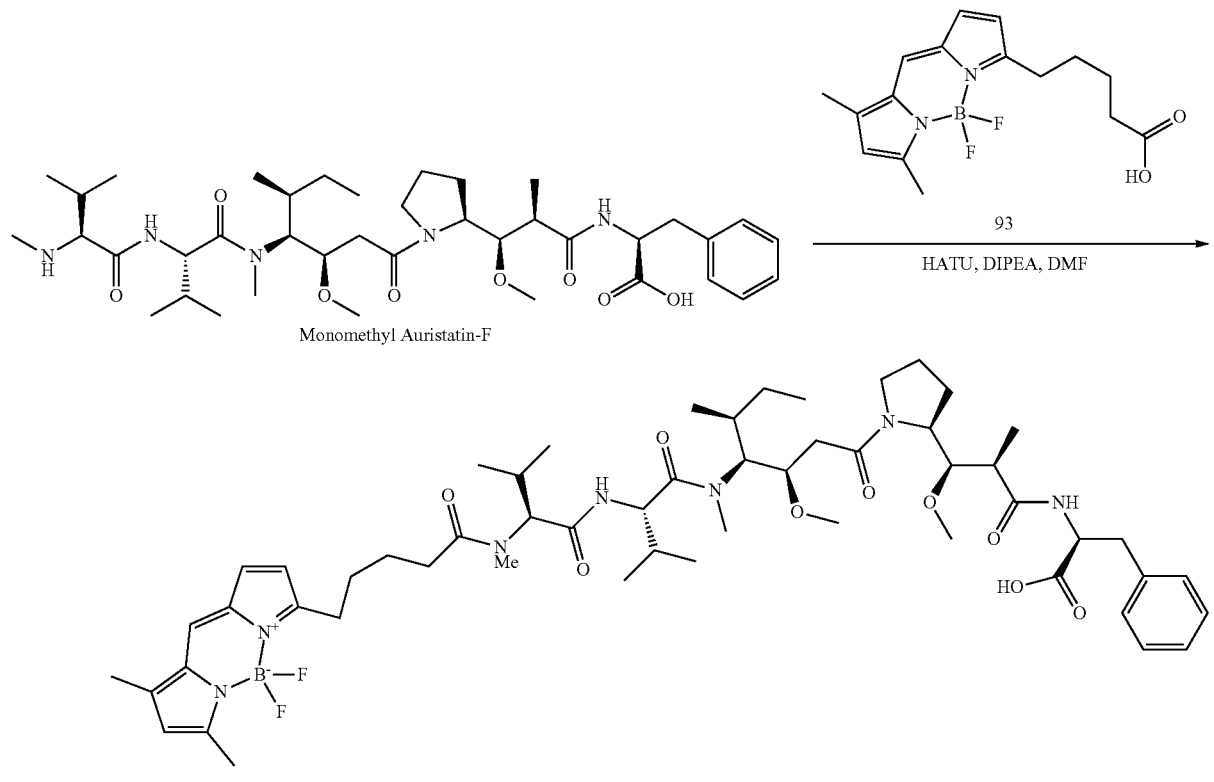

Sample dilution and mixing were done using a Beckman Biomek XF (Brea, Calif.). Porcine tubulin was purchased from Cytoskeleton, Inc. (Denver, Colo., Cat #T240) and RB3-SLD was expressed in *E. coli*. and purified on Q and then Superdex75 columns. The FP assay test for each compound was run in duplicates by mixing 6 μL of solution 1 containing 2.5× test compound (2.5× serial dilution from 7.8 μM maximum concentration, 11 total concentrations) and 7.5 nM of the FP probe in 80 mM PIPES, pH 7.0, 0.02% Tween 20, 2 mM $MgCl_2$, 1 mM EGTA and 3% DMSO with 9 μL of solution 2 containing 5 nM porcine tubulin and 167 nM of RB3-SLD-dm peptide (MADMEVIELNKATS-GQSWEVI-LKPPSFDGVPEFNASLPRRRDPSLEEIQK-KLEAAEERRKYQEAELLKHLAEKREHEREVIQKAIE ENNNFIKMAKEKLAQKMESNKENREAHLAAMLER-LQEKDKHAEEVRKNKELKEEASR) on ProxiPlate-384 micro-plates. The FP signals were read after five hours of incubation at 22° C. and fitted for dose response curve to obtain $IC_{50}$.

In Vitro Cell Assay Procedure

Target expressing (BT474 (breast cancer), N87 (gastric cancer), HCC1954 (breast cancer), MDA-MB-361-DYT2 (breast cancer)) or non-expressing (HT-29) cells were seeded in 96-well cell culture plates for 24 hours before treatment. Cells were treated with 3-fold serially diluted antibody-drug conjugates or free compounds (i. e. no antibody conjugated to the drug) in duplicate at 10 concentrations. Cell viability was determined by CellTiter 96® $AQ_{ueous}$ One Solution Cell Proliferation MTS Assay (Promega, Madison Wis.) 96 hours after treatment. Relative cell viability was determined as percentage of untreated control. $IC_{50}$ values were calculated using a four parameter logistic model #203 with XLfit v4. 2 (IDBS, Guildford, Surry, UK). Results are shown in Tables 1-3

In Vivo N87 Tumor Xenograft Model:

In vivo efficacy studies of antibody-drug conjugates were performed with target expressing xenograft models using the N87 cell lines. For efficacy study, 7.5 million tumor cells in 50% matrigel are implanted subcutaneously into 6-8 weeks old nude mice until the tumor sizes reach between 250 and 350 mm. Dosing is done through bolus tail vein injection. Depending on the tumor response to treatment, animals are injected with 1-10 mg/kg of antibody drug conjugates treated four times every four days. All experimental animals are monitored for body weight changes weekly. Tumor volume is measured twice a week for the first 50 days and once weekly thereafter by a Caliper device and calculated with the following formula: Tumor volume 5=(length× width)/2. Animals are humanely sacrificed before their tumor volumes reach 2500 mm. The tumor size is observed to decrease after the first week of treatment. Animals may be monitored continuously for tumor re-growth after the treatment has discontinued. Results of the testing of ADC 1, 3 and 10 in the N87 mouse xenograft in vivo screening model is shown in FIG. 1

In Vitro Plasma Stability Assay of ADCs

Figure 2:
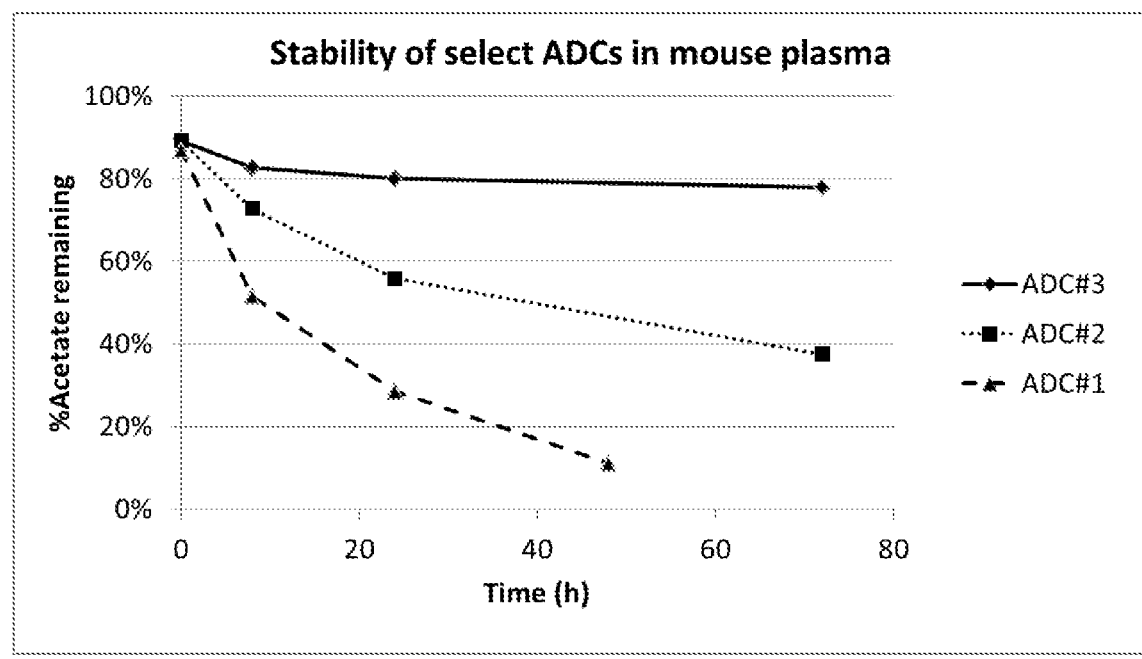
FIG. 2 provides plasma stability data for antibody drug conjugates of the present invention.

ADC samples (~1.5 mg/mL) were diluted into mouse plasma (Lampire Biological Laboratories, Pipersville, Pa.) to yield a final solution of 10% ADC, 90% plasma. Three time points were analyzed to determine their DAR (T-0, T-24 hr and T-48 hr). Each time point underwent an immunoprecipitation process to enrich the ADC. Briefly, each aliquot was diluted 1:1 in 20% MPER (Thermo Fisher Scientific, Waltham, Mass.) and equal amounts of biotinylated mouse anti-human Fc and goat anti-human kappa antibodies (SouthernBiotech, Birmingham, Ala.) were added. The samples were incubated for two hours at 4° C. followed by the addition of stretpadvidin Dynabeads (Thermo Fisher Scientific). Samples were processed on a KingFisher instrument with four washing steps consisting of 10% MPER, 0.05% TWEEN 20, and twice with PBS. The ADC was eluted off the beads with 0.15% formic acid. Samples were pH adjusted to 7.8 with 2M Tris pH 8.5 and their N-linked glycans were removed with PNGaseF (New England Biolabs, Ipswich, Mass.). The samples were reduced with TCEP and analyzed by LC-MS for % acetate hydrolysed ADC by height of mass shift of 993 (Parent) vs 951 (Deacetylated). The results are shown in FIG. 2. (Heavy chain or light chain containing the acetylated product (mass shift=993) was counted as "loaded" while those containing the deacetylated product (mass shift=951) was counted as "un-loaded" for DAR calculations). Results comparing ADC #1, ADC #2 (392 mutant), and ADC #3 (334 mutant) are shown in FIG. 2. No carbamate cleavage was observed for ADC #4. These results show that the labile ester of ADC #1 can be stabilized by judicious choice of the site of conjugation and by replacement of the ester a carbamate.

In Vivo Stability of ADCs

Blood samples were obtained at 72 h after the final dose of ADC from select tumor bearing mice from the previously mentioned N87 xenograft study. (see In vivo N87 Tumor Xenograft Model) Samples were taken from the 3 mpk dosing group. The ADC samples thus obtained were deglycosylated by treating with PNGase (New England Biolab) at 37° C. for 1 hour. Following the incubation, a capture antibody (biotinylated goat anti-human Fc at 1.0 mg/mL, Jackson ImmunoResearch) was added and the mixture was heated at 37° C. for one hour followed by gentle shaking at room temperature for a second hour. Dynabead MyOne Streptavidin T1 beads (Invitrogen) were added to the samples and incubated at rt for at least 30 minutes while gently shaking. The sample plate was then washed with 200 μL PBS+0.05% Tween 20, 200 μL PBS, and HPLC grade water. The bound ADC was eluted with 55 μL 2% of formic acid (v/v). Fifty microliters of each sample were transferred into a new plate followed by an additional 5 μL of 200 mM TCEP.

The intact protein analysis was carried out with Xevo G2 QTof mass spectrometer (Waters, Manchester, UK) coupled with Nano Acquity (waters) and BEH300 $C_4$, 1.7 μm, 0.3×100 mm column (Waters), using Masslynx v4.1 as acquisition software. The column temperature was set at 85° C. Mobile phase A consisted of 0.1% TFA (TFA) in water. Mobile phase B consisted of 0.1% TFA in acetonitrile: 1-propanol (1:1, v/v). The chromatographic separation was achieved at a flow rate of 18 μL/min using a linear gradient of mobile phase B from 5 to 90% over 7 minutes. Data analysis including deconvolution was performed using Biopharmalynx v1.33 (Waters). The results are shown in FIG. 3.

TABLE 7

Tubulin Peptide-Binding Site Competition Assay

| Example | Tubulin Peptide-Binding Site Competition Assay $IC_{50}$ (nM) |
|---|---|
| #B1 | 250.3 |
| #B2 | 92.2 |
| #B3 | 4.4 |
| #B4 | 4.6 |
| #B5 | 22.4 |
| #B6 | 118.829 |
| #B7 | 11.9 |
| #B8 | 1.8 |

TABLE 7-continued

Tubulin Peptide-Binding Site Competition Assay

| Example | Tubulin Peptide-Binding Site Competition Assay IC$_{50}$ (nM) |
|---|---|
| #B9 | 2.5 |
| #B12 | <0.458 |
| #B13 | 3.7 |
| #B14 | 11.5 |
| #B15 | 7 |
| #B16 | 10.4 |
| #B17 | 19.2 |
| #B21 | 1.9 |
| #B26 | <0.500 |
| #B27 | <0.648 |
| #B30 | 3.2 |
| #B31 | 3.1 |
| #B32 | 12.337 |
| #B34 | 24.8 |
| #B35 | 96.8 |
| #B36 | 1.7 |
| #B37 | 1.3 |
| #B38 | 4.8 |
| #B39 | 4.695 |
| #B40 | 2.4 |
| #B41 | 4.41 |
| #B42 | 27.6 |
| #B43 | 51.8 |
| #B44 | 47.6 |
| #B45 | 436.2 |
| #B46 | 282.3 |
| #B47 | 201.8 |
| #B48 | 110.4 |
| #B49 | 127.4 |
| #B50 | 8.6 |
| #B51 | 11.7 |
| #B52 | 61.8 |
| #B53 | 12.9 |
| #B54 | 60.6 |
| #B55 | 28.4 |
| #B56 | 33.6 |
| #B57 | 78.8 |
| #B58 | 5 |
| #B59 | 64.6 |
| #B60 | 108.2 |
| #B61 | 19.1 |
| #B62 | 4.7 |
| #B63 | 104.7 |
| #B64 | 73 |
| #B65 | 33.8 |
| #B66 | 52.2 |
| #B67 | 348.1 |
| #B68 | 84.7 |
| #B69 | 29.9 |
| #B70 | 56.3 |
| #B71 | 85.1 |
| #B72 | 32.9 |
| #B73 | 85.5 |
| #B74 | 89.3 |
| #B75 | 25.8 |
| #B76 | 19.9 |
| #B77 | 248.6 |
| #B78 | 9.3 |
| #B79 | 8.6 |
| #B80 | 6.5 |

TABLE 8

In vitro Cytotoxicity data for selected cytotoxic peptides of the invention

| Example | N87 IC50 (nM) | MDA-MB-361-DYT2 IC50 (nM) | HT29 IC50 (nM) |
|---|---|---|---|
| #B1 | 18.892 | 18.969 | |
| #B2 | 11.829 | 5.543 | |
| #B3 | 14.794 | 9.401 | |
| #B4 | 3.385 | 2.387 | |
| #B5 | 0.763 | 0.361 | 1.108 |
| #B6 | 29.306 | 18.586 | |
| #B7 | 9.528 | 5.152 | |
| #B8 | 0.104 | 0.063 | |
| #B9 | 1.071 | 0.765 | 0.642 |
| #B11 | 0.909 | 0.609 | 0.954 |
| #B12 | 2.985 | 2.974 | 4.516 |
| #B13 | <0.061 | <0.036 | <0.022 |
| #B14 | 0.337 | 0.017 | 0.063 |
| #B15 | >100.000 | >100.000 | >100.000 |
| #B16 | <0.042 | <0.064 | <0.026 |
| #B17 | 0.386 | 0.04 | 0.037 |
| #B18 | >100.000 | >100.000 | >100.000 |
| #B19 | 37.745 | 17.363 | 14.62 |
| #B20 | 6.111 | 2.578 | 3.369 |
| #B21 | 1.871 | 1.931 | 1.623 |
| #B22 | 12.073 | 11.173 | 14.41 |
| #B23 | 2.71 | 2.016 | 2.329 |
| #B24 | 1.219 | 1.244 | 1.143 |
| #B25 | 6.303 | 4.619 | 5.901 |
| #B26 | 7.777 | 8.269 | 8.828 |
| #B27 | 6.423 | 5.457 | 5.394 |
| #B28 | >100.000 | 81.477 | 74.91 |
| #B29 | 28.59 | 24.899 | 24.525 |
| #B30 | 2.671 | 3.265 | 1.807 |
| #B31 | 3.825 | 4.042 | 3.86 |
| #B32 | >100.000 | >100.000 | >100.000 |
| #B33 | >1000.000 | >1000.000 | >1000.000 |
| #B36 | 0.459 | 0.255 | |
| #B37 | 227.578 | 240.336 | |
| #B38 | 3.055 | 0.925 | |
| #B39 | 1.392 | 0.602 | |
| #B40 | 0.485 | 0.308 | |
| #B41 | 2.003 | 1.44 | |
| #B50 | 28.126 | 12.09 | 8.844 |
| #B51 | 7.776 | 2.937 | 2.198 |
| #B53 | 52.443 | 34.037 | 45.103 |
| #B58 | 5.629 | 2.26 | 1.492 |
| #B61 | 38.479 | 23.429 | 14.711 |
| #B62 | 10.428 | 2.652 | 2.256 |
| #B76 | 87.662 | 41.998 | 37.365 |
| #B78 | 39.902 | 19.858 | 14.473 |
| #B79 | 11.238 | 5.691 | 4.389 |
| #B80 | 18.542 | 4.205 | 4.63 |

TABLE 9
In vitro Cytotoxicity data for selected ADCs of the invention
| ADC# | N87 | | MDA-MB-361-DYT2 | | HT29 | |
|---|---|---|---|---|---|---|
| | $IC_{50}$ (nM) | $IC_{50}$ of Antibody (ng/mL) | $IC_{50}$ (nM) | $IC_{50}$ of Antibody (ng/mL) | $IC_{50}$ (nM) | $IC_{50}$ of Antibody (ng/mL) |
| ADC# 1 | 0.353 | 14.403 | 1.59 | 57.5 | 400.7 | 15835.752 |
| ADC# 2 | 0.568 | 43.106 | >1000.000 | >74977.416 | >1000.000 | >74977.416 |
| ADC# 3 | 0.454 | 33.943 | >1000.000 | >72740.113 | 809.98 | 59870.304 |
| ADC# 4 | 1.432 | 53.337 | >1610.738 | >60000.000 | >1610.738 | >60000.000 |
| ADC# 6 | 0.732 | 56.701 | 0.304 | 33.543 | 465.082 | 35436.334 |
| ADC# 7 | 0.684 | 55.316 | 0.139 | 9.588 | >1000.000 | >74031.891 |
| ADC# 8 | 104.337 | 7726.718 | 111.016 | 8221.314 | 83.283 | 6167.519 |
| ADC# 9 | >1000.000 | >77983.193 | >1000.000 | >77983.193 | >1000.000 | >77983.193 |
| ADC# 10 | 1.724 | 136.09 | >1000.000 | >77961.019 | >1000.000 | >77961.019 |
| ADC# 11 | 0.442 | 33.35 | 0.204 | 15.238 | >1000.000 | >72655.218 |
| ADC# 12 | 0.309 | 23.138 | 0.104 | 7.804 | >1000.000 | >74977.817 |
| ADC# 13 | 0.712 | 53 | >805.369 | >60,000 | >805.369 | >60,000 |
| ADC# 14 | 0.764 | 49 | >845.638 | >60,000 | >845.638 | >60,000 |
| ADC# 15 | 0.709 | 49 | >805.369 | >60,000 | >805.369 | >60,000 |
| ADC# 16 | 0.545 | 42 | 76.468 | 5696.811 | >805.369 | >60,000 |
We claim:
1. A compound presented below:
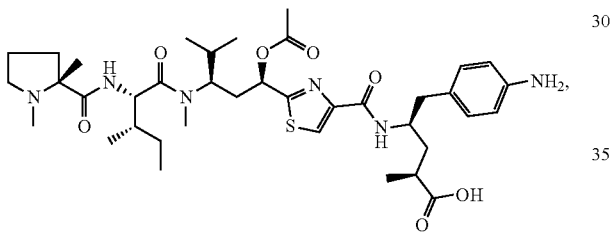
or a pharmaceutically acceptable salt thereof.
2. A compound selected from:
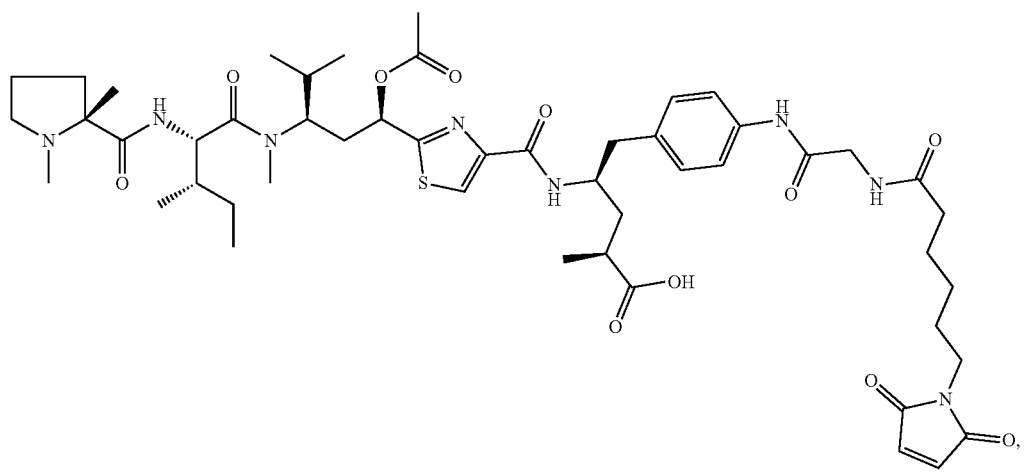

-continued
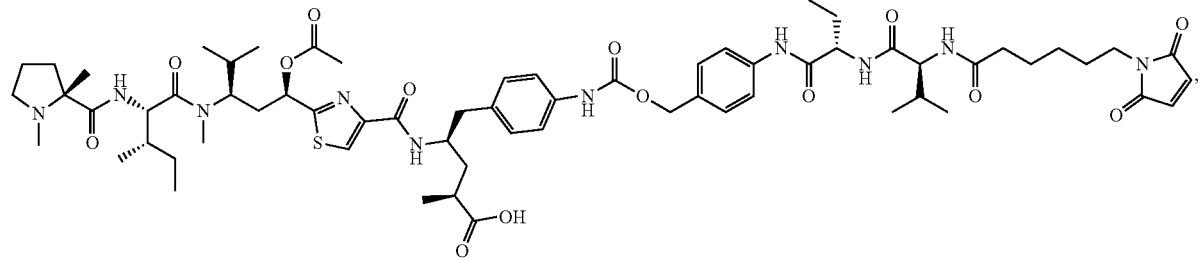
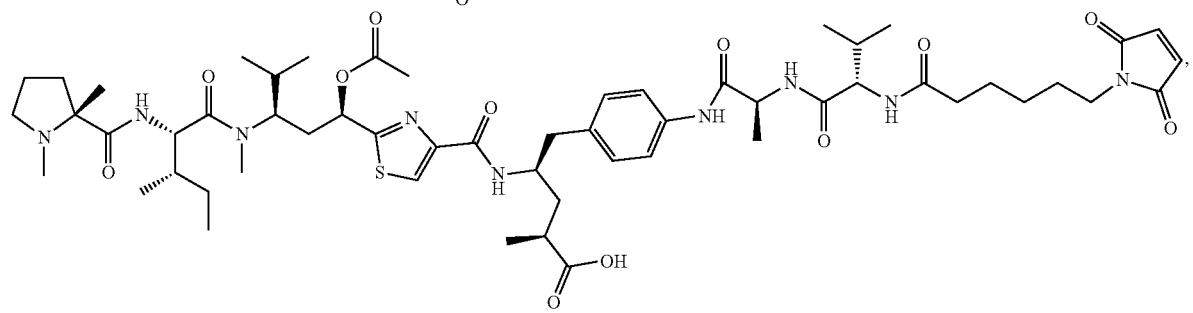
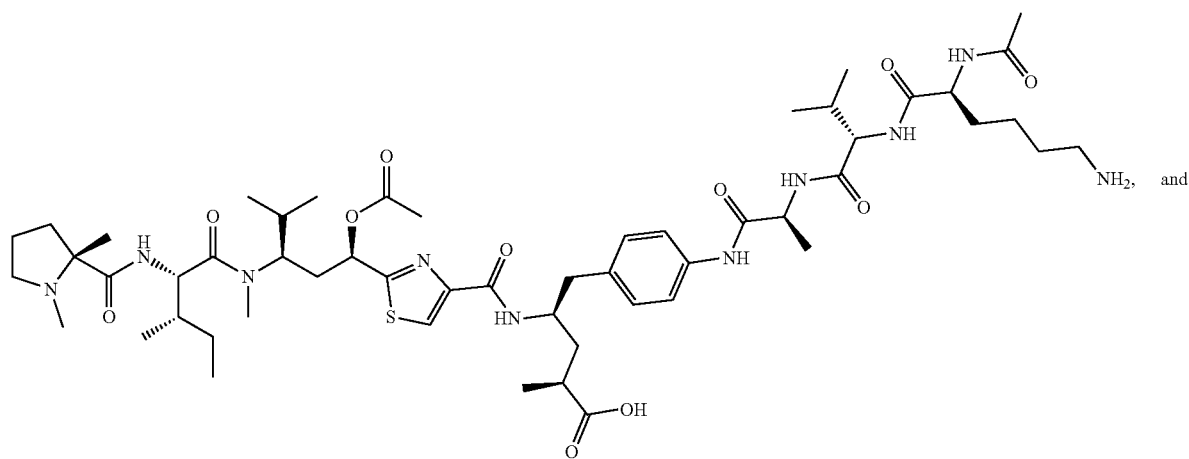
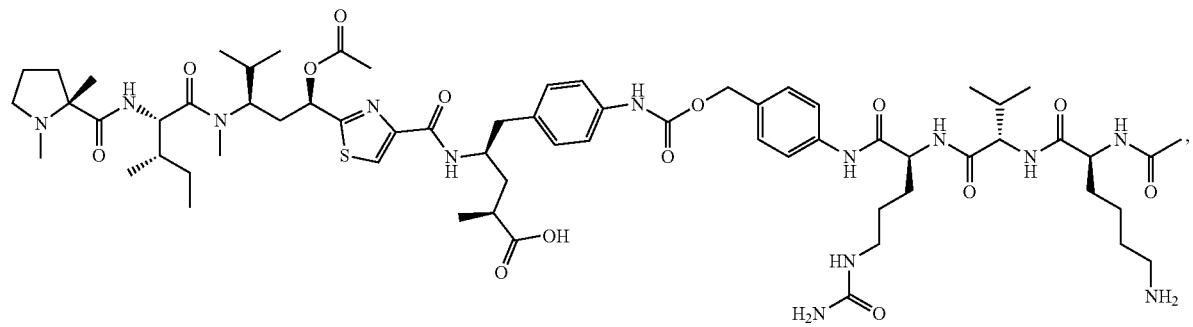 [SMILES: CC[C@H](C)[C@H](NC(=O)[C@@]1(C)CCCN1C)C(=O)N(C)[C@H](C[C@@H](OC(C)=O)c1nc(C(=O)N[C@@H](Cc2ccc(NC(=O)OCc3ccc(NC(=O)[C@H](CCCNC(N)=O)NC(=O)[C@@H](NC(=O)[C@H](CCCCN)NC(C)=O)C(C)C)cc3)cc2)C[C@H](C)C(=O)O)cs1)C(C)C]
or a pharmaceutically acceptable salt thereof.

3. A compound selected from:
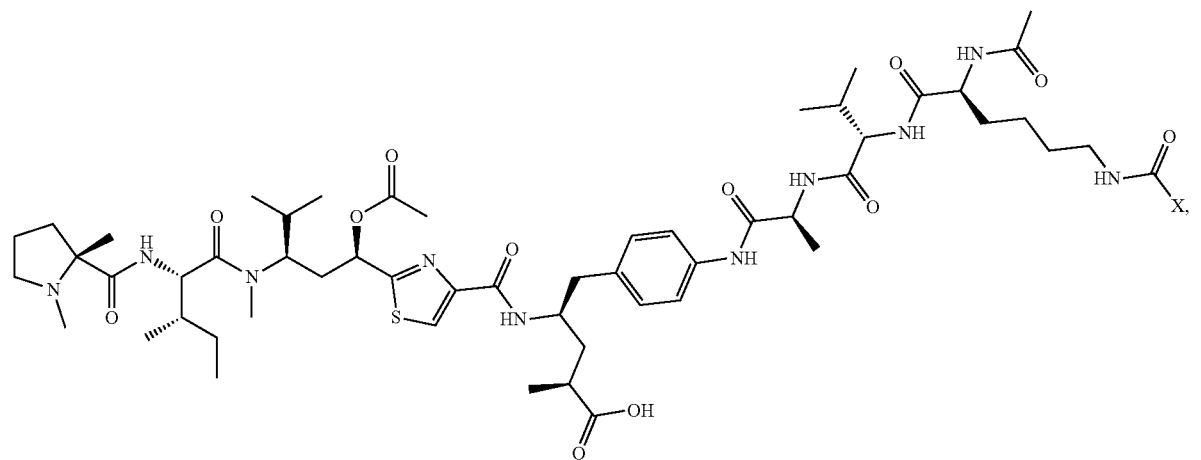
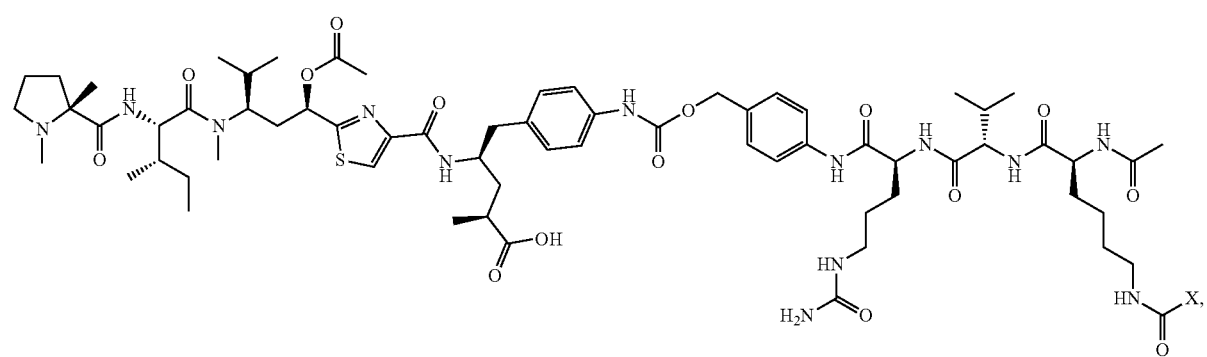
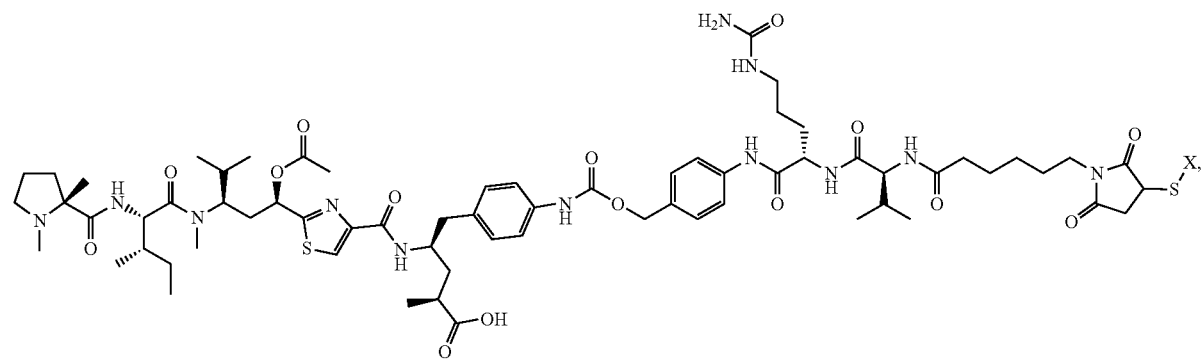
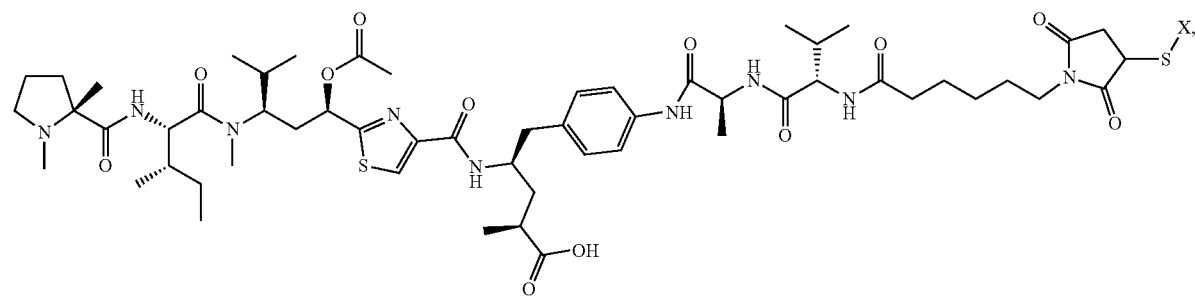

-continued

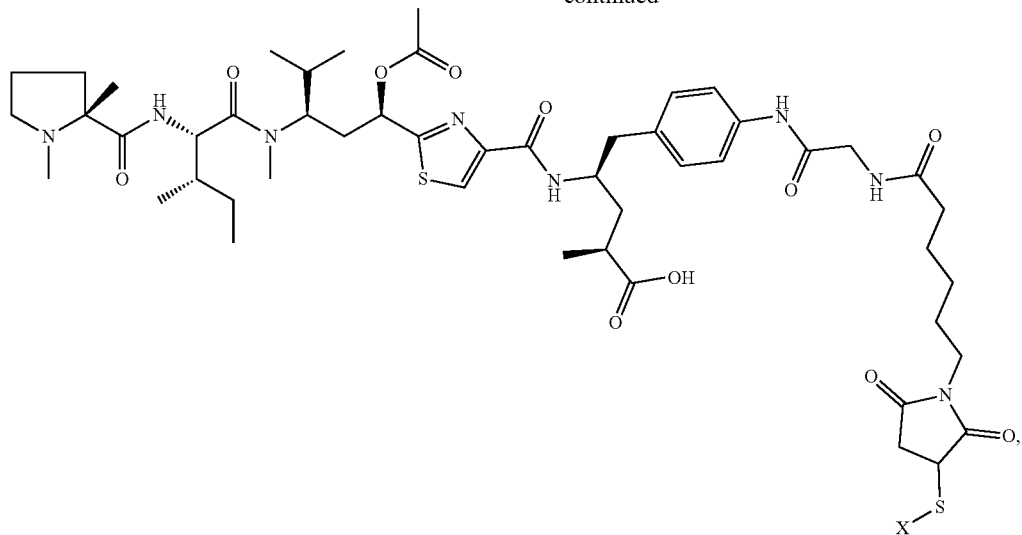

where X is an antibody, or a pharmaceutically acceptable salt thereof.

4. The compound or salt of claim 3, wherein said antibody is selected from: trastuzumab, trastuzumab mutants, oregovomab, edrecolomab, cetuximab, a humanized monoclonal antibody to the vitronectin receptor ($\alpha_v\beta_3$), alemtuzumab, a humanized anti-HLA-DR antibody for the treatment of non-Hodgkin's lymphoma, 131I Lym-1, a murine anti-HLA-Dr10 antibody for the treatment of non-Hodgkin's lymphoma, a humanized anti-CD2 mAb for the treatment of Hodgkin's Disease or non-Hodgkin's lymphoma, labetuzumab, bevacizumab, ibritumomab tiuxetan, ofatumumab, panitumumab, rituximab, tositumomab, ipilimumab, gemtuzumab, humanized monoclonal antibody to the oncofecal protein receptor 5T4, M1/70 (antibody to CD11b receptor), and other antibodies.

5. The compound of claim 3, wherein the antibody is bound via a Fc-containing or Fab-containing polypeptide engineered with an acyl donor glutamine-containing tag or an endogenous glutamine made reactive by polypeptide engineering in the presence of transglutaminase.

6. A pharmaceutical composition comprising an effective amount of the compound or salt of claim 3, or a pharmaceutically acceptable diluent, carrier or excipient.

7. The pharmaceutical composition of claim 6, further comprising a therapeutically effective amount of a chemotherapeutic agent selected from the group consisting of a tubulin-forming inhibitor, a topoisomerase inhibitor, and a DNA binder.

* * * * *